United States Patent
Umemura et al.

(10) Patent No.: US 7,871,982 B2
(45) Date of Patent: Jan. 18, 2011

(54) LINCOMYCIN DERIVATIVES AND ANTIMICROBIAL AGENTS COMPRISING THE SAME AS ACTIVE INGREDIENT

(75) Inventors: Eijirou Umemura, Chigasaki (JP); Yoshinari Wakiyama, Tokyo (JP); Kazutaka Ueda, Kitakami (JP); Kou Kumura, Yokohama (JP); Satomi Masaki, Saitama (JP); Takashi Watanabe, Yokohama (JP); Mikio Yamamoto, Kawasaki (JP); Chizuko Kaji, Kawasaki (JP); Keiichi Ajito, Kawasaki (JP)

(73) Assignee: Meiji Seika Kaisha, Ltd., Tokyo (JP)

( * ) Notice: Subject to any disclaimer, the term of this patent is extended or adjusted under 35 U.S.C. 154(b) by 377 days.

(21) Appl. No.: 12/086,279

(22) PCT Filed: Dec. 11, 2006

(86) PCT No.: PCT/JP2006/324698
§ 371 (c)(1),
(2), (4) Date: Aug. 6, 2008

(87) PCT Pub. No.: WO2007/066805
PCT Pub. Date: Jun. 14, 2007

(65) Prior Publication Data
US 2009/0156512 A1    Jun. 18, 2009

(30) Foreign Application Priority Data
Dec. 9, 2005    (JP) .............................. 2005-356053

(51) Int. Cl.
*A01N 43/04* (2006.01)
*A61K 31/70* (2006.01)
*C07H 15/16* (2006.01)

(52) U.S. Cl. ...................... 514/24; 536/16.2; 536/16.3; 536/16.4; 536/16.5

(58) Field of Classification Search ....................... None
See application file for complete search history.

(56) References Cited

U.S. PATENT DOCUMENTS 3,915,954 A   10/1975   Bannister 7,164,011 B2 *  1/2007  Lewis et al. ................ 536/16.5
7,199,105 B2 *  4/2007  Lewis et al. ................... 514/24
7,199,106 B2 *  4/2007  Lewis et al. ................... 514/24
7,256,177 B2 *  8/2007  Lewis et al. ................... 514/24
7,361,743 B2 *  4/2008  Lewis et al. ................ 536/16.3

OTHER PUBLICATIONS

International Search Report issued Jan. 23, 2007 in the International (PCT) Application PCT/JP2006/324698 of which the present application is the U.S. National Stage.
Ferenc Sztaricskai et al., "Semisynthetic modification of antibiotic lincomycin", Journal of Antibiotics, vol. 49, No. 9, pp. 941-943, 1996.
Ferenc Sztaricskai et al., "Chemical modification of antibiotic lincomycin", Magyar Kemiai Folyoirat, Database CAPLUS on STN, AN 1997:794464, DN 128:61724, vol. 103, No. 11, pp. 524-530, 1997.

* cited by examiner

*Primary Examiner*—Traviss C McIntosh, III
(74) *Attorney, Agent, or Firm*—Wenderoth, Lind & Ponack, L.L.P.

(57) ABSTRACT

This invention provides compounds of formula (I) or its pharmacologically acceptable salt or solvate, wherein A represents aryl or a monocyclic or bicyclic heterocyclic group, $R_1$ represents a halide, nitro, substituted $C_{1-6}$ alkyl, optionally substituted amino, $C_{1-6}$ alkyloxycarbonyl, optionally substituted aryl, a heterocyclic group, or heterocyclic carbonyl, $R_2$ represents a hydrogen atom or $C_{1-6}$ alkyl, $R_3$ represents $C_{1-6}$ alkyl, all of $R_4$, $R_5$, and $R_6$ represent a hydrogen atom, $R_7$ represents $C_{1-6}$ alkyl, m is 1 or 2, and n is 1. The compounds are novel lincomycin derivatives having a potent activity against resistant pneumococci. The compounds can be used as an antimicrobial agent and are useful for preventing or treating bacterial infectious diseases.

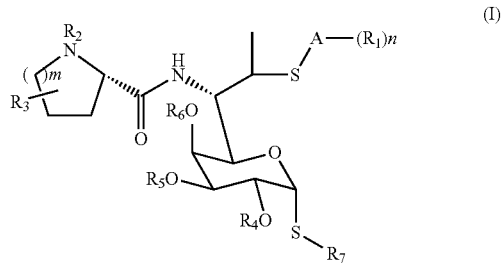

18 Claims, No Drawings

LINCOMYCIN DERIVATIVES AND ANTIMICROBIAL AGENTS COMPRISING THE SAME AS ACTIVE INGREDIENT

CROSS-REFERENCE TO RELATED APPLICATIONS

This application is based upon and claims the benefit of priority from the prior Japanese Patent Application No. 356053/2005, filed on Dec. 9, 2005, the entire contents of which are incorporated herein by reference.

BACKGROUND OF THE INVENTION

1. Field of the Invention

The present invention relates to novel lincomycin derivatives having antimicrobial activity or their pharmacologically acceptable salts thereof. The present invention also relates to a microbial agent comprising the compound as an active ingredient.

2. Related Art

Various compounds have hitherto been reported as lincomycin derivatives having antimicrobial activity. It is also disclosed that compounds having a structure similar to the compounds according to the present invention have antimicrobial activity. See, for example, U.S. Pat. No. 3,915,954, U.S. Pat. No. 3,870,699, U.S. Pat. No. 3,767,649, German Patent Laid-Open Publication No. 2229950, U.S. Pat. No. 3,689,474, U.S. Pat. No. 3,544,551, International Publication WO 2005/012320, J. Antibiotics, 49, (1996), 941, and Structure-Activity Relationships among the semisynthetic antibiotics, 601-651.

The compounds described in these documents, however, are ineffective against resistance pneumococci which have recently posed a clinical problem. Accordingly, the development of antimicrobial agents comprising lincomycin derivatives which are also effective against resistance pneumococci have been desired.

SUMMARY OF THE INVENTION

The present inventors have now found that a group of lincomycin derivatives of formula (I) have potent antimicrobial activity against resistance pneumococci against which lincomycin and clindamycin are ineffective. The present invention has been made based on such finding.

An object of the present invention is to provide novel lincomycin derivatives having potent activity against resistance pneumococci in the treatment of infectious diseases as a recent issue.

The compounds according to the present invention, that is, novel lincomycin derivatives according to the present invention are compounds of formula (I) or their pharmacologically acceptable salts or solvates:

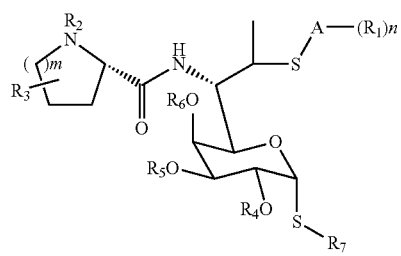

(I)

wherein
A represents
aryl optionally substituted by a group selected from the group consisting of benzyl and $C_{1-6}$ alky; or
a monocyclic or bicyclic heterocyclic group in which each ring is a four- to seven-membered ring and which is optionally substituted by a group selected from the group consisting of $C_{1-6}$ alkyl and halogenated $C_{1-6}$ alkyl,
wherein the heterocyclic group contains one to four heteroatoms selected from the group consisting of nitrogen, oxygen, and sulfur atoms,
$R_1$ represents
a halide;
cyano;
nitro;
substituted $C_{1-6}$ alkyl
wherein the $C_{1-6}$ alkyl group is substituted by one or more groups selected from the group consisting of hydroxy, halides, carbamoyl, $C_{1-6}$ alkyloxycarbonyl, cyano, di-$C_{1-6}$ alkylcarbamoyl, $C_{1-6}$ alkyloxy, heterocyclic carbonyl, and heterocyclic groups, and the heterocyclic carbonyl and heterocyclic groups are optionally substituted by one or more groups selected from the group consisting of halides, nitro, $C_{1-6}$ alkyl, $C_{1-6}$ alkylamino, amino, cyano, di-$C_{1-6}$ alkylamino, $C_{1-6}$ alkyloxy, hydroxy, acylamino, oxo, carbamoyl, di-$C_{1-6}$ alkylaminocarbonyl, and $C_{1-6}$ alkylaminocarbonyl;
optionally substituted amino
wherein the amino group is optionally substituted by one or more groups selected from the group consisting of $C_{1-6}$ alkyl, $C_{2-6}$ alkenyl, and $C_{1-6}$ acyl, optionally substituted heterocyclic groups, and optionally substituted aryl, the heterocyclic group, which can substitute the amino group, is optionally substituted by one or more groups selected from the group consisting of halides, nitro, cyano, di-$C_{1-6}$ alkylamino, $C_{1-6}$ alkyloxy, hydroxy, acylamino, $C_{1-6}$ alkyl, $C_{1-6}$ alkylamino, amino, oxo, carbamoyl, di-$C_{1-6}$ alkylaminocarbonyl, and $C_{1-6}$ alkylaminocarbony, and the aryl group is optionally substituted by one or more groups selected from the group consisting of halides, nitro, amino, $C_{1-6}$ alkyl, cyano, $C_{1-6}$ alkylthio, halogenated $C_{1-6}$ alkylthio, $C_{1-6}$ alkylsulfonyl, $C_{1-6}$ alkyloxy, hydroxy $C_{1-6}$ alkylamino, $C_{1-6}$ alkylamino, di-$C_{1-6}$ alkylamino, $C_{1-6}$ alkylsulfinyl, $C_{1-6}$ alkyloxycarbonyl, carbamoyl, and di-$C_{1-6}$ alkylaminocarbonyl;
N-amino-$C_{1-6}$ alkylcarbonyl-N—$C_{1-6}$ alkylamino;
N—$C_{1-6}$ alkyloxycarbonyl-$C_{1-6}$ alkyl-N—$C_{1-6}$ alkylamino;
N—$C_{1-6}$ alkyloxy substituted $C_{1-6}$ alkylcarbonyl-N—$C_{1-6}$ alkylamino;
$C_{1-6}$ alkylcarbonylamino optionally substituted by one or more groups selected from the group consisting of amino and hydroxy;
$C_{1-6}$ alkylamino-$C_{1-6}$ alkylcarbonylamino;
(di-$C_{1-6}$ alkylamino)-$C_{1-6}$ alkylcarbonylamino;
$C_{1-6}$ alkyloxy-$C_{1-6}$ alkylcarbonylamino;
N—$C_{2-6}$ alkenylcarbonylamino;
$C_{1-6}$ alkyloxycarbonylamino;
heterocyclic carbonylamino optionally substituted by one or more $C_{1-6}$ alkyl;
$C_{1-6}$ alkylsulfonylamino;
(S)-2-amino-3-succinamide;
carbamoyl;
N—$C_{1-6}$ alkyl substituted carbamoyl
N—$C_{1-6}$ alkyl-N—$C_{1-6}$ alkyloxy substituted carbamoyl;
N,N-di-$C_{1-6}$ alkyl substituted carbamoyl;

N—$C_{3-6}$ cycloalkyl substituted carbamoyl;
N-adamantyl substituted carbamoyl;
N-amino substituted carbamoyl;
N-heterocyclic $C_{1-6}$ alkyl substituted carbamoyl;
N-(hydroxy-$C_{1-6}$ alkyl) substituted carbamoyl;
N-(dihydroxy-$C_{1-6}$ alkyl) substituted carbamoyl;
N-(di-$C_{1-6}$ alkyloxy-$C_{1-6}$ alkyl) substituted carbamoyl;
N,N-di(hydroxy-$C_{1-6}$ alkyl) substituted carbamoyl;
N,N-di($C_{1-6}$ alkyloxy-$C_{1-6}$ alkyl) substituted carbamoyl;
carboxyl;
$C_{1-6}$ alkylcarbonyl;
heterocyclic-$C_{1-6}$ alkylcarbonyl;
$C_{1-6}$ alkyloxycarbonyl;
heterocyclic aminocarbonyl;
optionally substituted arylcarbonyl
  wherein the arylcarbonyl group is optionally substituted by one or more groups selected from the group consisting of halides, nitro, amino, $C_{1-6}$ alkyl, cyano, $C_{1-6}$ alkylthio, $C_{1-6}$ alkylsulfonyl, $C_{1-6}$ alkyloxy, hydroxy $C_{1-6}$ alkylamino, $C_{1-6}$ alkylamino, di-$C_{1-6}$ alkylamino, $C_{1-6}$ alkylsulfinyl, $C_{1-6}$ alkyloxycarbonyl, carbamoyl, and di-$C_{1-6}$ alkylaminocarbonyl;
optionally substituted four- to seven-membered heterocyclic carbonyl
  wherein the heterocyclic carbonyl group is optionally substituted by one or more groups selected from the group consisting of $C_{1-6}$ alkyl, hydroxy $C_{1-6}$ alkyl, cyano, di-$C_{1-6}$ alkylamino, $C_{1-6}$ alkyloxy, $C_{2-6}$ alkenyloxy-$C_{1-6}$ alkyl, hydroxy, $C_{1-6}$ alkylcarbonylamino, $C_{1-6}$ alkylthio-$C_{1-6}$ alkyl, amino-$C_{1-6}$ alkyl, $C_{1-6}$ alkyloxy-$C_{1-6}$ alkyl, OXO, $C_{1-6}$ alkylamino, carbamoyl, di-$C_{1-6}$ alkylaminocarbonyl, $C_{1-6}$ alkylaminocarbonyl, $C_{1-6}$ alkylamino-$C_{1-6}$ alkyl, di-$C_{1-6}$ alkylamino-$C_{1-6}$ alkyl, $C_{1-6}$ alkylsulfonyl-$C_{1-6}$ alkyl, cyano, halides, amino, acylamino $C_{1-6}$ alkyl, and acylamino;
$C_{1-6}$ alkylthio substituted by amino or carbamoyl;
pyridylthio;
$C_{1-6}$ alkylsulfonyl;
arylsulfonyl;
heterocyclic sulfonyl;
pyridyloxy;
optionally substituted aryl
  wherein the aryl group is optionally substituted by one or more groups, which may be the same or different, selected from the group consisting of a fluorine atom, a chlorine atom, nitro, amino, $C_{1-6}$ alkyl, cyano, $C_{1-6}$ alkyloxy, halogenated $C_{1-6}$ alkyloxy, hydroxy $C_{1-6}$ alkyl, hydroxy $C_{1-6}$ alkylamino, $C_{1-6}$ alkylamino, di-$C_{1-6}$ alkylamino, $C_{1-6}$ alkylthiocarbamoyl, $C_{1-6}$ alkylcarbonylamino, $C_{1-6}$ alkylsulfonylamino, formylamino, $C_{1-6}$ alkyloxycarbonyl, and azetidinyl;
an optionally substituted four- to seven-membered monocyclic heterocyclic group
  wherein the heterocyclic group is optionally substituted by one or more groups selected from the group consisting of halides, nitro, cyano, di-$C_{1-6}$ alkylamino, $C_{1-6}$ alkyloxy, hydroxy, acylamino, $C_{1-6}$ alkyl, $C_{1-6}$ alkylamino, amino, oxo, carbamoyl, di-$C_{1-6}$ alkylaminocarbonyl, $C_{1-6}$ alkylaminocarbonyl, $C_{1-6}$ alkyloxy-$C_{1-6}$ alkyl, and N-oxide; or
a bicyclic heterocyclic group in which each ring is a four- to seven-membered ring,
provided that, when n is 2, individual $R_1$s may be the same or different,
$R_2$ represents
a hydrogen atom;
optionally substituted $C_{1-6}$ alkyl;
optionally substituted $C_{2-6}$ alkenyl;
optionally substituted acyl; or
optionally substituted $C_{1-6}$ alkyloxycarbonyl
  wherein the $C_{1-6}$ alkyl, $C_{2-6}$ alkenyl, acyl, and $C_{1-6}$ alkyloxycarbonyl groups are optionally substituted by one or more groups selected from the group consisting of heterocyclic rings optionally substituted by $C_{1-6}$ alkyl; amino; hydroxy; and cyano,
$R_3$ represents
optionally substituted $C_{1-6}$ alkyl
  wherein the $C_{1-6}$ alkyl group is optionally substituted by one or more groups selected from the group consisting of halides, nitro, hydroxy, amino, $C_{1-6}$ alkyloxycarbonyl, carbamoyl, cyano, $C_{1-6}$ alkyloxy, oxo, heterocyclic ring, carbamoyl, azide, $C_{1-6}$ alkylaminocarbonyl, di-$C_{1-6}$ alkylaminocarbonyl, and optionally substituted aryl; or
$C_{2-6}$ alkenyl
$R_4$, $R_5$, and $R_6$, which may be the same or different, represent
a hydrogen atom;
optionally substituted $C_{1-6}$ alkyl; or
optionally substituted acyl
  wherein the $C_{1-6}$ alkyl group and a hydrogen atoms on the acyl group are optionally substituted by one or more groups selected from the group consisting of halides; nitro; hydroxy; amino; $C_{1-6}$ alkyloxycarbonyl; carbamoyl; cyano; nitro halide; $C_{1-6}$ alkyloxy; oxo; heterocyclic rings; carbamoyl; azide; $C_{1-6}$ alkylaminocarbonyl; di-$C_{1-6}$ alkylaminocarbonyl; and aryl optionally substituted by a halide, hydroxy or $C_{1-4}$ alkyl,
$R_7$ represents $C_{1-6}$ alkyl optionally substituted by one or more groups selected from the group consisting of halides and hydroxy,
m is 1 to 3, and
n is 1 or 2.

According to the present invention, there is provided a pharmaceutical composition comprising the compound of formula (I) or its pharmacologically acceptable salt or solvate. In a preferred embodiment of the present invention, there are provided pharmaceutical compositions comprising the above compound as an active ingredient together with an additive for a pharmaceutical preparation. These pharmaceutical compositions are useful for the prevention or treatment of bacterial infectious diseases (preferably bacterial infectious diseases in respiratory organs) and can be used as antimicrobial agents.

According to the present invention, there is also provided a method for preventing or treating bacterial infectious diseases, comprising administering a preventively or therapeutically effective amount of the compound according to the present invention or its pharmacologically acceptable salt or solvate together with a pharmaceutically acceptable carrier to a mammal.

Further, according to the present invention, there is provided use of the compound according to the present invention or its pharmacologically acceptable salt or solvate for the manufacture of a pharmaceutical composition for the prevention or treatment of bacterial infectious diseases. According to another aspect of the present invention, there is provided use of the compound according to the present invention or its pharmacologically acceptable salt or solvate as an active ingredient of an antimicrobial agent.

The lincomycin derivatives of formula (I) according to the present invention have potent antimicrobial activity against resistant pneumococci against which not only lincosamide-type antibiotics such as clindamycin but also other antibiotics such as microlide antibiotics are ineffective. Accordingly, the compounds according to the present invention are expected to be excellent therapeutic agents for infectious diseases in respiratory organs.

DETAILED DESCRIPTION OF THE INVENTION

Compounds of Formulae (I) and (II)

The term "$C_{1-6}$ alkyl" as used herein as a group or a part of a group means alkyl having 1 to 6 carbon atoms, which is of a straight chain or branched chain. $C_{1-6}$ alkyl is preferably $C_{1-4}$ alkyl, more preferably $C_{1-2}$ alkyl.

Examples of $C_{1-6}$ alkyl include methyl, ethyl, n-propyl, iso-propyl, n-butyl, iso-butyl, sec-butyl, tert-butyl, n-pentyl, and n-hexyl.

The alkenyl and the alkenyl moiety in the substituent containing the alkenyl group moiety may be, for example, vinyl, allyl, 1-propenyl, isopropenyl, 1-butenyl, 2-butenyl, propargyl, 1-butynyl, 1-pentynyl, or 2-butynyl which is of a straight chain, branched chain, or cyclic type or a combination thereof unless otherwise specified, preferably of a straight chain or branched chain type. The term "$C_{2-6}$ alkenyl" refers to alkenyl having 2 to 6 carbon atoms, preferably $C_{2-4}$ alkenyl. The number of double bonds contained in the alkenyl moiety is not particularly limited, and the double bond contained in the alkenyl moiety may be a Z configuration or an E configuration.

Acyl and the acyl moiety in the acyl moiety-containing substituent (for example, acyloxy such as acetoxy) as used herein refer to $C_2$ to $C_5$ straight-chain or branched-chain alkylcarbonyl or formyl, such as acetyl, propionyl, butyryl, isobutyryl, valeryl, or isovaleryl, unless otherwise specified.

The expression "alkyl optionally substituted by" as used herein refers to alkyl, wherein one or more hydrogen atoms on the alkyl group are substituted by one or more substituents which may be the same or different, and unsubstituted alkyl. It will be apparent to a person having ordinary skill in the art that the maximum number of substituents may be determined depending upon the number of substitutable hydrogen atoms on the alkyl group. This is true of groups containing substituents other than alkyl, for example, alkenyl, acyl, and aryl such as phenyl, and heterocyclic rings such as 1,3,4-thiadiazolyl.

The term "halide" (halogen atom) as used herein refers to a fluorine, chlorine, bromine, or iodine atom.

The term "halide" used herein, for example, in "alkyl halide" as a group or a part of a group means that one or more hydrogen atoms on each group have been substituted by a halogen atom.

The term "aryl" as used herein refers to a heteroatom-free six- to fourteen-membered (monocyclic to tricyclic, preferably monocyclic to bicyclic) aromatic ring, for example, phenyl, 1-naphthyl, 2-naphthyl, 1-anthryl, or 2-anthryl, unless otherwise specified. The six- to fourteen-membered aryl contains six to fourteen carbon atoms in the ring system.

The term "heterocyclic group" or "heterocyclic ring" as used herein may be a saturated, partially saturated, or unsaturated monocyclic or bicyclic heterocyclic ring which contains one to four heteroatoms selected from nitrogen, oxygen, and sulfur atoms with the remaining ring atoms being carbon atoms and wherein each ring is a four- to seven-membered (preferably 5- to 7-membered, more preferably five- or six-membered) ring. Examples of these heterocyclic groups include azetidino, pyrrolyl, pyrrolidinyl, pyrrolidino, furyl, thienyl, imidazolyl, isoxazolyl, oxazolyl, thiazolyl, isothiazolyl, triazolyl, thiadiazolyl, oxadiazolyl, tetrazolyl, pyridyl, pyrazolyl, pyrimidyl, pyrazinyl, piperazinyl, piperazino, piperidino, morpholinyl, morpholino, thiomorpholino, pyrazinyl, quinolyl, chromenyl, benzoxazolyl, benzothiazolyl, thiazolopyridyl, thiazolopyrimidinyl, and imidazothiazolyl wherein the binding position is not particularly limited.

Aryl represented by A is preferably phenyl.

The heterocyclic group represented by A is preferably
a four- to six-membered heterocyclic group containing one sulfur or nitrogen atom as the heteroatom,
a five- or six-membered unsaturated heterocyclic group containing two or three nitrogen atoms as the heteroatom,
a five-membered unsaturated heterocyclic group containing an oxygen or sulfur atom and two nitrogen atoms as the heteroatom, or
a bicyclic heterocyclic group formed of a five-membered unsaturated heterocyclic ring containing an oxygen or sulfur atom and one nitrogen atom as the heteroatom, and a benzene ring,
more preferably a ring group selected from the group consisting of azetidinyl, thienyl, imidazolyl, thiazolyl, oxazolyl, 1,3,4-thiadiazolyl, 1,2,4-thiadiazolyl, 1,3,4-oxadiazolyl, 1,2,4-triazolyl, pyridyl, pyrimidinyl, tetrazolyl, benzothiazolyl, benzoxazolyl, thiazolo[5,4-b]pyridyl, thiazolo[5,4-b]pyrimidinyl, imidazo[5,1-b]thiazolyl, quinolyl, and imidazo[1,2-a]pyridyl, more preferably azetidinyl, thienyl, imidazolyl, thiazolyl, 1,3,4-thiadiazolyl, 1,2,4-thiadiazolyl, 1,3,4-oxadiazolyl, 1,2,4-triazolyl, pyridyl, pyrimidinyl, benzoxazole, benzothiazole, and oxazole,
still more preferably, 1,3,4-thiadiazolyl.

Specific examples of heterocyclic groups represented by A include 3-azetidinyl, 2-thienyl, 2-imidazolyl, (2- or 5-)thiazolyl, 2-oxazolyl, 1,3,4-thiadiazol-2-yl, 1,2,4-thiadiazol-5-yl, 1,3,4-oxadiazol-2-yl, 1,2,4-triazol-3-yl, 2-pyridyl, 2-pyrimidinyl, 3-quinolyl, 2-benzothiazolyl, 2-benzoxazolyl, imidazo[5,1-b]thiazol-5-yl, imidazo[1,2-a]pyridin-6-yl, thiazolo[5,4-b]pyridin-2-yl, or thiazolo[5,4-b]pyrimidin-2-yl.

Specific examples of preferred heterocyclic groups represented by A include 1,3,4-thiadiazol-2-yl, 2-pyridyl, 2-thiazolyl, 2-pyrimidinyl, 2-azetidinyl, 2-benzothiazolyl, 2-oxazolyl, 1,3,4-oxadiazol-2-yl, or 1,2,4-triazol-3-yl.

In a preferred embodiment of the present invention, A represents a group selected from the group consisting of 1,3,4-thiadiazolyl, 1,2,4-thiadiazolyl, thiazolyl, thienyl, imidazolyl, azetidinyl, oxazolyl, 1,3,4-oxadiazolyl, 1,2,4-triazolyl, tetrazolyl, phenyl, pyridyl, pyrimidinyl, benzothiazolyl, benzoxazolyl, thiazolo[5,4-b]pyridyl, thiazolo[5,4-b]pyrimidinyl, imidazo[1,2-a]pyridyl, and imidazo[5,1-b]thiazolyl.

In a more preferred embodiment of the present invention, as described above, A represents phenyl or 1,3,4-thiadiazolyl (i.e., 1,3,4-thiadiazol-2-yl).

The halide represented by $R_1$ is preferably a fluorine atom or a chlorine atom.

The substituent in substituted $C_{1-6}$ alkyl represented by $R_1$ is preferably hydroxy, a halide, or $C_{1-6}$ alkyloxycarbonyl, more preferably hydroxy or a halide. The halide in the substituent is preferably a fluorine atom.

When $R_1$ represents heterocyclic-$C_{1-6}$ alkyl which substitutes the heterocyclic group, the heterocyclic ring is preferably a saturated six-membered ring containing an oxygen or sulfur atom and one nitrogen atom as the heteroatom. Accordingly, the heterocyclic-$C_{1-6}$ alkyl is preferably optionally substituted morpholino-$C_{1-6}$ alkyl, more preferably morpholino-$C_{1-6}$ alkyl.

The substituent for optionally substituted amino represented by $R_1$ is preferably $C_{1-6}$ alkyl (preferably n-$C_{1-6}$ alkyl), $C_{1-6}$ acyl, or a five- or six-membered monocyclic heterocyclic group (preferably pyridyl) containing one or two nitrogen atoms as the heteroatom. In particular, the heterocyclic substituted amino represented by $R_1$ is preferably N-pyridylamino or N-methyl-N-pyridylamino.

The heterocyclic-$C_{1-6}$ alkylcarbonyl represented by $R_1$ is preferably morpholino-$C_{1-6}$ alkylcarbonyl. In this case, the heterocyclic ring is optionally substituted by methyl, ethyl, or n-propyl.

The heterocyclic aminocarbonyl represented by $R_1$ is preferably (thiazol-2-yl)aminocarbonyl, (1,3,4-thiadiazol-2-yl)aminocarbonyl, or (3-pyridyl)aminocarbonyl.

The heterocyclic sulfonyl represented by $R_1$ is preferably morpholinosulfonyl or piperidinosulfonyl.

The arylcarbonyl and arylsulfonyl represented by $R_1$ are preferably benzoyl and benzenesulfonyl, respectively.

The optionally substituted four- to seven-membered heterocyclic carbonyl represented by $R_1$ is preferably a saturated five- or six-membered heterocyclic carbonyl containing one or two nitrogen atoms as the heteroatom, a saturated six-membered heterocyclic carbonyl group containing an oxygen or sulfur atom and one nitrogen atom as the heteroatom, more preferably azetidinylcarbonyl, morpholinocarbonyl, 1,4-perhydroxazepinylcarbonyl, piperidinocarbonyl, pyrrolidinocarbonyl, piperazinocarbonyl, or thiomorpholinocarbonyl, still more preferably azetidinylcarbonyl, morpholinocarbonyl, piperidinocarbonyl, or pyrrolidinocarbonyl. In another preferred embodiment of the present invention, the heterocyclic carbonyl is morpholinocarbonyl, 1,4-perhydroxazepinylcarbonyl, piperidinocarbonyl, or pyrrolidinocarbonyl. The substituent in the heterocyclic group is preferably $C_{1-6}$ alkyl, hydroxy $C_{1-6}$ alkyl, $C_{1-6}$ alkyloxy-$C_{1-6}$ alkyl, $C_{1-6}$ alkyloxy, $C_{2-6}$ alkenyloxy-$C_{1-6}$ alkyl, hydroxy, $C_{1-6}$ alkylthio-$C_{1-6}$ alkyl, $C_{1-6}$ alkylcarbonylamino-$C_{1-6}$ alkyl, amino-$C_{1-6}$ alkyl, $C_{1-6}$ alkylamino-$C_{1-6}$ alkyl, or di-$C_{1-6}$ alkylamino-$C_{1-6}$ alkyl. In still another preferred embodiment of the present invention, the substituent is $C_{1-6}$ alkyl, hydroxy $C_{1-6}$ alkyl, $C_{1-6}$ alkyloxy-$C_{1-6}$ alkyl, oxo, $C_{1-6}$ alkyloxy, hydroxy, $C_{1-6}$ alkylcarbonylamino, amino-$C_{1-6}$ alkyl, $C_{1-6}$ alkylamino-$C_{1-6}$ alkyl, di-$C_{1-6}$ alkylamino-$C_{1-6}$ alkyl, $C_{2-6}$ alkenyloxy-$C_{1-6}$ alkyl, or $C_{1-6}$ alkylthio-$C_{1-6}$ alkyl.

The optionally substituted aryl represented by $R_1$ is preferably optionally substituted phenyl, more preferably substituted phenyl. The substituent in the aryl is preferably a fluorine atom, a chlorine atom, nitro, amino, $C_{1-6}$ alkyl, cyano, $C_{1-6}$ alkyloxy, halogenated $C_{1-6}$ alkyloxy, hydroxy $C_{1-6}$ alkyl, hydroxy $C_{1-6}$ alkylamino, $C_{1-6}$ alkylamino, di-$C_{1-6}$ alkylamino, $C_{1-6}$ alkylthiocarbamoyl, $C_{1-6}$ alkylcarbonylamino, $C_{1-6}$ alkylsulfonylamino, formylamino, $C_{1-6}$ alkyloxycarbonyl, or azetidinyl. In a further preferred embodiment of the present invention, the substituent in the aryl is a fluorine atom, chlorine atom, nitro, amino, $C_{1-6}$ alkyl, cyano, $C_{1-6}$ alkylthio, $C_{1-6}$ alkylsulfonyl, $C_{1-6}$ alkyloxy, hydroxy $C_{1-6}$ alkylamino, $C_{1-6}$ alkylamino, di-$C_{1-6}$ alkylamino, $C_{1-6}$ alkylsulfinyl, $C_{1-6}$ alkyloxycarbonyl, carbamoyl, di-$C_{1-6}$ alkylaminocarbonyl, hydroxy, or azetidinyl. More preferably, the substituent is a group selected from a fluorine atom, nitro, and di-$C_{1-6}$ alkylamino.

The optionally substituted four- to seven-membered monocyclic heterocyclic group represented by $R_1$ is preferably an unsaturated five- or six-membered heterocyclic ring containing one oxygen, sulfur, or nitrogen atom as the heteroatom, a five- or six-membered heterocyclic ring containing two to four nitrogen atoms as the heteroatom, a saturated six-membered heterocyclic ring containing an oxygen or sulfur atom and one nitrogen atom as the heteroatom, or a five-membered unsaturated heterocyclic ring containing a sulfur atom and one or two nitrogen atoms as the heteroatom, and a preferred example of the group is a group selected from the group consisting of pyridyl, furyl, thiazolyl, pyrazolyl, imidazolyl, tetrazolyl, thiazolyl, 1,2,3-thiadiazolyl, and 1,3,6-triazinyl. More preferably, the heterocyclic group is 2-thienyl, 2-furyl, (2-, 4- or 5-)thiazolyl, 4-pyrazolyl, 5-pyrazolyl, 1,2,3-thiadiazol-4-yl, 1,2,3-thiadiazol-5-yl, 1,3,4-thiadiazol-2-yl, (2-, 3- or 4-)pyridyl, 2-pyrazinyl, 1,2,3-triazol-1-yl, 1,2,3-triazol-2-yl, 1,2,4-triazol-1-yl, 1,2,4-triazol-2-yl, tetrazol-1-yl, tetrazol-2-yl, imidazol-1-yl, imidazol-2-yl, or morpholino, still more preferably 2-furyl, (2-, 4- or 5-)thiazolyl, or (2-, 3- or 4-)pyridyl. The substituent in the heterocyclic group is preferably nitro, $C_{1-6}$ alkyl, $C_{1-6}$ alkyloxy, $C_{1-6}$ alkyloxy-$C_{1-6}$ alkyl, $C_{1-6}$ alkylamino, a halide, amino, oxo, or N-oxide.

The bicyclic heterocyclic group represented by $R_1$ is preferably a bicyclic group comprised of five- or six-membered unsaturated heterocyclic rings containing one or two oxygen, sulfur, or nitrogen atoms as the heteroatom, or a bicyclic group comprised of an unsaturated five- or six-membered heterocyclic ring containing one or two oxygen, sulfur, or nitrogen atoms as the heteroatom and an unsaturated five- or six-membered carbocyclic ring (for example, a benzene ring), more preferably, for example, quinoline, quinazoline, benzooxazole, or benzothiazole, still more preferably 3-quinolinyl or 2-benzoxazolyl.

In one preferred embodiment of the present invention, $R_1$ is selected from halides; cyano; nitro; substituted $C_{1-6}$ alkyl wherein the $C_{1-6}$ alkyl group is substituted by one or more groups selected from the group consisting of hydroxy, halide, carbamoyl, $C_{1-6}$ alkyloxycarbonyl, cyano, heterocyclic carbonyl, and di-$C_{1-6}$ alkylcarbamoyl; amino optionally substituted by $C_{1-6}$ alkyl and/or acyl; $C_{1-6}$ alkylcarbonylamino substituted by amino and/or hydroxy; $C_{1-6}$ alkylamino-$C_{1-6}$ alkylcarbonylamino; (di-$C_{1-6}$ alkylamino)-$C_{1-6}$ alkylcarbonylamino; $C_{1-6}$ alkyloxy-$C_{1-6}$ alkylcarbonylamino; (S)-2-amino-3-succinamide; $C_{1-6}$ alkylcarbonyl-N—$C_{1-6}$ alkylamino substituted by N—$C_{1-6}$ alkyloxy; carbamoyl substituted by N—$C_{1-6}$ alkyl; carbamoyl substituted by N,N-di-$C_{1-6}$ alkyl; carbamoyl; $C_{1-6}$ alkyloxycarbonyl; optionally substituted aryl wherein the aryl group is optionally substituted by one or more groups selected from the group consisting of halides, nitro, amino, $C_{1-6}$ alkyl, cyano, $C_{1-6}$ alkylthio, $C_{1-6}$ alkylsulfonyl, $C_{1-6}$ alkyloxy, hydroxy $C_{1-6}$ alkylamino, $C_{1-6}$ alkylamino, di-$C_{1-6}$ alkylamino, $C_{1-6}$ alkylsulfinyl, $C_{1-6}$ alkyloxycarbonyl, carbamoyl, and di-$C_{1-6}$ alkylaminocarbonyl; optionally substituted four- to seven-membered heterocyclic groups wherein the heterocyclic group is optionally substituted by one or more groups selected from the group consisting of halides, nitro, $C_{1-6}$ alkyl, $C_{1-6}$ alkylamino, amino, and oxo; optionally substituted four- to seven-membered heterocyclic carbonyl wherein the heterocyclic carbonyl group is optionally substituted by one or more groups selected from the group consisting of $C_{1-6}$ alkyl, hydroxy $C_{1-6}$ alkyl, $C_{1-6}$ alkyloxy-$C_{1-6}$ alkyl, oxo, and $C_{1-6}$ alkylamino; heterocyclic amino; heterocyclic-$C_{1-6}$ alkylcarbonyl; carbamoyl substituted by N-(hydroxy-$C_{1-6}$ alkyl); carbamoyl substituted by N-(dihydroxy-$C_{1-6}$ alkyl), carbamoyl substituted by N-(di-$C_{1-6}$ alkyloxy-$C_{1-6}$ alkyl); carbamoyl substituted by N,N-di(hydroxy-$C_{1-6}$ alkyl); and carbamoyl substituted by N,N-di($C_{1-6}$ alkyloxy-$C_{1-6}$ alkyl).

In one more preferred embodiment of the present invention, $R_1$ is selected from the group consisting of halides; nitro; substituted $C_{1-6}$ alkyl wherein the $C_{1-6}$ alkyl group is substituted by one or more groups selected from the group consisting of hydroxy and halides; amino optionally substituted by acyl; $C_{1-6}$ alkyloxycarbonyl; optionally substituted aryl wherein the aryl group is optionally substituted by one or more groups selected from the group consisting of halides, nitro, amino, $C_{1-6}$ alkyl, cyano, $C_{1-6}$ alkylthio, $C_{1-6}$ alkylsulfonyl, $C_{1-6}$ alkyloxy, hydroxy $C_{1-6}$ alkylamino, $C_{1-6}$ alkylamino, di-$C_{1-6}$ alkylamino, $C_{1-6}$ alkylsulfinyl, $C_{1-6}$ alkyloxycarbonyl, carbamoyl, and di-$C_{1-6}$ alkylaminocarbonyl; optionally substituted four- to seven-membered heterocyclic groups wherein the heterocyclic group is optionally substituted by one or more groups selected from the group consisting of nitro, $C_{1-6}$ alkyl, $C_{1-6}$ alkylamino, amino, and oxo; and optionally substituted four- to seven-membered heterocyclic carbonyl wherein the heterocyclic carbonyl group is optionally substituted by one or more groups selected from the group consisting of $C_{1-6}$ alkyl, hydroxy $C_{1-6}$ alkyl, $C_{1-6}$ alkyloxy-$C_{1-6}$ alkyl, and oxo.

In another preferred embodiment of the present invention, $R_1$ represents a group selected from the group consisting of
halides,
cyano,
nitro,
substituted $C_{1-6}$ alkyl wherein the substituent is as defined in formula (I),
amino optionally substituted by $C_{1-6}$ acyl,
N—$C_{1-6}$ alkylamino,
N,N-di-$C_{1-6}$ alkylamino,
pyridylamino,
$C_{1-6}$ alkylcarbonyl-N—$C_{1-6}$ alkylamino substituted by N—$C_{1-6}$ alkyloxy,
$C_{1-6}$ alkylcarbonylamino,
N—$C_{1-6}$ alkyl-N—$C_{1-6}$ alkylcarbonylamino,
$C_{1-6}$ alkyloxy-$C_{1-6}$ alkylcarbonylamino,
$C_{1-6}$ alkylcarbonylamino substituted by amino,
$C_{1-6}$ alkylcarbonylamino substituted by amino and hydroxy,
$C_{1-6}$ alkylamino-$C_{1-6}$ alkylcarbonylamino,
(di-$C_{1-6}$ alkylamino)-$C_{1-6}$ alkylcarbonylamino,
morpholino $C_{1-6}$ alkylcarbonyl,
(S)-2-amino-3-succinamide,
carbamoyl,
carbamoyl substituted by N—$C_{1-6}$ alkyl,
carbamoyl substituted by N,N-di-$C_{1-6}$ alkyl,
$C_{1-6}$ alkyloxycarbonyl,
azetidin-1-ylcarbonyl,
optionally substituted four- to seven-membered heterocyclic carbonyl wherein the substituent is as defined in formula (I), and the heterocyclic group in this group is selected from the group consisting of morpholino, 1,4-perhydroxazepinyl, piperidyl, and pyrrolidyl,
optionally substituted phenyl wherein the substituent is as defined in claim 1, and
optionally substituted four- to seven-membered heterocyclic groups wherein the substituent is as defined in formula (I), and the heterocyclic group is selected from the group consisting of pyridyl, furyl, thiazolyl, pyrazolyl, imidazolyl, tetrazolyl, thiazolyl, 1,2,3-thiadiazolyl, and 1,3,6-triazinyl.

In still another more preferred embodiment of the present invention, $R_1$ represents a group selected from the group consisting of
halides,
nitro,
$C_{1-6}$ alkyl substituted by hydroxy, halide or $C_{1-6}$ alkyloxy,
amino optionally substituted by $C_{1-6}$ acyl,
pyridylamino,
$C_{1-6}$ alkyloxycarbonyl,
morpholino $C_{1-6}$ alkylcarbonyl,
carbamoyl,
N—$C_{1-6}$ alkyl substituted carbamoyl,
N,N-di-$C_{1-6}$ alkyl substituted carbamoyl,
optionally substituted four- to seven-membered heterocyclic carbonyl wherein the heterocyclic carbonyl group is optionally substituted by one or more groups selected from the group consisting of $C_{1-6}$ alkyl, hydroxy $C_{1-6}$ alkyl, $C_{1-6}$ alkyloxy-$C_{1-6}$ alkyl, oxo, $C_{1-6}$ alkyloxy, hydroxy, $C_{1-6}$ alkylcarbonylamino, amino-$C_{1-6}$ alkyl, $C_{1-6}$ alkylamino-$C_{1-6}$ alkyl, di-$C_{1-6}$ alkylamino-$C_{1-6}$ alkyl, $C_{2-6}$ alkenyloxy-$C_{1-6}$ alkyl, and $C_{1-6}$ alkylthio-$C_{1-6}$ alkyl, and the heterocyclic group in this group is selected from the group consisting of morpholino, 1,4-perhydroxazepinyl, piperidyl, and pyrrolidyl,
optionally substituted phenyl wherein the phenyl is optionally substituted by one or more groups selected from the group consisting of a fluorine atom, a chlorine atom, nitro, amino, $C_{1-6}$ alkyl, cyano, $C_{1-6}$ alkylthio, $C_{1-6}$ alkylsulfonyl, $C_{1-6}$ alkyloxy, hydroxy $C_{1-6}$ alkylamino, $C_{1-6}$ alkylamino, $C_{1-6}$ alkylcarbonylamino, di-$C_{1-6}$ alkylamino, $C_{1-6}$ alkylsulfinyl, $C_{1-6}$ alkyloxycarbonyl, carbamoyl, di-$C_{1-6}$ alkylaminocarbonyl, hydroxy, and azetidinyl, and
optionally substituted four- to seven-membered heterocyclic group wherein the heterocyclic group is optionally substituted by one or more groups selected from the group consisting of nitro, $C_{1-6}$ alkyl, $C_{1-6}$ alkylamino, amino, $C_{1-6}$ alkyloxy, N-oxide, $C_{1-6}$ alkyloxy-$C_{1-6}$ alkyl, halides, and oxo, and the heterocyclic group is selected from the group consisting of pyridyl, furyl, thiazolyl, pyrazolyl, imidazolyl, tetrazolyl, thiazolyl, 1,2,3-thiadiazolyl, and 1,3,6-triazinyl.

In the present invention, preferably $R_2$ represents
a hydrogen atom;
optionally substituted $C_{1-6}$ alkyl
wherein the $C_{1-6}$ alkyl group is optionally substituted by one or more groups selected from the group consisting of amino; hydroxy; heterocyclic rings substituted by $C_{1-6}$ alkyl; and cyano;
$C_{2-6}$ alkenyl;
$C_{1-6}$ acyl
wherein the acyl group is optionally substituted by one or more groups selected from the group consisting of hydroxy, heterocyclic rings, and amino; or
$C_{1-6}$ alkyloxycarbonyl.
More preferably, $R_2$ represents
a hydrogen atom;
optionally substituted $C_{1-6}$ alkyl wherein the $C_{1-6}$ alkyl group is optionally substituted by one or more groups selected from the group consisting of amino; hydroxy; and heterocyclic rings substituted by $C_{1-6}$ alkyl,
still more preferably, a hydrogen atom or $C_{1-6}$ alkyl.

Preferably, $R_3$ represents $C_{1-6}$ alkyl (preferably n-$C_{1-6}$ alkyl) or $C_{2-6}$ alkenyl, more preferably $C_{1-6}$ alkyl.

The binding position of the group represented by $R_3$ is preferably the 4-position of 2-pyrrolidinyl (when m is 1), 2-piperidinyl (when m is 2), or 2-homopiperidinyl (when m is 3) to which $R_3$ is bonded.

Preferably, $R_4$, $R_5$, and $R_6$, which may be the same or different, represents
- a hydrogen atom; or
- optionally substituted $C_{1-6}$ alkyl
  wherein the $C_{1-6}$ alkyl group is optionally substituted by one or more groups selected from the group consisting of halides; nitro; hydroxy; amino; carbamoyl; cyano; and aryl optionally substituted by a halide.

More preferably, $R_4$ is as defined above, and both $R_5$ and $R_6$ represent a hydrogen atom, Still more preferably, $R_4$, $R_5$, and $R_6$ simultaneously represent a hydrogen atom.

$R_7$ preferably represents $C_{1-6}$ alkyl.

m is preferably 1 or 2.

n is preferably 1.

In a preferred embodiment of the present invention, when A represents 1,3,4-thiadiazolyl, $R_1$ represents a group selected from the group consisting of amino optionally substituted by acyl, $C_{1-6}$ alkyloxycarbonyl, four- to seven-membered heterocyclic carbonyl optionally substituted by $C_{1-6}$ alkyl, optionally substituted aryl
  wherein the aryl group is optionally substituted by one or more groups selected from the group consisting of a fluorine atom, a chlorine atom, nitro, amino, $C_{1-6}$ alkyl, cyano, $C_{1-6}$ alkylthio, $C_{1-6}$ alkylsulfonyl, $C_{1-6}$ alkyloxy, hydroxy $C_{1-6}$ alkylamino, $C_{1-6}$ alkylamino, di-$C_{1-6}$ alkylamino, $C_{1-6}$ alkylsulfinyl, $C_{1-6}$ alkyloxycarbonyl, carbamoyl, di-$C_{1-6}$ alkylaminocarbonyl, hydroxy, and azetidinyl, and optionally substituted four- to seven-membered monocyclic heterocyclic groups
  wherein the heterocyclic group is optionally substituted by one or more groups selected from the group consisting of nitro, $C_{1-6}$ alkyl, $C_{1-6}$ alkylamino, and amino. More preferably, in this case, $R_2$ represents
- a hydrogen atom or
- optionally substituted $C_{1-6}$ alkyl
  wherein the $C_{1-6}$ alkyl group is optionally substituted by one or more groups selected from the group consisting of amino, hydroxy, and $C_{1-6}$ alkyl substituted heterocyclic ring, $R_3$ represents n-$C_{1-6}$ alkyl, $R_4$, $R_5$, and $R_6$ simultaneously represent a hydrogen atom, $R_7$ represents $C_{1-6}$ alkyl, m is 1 or 2, and n is 1.

In another preferred embodiment of the present invention, when A represents phenyl, $R_1$ represents a group selected from the group consisting of halides, nitro, $C_{1-6}$ alkyl substituted by hydroxy, a halide, or $C_{1-6}$ alkyloxy, amino optionally substituted by acyl, heterocyclic amino, $C_{1-6}$ alkyloxycarbonyl, heterocyclic-$C_{1-6}$ alkylcarbonyl, and, N-(hydroxy-$C_{1-6}$ alkyl) substituted carbamoyl, N-(dihydroxy-$C_{1-6}$ alkyl) substituted carbamoyl, N-(di-$C_{1-6}$ alkyloxy-$C_{1-6}$ alkyl) substituted carbamoyl, N,N-di(hydroxy-$C_{1-6}$ alkyl) substituted carbamoyl, N,N-di($C_{1-6}$ alkyloxy-$C_{1-6}$ alkyl) substituted carbamoyl, optionally substituted four- to seven-membered heterocyclic carbonyl
  wherein the heterocyclic carbonyl group is optionally substituted by one or more groups selected from the group consisting of $C_{1-6}$ alkyl, hydroxy $C_{1-6}$ alkyl, $C_{1-6}$ alkyloxy-$C_{1-6}$ alkyl, oxo, $C_{1-6}$ alkyloxy, hydroxy, $C_{1-6}$ alkylcarbonylamino, amino-$C_{1-6}$ alkyl, $C_{1-6}$ alkylamino-$C_{1-6}$ alkyl, di-$C_{1-6}$ alkylamino-$C_{1-6}$ alkyl, $C_{2-6}$ alkenyloxy-$C_{1-6}$ alkyl, and $C_{1-6}$ alkylthio-$C_{1-6}$ alkyl, optionally substituted aryl
  wherein the aryl group is optionally substituted by one or more groups selected from the group consisting of cyano, amino, $C_{1-6}$ alkyl, $C_{1-6}$ alkylcarbonylamino, $C_{1-6}$ alkyloxy, $C_{1-6}$ alkylthio, and di-$C_{1-6}$ alkylamino, and optionally substituted four- to seven-membered monocyclic heterocyclic groups
  wherein the heterocyclic group is optionally substituted by one or more groups selected from the group consisting of $C_{1-6}$ alkyl, $C_{1-6}$ alkyloxy, N-oxide, nitro, $C_{1-6}$ alkyloxy-$C_{1-6}$ alkyl, amino, halide, and oxo.

More preferably, $R_1$ represents a group selected from the group consisting of
halides, nitro, $C_{1-6}$ alkyl substituted by hydroxy or a halide, amino optionally substituted by acyl, $C_{1-6}$ alkyloxycarbonyl, optionally substituted four- to seven-membered heterocyclic carbonyl wherein the heterocyclic carbonyl group is optionally substituted by one or more groups selected from the group consisting of $C_{1-6}$ alkyl, hydroxy $C_{1-6}$ alkyl, $C_{1-6}$ alkyloxy-$C_{1-6}$ alkyl, and oxo, aryl, and four- to seven-membered monocyclic heterocyclic groups optionally substituted by $C_{1-6}$ alkyl or oxo. More preferably, in this case, $R_2$ represents a hydrogen atom or $C_{1-6}$ alkyl, $R_3$ represents n-$C_{1-6}$ alkyl, $R_4$, $R_5$, and $R_6$ simultaneously represent a hydrogen atom, $R_7$ represents $C_{1-6}$ alkyl, m is 1 or 2, and n is 1.

In a further preferred embodiment of the present invention, -A-$(R_1)_n$ in formula (I) or (II) represents a group selected from the group consisting of:

optionally substituted phenyl-1,3,4-thiadiazol-2-yl, optionally substituted phenyloxazol-2-yl, optionally substituted pyrazolyl-1,3,4-thiadiazol-2-yl, optionally substituted pyridyloxazol-2-yl,
optionally substituted phenylthiazol-2-yl,
optionally substituted pyrrolidylcarbonylphenyl,
optionally substituted imidazolyl-1,3,4-thiadiazol-2-yl,
optionally substituted imidazolylphenyl,
optionally substituted 1,3,6-triazinylphenyl,
optionally substituted thiazolyl-1,3,4-oxadiazol-2-yl,
optionally substituted thiazolyl-1,3,4-thiadiazol-2-yl,
tetrazolyl phenyl,
1,4-perhydroxazepinecarbonylphenyl,
1,2,3-thiadiazolyloxazol-2-yl,
imidazo[5,1-b]thiazolylphenyl,
phenylimidazo[1,2-a]pyridin-6-yl,
optionally substituted phenyl-1,3,4-oxadiazol-2-yl,
optionally substituted pyridyl-1,3,4-thiadiazol-2-yl,
optionally substituted pyridylphenyl,
optionally substituted pyridylthiazol-2-yl,
optionally substituted pyridyloxazol-2-yl,
optionally substituted phenyloxazol-2-yl,
optionally substituted biphenyl,
optionally substituted morpholinocarbonylphenyl,
optionally substituted pyridylthiophen-2-yl,
optionally substituted pyrazolylphenyl,
optionally substituted phenylpyridyl,
optionally substituted morpholylphenyl, and pyridylcarbonylphenyl.

Asymmetric carbon, to which —S-A-$(R_1)_n$ in formula (I) is bonded, is present in the molecule of the compound of formula (I) according to the present invention, and the present invention includes any isolated substance in the stereoisomers and a mixtures of the stereoisomers. The carbon preferably has an S configuration.

Accordingly, in a preferred embodiment of the present invention, formula (I) is represented by formula (II):

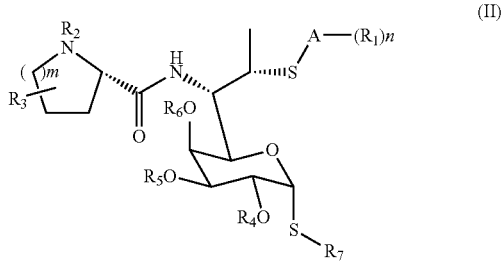

wherein A, $R_1$, $R_2$, $R_3$, $R_4$, $R_5$, $R_6$, $R_7$, m, and n are as defined in formula (I).

In another embodiment of the present invention, there is provided a lincomycin derivative of formula (I) or its pharmaceutically acceptable salt wherein A, $R_1$, $R_2$, $R_3$, $R_4$, $R_5$, $R_6$, $R_7$, m, and n are as defined below.

In formula (I),

A represents benzyl; or aryl optionally substituted by $C_{1-6}$ alky or a monocyclic or bicyclic heterocyclic group which contains one to four heteroatoms selected from nitrogen, oxygen, and sulfur atoms and optionally substituted by $C_{1-6}$ alkyl or halogenated $C_{1-6}$ alkyl, each ring being a four- to seven-membered ring, $R_1$ represents
a halide;
cyano;
nitro;
substituted $C_{1-6}$ alkyl
wherein the $C_{1-6}$ alkyl group is substituted by one or more groups selected from the group consisting of hydroxy, halides, carbamoyl, $C_{1-6}$ alkyloxycarbonyl, cyano, di-$C_{1-6}$ alkylcarbamoyl, $C_{1-6}$ alkyloxy, heterocyclic carbonyl, and heterocyclic groups, and the heterocyclic carbonyl and heterocyclic groups are optionally substituted by one or more groups selected from the group consisting of halides, nitro, $C_{1-6}$ alkyl, $C_{1-6}$ alkylamino, amino, cyano, di-$C_{1-6}$ alkylamino, $C_{1-6}$ alkyloxy, hydroxy, acylamino, oxo, carbamoyl, di-$C_{1-6}$ alkylaminocarbonyl, and $C_{1-6}$ alkylaminocarbonyl;
$C_{1-6}$ alkylcarbonyl,
heterocyclic-$C_{1-6}$ alkylcarbonyl,
amino optionally substituted by $C_{1-6}$ alkyl and acyl,
$C_{2-6}$ alkenylamino,
$C_{1-6}$ alkylcarbonylamino substituted by amino and/or hydroxy,
amino optionally substituted by one or more groups selected from heterocyclic rings optionally substituted by one or more groups selected from halides, nitro, cyano, di-$C_{1-6}$ alkylamino, $C_{1-6}$ alkyloxy, hydroxy, acylamino, $C_{1-6}$ alkyl, $C_{1-6}$ alkylamino, amino, oxo, carbamoyl, di-$C_{1-6}$ alkylaminocarbonyl, and $C_{1-6}$ alkylaminocarbonyl; aryl optionally substituted by one or more groups selected from halides, nitro, amino, $C_{1-6}$ alkyl, cyano, $C_{1-6}$ alkylthio, $C_{1-6}$ alkylsulfonyl, $C_{1-6}$ alkyloxy, hydroxy $C_{1-6}$ alkylamino, $C_{1-6}$ alkylamino, di-$C_{1-6}$ alkylamino, $C_{1-6}$ alkylsulfinyl, $C_{1-6}$ alkyloxycarbonyl, carbamoyl, and di-$C_{1-6}$ alkylaminocarbonyl; $C_{1-6}$ alkyl; and $C_{1-6}$ acyl,
$C_{1-6}$ alkylamino-$C_{1-6}$ alkylcarbonylamino,
(di-$C_{1-6}$ alkylamino)-$C_{1-6}$ alkylcarbonylamino,
N,N-di-$C_{1-6}$ alkylamino,
N-amino-$C_{1-6}$ alkylcarbonyl-N—$C_{1-6}$ alkylamino,
N—$C_{1-6}$ alkyloxycarbonyl-$C_{1-6}$ alkyl-N—$C_{1-6}$ alkylamino,
N—$C_{2-6}$ alkenylcarbonylamino,
heterocyclic carbonylamino optionally substituted by one or more $C_{1-6}$ alkyl,
$C_{1-6}$ alkyloxy-$C_{1-6}$ alkylcarbonylamino,
(S)-2-amino-3-succinamide,
N—$C_{1-6}$ alkyloxy substituted $C_{1-6}$ alkylcarbonyl-N—$C_{1-6}$ alkylamino,
$C_{1-6}$ alkylsulfonylamino,
arylamino optionally substituted by halogenated $C_{1-6}$ alkylthio,
carboxyl,
$C_{1-6}$ alkyloxycarbonylamino,
N—$C_{1-6}$ alkyl substituted carbamoyl,
N—$C_{1-6}$ alkyl-N—$C_{1-6}$ alkyloxy substituted carbamoyl,
N,N-di-$C_{1-6}$ alkyl substituted carbamoyl,
N—$C_{3-6}$ cycloalkyl substituted carbamoyl,
N-adamantyl substituted carbamoyl,
N-amino substituted carbamoyl,
N-heterocyclic $C_{1-6}$ alkyl substituted carbamoyl, N-hydroxy-$C_{1-6}$ alkyl substituted carbamoyl,
carbamoyl,
$C_{1-6}$ alkyloxycarbonyl,
heterocyclic aminocarbonyl,
substituted $C_{1-6}$ alkylthio wherein the $C_{1-6}$ alkylthio group is substituted by amino or carbamoyl,
pyridylthio,
heterocyclic sulfonyl,
$C_{1-6}$ alkylsulfonyl,
aryl,
arylcarbonyl wherein the aryl group and arylcarbonyl group are optionally substituted by one or more groups selected from halides, nitro, amino, $C_{1-6}$ alkyl, cyano, $C_{1-6}$ alkylthio, $C_{1-6}$ alkylsulfonyl, $C_{1-6}$ alkyloxy, hydroxy $C_{1-6}$ alkylamino, $C_{1-6}$ alkylamino, di-$C_{1-6}$ alkylamino, $C_{1-6}$ alkylsulfinyl, $C_{1-6}$ alkyloxycarbonyl, carbamoyl, and di-$C_{1-6}$ alkylaminocarbonyl,
arylsulfonyl,
four- to seven-membered heterocyclic groups wherein the heterocyclic group is optionally substituted by one or more groups selected from the group consisting of halides, nitro, cyano, di-$C_{1-6}$ alkylamino, $C_{1-6}$ alkyloxy, hydroxy, acylamino, $C_{1-6}$ alkyl, $C_{1-6}$ alkylamino, amino, oxo, carbamoyl, di-$C_{1-6}$ alkylaminocarbonyl, and $C_{1-6}$ alkylaminocarbonyl,
bicyclic heterocyclic groups,
pyridyloxy,
heterocyclic-$C_{1-6}$ alkyl, and
four- to seven-membered heterocyclic carbonyl wherein the heterocyclic carbonyl group is optionally substituted by one or more groups selected from the group consisting of $C_{1-6}$ alkyl, hydroxy $C_{1-6}$ alkyl, cyano, di-$C_{1-6}$ alkylamino, $C_{1-6}$ alkyloxy, hydroxy, $C_{1-6}$ alkyloxy-$C_{1-6}$ alkyl, oxo, $C_{1-6}$ alkylamino, carbamoyl, di-$C_{1-6}$ alkylaminocarbonyl, $C_{1-6}$ alkylaminocarbonyl, $C_{1-6}$ alkylamino-$C_{1-6}$ alkyl, di-$C_{1-6}$ alkylamino-$C_{1-6}$ alkyl, $C_{1-6}$ alkylsulfonyl-$C_{1-6}$ alkyl, cyano, halide, amino, acylamino $C_{1-6}$ alkyl, and acylamino, provided that, when n is 2, the $R_1$s may be the same or different, $R_2$ represents a hydrogen atom,
$C_{1-6}$ alkyl optionally substituted by one or more groups selected from amino, hydroxy, $C_{1-6}$ alkyl substituted heterocyclic ring, and cyano,
$C_{2-6}$ alkenyl,
acyl optionally substituted by one or more groups selected from hydroxy, heterocyclic ring, and amino, or
$C_{1-6}$ alkyloxycarbonyl, $R_3$ represents $C_{1-6}$ alkyl optionally substituted by one or more groups selected from halides, nitro, hydroxy, amino, $C_{1-6}$ alkyloxycarbonyl, carbamoyl, cyano, nitro halide, $C_{1-6}$ alkyloxy, oxo, heterocyclic rings, carbamoyl, azide, $C_{1-6}$ alkylaminocarbonyl, di-$C_{1-6}$ alkylaminocarbonyl, and optionally substituted aryl, or
$C_{2-6}$ alkenyl, $R_4$, $R_5$, and $R_6$, which may be the same or different, represent a hydrogen atom,
acyl wherein hydrogen atoms on the acyl group is optionally substituted by one or more groups selected from the group consisting of halides, nitro, hydroxy, amino, $C_{1-6}$ alkyloxycarbonyl, carbamoyl, cyano, nitro halides, $C_{1-6}$ alkyloxy, oxo, heterocyclic ring, carbamoyl, azide, $C_{1-6}$ alkylaminocarbonyl, di-$C_{1-6}$ alkylaminocarbonyl, and optionally substituted aryl, or $C_{1-6}$ alkyl optionally substituted by one or more groups selected from the group consisting of halides, nitro, hydroxy, amino, $C_{1-6}$ alkyloxycarbonyl, carbamoyl, cyano, nitro halide, $C_{1-6}$ alkyloxy, oxo, heterocyclic rings, carbamoyl, azide, $C_{1-6}$ alkylaminocarbonyl, di-$C_{1-6}$ alkylaminocarbonyl, and optionally substituted aryl, $R_7$ represents $C_{1-6}$ alkyl,
m is 1 to 3, and
n is 1 or 2.

The compounds according to the present invention may form pharmacologically acceptable salts thereof. Preferred examples of such salts include: alkali metal or alkaline earth metal salts such as sodium salts, potassium salts, or calcium salts; hydrohalogenic acid salts such as hydrofluoride salts, hydrochloride salts, hydrobromide salts, or hydroiodide salts; inorganic acid salts such as nitric acid salts, perchloric acid salts, sulfuric acid salts, or phosphoric acid salts; lower alkylsulfonic acid salts such as methanesulfonic acid salts, trifluoromethanesulfonic acid salts, or ethanesulfonic acid salts; arylsulfonic acid salts such as benzenesulfonic acid salts or p-toluenesulfonic acid salts; organic acid salts such as fumaric acid salts, succinic acid salts, citric acid salts, tartaric acid salts, oxalic acid salts, maleic acid salts, acetic acid salts, malic acid salts, lactic acid salts, or ascorbic acid salts; and amino acid salts such as glycine salts, phenylalanine salts, glutamic acid salts, or aspartic acid salts.

The compounds according to the present invention may form solvates. Such solvates include, for example, hydrates, alcoholates, for example, methanolates and ethanolates, and etherates, for example, diethyl etherates.

Use of Compounds/Pharmaceutical Composition

The compounds according to the present invention can inhibit the growth of bacteria, particularly resistant pneumococci, in vitro and actually exhibit antimicrobial activity (see Test Example 1).

The compounds according to the present invention are lincomycin derivatives having a very high level of antimicrobial activity, for example, against various bacteria, for example, resistant bacteria-containing pneumococci (*S. pneumoniae*). The compounds according to the present invention are lincomycin derivatives and thus have antimicrobial activity against various bacteria, which have hitherto been reported, and, at the same time, have potent antimicrobial activity against resistant pneumococci which pose a clinical problem. Accordingly, the compounds according to the present invention can be said to be very useful for the prevention or treatment of various bacterial infectious diseases including infectious diseases in respiratory organs.

Accordingly, the compounds according to the present invention can be used for the prevention or treatment of bacterial infectious diseases. Such bacterial infectious diseases include, for example, pneumonia, chronic bronchitis, acute otitis media, and acute sinusitis.

According to the present invention, there is provided a pharmaceutical composition comprising a compound according to the present invention or its pharmacologically acceptable salt or solvate and a pharmaceutically acceptable carrier. In a preferred embodiment of the present invention, there is provided a pharmaceutical composition comprising the above compound as an active ingredient and additionally an additive for a pharmaceutical preparation. The pharmaceutical composition is useful for the prevention or treatment of bacterial infectious diseases, preferably bacterial infectious diseases in respiratory organs and can be used as antimicrobial agents (that is, antimicrobial agent compositions).

According to another aspect of the present invention, there is provided an antimicrobial agent comprising a compound according to the present invention or its pharmacologically acceptable salt or solvate as an active ingredient.

According to still another aspect of the present invention, there is provided a method for preventing or treating bacterial infectious diseases, comprising administering a preventively or therapeutically effective amount of a compound according to the present invention or its pharmacologically acceptable salt or solvate together with a pharmaceutically acceptable carrier to a mammal.

According to a further aspect of the present invention, there is provided use of a compound according to the present invention or its pharmacologically acceptable salt or solvate for the production of a pharmaceutical composition for preventing or treating bacterial infectious diseases. According to a still further aspect of the present invention, there is provided use of a compound according to the present invention or its pharmacologically acceptable salt or solvate as an active ingredient of an antimicrobial agent.

Preferably, the infectious disease is an infectious disease in a respiratory organ.

The compounds according to the present invention can be administered to human and non-human animals orally or parenterally by administration routes, for example, intravenous administration, intramuscular administration, subcutaneous administration, rectal administration, or percutaneous administration.

Therefore, the pharmaceutical composition comprising a compound according to the present invention may be formulated into suitable dosage forms according to the administration routes. Specifically, oral preparations include tablets, capsules, powders, granules, pills, subtilized granules, troches, and syrups. Parental preparations include injections such as intravenous injections or intramuscular injections, suppositories, tapes, and ointments.

These various preparations may be prepared by conventional methods, for example, with pharmaceutically acceptable additives (carriers), that is, commonly used excipients, extenders, disintegrants, binders, lubricants, colorants, diluents, wetting agents, surfactants, dispersants, buffer agents, preservatives, solubilizers, antiseptics, flavoring agents, soothing agents, and stabilizers.

Excipients include, for example, lactose, fructose, glucose, corn starch, sorbit, and crystalline cellulose. Disintegrants include, for example, starch, sodium alginate, calcium carbonate, calcium citrate, and dextrin. Binders include, for example, dimethylcellulose or its salts, polyvinyl alcohol, polyvinyl ether, methylcellulose, ethylcellulose, gum arabic, gelatin, hydroxypropylcellulose, and polyvinyl pyrrolidone. Lubricants include, for example, talc, magnesium stearate, polyethylene glycol, and hydrogenated vegetable oils. Other nontoxic additives usable herein include, for example, syrup, vaseline, lanoline, glycerin, ethanol, propylene glycol, citric acid, sodium chloride, sodium sulfite, sodium phosphate, β-cyclodextrin, hydroxypropyl-β-cyclodextrin, and Tween 80.

In preparing the above injections, if necessary, for example, buffering agents, pH adjustors, stabilizers, tonicity adjusting agents, and preservatives may be added.

The content of a compound according to the present invention in the pharmaceutical composition according to the present invention may vary according to the dosage form. The content, however, is generally 10 to 95% by weight, preferably 30 to 80% by weight, based on the whole composition.

The dose may be appropriately determined in consideration of particular conditions, for example, the age, weight, sex, type of disease, and severity of condition of patients. For example, for the treatment of infectious diseases induced by pneumococci, the pharmaceutical composition can be administered, for example, through an oral route at a dose of about 1 to 2000 mg, preferably 10 to 1000 mg per adult per day, in terms of the weight of the compound according to the present invention. This dose may be administered at a time daily or divided doses of two to six times daily depending upon the symptom.

Compounds according to the present invention may be administered in combination with other medicaments, for example, other antimicrobial agents, for example, penicillin, carbapenem, and quinolone. The administration can be carried out simultaneously or sequentially. The kind, administration interval and the like of other medicaments can be determined by taking into consideration the kind of symptoms and the conditions of the patient.

Production of Compounds of Formula (I)

The compounds of general formula (I) according to the present invention may be produced according to production processes which will be described later. The production process of the compound according to the present invention is not limited to these production processes. The compounds of the present invention are not limited to the compounds produced by the following production processes. Specific examples of the production process of compounds according to the present invention are described in the working example of the present specification. Accordingly, all the compounds of formula (I) can easily be produced by a person having ordinary skill in the art by properly selecting starting compounds, reaction conditions, reagents and the like while referring to the following general description of production process and detailed description of the working examples and, if necessary, by conducting proper modification or improvement. The production process of the present invention include all of processes for producing compounds based on the properties of the compounds clarified by the present invention by conventional means.

In the following description, characters of A, $R_1$ to $R_7$, m, and n in structural formulae are as defined in formula (I). It should be noted that B, $R_8$ to $R_{20}$, and P means a partial structure in $R_1$ and thus are not beyond the range defined in formula (I). Regarding additional characters, other than those in formula (I), which appear as needed, the meaning will be defined in each case, and, when the defined character appears after that, the definition is applied. Further, it should be noted that, in all the following reaction steps, the reaction step identified with the same number represents is carried out under the same reaction conditions.

At the outset, a group of compounds of formula (I), wherein $R_2$ represents methyl (hereinafter abbreviated to "Me"), $R_3$ represents propyl (hereinafter abbreviated to "Pr"), $R_4$, $R_5$, and $R_6$ represent a hydrogen atom (hereinafter abbreviated to "H"), and m is 1, can be produced, for example, by the following general process.

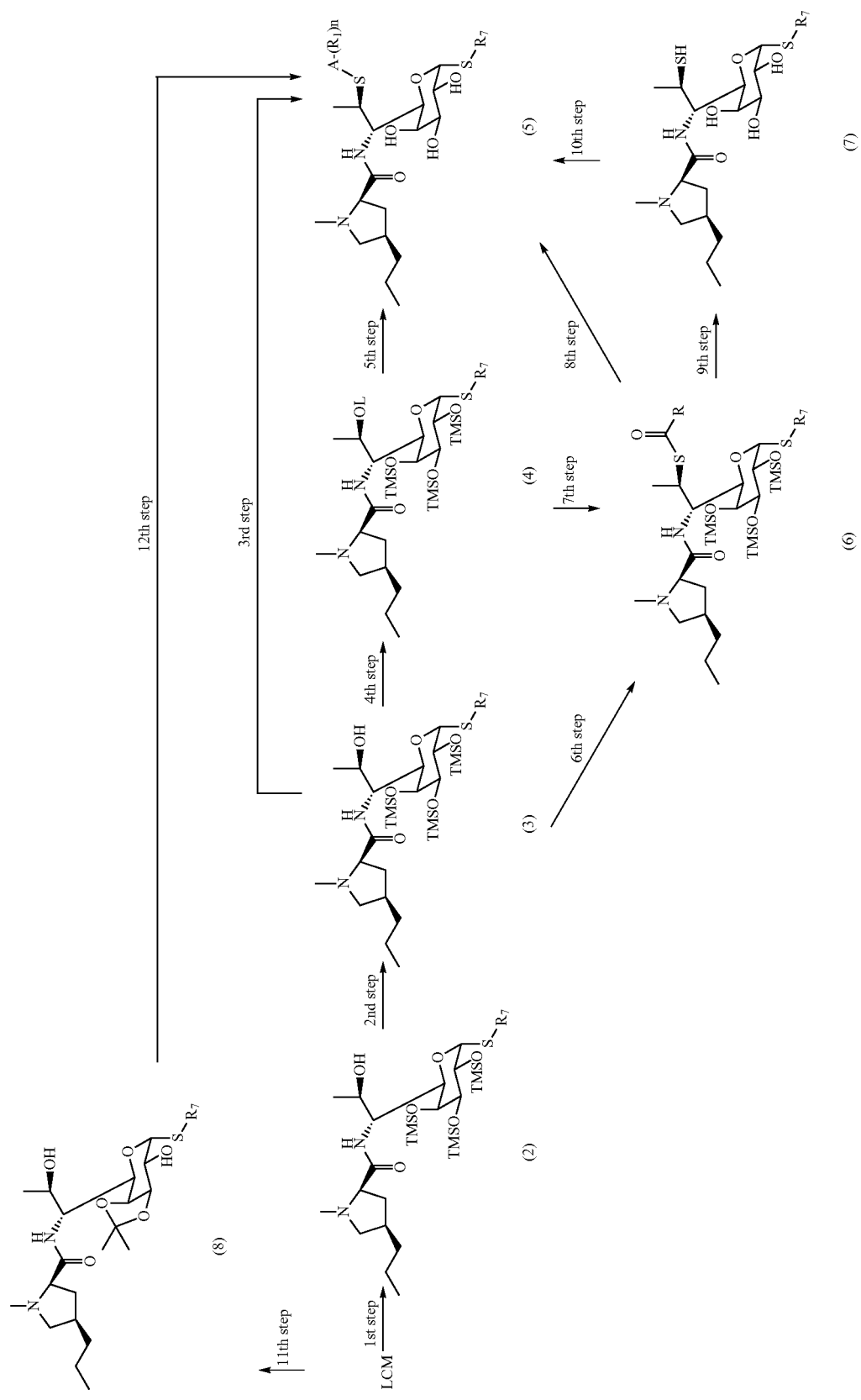

In formula (4), L represents a leaving group such as $C_{1-6}$ alkylsulfonyl or arylsulfonyl. In formula (6), R represents $C_{1-6}$ alkyl or aryl, and TMS represents trimethylsilyl.

In the first and second steps, the conversion of lincomycin (hereinafter abbreviated to "LCM") to a compound of formula (2) and the conversion of the compound of formula (2) to a compound of formula (3) can be produced by a process described, for example, in U.S. Pat. No. 3,418,414.

In the third step, the conversion of the compound of formula (3) to the compound of formula (5) can be produced, for example, by properly selecting either process (i) or process (ii) depending upon whether the reaction reagent used is thiol(HS-A-($R_1$)n) or disulfide(($R_1$)n-A-S—S-A-($R_1$)n).

(i) The compound of formula (5) can be produced by conducting a reaction using 1 to 10 equivalents of either the above thiol or the above disulfide in the presence of the compound of formula (3), triphenylphosphine, and diethyl azodicarboxylate in a tetrahydrofuran solution and then removing the trimethylsilyl group, for example, using a dilute hydrochloric acid-methanol solution. Regarding the reaction solvent in this reaction, in addition to tetrahydrofuran, conventional reaction solvents may be used, and preferred examples thereof include benzene, toluene, trifluoromethyl benzene, and acetonitrile. The phosphine reagent may be any phosphine reagent commonly known in literatures in addition to triphenylphosphine, preferably tolylphosphine, tri-n-butylphosphine, tri-tert-butylphosphine and the like, and the amount of the phosphine reagent is preferably 1 to 5 equivalents. The azo reagent may be any azo reagent commonly known in literatures in addition to diethyl azodicarboxylate, preferably diisopropyl azodicarboxylate, 1,1'-(azodicarbonyl)dipiperidine and the like, and the amount of the azo reagent is preferably 1 to 5 equivalents. The reaction temperature is 0 to 50° C., and the reaction time is 0.5 to 24 hr.

(ii) The compound of formula (5) can be produced by reacting the above thiol in the presence of the compound of formula (3) and cyanomethylenetri-n-butylphosphorane in a benzene solution and then removing the trimethylsilyl group, for example, using a dilute hydrochloric acid-methanol solution. Regarding the reaction solvent in this reaction, in addition to benzene, conventional reaction solvents may be used, and preferred examples thereof include tetrahydrofuran, toluene, trifluoromethyl benzene, and acetonitrile. The reaction accelerator may be, for example, phosphinylide commonly known in literatures and the like in addition to cyanomethylenetri-n-butylphosphorane, and preferred examples thereof include cyanomethylenetrimethylphosphorane. The amount of the reaction accelerator is preferably 1 to 5 equivalents. The reaction temperature is 0 to 150° C., and the reaction time is 0.5 to 24 hr.

In the fourth step, the conversion of the compound of formula (3) to the compound of formula (4) can be carried out, for example, by the following process. Specifically, the compound of formula (4) can be produced by reacting the compound of formula (3) with a sulfonylating agent in a chloroform solvent in the presence of a base. The reaction solvent in this reaction may be a conventional reaction solvent in addition to chloroform, and preferred examples thereof include halogenic solvents such as methylene chloride and carbon tetrachloride, and polar solvents such as dimethyl sulfoxide, pyridine, and 1-methylpyrrolidone. The base is a conventional inorganic base or organic base, and preferred examples thereof include potassium carbonate, sodium hydrogencarbonate, triethylamine, diisopropylethylamine, and pyridine. The amount of the base is preferably 1 to 10 equivalents. The sulfonylating agent refers to conventional sulfonylating agents, that is, alkylsulfonyl chloride, arylsulfonyl chloride, or sulfonic anhydride, and preferred examples thereof include methanesulfonyl chloride, toluenesulfonyl chloride, and trifluoromethanesulfonic anhydride. The amount of the sulfonylating agent is preferably 1 to 10 equivalents. The reaction temperature is −10 to 50° C., and the reaction time is 0.5 to 24 hr.

In the fifth step, the conversion of the compound of formula (4) to the compound of formula (5) can be carried out, for example, by the following process. Specifically, the compound of formula (5) can be produced by reacting the compound of formula (4) with 1 to 10 equivalents of the above thiol in an N,N-dimethylformamide solvent in the presence of a base and then removing the trimethylsilyl group, for example, using a diluted hydrochloric acid-methanol solution. The reaction solvent in this reaction may be a conventional reaction solvent in addition to N,N-dimethylformamide, and preferred examples thereof include polar solvents such as dimethyl sulfoxide, pyridine, and 1-methylpyrrolidone. The base is a commonly known inorganic base or organic base, and preferred examples thereof include potassium carbonate, sodium hydrogencarbonate, triethylamine, diisopropylamine, and pyridine. The amount of the base is preferably 1 to 10 equivalents. The reaction temperature is −10 to 120° C., and the reaction time is 0.5 to 24 hr.

In the sixth step, the conversion of the compound of formula (3) to the compound of formula (6) can be carried out, for example, in the same manner as in the third step except that the thiol is changed to 1 to 10 equivalents of a commonly known alkylthio carboxylic acid or a commonly known arylthio carboxylic acid, preferably, for example, thioacetic acid, thiopropionic acid, or thiobenzoic acid.

In the seventh step, the conversion of the compound of formula (4) to the compound of formula (6) can be carried out, for example, in the same manner as in the fifth step except that the thiol is changed to 1 to 10 equivalents of a commonly known alkylthio carboxylic acid or its salt or a commonly known arylthio carboxylic acid or its salt, preferably thioacetic acid, thiopropionic acid or its potassium salt, sodium salt or the like, or thiobenzoic acid or its potassium salt, sodium salt or the like.

In the eighth step, the conversion of the compound of formula (6) to the compound of formula (5) can be carried out, for example, by the following process. Specifically, the compound of formula (5) can be produced by removing the acyl group in the system in a methanol solvent in the presence of a base, reacting this compound, for example, with 1 to 10 equivalents of an alkyl halide, aryl halide, or a heterocyclic halide, then removing the trimethylsilyl group, for example, using a diluted hydrochloric acid-methanol solution. The reaction solvent in this reaction may be a conventional polar solvent in addition to methanol, and preferred solvents include ethanol, propanol, butanol, N,N-dimethylformamide, dimethyl sulfoxide, and 1-methylpyrrolidone. The base is a commonly known inorganic base, an alkali metal methoxide, or an alkali metal ethoxide, and preferred examples thereof include sodium hydrogencarbonate, potassium carbonate, calcium carbonate, sodium methoxide, and sodium ethoxide. The amount of the base is preferably 1 to 10 equivalents. The reaction temperature is 0 to 120° C., and the reaction time is 0.5 to 24 hr.

In the ninth step, the conversion of the compound of formula (6) to the compound of formula (7) can be produced, for example, by the following process. Specifically, the compound of formula (7) can be produced by removing the trimethylsilyl group in the compound of formula (6), for example, using a diluted hydrochloric acid-methanol solution in a methanol solvent and then deprotecting the acyl group in the compound of formula (6) with a base. The reaction solvent in this reaction may be a conventional polar solvent in addition to methanol, and preferred examples thereof include ethanol, propanol, butanol, N,N-dimethylformamide, dimethyl sulfoxide, and 1-methylpyrrolidone. The base may be a commonly known inorganic base, an alkali metal methoxide, or an alkali metal ethoxide, and preferred examples thereof include sodium hydroxide, potassium hydroxide, sodium methoxide, and sodium ethoxide. The amount of the base is preferably 1 to 10 equivalents. The reaction temperature is 0 to 40° C., and the reaction time is 0.5 to 24 hr.

In the tenth step, the conversion of the compound of formula (7) to the compound of formula (5) can be carried out, for example, by properly selecting either process (i) or process (ii).

(i) The compound of formula (5) can be produced by reacting the compound of formula (7) with 1 to 10 equivalents of a reactant represented by $X_1$-A-$(R_1)_n$, wherein $X_1$ represents an $RSO_2$ group or a halide, in an N,N-dimethylformamide solvent in the presence of a base. The reaction solvent in this reaction may be a conventional reaction solvent in addition to N,N-dimethylformamide, and preferred examples thereof include dimethyl sulfoxide, tetrahydrofuran, diethyl ether, and 1-methylpyrrolidone. The base may be a commonly known inorganic base or organic base, and preferred examples thereof include sodium hydrogencarbonate, sodium carbonate, potassium phosphate, sodium tert-butoxide, potassium tert-butoxide, diisopropylethylamine, and triethylamine. The amount of the base is preferably 1 to 10 equivalents. The reaction temperature may be room temperature to 150° C., and the reaction time is 1 to 24 hr.

(ii) The compound of formula (5) can be produced by reacting the compound of formula (7) in a dioxane solvent in the presence of a base, a reactant represented by $X_2$-A-$(R_1)_n$, wherein $X_2$ represents I, Br, Cl, OTf, or OTs wherein Tf represents trifluoromethanesulfonyl and Ts represents tosyl, an additive, and a conventional palladium catalyst. The reaction solvent in this reaction may be a conventional reaction solvent in addition to dioxane, and preferred examples thereof include N,N-dimethylformamide, benzene, toluene, cyclopentyl methyl ether, tetrahydrofuran, butanol, and dimethyl sulfoxide. The base may be a commonly known inorganic base or organic base, and preferred examples thereof include sodium carbonate, potassium phosphate, potassium fluoride, cesium fluoride, sodium tert-butoxide, potassium tert-butoxide, diisopropylethylamine, and triethylamine. The amount of the base is preferably 1 to 10 equivalents. The additive may be a conventional phosphine ligand, and preferred examples thereof include 4,5-bis(diphenylphosphino)-9,9-dimethylsantene, 2,2'-bis(diphenylphosphino)-1,1'-binaphthyl, triphenylphosphine, and tritert-butylphosphine. The amount of the additive is preferably 0.01 to 0.5 equivalent. Preferred examples of such palladium catalysts include tris(dibenzylideneacetone)dipalladium, palladium acetate, and dichlorobis(diphenylphosphino)ferrocene palladium. In addition to the palladium catalyst, metallic catalysts such as copper catalysts may be used, and the amount of the catalyst is preferably 0.01 to 0.5 equivalent. The reaction temperature is room temperature to 150° C., and the reaction time is 1 to 48 hr.

In the eleventh step, the conversion of LCM to the compound of formula (8) can be produced, for example, by the method described in J. Med. Chem., 13 (1970), 616.

In the twelfth step, the conversion of the compound of formula (8) to the compound of formula (5) can be carried out, for example, by introducing an —S-A-$(R_1)_n$ group in the same manner as in the third step and then removing 3,4-isopropylidene as a protective group of the hydroxyl group, for example, with a diluted hydrochloric acid-methanol solution or trifluoroacetic acid.

Secondly, among a group of compounds of formula (5) wherein $R_1$ represents —B—$NH_2$, wherein B represents a bond or optionally substituted aryl or heterocyclic ring and, when B represents a bond, the $NH_2$ group is bonded directly to A, a group of compounds (formula (10)) cannot be efficiently produced by the process shown in scheme 1, for example, for production or purification reasons. The group of compounds (formula (10)) can also be produced by an alternative process, for example, by producing the compound of formula (9) as a precursor of the compound of formula (10) by the process shown in scheme 1 and then subjecting the precursor to the following process.

Scheme 2

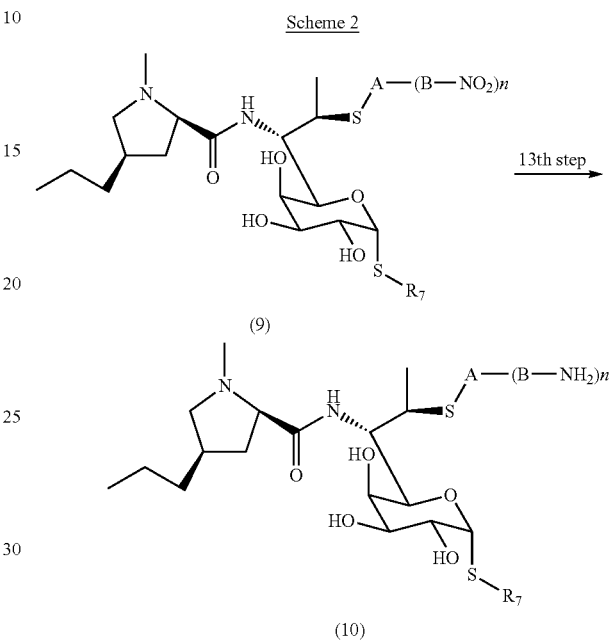

Specifically, in the thirteenth step, the conversion of the compound of formula (9) to the compound of formula (10) can be carried out, for example, by properly selecting either process (i) or process (ii).

(i) The compound of formula (10) can be produced by reacting the compound of formula (9) with a reducing agent in an ethanol solvent in the presence of 1 to 10 equivalents of stannic chloride dihydrate. The reaction solvent in this reaction may be a conventional reaction solvent in addition to ethanol, and preferred examples thereof include protic polar solvents such as methanol, propanol, and butanol. The reducing agent may be a conventional reducing reagent, and preferred examples thereof include sodium borohydride and lithium aluminum hydride. The amount of the reducing agent is preferably 1 to 10 equivalents. The reaction temperature is 0 to 50° C., and the reaction time is 0.5 to 24 hr.

(ii) The compound of formula (10) can be produced by adding stannic chloride dihydrate to the compound of formula (9) and allowing a reaction to proceed in the presence of tetrabutylammonium bromide. The reaction temperature is 0 to 100° C., and the reaction time is 0.5 to 24 hr.

Thirdly, among a group of compounds of formula (5) wherein $R_1$ represents —B—$NHCOR_8$, a group of compounds (formulae (12) and (13)) cannot be efficiently produced by the process shown in scheme 1, for example, for production or purification reasons. The group of these compounds (formulae (12) and (13)) can also be produced by an alternative process, for example, by producing the compound of formula (10) as a precursor of the compound of formula (12) or (13) by the process shown in scheme 1 or 2 and then subjecting the precursor to the following process.

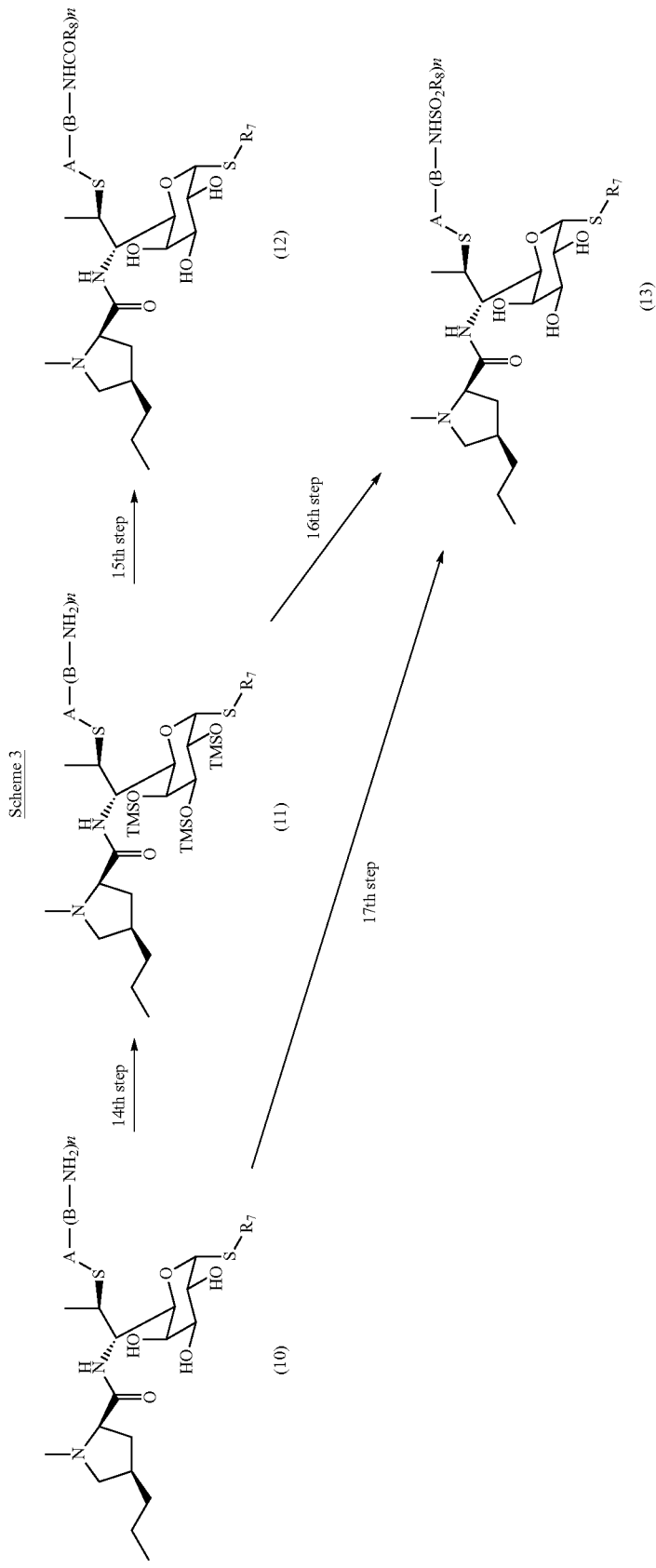

Specifically, in the fourteenth step, the conversion of the compound of formula (10) to the compound of formula (11) can be carried out, for example, according to the process described in U.S. Pat. No. 3,418,414.

Next, in the fifteenth step, the conversion of the compound of formula (11) to the compound of formula (12) can be carried out, for example, by reacting the compound of formula (11), for example, with 1 to 10 equivalents of an alkylcarbonyl chloride or arylcarbonyl chloride represented by $R_8COCl$ in an N,N-dimethylformamide solvent in the presence of a base and then removing the trimethylsilyl group, for example, using a diluted hydrochloric acid-methanol solution. The reaction solvent in this reaction may be a conventional solvent in addition to N,N-dimethylformamide, and preferred examples thereof include tetrahydrofuran, diethyl ether, dimethyl sulfoxide, and 1-methylpyrrolidone. The base may also be a commonly known organic base, and preferred examples thereof include triethylamine, diisopropylethylamine, and 1,8-diazabicyclo[5.4.0]-7-undecene. The amount of the base is preferably 1 to 10 equivalents. The reaction temperature is 0 to 50° C., and the reaction time is 0.5 to 24 hr.

Next, in the sixteenth step, the conversion of the compound of formula (11) to the compound of formula (13) can be carried out, for example, by reacting the compound of formula (11), for example, with 1 to 10 equivalents of an alkylsulfonyl chloride or an arylsulfonyl chloride represented by formula $R_8SO_2Cl$ in an N,N-dimethylformamide solvent in the presence of a base and then removing the trimethylsilyl group, for example, using a diluted hydrochloric acid-methanol solution. The reaction solvent in this reaction may be a conventional solvent in addition to N,N-dimethylformamide, and preferred examples thereof include tetrahydrofuran, diethyl ether, dimethyl sulfoxide, and 1-methylpyrrolidone. The base may be a commonly known organic base, and preferred examples thereof include triethylamine, diisopropylethylamine, and 1,8-diazabicyclo[5.4.0]-7-undecene. The amount of the base is preferably 1 to 10 equivalents. The reaction temperature is 0 to 50° C., and the reaction time is 0.5 to 24 hr.

Next, in the seventeenth step, the conversion of the compound of formula (10) to the compound of formula (13) can be carried out, for example, by reacting the compound of formula (10), for example, with 1 to 10 equivalents of an alkylsulfonyl chloride or an arylsulfonyl chloride represented by formula $R_8SO_2Cl$ in an N,N-dimethylformamide solvent in the presence of a base. The reaction solvent in this reaction may be a conventional solvent in addition to N,N-dimethylformamide, and preferred examples thereof include tetrahydrofuran, diethyl ether, dimethyl sulfoxide, and 1-methylpyrrolidone. The base may be a commonly known organic base, and preferred examples thereof include triethylamine, diisopropylethylamine, and 1,8-diazabicyclo[5.4.0]-7-undecene. The amount of the base is preferably 1 to 10 equivalents. The reaction temperature is 0 to 50° C., and the reaction time is 0.5 to 24 hr.

Fourthly, among a group of the compounds of formula (5) wherein $R_1$ represents —B—$NHR_9$, a group of compounds (formula (18)) cannot be efficiently produced by the process shown in scheme 1, for example, for production or purification reasons. The group of these compounds (formula (18)) can also be produced by an alternative method, for example, by producing the compound of formula (11) as a precursor of the compound of formula (18) by the process shown in scheme 3 and then subjecting the compound of formula (11) to the following process.

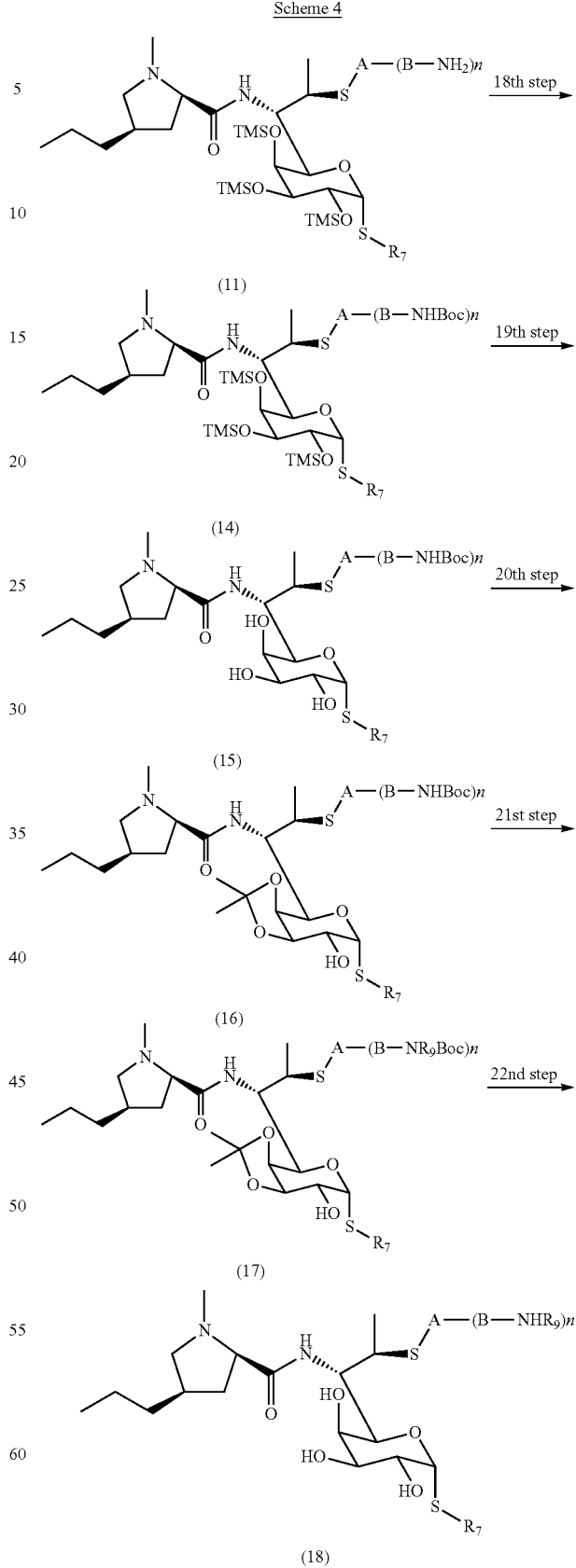

Scheme 4

Specifically, in the eighteenth step, the conversion of the compound of formula (11) to the compound of formula (14)

can be carried out, for example, by reacting the compound of formula (11) with 1 to 10 equivalents of tert-butyl dicarbonate in an N,N-dimethylformamide solvent in the presence of a base. The reaction solvent in this reaction may be a conventional reaction solvent in addition to N,N-dimethylformamide, and preferred examples thereof include tetrahydrofuran, diethyl ether, dimethyl sulfoxide, and 1-methylpyrrolidone. The base may be a commonly known inorganic base or organic base, and preferred examples thereof include sodium hydroxide, potassium hydroxide, barium hydroxide, triethylamine, and diisopropylethylamine. The amount of the base is preferably 1 to 10 equivalents. The reaction temperature is 0 to 50° C., and the reaction time is 0.5 to 24 hr.

Next, in the nineteenth step, the conversion of the compound of formula (14) to the compound of formula (15) can be carried out, for example, by reacting the compound of formula (14) with a dilute acid in a methanol solvent. The reaction solvent in this reaction may be a conventional solvent in addition to methanol, and preferred examples thereof include ethanol, propanol, tetrahydrofuran, diethyl ether, dimethyl sulfoxide, and 1-methylpyrrolidone. The acid may be a commonly known dilute acid, and preferred examples thereof include 1 N hydrochloric acid. The reaction temperature is 0 to 50° C., and the reaction time is 0.5 to 3 hr.

Next, in the twentieth step, the conversion of the compound of formula (15) to the compound of formula (16) can be carried out, for example, by reacting the compound of formula (15) with an excessive amount of acetone dimethyl acetal in an N,N-dimethylformamide solvent in the presence of an acid. The reaction solvent in this reaction may be a conventional reaction solvent in addition to N,N-dimethylformamide, preferred examples thereof include tetrahydrofuran, diethyl ether, dimethyl sulfoxide, and 1-methylpyrrolidone. The acid may be a commonly known strong acid or weak acid, and preferred examples thereof include p-toluenesulfonic acid monohydrate, sulfuric acid, and hydrochloric acid. The amount of the acid is preferably 1 to 10 equivalents. The reaction temperature is 0 to 50° C., and the reaction time is 0.5 to 24 hr.

Next, in the twenty-first step, the conversion of the compound of formula (16) to the compound of formula (17) can be carried out, for example, by reacting the compound of formula (16) with 1 to 3 equivalents of an alkyl halide represented by $R_9$—X in an N,N-dimethylformamide solvent in the presence of a base. The reaction solvent in this reaction may be a conventional reaction solvent in addition to N,N-dimethylformamide, and preferred examples thereof include tetrahydrofuran, diethyl ether, dimethyl sulfoxide, and 1-methylpyrrolidone. The base may be a commonly known inorganic base or organic base, and preferred examples thereof include sodium hydroxide, potassium hydroxide, barium hydroxide, lithium hydride, sodium hydride, calcium hydride, triethylamine, and diisopropylethylamine. The amount of the base is preferably 1 to 10 equivalents. The reaction temperature is 0 to 100° C., and the reaction time is 0.5 to 24 hr.

In the twenty-second step, the conversion of the compound of formula (17) to the compound of formula (18) can be carried out, for example, by reacting the compound of formula (17) in either a 95% aqueous trifluoroacetic acid solution or a 4 N hydrochloric acid-dioxane solution. The reaction temperature is −15° C. to room temperature, and the reaction time is 0.5 to 24 hr.

Fifthly, among a group of compounds of formula (5) wherein $R_1$ represents —B—$CONR_{11}R_{12}$, a group of compounds (formula (20)) cannot be efficiently produced by the process shown in scheme 1, for example, for production or purification reasons. The group of these compounds (formula (20)) can also be produced by an alternative process, for example, by producing the compound of formula (19) as a precursor of the compound of formula (20) by the process shown in scheme 1 and then subjecting the precursor to the following process.

Scheme 5

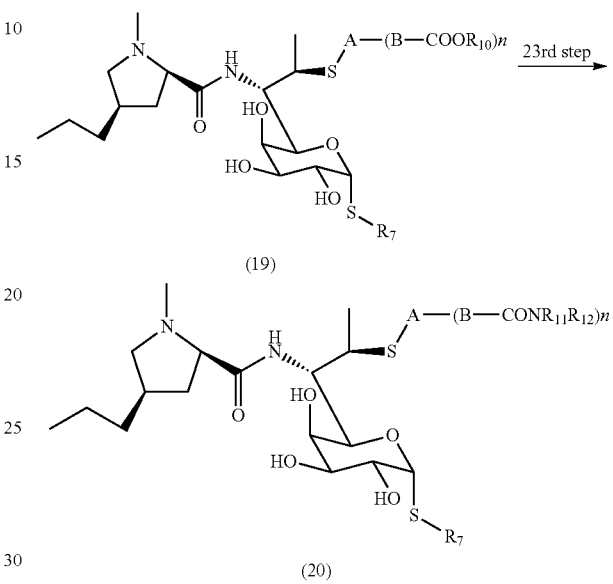

Specifically, in the twenty-third step, the conversion of the compound of formula (19) to the compound of formula (20) can be produced, for example, by reacting the compound of formula (19) with a large excessive amount of various primary or secondary amines in a methanol solvent. The reaction solvent in this reaction may be a conventional polar solvent in addition to methanol, and preferred examples thereof include ethanol, water, tetrahydrofuran, diethyl ether, dimethyl sulfoxide, and 1-methylpyrrolidone. The reaction temperature is room temperature to 150° C., and the reaction time is 0.5 to 24 hr.

Scheme 6

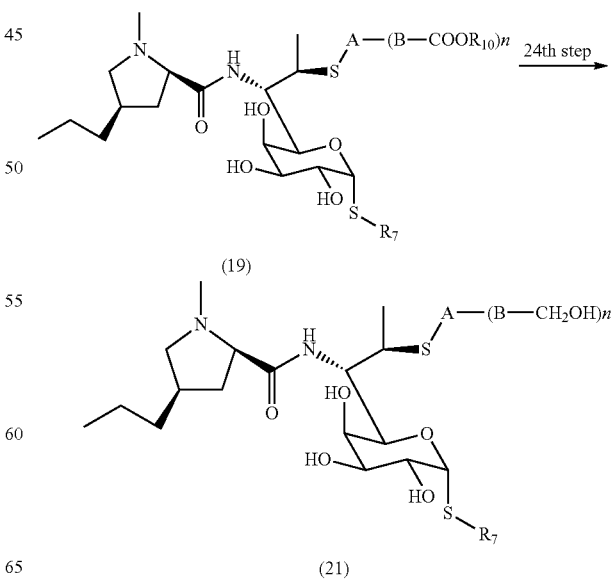

Sixthly, among a group of compounds of formula (5) wherein $R_1$ represents —B—$CH_2OH$, a group of compounds (formula (21)) cannot be efficiently produced by the process shown in scheme 1 for production or purification reasons. The group of these compounds (formula (21)) can also be produced by an alternative process, for example, by producing the compound of formula (19) as a precursor of the compound of formula (21) by the process shown in scheme 1 and then subjecting the precursor to the following process.

Specifically, in the twenty-fourth step, the conversion of the compound of formula (19) to the compound of formula (21) can be carried out, for example, by reacting the compound of formula (19) with 1 to 10 equivalents of lithium aluminum hydride in a tetrahydrofuran solvent. The reaction solvent in this reaction may be an ether solvent or a halogen solvent in addition to tetrahydrofuran, and preferred examples thereof include diethyl ether and methylene chloride. The reducing agent may be a commonly known reducing agent, and preferred examples thereof include sodium borohydride, sodium hydride, and bis(2-methoxyethoxy)aluminum. The amount of the reducing agent is preferably 1 to 10 equivalents. The reaction temperature is −78 to 0° C., and the reaction time is 0.5 to 24 hr.

Seventhly, among a group of compounds of formula (5) wherein $R_1$ represents —B—$CONR_{11}R_{12}$, a group of compounds (formula (20)) cannot be efficiently produced by the process shown in scheme 1 or 5 for production or purification reasons. The group of these compounds (formula (20)) can also be produced by an alternative process, for example, by producing the compound of formula (19) or (22) as a precursor of the compound of formula (20) by the process shown in scheme 1 and then subjecting the precursor to the following process.

Specifically, in the twenty-fifth step, the conversion of the compound of formula (19) to the compound of formula (22) can be produced, for example, by hydrolyzing the compound of formula (19) in a methanol solvent under basic conditions. The reaction solvent in this reaction may be a conventional polar solvent in addition to methanol, and preferred examples thereof include ethanol, water, dimethyl sulfoxide, and 1-methylpyrrolidone. The base is preferably, for example, an aqueous sodium hydroxide solution, an aqueous potassium hydroxide solution, or an aqueous barium hydroxide solution. The amount of the base is preferably 1 to 10 equivalents. The reaction temperature is 0 to 150° C., and the reaction time is 0.5 to 24 hr.

Next, in the twenty-sixth step, the conversion of the compound of formula (22) to the compound of formula (20) can be carried out, for example, by reacting the compound of formula (22) with 1 to 10 equivalents of a primary or secondary amine in an N,N-dimethylformamide solvent in the presence of 1-ethyl-3-(3-dimethylaminopropyl)carbodiimide hydrochloride and 1-hydroxybenzotriazole. The reaction solvent in this reaction may be a conventional solvent in addition to N,N-dimethylformamide, and preferred examples thereof include polar solvents such as tetrahydrofuran, diethyl ether, dimethyl sulfoxide, and 1-methylpyrrolidone. The condensing agent may be a conventional condensing agent in addition to a combination of 1-ethyl-3-(3-dimethylaminopropyl)carbodiimide hydrochloride with 1-hydroxybenzotriazole. Preferably, 1 to 10 equivalents of a combination of dicyclohexylcarbodiimide with 4-dimethylaminopyridine is used. The reaction temperature is 0 to 120° C., and the reaction time is 0.5 to 24 hr.

Eighthly, among a group of compounds of formula (5) wherein A represents a thiazole ring group, a group of compounds (formula (24)) cannot be efficiently produced by the process shown in scheme 1, for example, for production or purification reasons. The group of these compounds (formula (24)) can also be produced by an alternative method, for example, by producing the compound of formula (23) as a precursor of the compound of formula (24) by the process shown in scheme 1 and subjecting the compound of formula (23) to the following process.

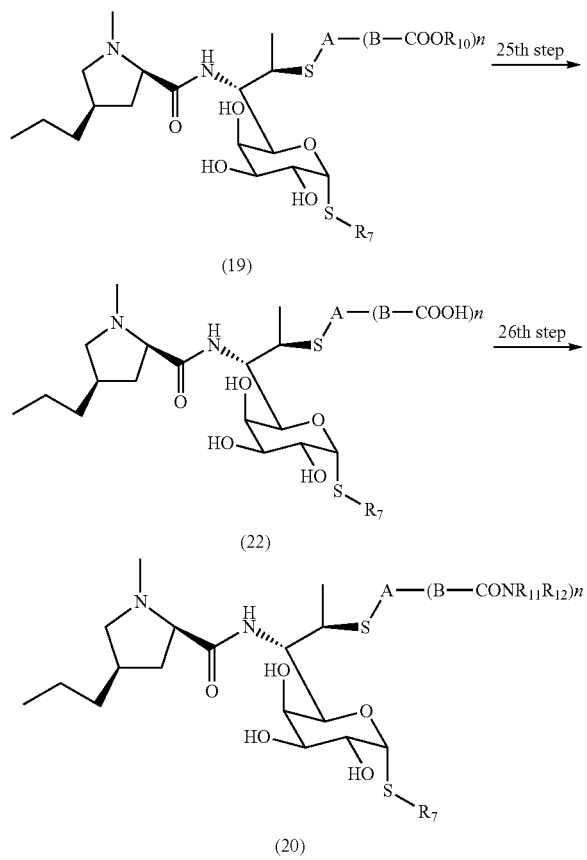

Scheme 7

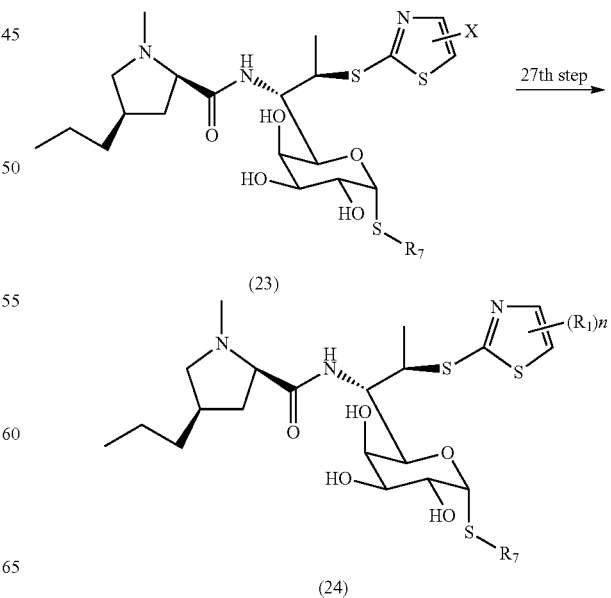

Scheme 8

In scheme 8, X represents, for example, a leaving group such as a halide, trifluoromethanesulfonyl, or toluenesulfonyl.

Specifically, the twenty-seventh step, the conversion of the compound of formula (23) to the compound of formula (24) can be produced, for example, by reacting the compound of formula (23) with an arylborane reagent or a heteroarylborane reagent in an isopropanol-water solvent in the presence of a base, an additive, and a conventional palladium catalyst. The reaction solvent in this reaction may be a conventional reaction solvent in addition to isopropanol, and preferred examples thereof include N,N-dimethylformamide, benzene, toluene, tetrahydrofuran, butanol, and dimethyl sulfoxide. The base may be a commonly known inorganic base or organic base, and preferred examples thereof include potassium carbonate, sodium carbonate, potassium phosphate, potassium fluoride, cesium fluoride, sodium tert-butoxide, potassium tert-butoxide, diisopropylethylamine, and triethylamine. The amount of the base is preferably 1 to 10 equivalents. The additive is a commonly known phosphine ligand, and preferred examples thereof include 4,5-bis(diphenylphosphino)-9,9-dimethylsantene, 2,2'-bis(diphenylphosphino)-1,1'-binaphthyl, triphenylphosphine, and tri-tert-butylphosphine. The amount of the additive is preferably 0.01 to 0.5 equivalent. The conventional palladium catalyst refers to palladium catalysts known, for example, in literatures, and preferred examples thereof include tetrakistriphenylphosphine palladium, tris(dibenzylideneacetone)dipalladium, palladium acetate, dichloro-bis(diphenylphosphino)ferrocene palladium. A tin reagent may be used instead of the borane reagent. The reaction temperature is room temperature to 150° C., and the reaction time is 1 to 48 hr.

Ninthly, among a group of compounds of formula (5) wherein $R_1$— represents —B—$NR_{13}R_{14}$, a group of compounds (formula (26)) cannot be efficiently produced by the process shown in scheme 1, for example, for production or purification reasons. The group of these compounds (formula (26)) can also be produced by an alternative process, for example, by producing the compound of formula (25) as a precursor of the compound of formula (26) by the process shown in scheme 1 and then subjecting the precursor to the following process.

Scheme 9

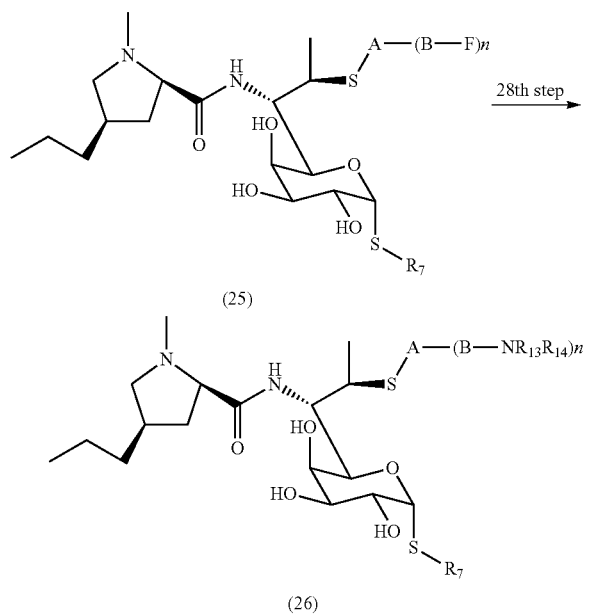

Specifically, in the twenty-eighth step, the conversion of the compound of formula (25) to the compound of formula (26) can be carried out, for example, by reacting the compound of formula (25) with 1 to 10 equivalents of a primary or secondary amine in a methanol solvent. The reaction solvent in this reaction may be a conventional solvent in addition to methanol, and preferred examples thereof include polar solvents such as tetrahydrofuran, diethyl ether, dimethyl sulfoxide, and 1-methylpyrrolidone. The reaction temperature is 0 to 120° C., and the reaction time is 0.5 to 24 hr.

Tenthly, among a group of the compounds of formula (5) wherein $R_1$ represents —B—$OR_{15}$, a group of compounds, which cannot be efficiently produced by the process shown in scheme 1, for example, for production or purification reasons, can also be produced by an alternative process, for example, by producing the compound of formula (25) as a precursor of the contemplated compound by the process shown in scheme 1 and then subjecting the precursor to the following process.

Scheme 10

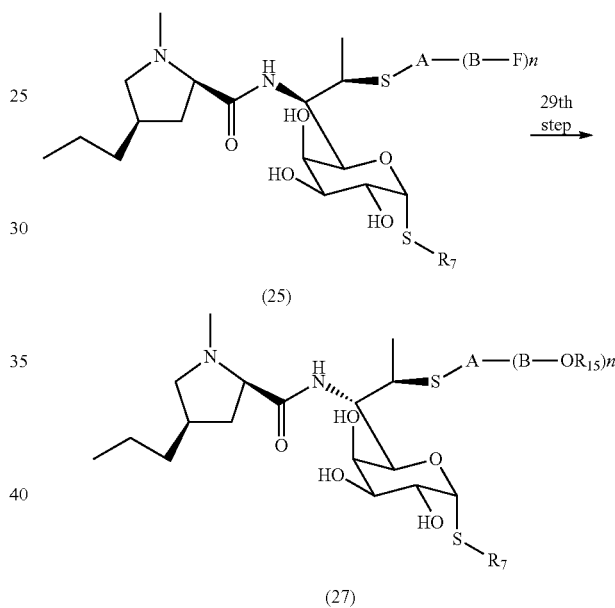

Specifically, in the twenty-ninth step, the conversion of the compound of formula (25) to the compound of formula (27) can be carried out, for example, by reacting the compound of formula (25) with 1 to 10 equivalents of a reaction reagent represented by $NaOR_{15}$ or $KOR_{15}$ in a methanol solvent. The reaction solvent in this reaction may be a conventional solvent in addition to methanol. Preferred examples thereof include polar solvents such as ethanol, dimethyl sulfoxide, and 1-methylpyrrolidone. The reaction temperature is 0 to 120° C., and the reaction time is 0.5 to 24 hr.

Eleventhly, among a group of the compounds of formula (5) wherein A represents an azetidine ring, a group of compounds (formulae (31) to (36)) cannot be efficiently produced by the process shown in scheme 1, for example, for production or purification reasons. The group of these compounds (formulae (31) to (36)) can also be produced by an alternative method, for example, by producing the compound of formula (28) as a precursor of the contemplated compound by the process shown in scheme 1 and then subjecting the compound of formula (28) to the following process.

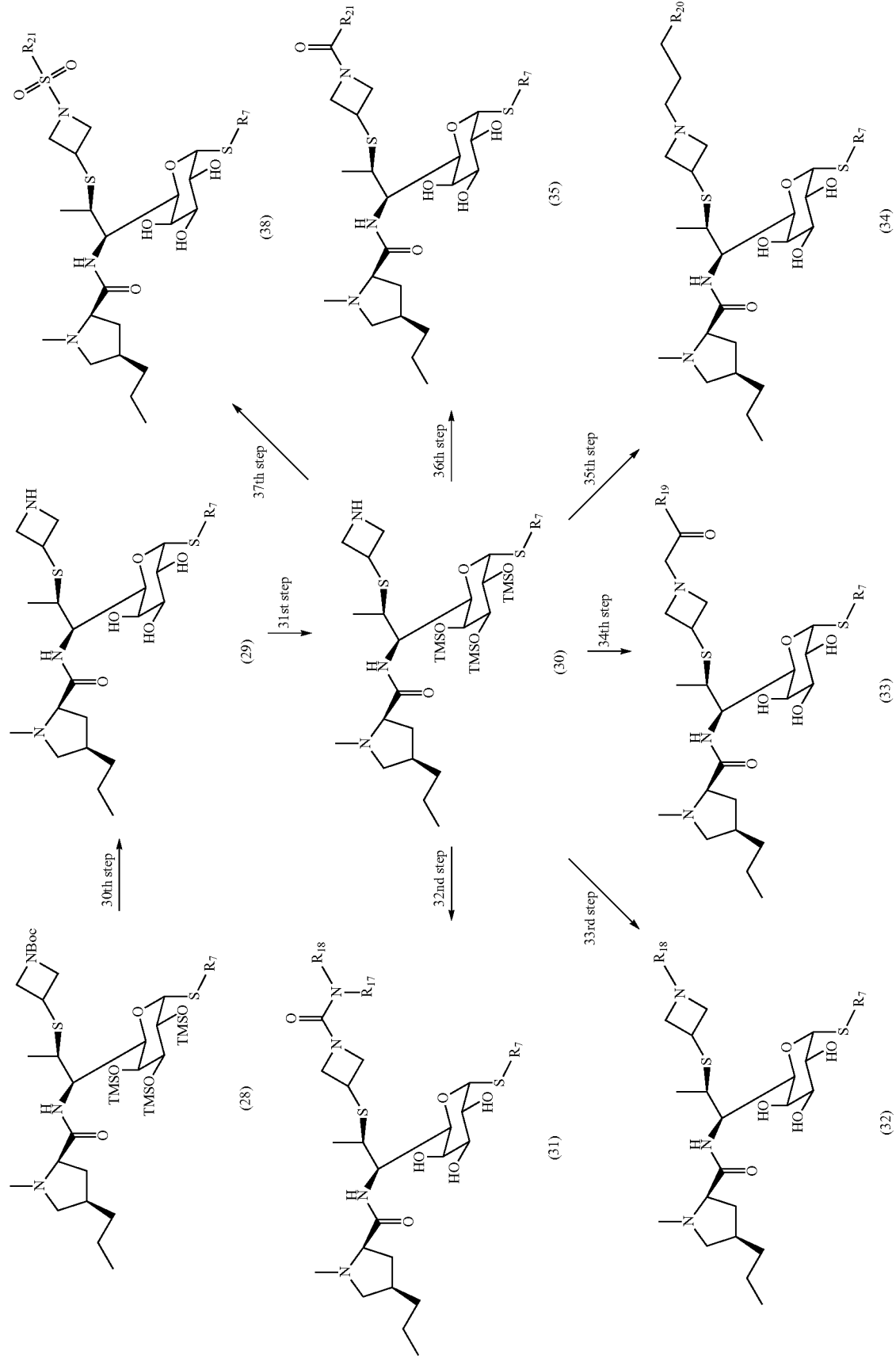

Specifically, in the thirtieth step, the conversion of the compound of formula (28) to the compound of formula (29) can be produced, for example, by removing both the trimethylsilyl and tert-butoxycarbonyl groups with a large excessive amount of 4 N hydrochloric acid-ethyl acetate or trifluoroacetic acid. In this reaction, the reaction temperature is 0 to 50° C., and the reaction time is 0.5 to 24 hr.

Next, in the thirty-first step, the conversion of the compound of formula (29) to the compound of formula (30) can be produced, for example, by reacting the compound of formula (29) with 3 to 10 equivalents of triethylsilane chloride in a pyridine solvent in the presence of 1 to 10 equivalents of hexamethyldisilazane. The reaction solvent in this reaction may be a conventional solvent in addition to pyridine, and preferred examples thereof include polar solvents such as N,N-dimethylformamide, dimethyl sulfoxide, and 1-methylpyrrolidone. The reaction temperature is 0 to 50° C., and the reaction time is 0.5 to 24 hr.

Next, in the thirty-second step, the conversion of the compound of formula (30) to the compound of formula (31) can be carried out, for example, by either the following process (i) or (ii).

(i) The compound of formula (31) can be produced, for example, by reacting the compound of formula (30) with 1 to 10 equivalents of various primary or secondary amines in a pyridine solvent in the presence of 1 to 10 equivalents of triphosgene and then removing the trimethylsilyl group, for example, using a diluted hydrochloric acid-methanol solution. The reaction solvent in this reaction may be a conventional solvent in addition to pyridine, and preferred examples thereof include methylene chloride, tetrahydrofuran, diethyl ether, dimethyl sulfoxide, and 1-methylpyrrolidone. The reaction temperature is 0 to 50° C., and the reaction time is 0.5 to 24 hr.

(ii) The compound of formula (31) can be produced, for example, by reacting the compound of formula (30) with 1 to 10 equivalents of a substituted aminocarbonyl halide represented by X—CONR$_{16}$R$_{17}$, wherein X represents a halide, in a chloroform solvent in the presence of a base and then removing the trimethylsilyl group, for example, using a diluted hydrochloric acid-methanol solution. The reaction solvent in this reaction may be a conventional solvent in addition to chloroform, and preferred examples thereof include methylene chloride, tetrahydrofuran, diethyl ether, dimethyl sulfoxide, and 1-methylpyrrolidone. The base may be a commonly known inorganic base or organic base, and preferred examples thereof include potassium carbonate, sodium hydroxide, potassium hydroxide, triethylamine, diisopropylethylamine, and 4-dimethylaminopyridine. The amount of the base is preferably 1 to 10 equivalents. The reaction temperature is 0 to 50° C., and the reaction time is 0.5 to 24 hr.

Next, in the thirty-third step, the conversion of the compound of formula (30) to the compound of formula (32) can be carried out, for example, by reacting the compound of formula (30) with 1 to 10 equivalents of a reaction reagent represented by MeSO$_2$Ar, wherein Ar represents aryl, or a reaction reagent represented by XR, in an N,N-dimethylformamide solvent in the presence of 1 to 10 equivalents of a base and then removing the trimethylsilyl group, for example, using a diluted hydrochloric acid-methanol solution. The reaction solvent in this reaction may be a conventional solvent in addition to N,N-dimethylformamide, and preferred examples thereof include methylene chloride, tetrahydrofuran, diethyl ether, dimethyl sulfoxide, and 1-methylpyrrolidone. The base may be a commonly known inorganic base or organic base, and preferred examples thereof include potassium carbonate, sodium hydroxide, potassium hydroxide, triethylamine, diisopropylethylamine, and 4-dimethylaminopyridine. The amount of the base is 1 to 10 equivalents. The reaction temperature is 0 to 50° C., and the reaction time is 0.5 to 24 hr.

Next, in the thirty-fourth step, the conversion of the compound of formula (30) to the compound of formula (33) can be carried out, for example, by reacting the compound of formula (30) with 1 to 10 equivalents of a reaction reagent represented by RCOCH$_2$X in a chloroform solvent in the presence of 1 to 10 equivalents of a base and then removing the trimethylsilane group, for example, with a diluted hydrochloric acid-methanol solution. The reaction solvent in this reaction may be a conventional solvent in addition to chloroform, and preferred examples thereof include N,N-dimethylformamide, methylene chloride, tetrahydrofuran, diethyl ether, dimethyl sulfoxide, and 1-methylpyrrolidone. The base may be a commonly known inorganic base or organic base, and preferred examples thereof include potassium carbonate, sodium hydroxide, potassium hydroxide, triethylamine, diisopropylethylamine, and 4-dimethylaminopyridine. The amount of the base is preferably 1 to 10 equivalents. The reaction temperature is 0 to 50° C., and the reaction time is 0.5 to 24 hr.

Next, in the thirty-fifth step, the conversion of the compound of formula (30) to the compound of formula (34) can be carried out, for example, by reacting the compound of formula (30) with 1 to 10 equivalents of a reaction reagent represented by CH$_2$=CHE$_1$ (E$_1$ represents an electron withdrawing group such as cyano, carbonyl, or a carboxylic acid ester, in an ethanol solvent and then removing the trimethylsilyl group, for example, using a diluted hydrochloric acid-methanol solution. The reaction solvent in this reaction may be a conventional solvent in addition to ethanol, and preferred examples thereof include methylene chloride, tetrahydrofuran, diethyl ether, dimethyl sulfoxide, and 1-methylpyrrolidone. The reaction temperature is 0 to 50° C., and the reaction time is 0.5 to 24 hr.

Next, in the thirty-sixth step, the conversion of the compound of formula (30) to the compound of formula (35) can be produced, for example, according to the process shown in the fifteenth step.

In the thirty-seventh step, the conversion of the compound of formula (30) to the compound of formula (36) can be produced, for example, according to the process described in the sixteenth step or seventeenth step.

Twelfthly, a group of compounds of formula (I), wherein R$_4$, R$_5$, and R$_6$ represent H and m is 1 or 2, can be produced, for example, by the following general process.

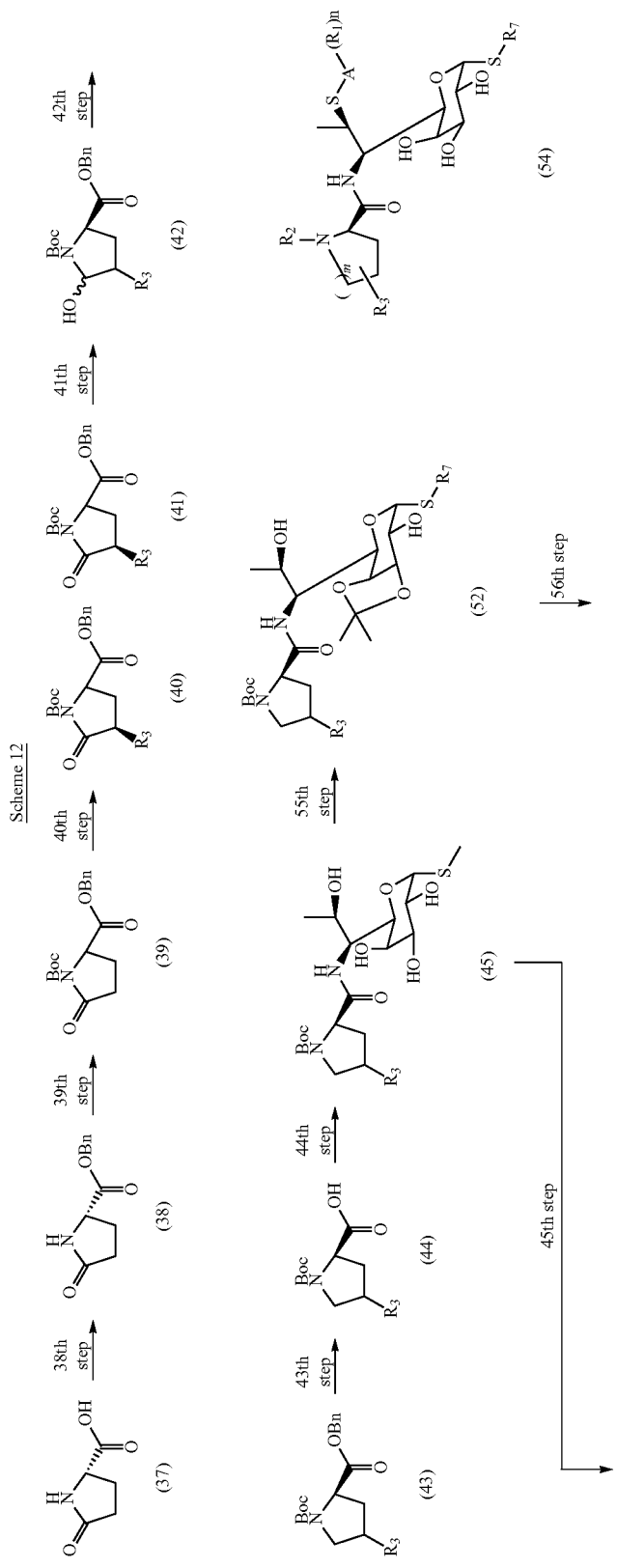

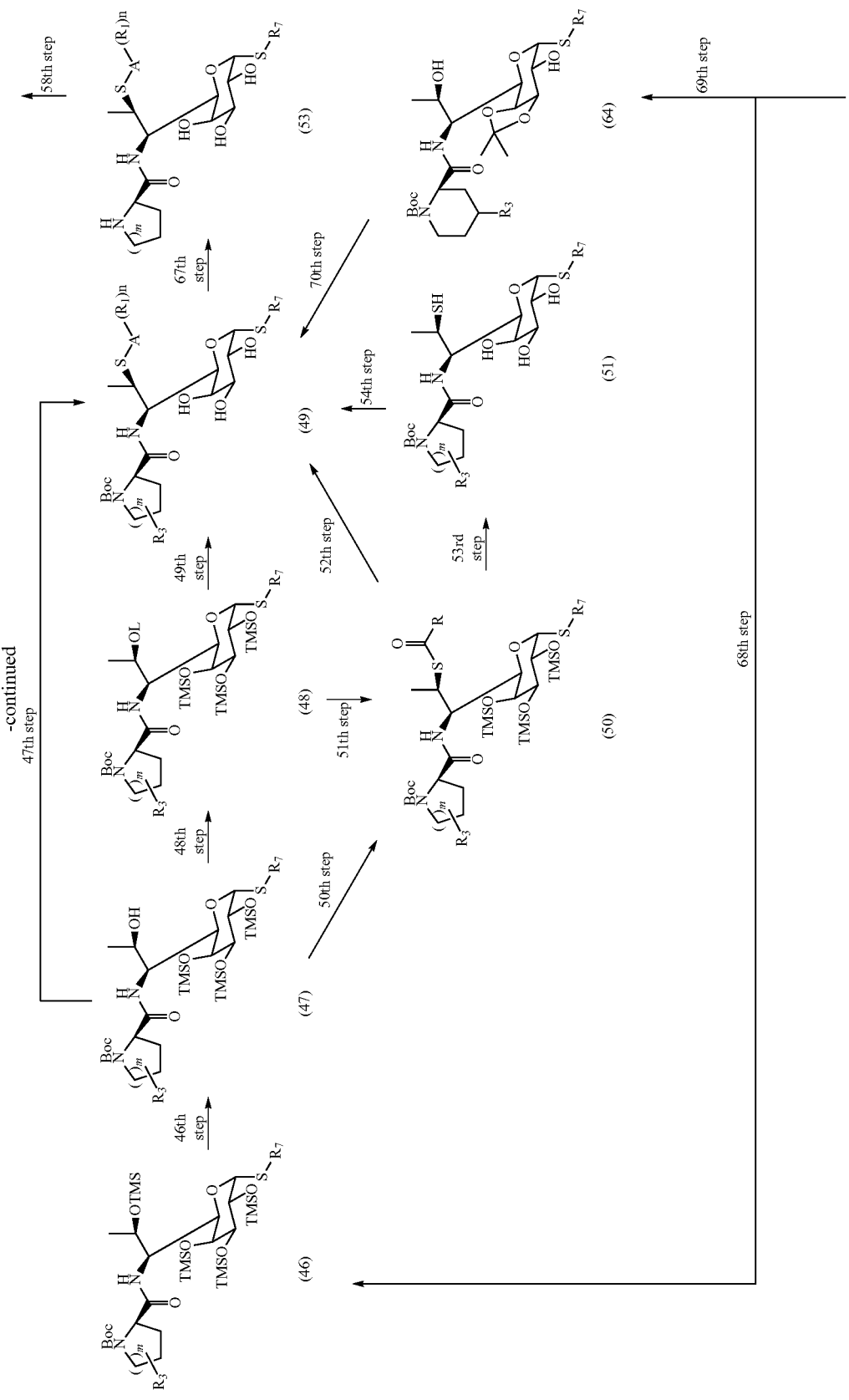

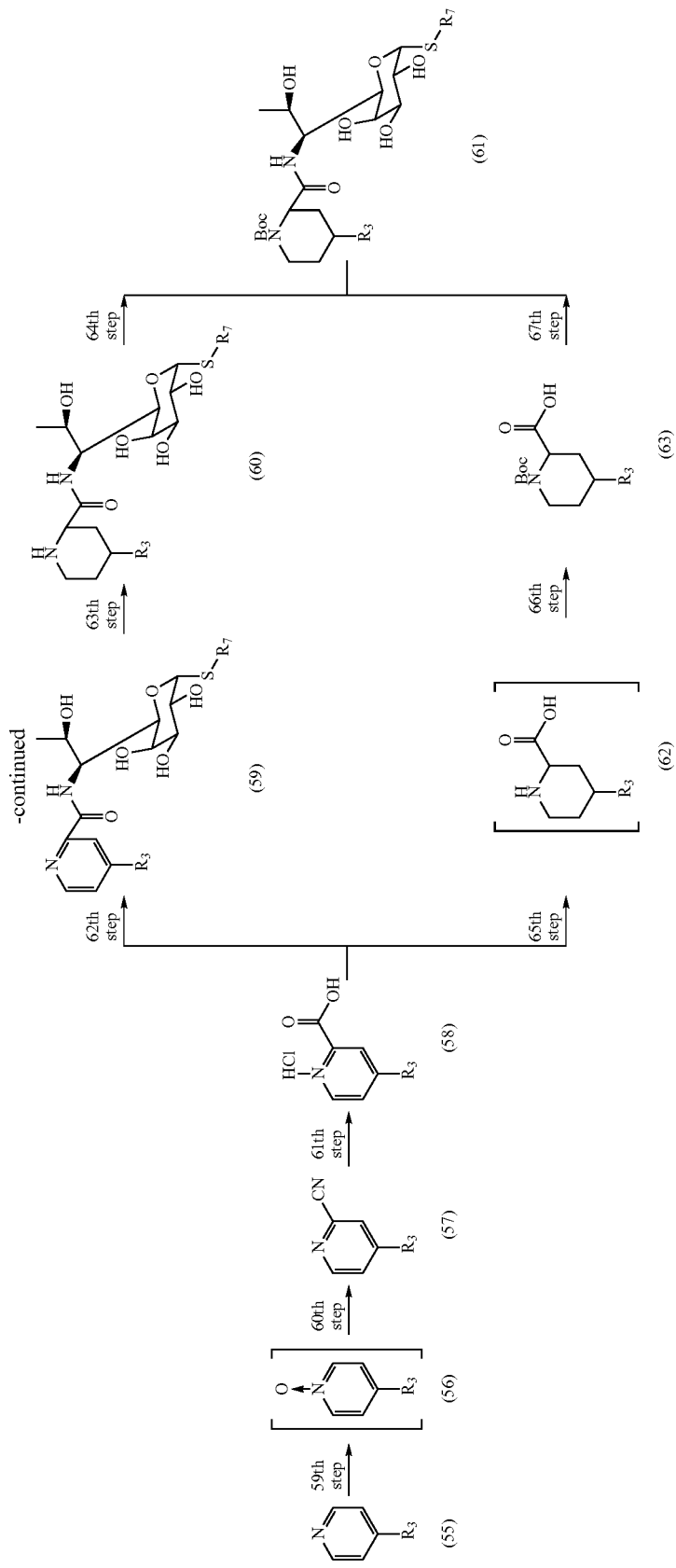

In the thirty-eighth and thirty-ninth steps, the conversion of the compound of formula (37) to the compound of formula (38) and the conversion of the compound of formula (38) to the compound of formula (39) can be produced, for example, by the process described in Tetrahedron Lett., 43, (2002), 3499.

In the fortieth, forty-first, and forty-second steps, the conversion of the compound of formula (39) to the compound of formula (40) and the compound of formula (41), the conversion of the compound of formula (40) to the compound of formula (42), and the conversion of the compound of formula (42) to the compound of formula (43) can be carried out, for example, according to the process described in Tetrahedron Lett., 35, (1994), 2053 and J. Am. Chem. Soc., 110, (1998), 3894.

In the forty-third step, the conversion of the compound of formula (43) to the compound of formula (44) can be carried out by properly selecting whether, $R_3$ in formula (44), the double bond (i) allows to remain unremoved or (ii) is removed and subjecting the compound of formula (43), for example, to the following process.

(i) The compound of formula (44) can be produced by hydrolyzing the compound of formula (43) in a methanol solvent in the presence of a base. The reaction solvent in this reaction may be a conventional alcohol solvent in addition to methanol, and preferred examples thereof include ethanol, propanol, and butanol. The reaction temperature is 0 to 120° C., and the reaction time is 0.5 to 24 hr. (ii) The compound of formula (44) can be produced by the process described in J. Am. Chem. Soc., 110, (1998), 3894.

In the forty-fourth step, the conversion of the compound of formula (44) to the compound of formula (45) can be carried out, for example, by reacting the compound of formula (44) with 1 to 10 equivalents of methyl1-thio-α-lincosamide (hereinafter abbreviated to "MTL") in an N,N-dimethylformamide solvent in the presence of 1-ethyl-3-(3-dimethylaminopropyl)carbodiimide hydrochloride and 1-hydroxybenzotriazole. The reaction solvent in this reaction may be a conventional solvent in addition to N,N-dimethylformamide, and preferred examples thereof include polar solvents such as tetrahydrofuran, diethyl ether, dimethyl sulfoxide, and 1-methylpyrrolidone. The condensing agent may be a conventional condensing agent in addition to a combination of 1-ethyl-3-(3-dimethylaminopropyl)carbodiimide hydrochloride with 1-hydroxybenzotriazole. Preferably, 1 to 10 equivalents of, for example, a combination of dicyclohexylcarbodiimide with 4-dimethylaminopyridine is used. The reaction temperature is 0 to 120° C., and the reaction time is 0.5 to 24 hr.

In the forty-fifth step, the conversion of the compound of formula (45) to the compound of formula (46) can be produced, for example, according to the process in the first step.

In the forty-sixth step, the conversion of the compound of formula (46) to the compound of formula (47) can be carried out, for example, according to the process in the second step.

In the forty-seventh step, the conversion of the compound of formula (47) to the compound of formula (49) can be carried out, for example, according to the process in the third step.

In the forty-eighth step, the conversion of the compound of formula (47) to the compound of formula (48) can be carried out, for example, according to the process in the fourth step.

In the forty-ninth step, the conversion of the compound of formula (48) to the compound of formula (49) can be carried out, for example, according to the process in the fifth step.

In the fiftieth step, the conversion of the compound of formula (47) to the compound of formula (50) can be carried out, for example, according to the process in the sixth step.

In the fifty-first step, the conversion of the compound of formula (48) to the compound of formula (50) can be carried out, for example, according to the process in the seventh step.

In the fifty-second step, the conversion of the compound of formula (50) to the compound of formula (49) can be carried out, for example, according to the process in the eighth step.

In the fifty-third step, the conversion of the compound of formula (50) to the compound of formula (51) can be carried out, for example, according to the process in the ninth step.

In the fifty-fourth step, the conversion of the compound of formula (51) to the compound of formula (49) can be carried out, for example, according to the process in the tenth step.

In the fifty-fifth step, the conversion of the compound of formula (45) to the compound of formula (52) can be carried out, for example, according to the process in the eleventh step.

In the fifty-sixth step, the conversion of the compound of formula (52) to the compound of formula (49) can be carried out, for example, according to the process in the twelfth step.

In the fifty-seventh step, the conversion of the compound of formula (49) to the compound of formula (53) can be carried out, for example, by reacting the compound of formula (49) with either a 95% aqueous trifluoroacetic acid solution or a 4 N hydrochloric acid-dioxane solution. The reaction temperature is −15° C. to room temperature, and the reaction time is 0.5 to 24 hr.

In the fifty-eighth step, the conversion of the compound of formula (53) to the compound of formula (54) can be carried out, for example, by properly selecting any one of processes (i), (ii), and (iii).

(i) The compound of formula (54) can be produced by reacting 1 to 10 equivalents of a ketone or an aldehyde with the compound of formula (53) in a 1,2-dichloroethane solvent in the presence of an acid and a reducing agent. The reaction solvent in this reaction may be a conventional solvent in addition to 1,2-dichloroethane, and preferred examples thereof include solvents such as methylene chloride, chloroform, tetrahydrofuran, diethyl ether, methanol, ethanol, and butanol. The acid is preferably acetic acid, hydrochloric acid, sulfuric acid or the like. The reducing agent may be a commonly known the reducing agent, and preferred examples thereof include sodium triacetoxyboron. The amount of the reducing agent is preferably 1 to 10 equivalents. The reaction temperature is 0 to 120° C., and the reaction time is 0.5 to 4 hr.

(ii) The compound of formula (54) can be produced by reacting the compound of formula (53) with 1 to 10 equivalents of an alkyl halide in an acetonitrile solvent in the presence of a base. The reaction solvent in this reaction may be a conventional solvent in addition to acetonitrile, and preferred examples thereof include polar solvents such as N,N-dimethylformamide, dimethyl sulfoxide, and 1-methylpyrrolidone. The base may be a commonly known inorganic base or organic base, and preferred examples thereof include potassium carbonate, sodium hydroxide, potassium hydroxide, triethylamine, diisopropylethylamine, and 4-dimethylaminopyridine. The amount of the base is preferably 1 to 10 equivalents. The reaction temperature is 0 to 50° C., and the reaction time is 0.5 to 24 hr.

(iii) The compound of formula (54) can be produced by reacting the compound of formula (53) with 1 to 10 equivalents of an alkylcarboxylic acid or an arylcarboxylic acid in an N,N-dimethylformamide solvent in the presence of 1-ethyl-3-(3-dimethylaminopropyl)carbodiimide hydrochloride and 1-hydroxybenzotriazole. The reaction solvent in this reaction may be a conventional solvent in addition to N,N-dimethylformamide, and preferred examples thereof include polar solvents such as dimethyl sulfoxide and 1-methylpyrrolidone. The condensing agent may be a conventional condensing agent in addition to a combination of 1-ethyl-3-(3-dimethylaminopropyl)carbodiimide hydrochloride with 1-hydroxybenzotriazole. Preferably, for example, 1 to 10 equivalents of a combination of dicyclohexylcarbodiimide with 4-dimethylaminopyridine is used. The reaction temperature is 0 to 120° C., and the reaction time is 0.5 to 24 hr.

In the fifty-ninth, sixtieth, and sixty-first steps, the conversion of the compound of formula (55) to the compound of formula (56), the conversion of the compound of formula (56) to the compound of formula (57), and the conversion of the compound of formula (57) to the compound of formula (58) can be carried out, for example, according to the process described in J. Med. Chem., 32, (1989), 829.

In the sixty-second step, the conversion of the compound of formula (58) to the compound of formula (59) can be carried out, for example, according to the process in the forty-fourth step.

In the sixty-third step, the conversion of the compound of formula (59) to the compound of formula (60) can be carried out, for example, by adding the compound of formula (59), an acid, and platinum oxide to a methanol-water mixed solvent and allowing a reaction to proceed under a hydrogen atmosphere (206850 to 689500 Pa). The reaction solvent in this reaction may be a conventional alcohol solvent in addition to the methanol-water mixed solvent, and preferred examples thereof include solvents such as methanol and ethanol. The acid may be a conventional acid, and preferred examples thereof include hydrochloric acid, sulfuric acid, and acetic acid. The amount of the acid is preferably 1 to 10 equivalents. The reaction temperature is 0° C. to room temperature, and the reaction time is 0.5 to 24 hr.

In the sixty-fourth step, the conversion of the compound of formula (60) to the compound of formula (61) can be carried out, for example, by reacting the compound of formula (60) with 1 to 10 equivalents of di-tert-butyl dicarbonate in a dioxane solvent in the presence of a base. The reaction solvent in this reaction may be a conventional solvent in addition to dioxane, and preferred examples thereof include polar solvents such as tert-butanol, tetrahydrofuran, diethyl ether, N,N-dimethylformamide, dimethyl sulfoxide, 1-methylpyrrolidone. The base may be a conventional organic base or inorganic base, and preferred examples thereof include 4-dimethylaminopyridine, sodium hydroxide, potassium hydroxide, and barium hydroxide. The base is used in an excessive amount. The reaction temperature is 0 to 50° C., and the reaction time is 0.5 to 24 hr.

In the sixty-fifth step, the conversion of the compound of formula (58) to the compound of formula (62) can be carried out, for example, by adding the compound of formula (58) and platinum oxide to an acetic acid solvent and allowing a reaction to proceed under a hydrogen atmosphere (ordinary pressure). The reaction temperature is 0 to 50° C., and the reaction time is 0.5 to 24 hr.

In the sixty-sixth step, the conversion of the compound of formula (62) to the compound of formula (63) can be carried out according to the process in the sixty-fourth step.

In the sixty-seventh step, the conversion of the compound of formula (63) to the compound of formula (61) can be carried out, for example, according to the process described in the forty-fourth step.

In the sixty-eighth step, the conversion of the compound of formula (61) to the compound of formula (46) can be carried out, for example, according to the process described in the first step.

In the sixty-ninth step, the conversion of the compound of formula (61) to the compound of formula (64) can be carried out, for example, according to the process in the eleventh step.

In the seventieth step, the conversion of the compound of formula (64) to the compound of formula (49) can be carried out, for example, according to the process in the twelfth step.

Thirteenthly, a group of compounds of formula (I), wherein $R_2$ represents Me, $R_3$ represents Pr, $R_4$, $R_5$, and $R_6$ represent H, and m is 1, can be produced, for example, by the process shown in schemes 1 to 11. However, a group of compounds (formula (5)) cannot be efficiently produced, for example, for production or purification reasons. The group of these compounds (formula (5)) can be produced by an alternative process, for example, by N-methylation in the fifty-eighth step in the process shown in scheme 12 to the compound of formula (5) corresponding to the compound of formula (54).

Fourteenthly, a group of compounds of formula (I), wherein $R_3$ has no double bond, $R_4$, $R_5$ and $R_6$ represent H, and m is 1, can be produced by the process shown in scheme 12. However, a group of compounds (formulae (53) and (54)), wherein $R_3$ has no double bond, $R_4$, $R_5$ and $R_6$ represent H, and m is 1, cannot be efficiently produced, for example, for production or purification reasons. The group of these compounds (formulae (53) and (54)) can be produced by once producing a compound having a double bond in $R_3$ (formula (49-1)) according to the process shown in scheme 12 and then subjecting the resultant compound to the following process.

Scheme 13

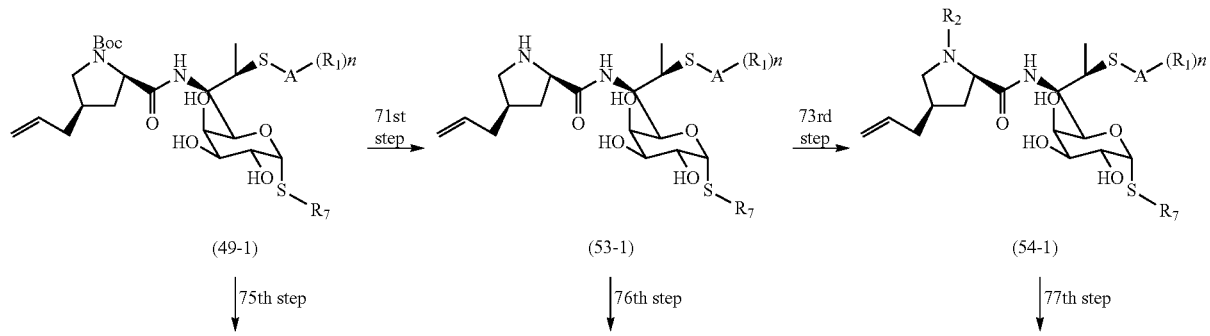

-continued

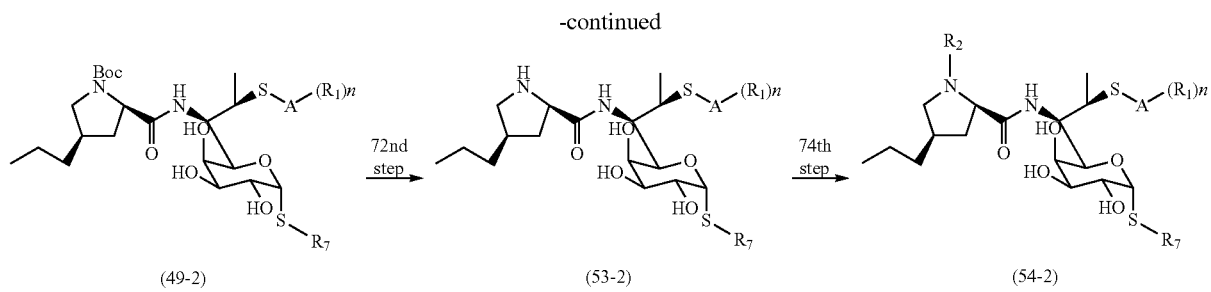

In the formulae (53) and (54), a group of compounds (formulae (53-2) and (54-2)), wherein R₃ has no double bond, R₄, R₅ and R₆ represent H, and m is 1, may be produced by reducing the double bond in the forty-third step in scheme 12 and then deriving the compound, or alternatively may be produced by deriving the compound in the process shown in scheme 13 without reducing the double bond in the forty-third step in scheme 12. In scheme 13, an embodiment, wherein R₃ represents propenyl or propyl, is shown. However, it should be noted that R₃ is not limited to propenyl.

In the seventy-first and seventy-second steps, the conversion of the compound of formula (49-1) to the compound of formula (53-1) and the conversion of the compound of formula (49-2) to the compound of formula (53-2) can be produced, for example, according to the process in the fifty-seventh step.

In the seventy-third and seventy-fourth steps, the conversion of the compound of formula (53-1) to the compound of formula (54-1) and the conversion of the compound of formula (53-2) to the compound of formula (54-2) can be produced, for example, according to the process in the fifty-eighth step.

In the seventy-fifth, seventy-sixth and seventy-seventh steps, the conversion of the compound of formula (49-1) to the compound of formula (49-2), the conversion of the compound of formula (53-1) to the compound of formula (53-2), and the conversion of the compound of formula (54-1) to the compound of formula (54-2) can be produced, for example, according to the process in the forty-third (ii) step.

Fifteenthly, among a group of compounds of formula (54), a group of some compounds (formula (54)) cannot be efficiently produced by the process shown in schemes 1 to 12, for example, for production or purification reasons. The group of these compounds (formula (54)) can also be produced by an alternative process, for example, by producing the compound of formula (43) as a precursor of the compound of formula (54) by the process shown in scheme 12 and then subjecting the precursor to the following process.

Scheme 14

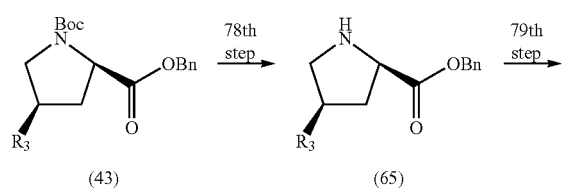

-continued

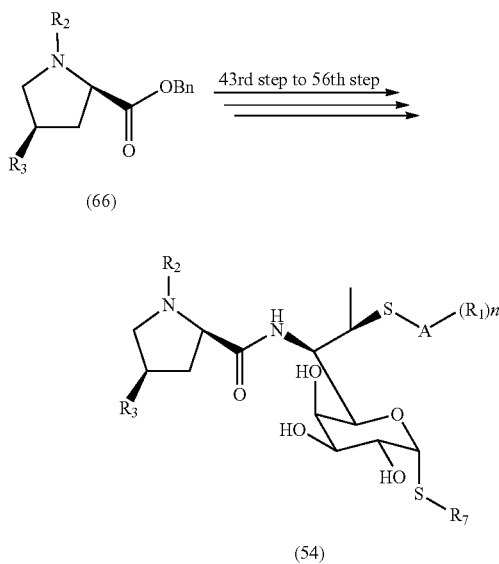

In the seventy-eighth and seventy-ninth steps, the conversion of the compound of formula (43) to the compound of formula (65) and the conversion of the compound of formula (65) to the compound of formula (66) can be produced, for example, according to the process in the fifty-seventh step and fifty-eighth step in scheme 12.

Next, regarding the conversion of the compound of formula (66) to the compound of formula (54) in scheme 14, the compound of formula (54) can be produced through the same production route as in the forty-third step to fifty-sixth step in scheme 12. Further, for a group of compounds of formula (54) wherein R₃ moiety has no double bond, the compound of formula (54-2) can be produced from the compound of formula (54-1) in the same manner as in scheme 13.

Sixteenthly, among a group of compounds of formulae (53) and (54) wherein R₁ represents —B—NH₂, a group of compounds (formulae (69) and (71)) cannot be efficiently produced by the process shown in scheme 12, for example, for production or purification reasons. The group of these compounds (formulae (69) and (71)) can also be produced by an alternative process, for example, by producing the compound of formula (67) or (70) as a precursor of the compound of formula (69) or (71) by the process shown in scheme 12 and then subjecting the precursor to the following process.

Scheme 15

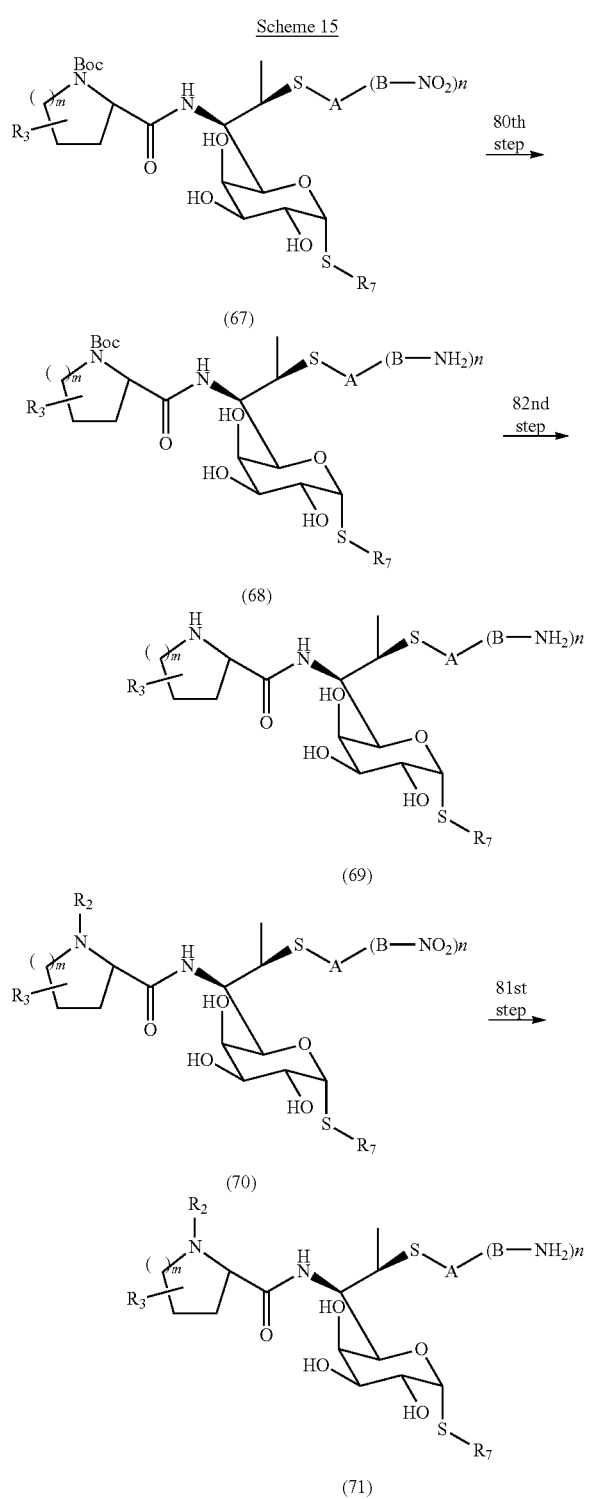

In the eightieth and eighty-first steps, the conversion of the compound of formula (67) to the compound of formula (68) and the conversion of the compound of formula (70) to the compound of formula (71) can be produced, for example, according to the process in the thirteenth step.

In the eighty-second step, the conversion of the compound of formula (68) to the compound of formula (69) can be produced, for example, according to the process in the fifty-seventh step.

Seventeenthly, among a group of compounds of formulae (53) and (54) wherein $R_1$ represents —B—NHCOR$_8$, a group of compounds (formulae (74) and (76)) cannot be efficiently produced by the process shown in scheme 12, for example, for production or purification reasons. The group of these compounds (formulae (74) and (76)) can also be produced by an alternative process, for example, by producing the compound of formula (68) or (71) as a precursor of the compound of formula (74) or (76) by the process shown in schemes 12 and 15 and then subjecting the precursor to the following process.

Scheme 16

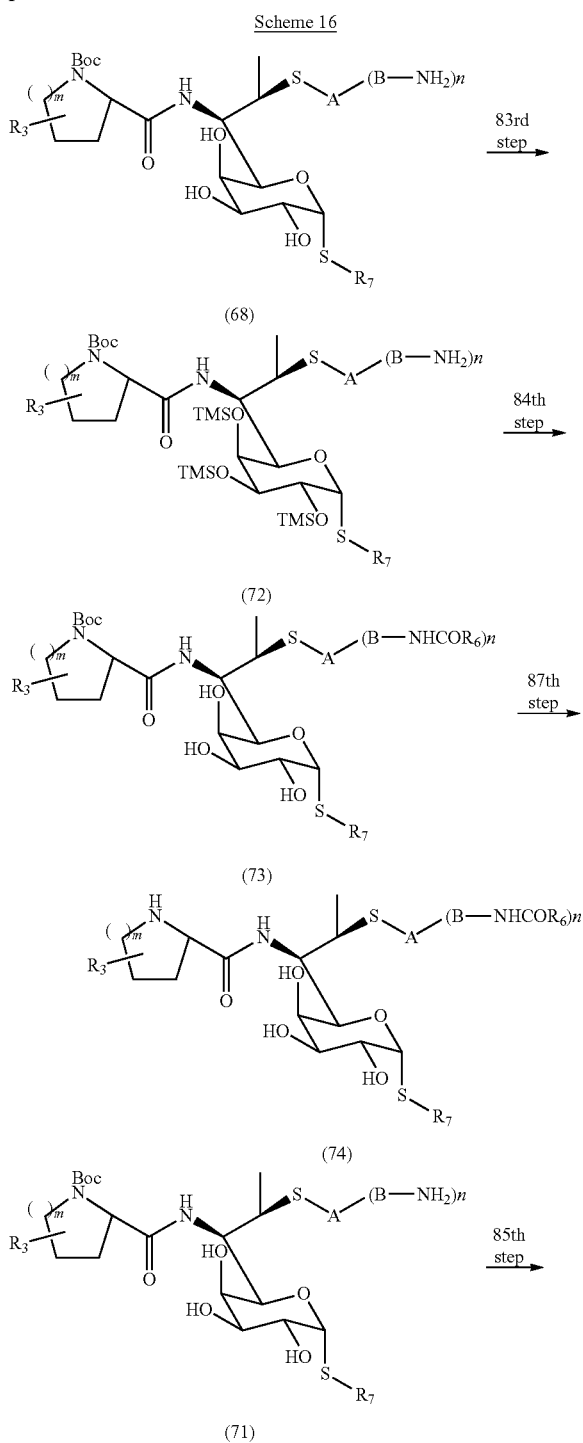

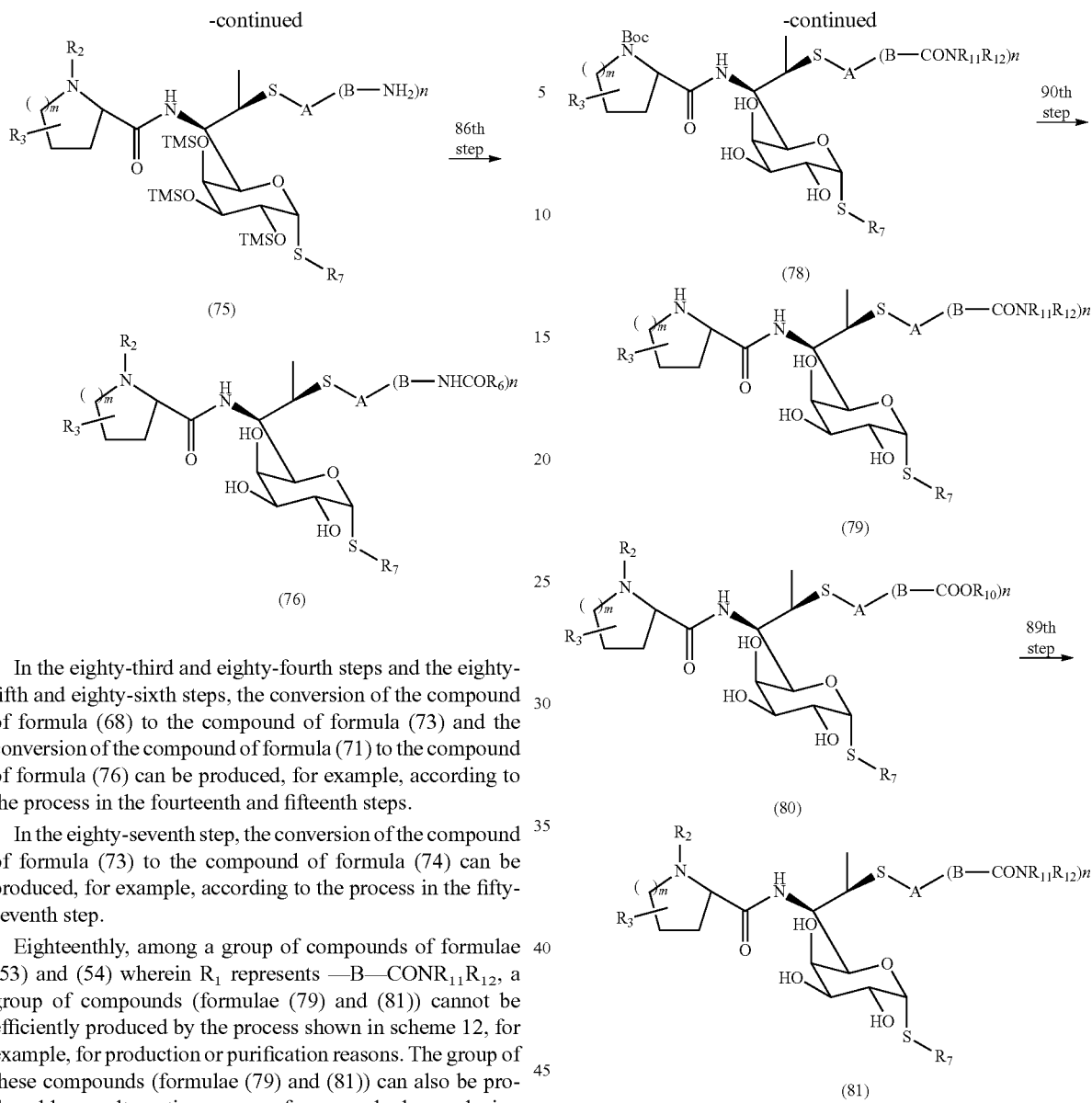

In the eighty-third and eighty-fourth steps and the eighty-fifth and eighty-sixth steps, the conversion of the compound of formula (68) to the compound of formula (73) and the conversion of the compound of formula (71) to the compound of formula (76) can be produced, for example, according to the process in the fourteenth and fifteenth steps.

In the eighty-seventh step, the conversion of the compound of formula (73) to the compound of formula (74) can be produced, for example, according to the process in the fifty-seventh step.

Eighteenthly, among a group of compounds of formulae (53) and (54) wherein $R_1$ represents —B—CONR$_{11}$R$_{12}$, a group of compounds (formulae (79) and (81)) cannot be efficiently produced by the process shown in scheme 12, for example, for production or purification reasons. The group of these compounds (formulae (79) and (81)) can also be produced by an alternative process, for example, by producing the compound of formula (77) or (80) as a precursor of the compound of formula (79) or (81) by the process shown in scheme 12 and then subjecting the precursor to the following process.

Scheme 17

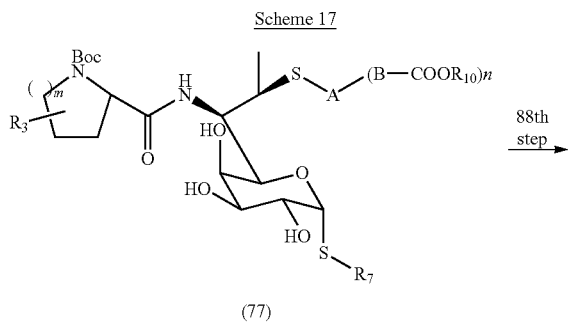

In the eighty-eighth and eighty-ninth steps, the conversion of the compound of formula (77) to the compound of formula (78) and the conversion of the compound of formula (80) to the compound of formula (81) can be produced, for example, according to the process in the twenty-third step.

In the ninetieth step, the conversion of the compound of formula (78) to the compound of formula (79) can be produced, for example, according to the process in the fifty-seventh step.

Ninteenthly, among a group of compounds of formulae (53) and (54) wherein $R_1$ represents —B—CONR$_{11}$R$_{12}$, a group of compounds (formulae (84) and (86)) cannot be efficiently produced by the process shown in scheme 12 or 16, for example, for production or purification reasons. The group of these compounds (formulae (84) and (86)) can also be produced by an alternative process, for example, by producing the compound of formula (77) or (80) as a precursor of the compound of formula (84) or (86) by the process shown in scheme 11 and then subjecting the precursor to the following process.

Scheme 18

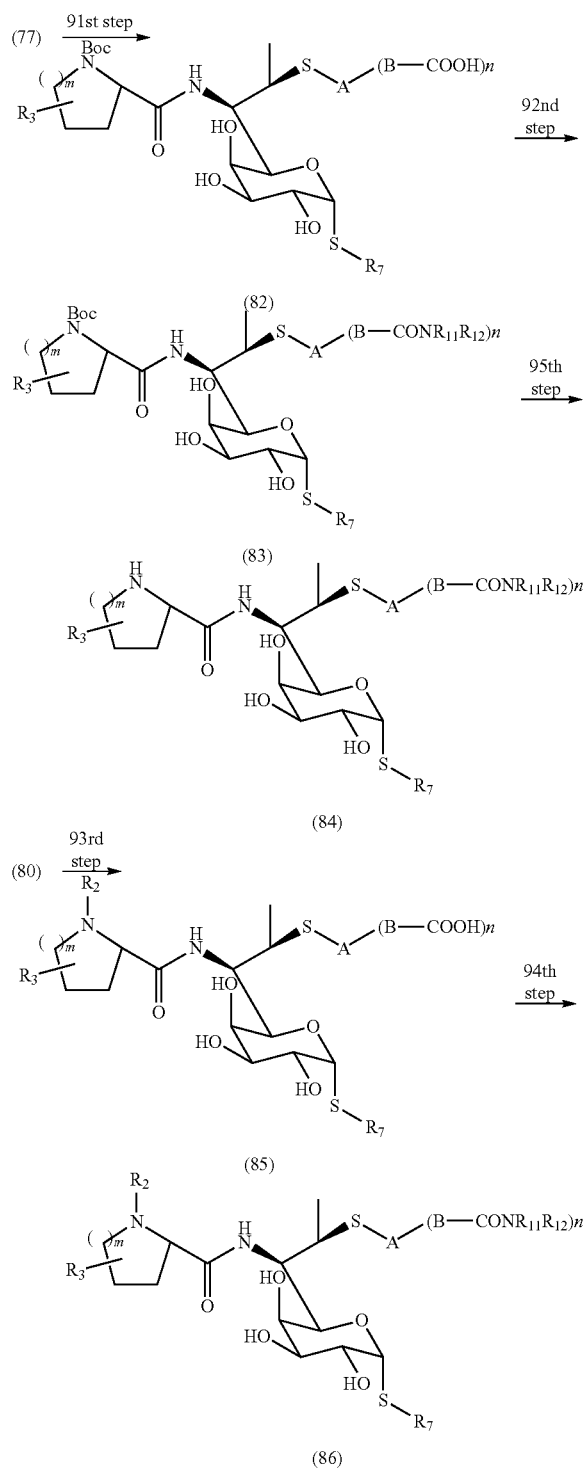

In the ninety-first and ninety-second steps and the ninety-third and ninety-fourth steps, the conversion of the compound of formula (77) to the compound of formula (83) and the compound of formula (80) to the compound of formula (86) can be produced, for example, according to the process in the twenty-fifth and twenty-sixth steps.

In the ninety-fifth step, the conversion of the compound of formula (83) to the compound of formula (84) can be produced, for example, according to the process in the fifty-seventh step.

Twentiethly, among a group of compounds of formulae (53) and (54) wherein $R_1$ represents —B—$NR_{13}R_{14}$, a group of compounds (formulae (89) and (91)) cannot be efficiently produced by the process shown in scheme 12, for example, for production or purification reasons. The group of these compounds (formulae (89) and (91)) can also be produced by an alternative process, for example, by producing the compound of formula (87) or (90) as a precursor of the compound of formula (89) or (91) by the process shown in scheme 12 and then subjecting the precursor to the following process.

Scheme 19

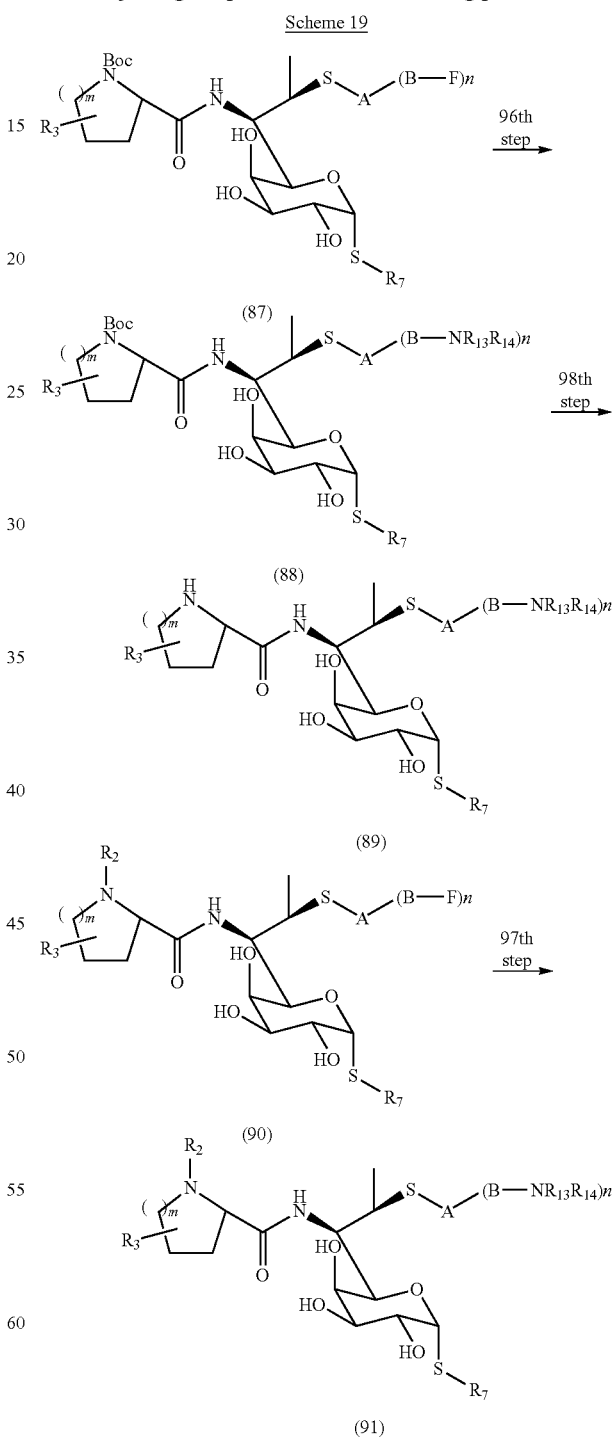

In the ninety-sixth and ninety-seventh steps, the conversion of the compound of formula (87) to the compound of formula

(88) and the conversion of the compound of formula (90) to the compound of formula (91) can be produced, for example, according to the process in the twenty-eighth step.

In the ninety-eighth step, the conversion of the compound of formula (88) to the compound of formula (89) can be produced, for example, according to the process in the fifty-seventh step.

Twenty-firstly, among a group of compounds of formulae (53) and (54) wherein $R_1$ represents —B—$OR_{15}$, a group of compounds (formulae (93) and (94)) cannot be efficiently produced by the process shown in scheme 12, for example, for production or purification reasons. The group of these compounds (formulae (93) and (94)) can also be produced by an alternative process, for example, by producing the compound of formula (87) or (90) as a precursor of the compound of formula (93) or (94) by the process shown in scheme 12 and then subjecting the precursor to the following process.

In the ninety-ninth and hundredth steps, the conversion of the compound of formula (87) to the compound of formula (92) and the conversion of the compound of formula (90) to the compound of formula (94) can be produced, for example, according to the process in the twenty-second step.

In one hundred and first step, the conversion of the compound of formula (92) to the compound of formula (93) can be carried out, for example, according to the process in the fifty-seventh step.

A group of compounds of formula (69), formula (71), formula (74), formula (76), formula (79), formula (81), formula (84), formula (86), formula (89), formula (91), formula (93), and formula (94) can also be produced in the same manner as in scheme 13.

Twenty-secondly, among a group of compounds of formula (I) wherein $R_2$ represents Me, $R_3$ represents Pr, and m is 1, a group of compounds having a stereochemical property (wherein the stereochemistry of sulfur atom at the 7-position is in an R form) different from the group of compounds produced by the process in schemes 1 to 20 can be produced from clindamycin by the following process.

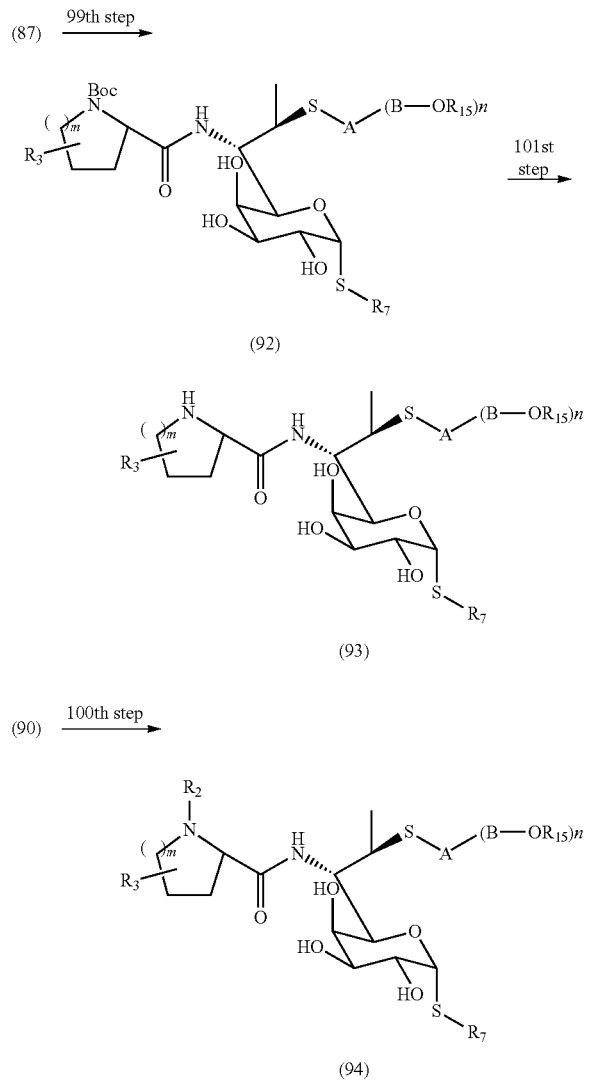

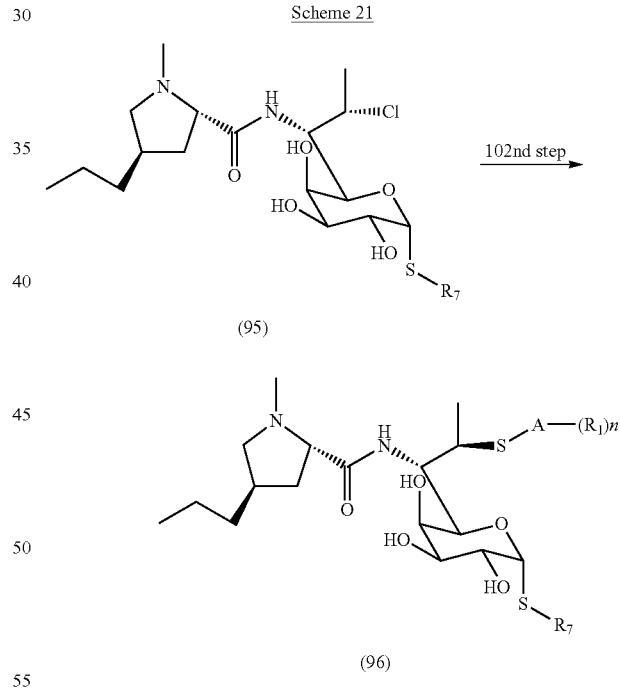

In the one hundred and second step, the conversion of the compound of formula (95) to the compound of formula (96) can be produced, for example, according to the process described in J. Antibiotics., 49, 941.

Twenty-thirdly, a group of compounds of formula (I) wherein $R_5$ and $R_6$ represent H, can be produced, for example, by producing the compound of formula (97) as a precursor of the contemplated compound by the process in scheme 12 and then subjecting the compound to the following process.

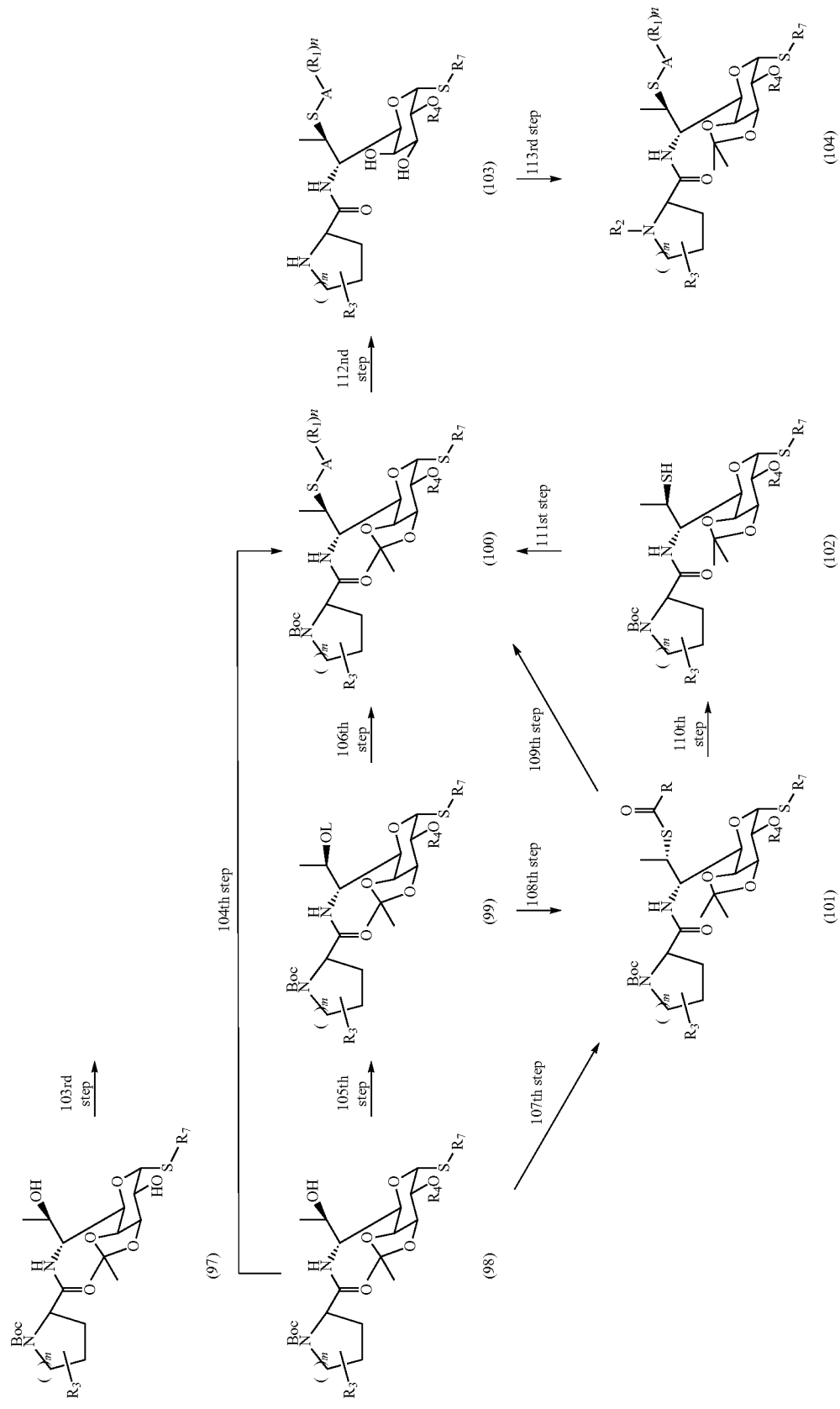
Scheme 22

In the one hundred and third step, the conversion of the compound of formula (97) to the compound of formula (98) can be carried out, for example, by reacting the compound of formula (97) with 1 to 10 equivalents of an optionally substituted alkyl halide in a benzene solvent in the presence of a base. The reaction solvent in this reaction may be a conventional solvent in addition to benzene, and preferred examples thereof include solvents such as toluene, tetrahydrofuran, diethyl ether, dimethyl sulfoxide, 1-methylpyrrolidone, and dimethylformamide. The base may be a conventional inorganic base, and preferred examples thereof include potassium tert-butoxide, sodium tert-butoxide, sodium hydroxide, potassium hydroxide, and sodium hydride. The base is used in an excessive amount. The reaction temperature is 0 to 50° C., and the reaction time is 0.5 to 24 hr.

In the one hundred and fourth step to one hundred and thirteenth step, the conversion of the compound of formula (98) to the compound of formula (103) and the compound of formula (104) can be carried out, for example, according to the process in the forty-seventh to fifty-eighth steps shown in scheme 12.

A group of compounds of formulae (103) and (104) in scheme 22 can also be produced in the same manner as in scheme 13.

Twenty-fourthly, a group of compounds of formula (I), wherein $R_4$, $R_5$ and $R_6$ represent (i) optionally substituted acyl or (ii) optionally substituted $C_{1-6}$ alkyl, can be produced, for example, by producing the compound of formula (49) or (54) as a precursor of the contemplated compound by the process shown in scheme 12 and then subjecting the compound to the following process.

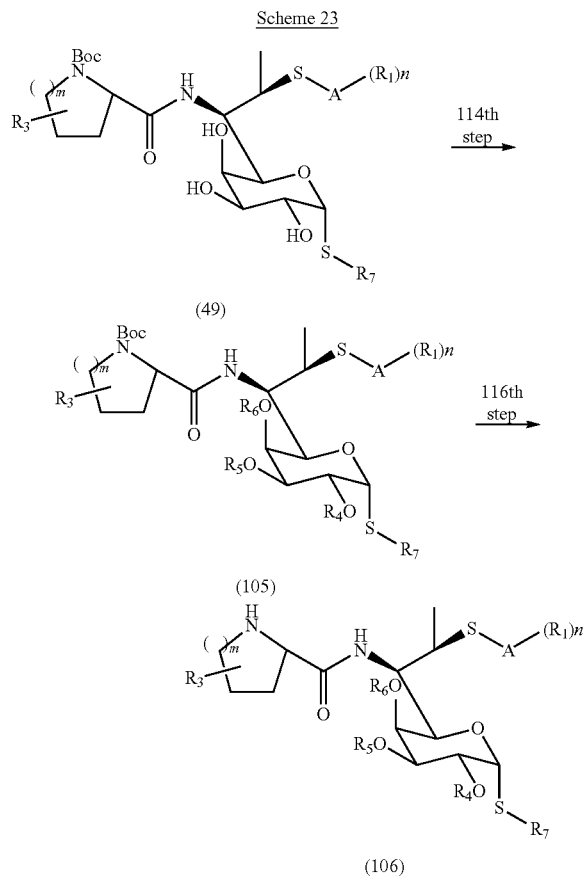

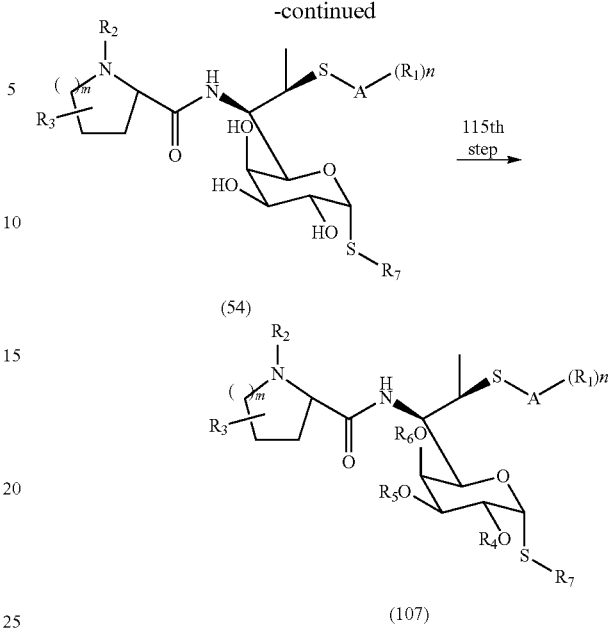

In the one hundred and fourteenth and one hundred and fifteenth steps, the conversion of the compound of formula (49) to the compound of formula (105) and the conversion of the compound of formula (54) to the compound of formula (107) can be carried out, for example, by the following process. (i) The contemplated compound can be produced by reacting the compound of formula (49) or the compound of formula (54) with 1 to 10 equivalents of an optionally substituted acid anhydride or acyl halide in a pyridine solvent in the presence of a base. The reaction solvent in this reaction may be a conventional polar solvent in addition to pyridine, and preferred examples thereof include solvents such as tetrahydrofuran, dimethyl sulfoxide, and 1-methylpyrrolidone, dimethylformamide. The base may be a conventional organic base or inorganic base, and preferred examples thereof include dimethylaminopyridine, triethylamine, sodium hydroxide, and potassium hydroxide. The base is preferably used in an excessive amount. The reaction temperature is 0 to 100° C., and the reaction time is 0.5 to 24 hr. (ii) The contemplated compound can be produced according to the process in the one hundred and third step.

In the one hundred and sixteenth step, the conversion of the compound of formula (105) to the compound of formula (106) can be carried out, for example, according to the process in the fifty-seventh step.

A group of compounds of formula (106) and a group of compounds of formula (107) in scheme 23, can also be produced in the same manner as in scheme 13.

A group of compounds cannot be efficiently produced by the process in scheme 23, for example, for production or purification reasons. The group of these compounds (formulae (106) and (107)) can also be produced by an alternative process, for example, by the process in schemes 15 to 20.

Twenty-fifthly, a group of compounds of formula (I), wherein $R_4$, $R_5$, and $R_6$ represent H and m is 3, can be produced, for example, by the following general process.

Scheme 24
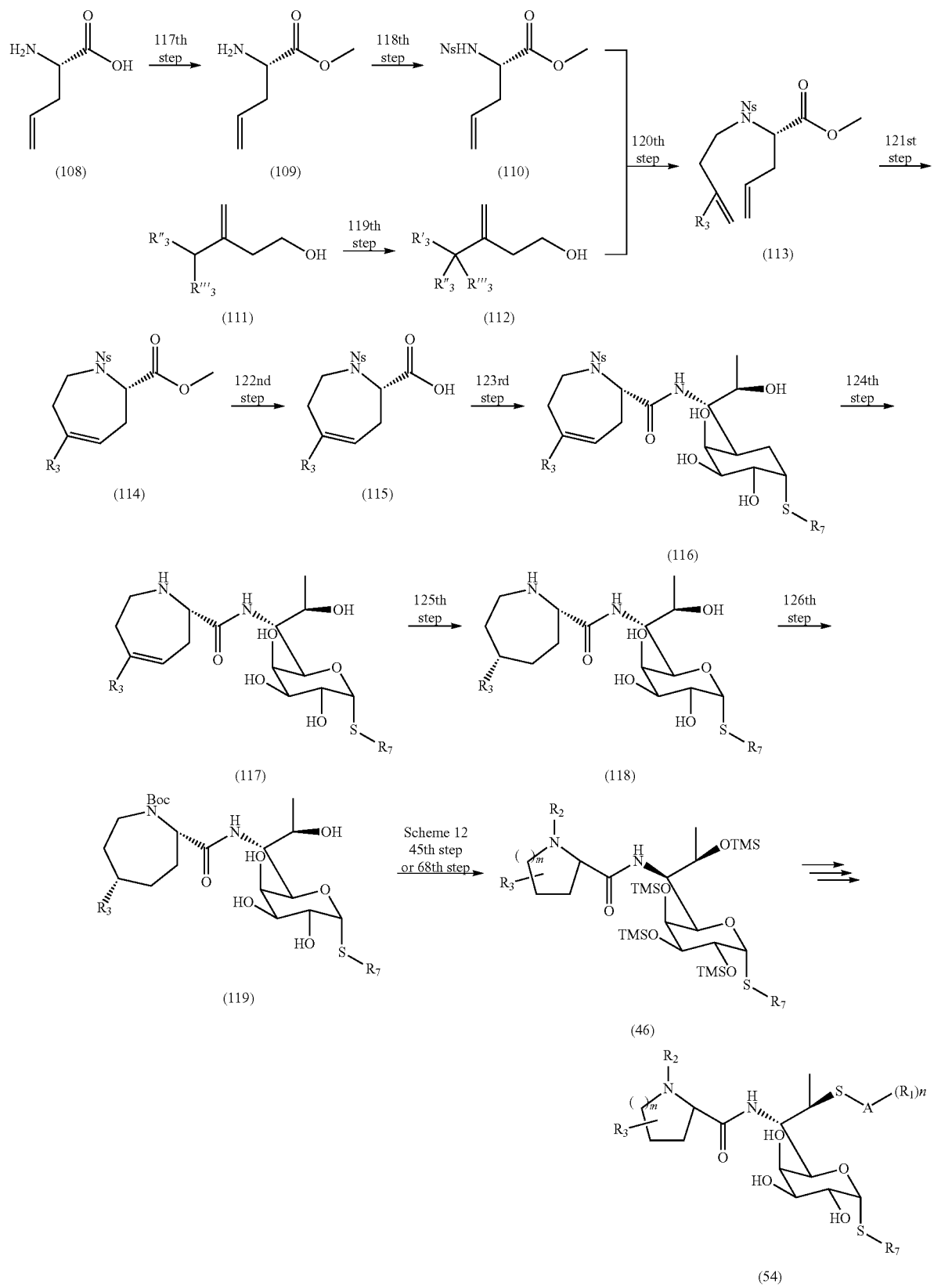

In scheme 24, $R_3$ represents $CR'_3(R''_3)(R'''_3)$.

In the one hundred and seventeenth step, the conversion of the compound of formula (108) to the compound of formula (109) can be carried out, for example, by either process (i) or (ii).

(i) The compound of formula (109) can be produced by reacting the compound of formula (108) in a methanol solvent in the presence of 1 to 10 equivalents of 4 N hydrochloric acid-dioxane. The acid in this reaction may be a commonly known strong acid in addition to hydrochloric acid, and preferred examples thereof include sulfuric acid. The amount of the acid is 1 to 10 equivalents. The reaction temperature is 0 to 50° C., and the reaction time is 0.5 to 120 hr.

(ii) The compound of formula (109) can be produced by reacting the compound of formula (108) in a methanol solvent in the presence of 1 to 10 equivalents of thionyl chloride. The reaction reagent in this reaction may be a commonly known carboxylic acid activating agent in addition to thionyl chloride, and preferred examples thereof include thionyl bromide, oxazalyl chloride, and dicyclohexylcarbodiimide-4-dimethylaminopyridine composite condensing agents. The amount of the reaction reagent is preferably 1 to 10 equivalents. The reaction temperature is 0 to 50° C., and the reaction time is 0.5 to 24 hr.

In scheme 24, Ns represents o-nitrobenzenesulfonyl.

In one hundred and eighteenth step, the conversion of the compound of formula (109) to the compound of formula (110) can be carried out, for example, by reacting the compound of formula (109) with 1 to 10 equivalents of o-nitrobenzenesulfonyl chloride in a diethyl ether solvent in the presence of a base. The reaction solvent in this reaction may be a conventional solvent in addition to diethyl ether, and preferred examples thereof include tetrahydrofuran, dimethyl sulfoxide, 1-methylpyrrolidone, N,N-dimethylformamide, and methylene chloride. The base may be a commonly known inorganic base or organic base, and preferred examples thereof include sodium hydrogencarbonate, potassium carbonate, potassium phosphate, lithium hydroxide, sodium hydroxide, triethylamine, diisopropylethylamine, 1,3,4,6,7,8-hexahydro-1-methyl-2H-pyrimido[1,2-a]pyridine, and 1,8-diazabicyclo[5.4.0]-7-undecene. The amount of the base is preferably 1 to 10 equivalents. The reaction temperature is 0 to 50° C., and the reaction time is 0.5 to 24 hr.

In the one hundred and nineteenth step, the conversion of the compound of formula (111) to the compound of formula (112) can be carried out, for example, by reacting the compound of formula (111) with 3-methyl-3-buten-1-ol in a diethyl ether solvent in the presence of N,N,N',N'-tetramethylethylenediamine and n-butyllithium at 0° C., then adding 1 to 5 equivalents of an alkyl bromide represented by $R_3$'Br at −78° C., and raising the temperature of the reaction system to room temperature. The reaction solvent in this reaction may be a conventional ether solvent in addition to diethyl ether, and preferred examples thereof include tetrahydrofuran. The reaction temperature is −78° C. to room temperature, and the reaction time is 15 to 36 hr.

In the one hundred and twentieth step, the conversion of the compound of formula (110) and the compound of formula (112) to the compound of formula (113) can be carried out, for example, by allowing a reaction to proceed using 1 to 10 equivalents of the compound of formula (110) in a tetrahydrofuran solution in the presence of the compound of formula (112), triphenylphosphine, and diisopropyl azodicarboxylate. The reaction solvent in this reaction may be a conventional reaction solvent in addition to tetrahydrofuran, and preferred examples thereof include benzene, toluene, trifluoromethyl benzene, and acetonitrile. The phosphine reagent may be a conventional phosphine reagent commonly known in literatures and the like in addition to triphenylphosphine, and preferred examples thereof include o-tolylphosphine and tri-n-butylphosphine. The amount of the phosphine reagent is preferably 1 to 5 equivalents. The azo reagent may be a conventional azo reagent commonly known in literatures and the like in addition to diisopropyl azodicarboxylate, and preferred examples thereof include diethyl azodicarboxylate and 1,1'-(azodicarbonyl)dipiperidine. The amount of the azo reagent is preferably 1 to 5 equivalents. The reaction temperature is 0 to 50° C., and the reaction time is 0.5 to 24 hr.

In the one hundred and twenty-first step, the conversion of the compound of formula (113) to the compound of formula (114) can be carried out, for example, by ring-closing the compound of formula (113) in a methylene chloride solvent in the presence of 0.01 to 0.1 equivalent of benzylidene[1,3-bis(2,4,6-trimethylphenyl)-2-imidazolidinylidene]dichloro(tricyclohexylphosphine)ruthenium. The reaction solvent in this reaction may be a conventional halogenic solvent in addition to the methylene chloride solvent, and preferred examples thereof include chloroform, carbon tetrachloride, and 1,2-dichloroethane. The reaction temperature is room temperature to 100° C., and the reaction time is 0.5 to 24 hr.

In the one hundred and twenty-second step, the conversion of the compound of formula (114) to the compound of formula (115) can be carried out, for example, by hydrolyzing the compound of formula (114) in a dioxane-water mixed solvent in the presence of a base. The reaction solvent in this reaction may be a conventional alcohol-water mixed solvent in addition to the dioxane-water mixed solvent, and a mixed solvent composed of methanol, ethanol, propanol, or butanol with water is preferred. The base may be a commonly known inorganic base, and preferred examples thereof include lithium hydroxide, sodium hydroxide, potassium hydroxide, and barium hydroxide. The amount of the base is preferably 1 to 10 equivalents. The reaction temperature is 0 to 120° C., and the reaction time is 0.5 to 24 hr.

In the one hundred and twenty-third step, the conversion of the compound of formula (115) to the compound of formula (116) can be carried out, for example, according to the process in the forty-fourth step in scheme 12.

In the one hundred and twenty-fourth step, the conversion of the compound of formula (116) to the compound of formula (117) can be carried out, for example, by reacting the compound of formula (116) with 1 to 10 equivalents of benzenethiol in an N,N-dimethylformamide solvent in the presence of a base. The reaction solvent in this reaction may be a conventional solvent in addition to N,N-dimethylformamide, and preferred examples thereof include tetrahydrofuran, dimethyl sulfoxide, 1-methylpyrrolidone, and diethyl ether. The base may be a commonly known inorganic base or organic base, and preferred examples thereof include potassium carbonate, sodium hydroxide, triethylamine, diisopropylethylamine, 1,8-diazabicyclo[5.4.0]-7-undecene, and 7-methyl-1,5,7-triazabicyclo-[4,4,0]dec-5-ene. The amount of the base is preferably 1 to 10 equivalents. The thiol may be a commonly known alkylthiol or arylthiol in addition to benzenethiol, and preferred examples thereof include 4-bromobenzenethiol and 4-t-butylbenzenethiol. The amount of the thiol is preferably 1 to 10 equivalents. The reaction temperature is 0 to 50° C., and the reaction time is 0.5 to 24 hr.

In the one hundred and twenty-fifth step, the conversion of the compound of formula (117) to the compound of formula (118) can be carried out, for example, by allowing a reaction to proceed in a methanol solvent in the presence of a metallic catalyst under a hydrogen atmosphere. The metallic catalyst in this reaction may be a metallic catalyst commonly used in hydrogen reduction, and preferred examples thereof include Raney nickel, palladium/carbon, and palladium hydroxide/carbon. The reaction temperature is 0 to 50° C., and the reaction time is 0.5 to 24 hr.

In the one hundred and twenty-sixth step, the conversion of the compound of formula (118) to the compound of formula (119) can be carried out, for example, according to the process in the sixty-fourth step in scheme 12.

The conversion of the compound of formula (119) to the compound of formula (46) can be carried out, for example, according to the process in the forty-fifth step or sixty-eighth step in scheme 12.

The conversion of the compound of formula (46) (m=3) to the compound of formula (54) in scheme 24 can be carried out, for example, according to the process in scheme 12.

EXAMPLES

The present invention is further illustrated by the following Examples. However, it should be noted that embodiments described in the Examples are not intended as a limitation of the invention. Reference Examples and Examples for producing the compounds of the present invention and the physicochemical properties of the compounds of the present invention will be described.

Reference Example 1

5-Phenyl-1,3,4-thiadiazole-2-thiol

Phosphorus oxychloride (7 ml) was added to 3.67 g (30 mmol) of benzoic acid and 2.73 g (30 mmol) of thiosemicarbazide, and the mixture was stirred at 80° C. for one hr. The reaction solution was added dropwise to 500 ml of a saturated aqueous sodium hydrogencarbonate solution. The resultant precipitate was collected by filtration and was dried. The dried precipitate was suspended in 20 ml of acetonitrile. Cupric chloride (6 g, 45 mmol) and 5.3 g (45 mmol) of tert-butyl nitrite were added to the suspension, and the mixture was stirred at room temperature for 3 hr. The solvent was removed by distillation. Ethyl acetate (100 ml) was added to the residue, and the mixture was washed with 30 ml of 1 N hydrochloric acid and 50 ml of distilled water in that order. The solvent was removed by distillation. The residue was dissolved in 20 ml of ethanol, 3.4 g (45 mmol) of thiourea was added to the solution, and the mixture was heated under reflux for 3 hr. The solvent was removed by distillation, 100 ml of ethyl acetate was added to the residue, and the mixture was washed with 50 ml of distilled water. The solvent was removed by distillation, and the residue was then purified by column chromatography on silica gel (chloroform:methanol=30:1) to give 3.17 g (yield 55%) of the title compound.

The following compounds were synthesized in the same manner as in Reference Example 1 and were used in the Examples.
5-(Naphthalen-3-yl)-1,3,4-thiadiazole-2-thiol,
5-(quinolin-3-yl)-1,3,4-thiadiazole-2-thiol,
5-(2,4-dinitrophenyl)-1,3,4-thiadiazole-2-thiol,
5-(4-fluoro-2-nitrophenyl)-1,3,4-thiadiazole-2-thiol,
5-(2-cyanophenyl)-1,3,4-thiadiazole-2-thiol,
5-(3,4-difluoro-2-nitrophenyl)-1,3,4-thiadiazole-2-thiol,
5-(5-fluoro-2-nitrophenyl)-1,3,4-thiadiazole-2-thiol,
5-(5-methyl-2-nitrophenyl)-1,3,4-thiadiazole-2-thiol,
5-(5-(azetidin-1-yl)-2-nitrophenyl)-1,3,4-thiadiazole-2-thiol,
5-(1-methyl-5-nitro-1H-pyrazol-4-yl)-1,3,4-thiadiazole-2-thiol,
5-(4-amino-2-nitrophenyl)-1,3,4-thiadiazole-2-thiol,
5-(1-methyl-4-nitro-1H-pyrazol-5-yl)-1,3,4-thiadiazole-2-thiol,
5-(1-methyl-4-nitro-1H-imidazol-2-yl)-1,3,4-thiadiazole-2-thiol, and
5-(1-methyl-4-nitro-1H-pyrazol-3-yl)-1,3,4-thiadiazole-2-thiol.

Reference Example 2

5-(2-Nitrophenyl)-1,3,4-thiadiazole-2-thiol

Carbon bisulfide (4 ml) was added to a solution of 1.81 g (10 mmol) of 2-nitrobenzohydrazide in 8 ml of methanol. A solution of 616 mg (11 mmol) of potassium hydroxide in methanol (10 ml) was added thereto, and the mixture was stirred at room temperature for 6 hr. The precipitated crystal was collected by filtration and was dried. The dried crystal was added dropwise to 5 ml of concentrated sulfuric acid, and the mixture was stirred at room temperature for 3 hr. The reaction solution was added dropwise to 100 ml of ice water, and the resultant precipitate was collected by filtration and was dried to give 1.21 g (51%) of the title compound.

The following compounds were synthesized in the same manner as in Reference Example 2 and were used in the Examples.
5-(2-Nitrophenyl)-1,3,4-thiadiazole-2-thiol,
5-(3-nitrophenyl)-1,3,4-thiadiazole-2-thiol,
5-(4-nitrophenyl)-1,3,4-thiadiazole-2-thiol,
5-(2-chlorophenyl)-1,3,4-thiadiazole-2-thiol,
5-(4-chlorophenyl)-1,3,4-thiadiazole-2-thiol,
5-(2-fluorophenyl)-1,3,4-thiadiazole-2-thiol,
5-(2-methylthiophenyl)-1,3,4-thiadiazole-2-thiol,
5-(2-methylsulfonylphenyl)-1,3,4-thiadiazole-2-thiol,
5-(2-methoxyphenyl)-1,3,4-thiadiazole-2-thiol,
5-(2-methylphenyl)-1,3,4-thiadiazole-2-thiol,
5-(4-chloro-2-nitrophenyl)-1,3,4-thiadiazole-2-thiol,
5-(4,5-dimethoxy-2-nitrophenyl)-1,3,4-thiadiazole-2-thiol,
5-(pyridin-2-yl)-1,3,4-thiadiazole-2-thiol,
5-(pyridin-3-yl)-1,3,4-thiadiazole-2-thiol,
5-(pyridin-4-yl)-1,3,4-thiadiazole-2-thiol,
5-(3,5-diaminophenyl)-1,3,4-thiadiazole-2-thiol,
5-(3,4-diaminophenyl)-1,3,4-thiadiazole-2-thiol,
5-(thiazol-4-yl)-1,3,4-thiadiazole-2-thiol,
5-(5-(methylamino)thiazol-4-yl)-1,3,4-thiadiazole-2-thiol,
5-(5-aminothiazol-4-yl)-1,3,4-thiadiazole-2-thiol,
5-(2-aminothiazol-4-yl)-1,3,4-thiadiazole-2-thiol,
5-(thiophen-2-yl)-1,3,4-thiadiazole-2-thiol,
5-(3-aminothiophen-2-yl)-1,3,4-thiadiazole-2-thiol,
5-(5-amino-1-methyl-1H-pyrazol-4-yl)-1,3,4-thiadiazole-2-thiol,
5-(1,2,3-thiadiazol-4-yl)-1,3,4-thiadiazole-2-thiol,
5-(4-methyl-1,2,3-thiadiazol-5-yl)-1,3,4-thiadiazole-2-thiol,
5-(furan-2-yl)-1,3,4-thiadiazole-2-thiol,
5-(pyrazin-2-yl)-1,3,4-thiadiazole-2-thiol,
5-(3-aminopyrazin-2-yl)-1,3,4-thiadiazole-2-thiol,
5-(2-amino-1,3,4-thiadiazol-5-yl)-1,3,4-thiadiazole-2-thiol,
5-(2-aminopyridin-3-yl)-1,3,4-thiadiazole-2-thiol,
5-(2-aminopyridin-5-yl)-1,3,4-thiadiazole-2-thiol, and
5-(2-methylaminophenyl)-1,3,4-thiadiazole-2-thiol.

Reference Example 3

2-(4,5-Dimethoxy-2-nitrophenyl)-5-methylthio-1,3,4-thiadiazole

Potassium carbonate (13.8 mg, 1.0 mmol) and 0.0624 ml (1.0 mmol) of methyl iodide were added to a solution of 150 mg (0.510 mmol) of 5-(4,5-dimethoxy-2-nitrophenyl)-1,3,4-thiadiazole-2-thiol produced in Reference Example 2 in N,N-dimethylformamide (2 ml), and the mixture was stirred at room temperature for 10 min. The mixture was diluted with 30 ml of ethyl acetate, and the diluted solution was washed with 30 ml of a 10% aqueous ammonium chloride solution and 30 ml of saturated brine. The organic layer was dried over anhydrous sodium sulfate and was then filtered. The filtrate was concentrated under the reduced pressure, and the resultant crystal was washed with diisopropyl ether to give 140 mg (yield 89%) of the title compound.

$^1$H-NMR (400 MHz, CDCl$_3$) δ: 2.85 (3H, s), 3.99 (3H, s), 4.02 (3H, s), 7.17 (1H, s), 7.66 (1H, s).

MS (FAB$^+$) m/z: 314 (M$^+$+1).

Reference Example 4

2-(4,5-Dimethoxy-2-nitrophenyl)-5-methylsulfonyl-1,3,4-thiadiazole m-Chlorobenzoic acid (405 mg, 2.35 mmol) was added to a solution of 135 mg (0.431 mmol) of the title compound produced in Reference Example 3 in dichloromethane (2 ml) under ice cooling, and the mixture was stirred at room temperature for one hr. The reaction solution was diluted with 30 ml of chloroform and was washed with 30 ml of a 10% aqueous thiosulfric acid solution and 30 ml of a 10% aqueous sodium hydrogencarbonate solution. The organic layer was dried over anhydrous sodium sulfate and was then filtered. The filtrate was concentrated under the reduced pressure, and the resultant crystal was washed with diisopropyl ether to give 149 mg (yield 100%) of the title compound.

$^1$H-NMR (400 MHz, CDCl$_3$) δ: 3.54 (3H, s), 4.02 (3H, s), 4.05 (3H, s), 7.16 (1H, s), 7.75 (1H, s).

Reference Example 5

2-(5-Amino-1,3,4-thiadiazol-2-yl)methyl Benzoate

Phosphorus oxychloride (20 ml) was added to 5 g (27.8 mmol) of monomethyl phthalate and 2.53 g (30 mmol) of thiosemicarbazide, and the mixture was stirred at 80° C. for 4 hr. The reaction solution was added dropwise to 250 ml of ice water, and the mixture was neutralized with potassium carbonate, was extracted twice with 250 ml of ethyl acetate, was dried over anhydrous sodium sulfate, and was then filtered. The filtrate was concentrated under the reduced pressure, and the residue was washed with ethyl acetate and chloroform to give 860 mg (yield 13%) of the title compound.

MS (FAB$^+$) m/z: 236 (M$^+$+1).

$^1$H-NMR (400 MHz, DMSO-d6) δ: 3.20-3.60 (2H, br), 3.72 (3H, s), 7.50-7.75 (4H, m).

Reference Example 6

2-(5-Chloro-1,3,4-thiadiazol-2-yl)methyl Benzoate

The title compound (850 mg, 3.61 mmol) produced in Reference Example 5 was suspended in 20 ml of acetonitrile, 972 mg (7.23 mmol) of cupric chloride and 0.644 ml (5.42 mmol) of tert-butyl nitrite were added to the suspension, and the mixture was stirred at room temperature for 40 min. Ethyl acetate (100 ml) and water (50 ml) were added thereto, and insolubles were separated by filtration, followed by washing with saturated brine (50 ml). The washed product was then dried over anhydrous sodium sulfate and was then filtered. The filtrate was concentrated under the reduced pressure, and the residue was purified by column chromatography on silica gel (hexane:ethyl acetate=100:0 to 80:20) to give 442 mg (yield 48%) of the title compound.

MS (FAB$^+$) m/z: 255 (M$^+$+1).

$^1$H-NMR (400 MHz, DMSO-d6) δ: 3.83 (3H, s), 7.60-7.75 (3H, m), 7.95-8.05 (1H, m).

The following compound was synthesized in the same manner as in Reference Example 6 and was used in the Examples.
2-Chloro-5-(nitropyridin-2-yl)-1,3,4-thiadiazole.

Reference Example 7

(i) N-(4-Bromophenyl)acetamide

Triethylamine (0.65 ml, 4.65 mmol) was added to a solution of 200 mg (1.16 mmol) of 4-bromoaniline in tetrahydrofuran (2 ml), and the mixture was stirred at room temperature for 5 min. Acetyl chloride (0.165 ml, 2.33 mmol) was added thereto, and the mixture was stirred at room temperature for 17 hr. The reaction was stopped by adding a saturated aqueous sodium hydrogencarbonate solution, and the reaction solution Was extracted with ethyl acetate. The organic layer was washed with water and saturated brine in that order, was dried over anhydrous sodium sulfate and was filtered. The filtrate was concentrated under the reduced pressure, and the residue was purified by column chromatography on silica gel (chloroform:methanol=20:1) to give 249 mg (yield 99%) of the title compound.

The following compounds were synthesized in the same manner as in step (i) of Reference Example 7 and were used in the Examples.
N-(4-Bromophenyl)propionamide,
N-(4-bromophenyl)pentanamide, and
N-(4-bromophenyl)-2-methoxyacetamide.

(ii) N-(4-Bromophenyl)-N-methylacetamide

Sodium hydride (101.5 mg, 2.33 mmol) (55% in paraffin liquid) was added to a solution of 249 mg (1.16 mmol) of the title compound produced in step (i) of Reference Example 7 in N,N-dimethylformamide (2.5 ml), and the mixture was stirred at room temperature for 30 min. Thereafter, methyl iodide was added, and the mixture was stirred at room temperature for 1 hr. The reaction was stopped by adding a saturated aqueous sodium hydrogencarbonate solution, and the reaction solution was extracted with ethyl acetate. The organic layer was washed with water and saturated brine in that order, was dried over anhydrous sodium sulfate, and was filtered. The filtrate was concentrated under the reduced pressure, and the residue was purified by column chromatography on silica gel (hexane:ethyl acetate=2:1) to give 239 mg (yield 90%) of the title compound.

$^1$H-NMR (400 MHz, CDCl$_3$) δ: 1.88 (3H, s), 3.24 (3H, s), 7.08 (2H, d, J=8.5 Hz), 7.54 (2H, d, J=8.5 Hz).

MS (FAB$^+$) m/z: 227 (M$^+$+1).

The following compounds were synthesized in the same manner as in step (ii) of Reference Example 7 and were used in the Examples.
N-(4-Bromophenyl)-2-methoxy-N-methylacetamide
and N-(4-bromophenyl2-methoxy-N-propylacetamide.

Reference Example 8

(i) (4-Bromophenyl)(morpholino)methanone

1-Hydroxybenzotriazole (2.02 g, 14.9 mmol) and 2.86 g (14.9 mmol) of 1-ethyl-3-(3-dimethylaminopropyl)carbodiimide hydrochloride were added to a solution of 2.0 g (9.95 mmol) of 4-bromobenzoic acid in N,N-dimethylformamide (15 ml), and the mixture was stirred at room temperature for 10 min. Thereafter, 1.3 ml (14.9 mmol) of morpholine was added thereto, and the mixture was stirred at room temperature for 18 hr. The reaction was stopped by adding a saturated aqueous sodium hydrogencarbonate solution, and the reaction solution was extracted with ethyl acetate. The organic layer was washed with water and saturated brine in that order, was dried over anhydrous sodium sulfate, and was then filtered. The filtrate was concentrated under the reduced pressure, and the residue was purified by column chromatography on silica gel (hexane:ethyl acetate=1:2) to give 2.66 g (yield 99%) of the title compound.

$^1$H-NMR (400 MHz, CDCl$_3$) δ: 3.76 (8H, brs), 7.30 (2H, ddd, J=8.3, 1.7, 1.7 Hz), 7.56 (2H, ddd, J=8.3, 1.7, 1.7 Hz).
MS (ESI$^+$) m/z: 270 (M$^+$+1).

The following compounds were synthesized in the same manner as in step (i) of Reference Example 8, except that morpholine was changed to various amines. The compounds thus obtained were used in the Examples.
(4-Bromophenyl)(piperidin-1-yl)methanone,
(4-bromophenyl)(pyrrolidin-1-yl)methanone,
(S)-(4-bromophenyl)(2-(hydroxymethyl)pyrrolidin-1-yl)methanone,
(S)-(4-bromophenyl)(2-(methoxymethyl)pyrrolidin-1-yl)methanone,
(R)-(4-bromophenyl)(2-(hydroxymethyl)pyrrolidin-1-yl)methanone, (R)-(4-bromophenyl)(3-hydroxypyrrolidin-1-yl)methanone,
4-bromo-N-(1,3-dihydroxypropan-2-yl)benzamide,
4-bromo-N-(3-hydroxypropyl)benzamide,
4-bromo-N-(2-hydroxyethyl)-N-(3-hydroxypropyl)benzamide,
and (S)-4-bromo-N-(1-hydroxybutan-2-yl)benzamide.

The following compounds were synthesized in the same manner as in step (i) of Reference Example 8, except that 4-bromobenzoic acid was changed to various 4-bromobenzoic acids containing a substituent on their phenyl. The compounds thus obtained were used in the Examples.
(4-Bromo-2-fluorophenyl)(morpholino)methanone,
(4-bromo-2-nitrophenyl)(morpholino)methanone,
(4-bromo-3-fluorophenyl)(morpholino)methanone,
(4-bromo-2-methylphenyl)(morpholino)methanone,
(4-bromo-2-fluorophenyl)(piperidin-1-yl)methanone, and
(4-bromo-3-fluorophenyl)(piperidin-1-yl)methanone.

(ii) (R)-(4-Bromophenyl)(3-methoxypyrrolidin-1-yl)methanone

Sodium hydroxide (10.6 mg, 0.264 mmol) was added to a solution of 54 mg (0.176 mmol) of (R)-(4-bromophenyl)(3-hydroxypyrrolidin-1-yl)methanone in dimethyl sulfoxide (1 ml) synthesized in the same manner as in step (i) of Reference Example 8, 0.11 ml (1.76 mmol) of methyl iodide was then added thereto, and the mixture was stirred at 100° C. for 20 hr. A saturated aqueous sodium hydrogencarbonate solution was added thereto, and the mixture was extracted with ethyl acetate. The organic layer was washed with water and saturated brine in that order, was dried over anhydrous sodium sulfate, and was then filtered. The filtrate was concentrated under the reduced pressure, and the residue was purified by preparative thin layer chromatography (chloroform:methanol:28% aqueous ammonia=9:2:0.2) to give 45 mg (yield 90%) of the title compound.

The following compound was synthesized in the same manner as in step (ii) of Reference Example 8 and was used in the Examples.
4-Bromo-N-(1,3-dimethoxypropan-2-yl)benzamide.

(iii) (S)-(2-(Allyloxymethyl)pyrrolidin-1-yl)(4-bromophenyl)methanone

Sodium hydride (61.5 mg, 1.41 mmol) (55% in paraffin liquid) was added to a solution of 200 mg (0.704 mmol) of (S)-(4-bromophenyl)(2-(hydroxymethyl)pyrrolidin-1-yl)methanone in N,N-dimethylformamide (2 ml) synthesized in the same manner as in step (i) of Reference Example 8, and the mixture was stirred at room temperature for 30 min. Thereafter, allyl iodide was added thereto, and the mixture was stirred at room temperature for 1 hr. The reaction was stopped by adding a saturated aqueous sodium hydrogencarbonate solution, and the reaction solution was extracted with ethyl acetate. The organic layer was washed with water and saturated brine in that order, was dried over anhydrous sodium sulfate, and was then filtered. The filtrate was concentrated under the reduced pressure, and the residue was purified by column chromatography on silica gel (hexane:ethyl acetate=1:2) to give 155 mg (yield 68%) of the title compound.

(iv) (S)—S-(1-(4-Bromobenzoyl)pyrrolidin-2-yl)methyl Ethanethioate

Triethylamine (0.2 ml, 1.41 mmol) was added to a solution of 200 mg (0.704 mmol) of (S)-(4-bromophenyl)(2-(hydroxymethyl)pyrrolidin-1-yl)methanone synthesized in step (i) of Reference Example 8 in chloroform (2 ml), and the mixture was stirred at room temperature for 10 min. Thereafter, 0.11 ml (1.41 mmol) of methanesulfonyl chloride was added thereto, and the mixture was stirred at room temperature for 10 min. The reaction was stopped by adding a saturated aqueous sodium hydrogencarbonate solution, and the reaction solution was extracted with chloroform. The organic layer was washed with water and saturated brine in that order, was dried over anhydrous sodium sulfate, and was then filtered. The filtrate was concentrated under the reduced pressure and was then dried. Potassium thioacetate (160.8 mg, 1.41 mmol) was added to a solution of the crude product in N,N-dimethylformamide (4 ml), and the mixture was stirred at 100° C. for 2 hr. The reaction was stopped by adding a saturated aqueous sodium hydrogencarbonate solution, and the reaction solution was extracted with ethyl acetate. The organic layer was washed with water and saturated brine in that order, was dried over anhydrous sodium sulfate, and was then filtered. The filtrate was concentrated under the reduced pressure, and the residue was then purified by preparative thin layer chromatography (hexane:ethyl acetate=1:2) to give 100 mg (yield 42%) of the title compound.

(v) (S)-(4-Bromophenyl)(2-(methylthiomethyl)pyrrolidin-1-yl)methanone

Sodium methoxide (0.22 ml, 0.876 mmol) (28% in methanol) was added to a solution of 100 mg (0.292 mmol) of the title compound produced in step (iv) of Reference Example 8 in methanol (1 ml), and the mixture was stirred at room temperature for 15 min. Thereafter, 0.11 ml (1.75 mmol) of methyl iodide was added thereto, and the mixture was stirred at room temperature for 20 hr. The reaction was stopped by adding a saturated aqueous sodium hydrogencarbonate solution, and the reaction solution was extracted with ethyl acetate. The organic layer was washed with water and saturated brine in that order, was dried over anhydrous sodium sulfate, and was then filtered. The filtrate was concentrated under the reduced pressure, and the residue was purified by preparative thin layer chromatography (hexane:ethyl acetate=1:4) to give 55 mg (yield 60%) of the title compound.

¹H-NMR (400 MHz, CDCl₃) δ: 1.73-1.80 (1H, m), 1.89-1.98 (2H, m), 2.15-2.21 (4H, m), 2.78 (1H, dd, J=13.2, 8.3 Hz), 3.04 (1H, dd, J=13.2, 2.9 Hz), 3.40-3.54 (2H, m), 4.45-4.46 (1H, m), 7.41 (2H, d, J=8.3 Hz), 7.54 (2H, d, J=8.3 Hz).
MS (EI⁺) m/z: 313 (M⁺).

(vi) (S)-(2-(Azidomethyl)pyrrolidin-1-yl)(4-bromophenyl)methanone

Diisopropylethylamine (0.36 ml, 2.1 mmol) and 0.15 ml (1.9 mmol) of methanesulfonyl chloride were added under ice cooling to a solution of 397 mg (1.4 mmol) of (S)-(4-bromophenyl)(2-(hydroxymethyl)pyrrolidin-1-yl)methanone synthesized in the same manner as in step (i) of Reference Example 8 in methylene chloride (15 ml) solution, and the mixture was stirred for 2 hr. The reaction solution was diluted with 45 ml of ethyl acetate and was washed with a saturated aqueous ammonium chloride solution. The aqueous layer was extracted twice with 5 ml of ethyl acetate. The organic layers were combined and were washed with 25% brine. The organic layer was dried over anhydrous sodium sulfate and was filtered. The filtrate was concentrated under the reduced pressure, and the residue was dissolved in 10 ml of N,N-dimethylformamide. Sodium azide (146 mg, 2.2 mmol) was added to the solution, and the mixture was stirred at 50° C. for 5 hr. The reaction solution was diluted with 20 ml of ethyl acetate, and the diluted solution was washed five times with 10 ml of 12.5% brine. The organic layer was dried over anhydrous sodium sulfate and was filtered, and the filtrate was concentrated under the reduced pressure. The residue was purified by column chromatography on silica gel (n-hexane:ethyl acetate=2:1) to give 194 mg (yield 45%) of the title compound.

(vii) (S)-(2-(Aminomethyl)pyrrolidin-1-yl)(4-bromophenyl)methanone

The title compound (194 mg, 0.63 mmol) produced in step (vi) of Reference Example 8 was dissolved in 10 ml of tetrahydrofuran and 1 ml of water, 852 mg (3.1 mmol) of triphenylphosphine was added to the solution, and the mixture was stirred at 60° C. for 5 hr. The reaction solution was concentrated under the reduced pressure, and the residue was purified by column chromatography on silica gel (chloroform:methanol=40:1 to 5:1) to give 177 mg (yield 100%) of the title compound.
¹H-NMR (300 MHz, CDCl₃) δ: 1.71-2.17 (4H, m), 2.89 (1H, dd, J=6.3, 12.6 Hz), 3.05 (1H, dd, J=4.8, 12.6 Hz), 3.40-3.47 (2H, m), 4.29 (1H, t, J=6.0 Hz), 7.40 (2H, d, J=8.1 Hz), 7.54 (2H, d, J=8.4 Hz).
MS (FAB) m/z: 283 (M⁺+1).

(viii) (S)-(4-Bromophenyl)(2-((N,N-dimethylamino)methyl)pyrrolidin-1-yl)methanone Acetic acid (105 μl, 1.8 mmol), 0.15 ml (2.0 mmol) of a 37% aqueous formaldehyde solution, and 416 mg (1.9 mmol) of sodium triacetoxyboron were added to a solution of the title compound (104 mg, 0.37 mmol) produced in step (vii) of Reference Example 8 in methanol (3 ml) solution, and the mixture was stirred at room temperature for 7 hr. The solvent was removed by distillation, and the residue was purified by column chromatography on silica gel (chloroform:methanol=20:1 to 7:1) to give 104 mg (yield 90%) of the title compound.
¹H-NMR (300 MHz, CDCl₃) δ: 1.74-2.00 (3H, m), 2.12-2.25 (1H, m), 2.53 (6H, s), 2.57-2.67 (1H, m), 3.01 (1H, dd, J=3.0, 11.7 Hz), 3.35-3.54 (2H, m), 4.43-4.54 (1H, br), 7.40 (2H, d, J=8.1 Hz), 7.54 (2H, d, J=8.4 Hz).
MS (FAB) m/z: 310 (M⁺+1).

(ix) (S)-(4-Bromophenyl)(2-(iodomethyl)pyrrolidin-1-yl)methanone

A solution of imidazole (310 mg, 4.5 mmol), 1.75 g (6.5 mmol) of triphenylphosphine, and 568 mg (2.2 mmol) of iodine in tetrahydrofuran (12 ml) was added under ice cooling to a solution of 504 mg (1.8 mmol) of (S)-(4-bromophenyl)(2-(hydroxymethyl)pyrrolidin-1-yl)methanone synthesized in step (i) of Reference Example 8 in methylene chloride (40 ml), and the mixture was stirred under ice cooling for 3 hr and then at room temperature for 4 hr. The reaction solution was diluted with 60 ml of ethyl acetate and was washed with an 8% aqueous sodium hydrogencarbonate solution. The aqueous layer was washed twice with 8 ml of ethyl acetate. The organic layers were combined and were washed with 25% brine. The organic layer was dried over anhydrous sodium sulfate and was filtered. The filtrate was concentrated under the reduced pressure, and the residue was purified by column chromatography on silica gel (n-hexane:ethyl acetate=4:1) to give 438 mg (yield 63%) of the title compound.

(x) (S)-(4-Bromophenyl)(2-((methylamino)methyl)pyrrolidin-1-yl)methanone

The title compound (80 mg, 0.20 mmol) produced in step (ix) of Reference Example 8 was dissolved in 1 ml of a 40% methylamine methanol solution, and the mixture was stirred at room temperature for 44 hr. The reaction solution was concentrated under the reduced pressure, and the residue was purified by preparative thin layer chromatography (chloroform:methanol:28% aqueous ammonia=5:1:0.1) to give 36 mg (yield 59%) of the title compound.
¹H-NMR (300 MHz, CDCl₃) δ: 1.72-2.00 (3H, m), 2.10-2.25 (1H, m), 2.53 (3H, s), 2.87 (1H, dd, J=5.4, 12.0 Hz), 3.02 (1H, dd, J=5.4, 12.0 Hz), 3.40-3.56 (2H, m), 4.44 (1H, t, J=6.0 Hz), 7.43 (2H, d, J=8.4 Hz), 7.55 (2H, d, J=8.4 Hz).
MS (FAB) m/z: 297 (M⁺+1).

Reference Example 9

(i) (S)—N-(1-Hydroxybutan-2-yl)-2-nitrobenzenesulfonamide

Triethylamine (0.94 ml, 6.74 mmol) was added to a solution of 400 mg (4.49 mmol) of (S)-2-aminobutan-1-ol in tetrahydrofuran (5 ml), and the mixture was stirred at room temperature for 10 min. 2-Nitrobenzenesulfonyl chloride (995.1 mg, 4.49 mmol) was added to the solution, and the mixture was stirred at room temperature for 15 min. A saturated aqueous sodium hydrogencarbonate solution was added thereto to stop the reaction, and the reaction solution was then extracted with ethyl acetate, was dried over anhydrous sodium sulfate, and was filtered. The filtrate was concentrated under the reduced pressure, and the residue was purified by column chromatography on silica gel (hexane:ethyl acetate=2:1) to give 1.22 g (yield 99%) of the title compound.

(ii) (S)—N-(1-Hydroxybutan-2-yl)-N-(2-hydroxyethyl)-2-nitrobenzenesulfonamide

Sodium hydride (60% in paraffin liquid) (19.2 mg, 0.441 mmol) was added to a solution of 100.7 mg (0.367 mmol) of the title compound produced in step (i) of Reference Example 9 in N,N-dimethylformamide (1.0 ml), and the mixture was stirred at room temperature for 30 min. Tert-butyl(2-iodoethoxy)dimethylsilane (126.2 mg, 0.441 mmol) was added thereto, and the mixture was stirred at room temperature for 5 days. A saturated aqueous sodium hydrogencarbonate solution was added to stop the reaction, and the reaction solution was extracted with ethyl acetate. The extract was dried over anhydrous sodium sulfate and was filtered. The filtrate was concentrated under the reduced pressure, and the concentrate was purified by preparative thin layer chromatography (hexane:ethyl acetate=1:4) to give 154 mg of a crude compound.

To a solution of 154 mg (0.356 mmol) of this crude compound in methanol (3.0 ml) was added 1 ml of 1 N hydrochloric acid. The mixture was stirred at room temperature for 35 min. The aqueous methanol solution was removed under the reduced pressure, and the residue was purified by preparative thin layer chromatography (chloroform:methanol:28% aqueous ammonia=9:2:0.2) to give 97 mg (2 steps, yield 83%) of the title compound.

(iii) (S)-3-Ethyl-4-(2-nitrophenylsulfonyl)morpholine

A 1 M solution of 0.558 ml (0.558 mmol) of (cyanomethylene)tributylphosphorane in toluene was added to a solution of 95 mg (0.298 mmol) of the title compound produced in step (ii) of Reference Example 9 in toluene (3 ml), and the mixture was stirred with heating under reflux for 1 hr 20 min. Thereafter, the reaction solution was cooled to room temperature, and the solvent was removed under the reduced pressure. The residue was purified by column chromatography on silica gel (hexane:ethyl acetate=1:4) to give 89 mg (yield 99%) of the title compound.

(iv) (S)-(4-Bromophenyl)(3-ethylmorpholino)methanone

Potassium carbonate (49.1 mg, 0.355 mmol) was added to a solution of 89 mg (0.296 mmol) of the title compound produced in step (iii) of Reference Example 9 in N,N-dimethylformamide (1.0 ml), and the mixture was stirred at room temperature for 5 min. 4-Bromobenzenethiol (56.0 mg, 0.296 mmol) was added thereto, and the mixture was stirred at room temperature for 5 hr. Thereafter, N,N-dimethylformamide (1.0 ml), 119.0 mg (0.592 mmol) of 4-bromobenzoic acid, 80.0 mg (0.592 mmol) of 1-hydroxybenzotriazole, and 119.0 mg (0.592 mmol) of 1-ethyl-3-(3-dimethylaminopropyl)carbodiimide hydrochloride were successively added thereto, and the mixture was stirred at room temperature for 4.5 hr. A saturated aqueous sodium hydrogencarbonate solution was added thereto to stop the reaction, followed by extraction with ethyl acetate. The extract was dried over anhydrous sodium sulfate and was then filtered. The filtrate was concentrated under the reduced pressure and was then purified by preparative thin layer chromatography (hexane:ethyl acetate=1:4) to give 64 mg (2 steps, yield 72%) of the title compound.

$^1$H-NMR (400 MHz, CD$_3$OD) δ: 1.73-1.82 (1H, m), 1.92-2.01 (1H, m), 3.47-3.54 (2H, m), 3.63-3.68 (1H, m), 3.72-3.86 (5H, m), 7.30-7.37 (2H, m), 7.58-7.65 (2H, m).

MS (FAB$^+$) m/z: 284 (M$^+$+1).

The following compound was synthesized in the same manner as in Reference Example 9, except that 2-aminoethanol and tert-butyl(3-iodopropoxy)dimethylsilane were used respectively instead of (S)-2-aminobutan-1-ol in step (i) of Reference Example 9 and tert-butyl(2-iodoethoxy)dimethylsilane in step (ii) of Reference Example 9. The synthesized compound was used in the Examples.

(4-Bromophenyl)(1,4-oxazepan-4-yl)methanone.

Reference Example 10

(i) (4-Bromophenyl)(3-(hydroxymethyl)morpholino)methanone

The title compound was produced in the same manner as in Reference Example 9, except that 2-aminopropane-1,3-diol was used instead of (S)-2-aminobutan-1-ol in step (i) of Reference Example 9.

(ii) (4-Bromophenyl)(3-(methoxymethyl)morpholino)methanone

Sodium hydroxide (10.2 mg, 0.256 mmol) was added to a solution of 22 mg (0.073 mmol) of the title compound produced in step (i) of Reference Example 10 in dimethyl sulfoxide (1.0 ml), 0.091 ml (1.46 mmol) of methyl iodide was added thereto, and the mixture was heated at 100° C. for 23 hr. A saturated aqueous sodium hydrogencarbonate solution was added thereto, and the mixture was extracted with ethyl acetate. The organic layer was successively washed with water and saturated brine, was dried over anhydrous sodium sulfate, and was then filtered. The filtrate was concentrated under the reduced pressure and was purified by preparative thin layer chromatography (chloroform:methanol=20:1) to give 18 mg (yield 78%) of the title compound.

Reference Example 11

(i) N-(2-Hydroxyethyl)-N-(3-hydroxypropyl)-2-nitrobenzenesulfonamide

The title compound (289 mg) (three steps, yield 43%) was produced in the same manner as in steps (i) and (ii) of Reference Example 9, except that 2-aminoethanol was used instead of (S)-2-aminobutan-1-ol in step (i) of Reference Example 9 and tert-butyl(3-iodopropyl)dimethylsilane was used instead of tert-butyl(2-iodoethoxy)dimethylsilane in step (ii) of Reference Example 9.

(ii) N-(2-Methoxyethyl)-N-(3-methoxypropyl)-2-nitrobenzenesulfonamide

The title compound (70 mg, yield 59%) was produced in the same manner as in step (ii) of Reference Example 10, except that 109 mg (0.358 mmol) of the title compound produced in step (i) of Reference Example 11 was used.

(iii) 4-Bromo-N-(2-methoxyethyl)-N-(3-methoxypropyl)benzamide

The title compound (34 mg, yield 49%) was produced in the same manner as in step (iv) of Reference Example 9, except that 70 mg (0.211 mmol) of the title compound produced in step (ii) of Reference Example 11 was used and 3H-1,2,3-triazolo-[4,5-b]pyridin-3-ol was used instead of 1-hydroxybenzotriazole in step (iv) of Reference Example 9.

Reference Example 12

(i) 4-(1-Hydroxy-2-(2-nitrophenylsulfonamido)ethyl)phenyl 2-nitrobenzenesulfonate A 1 N aqueous solution of sodium hydroxide (79.1 ml, 79.1 mmol) solution was added to a solution of 5 g (26.4 mmol) of 4-(2-amino-1-hydroxyethyl)phenol in dioxane (50 ml), and the mixture was stirred at room temperature for 5 min. 2-Nitrobenzenesulfonyl chloride (14.6 g, 65.9 mmol) was added to this solution, and the mixture was stirred at room temperature for 17 hr. Dioxane as the solvent was removed under the reduced pressure, and the residue was extracted with methylene chloride. The extract was dried over anhydrous sodium sulfate and was then filtered. The filtrate was concentrated under the reduced pressure, and the residue was purified by column chromatography on silica gel (hexane:ethyl acetate=2:1) to give 13.3 g (yield 97%) of the title compound.

(ii) 4-(1-Hydroxy-2-(N-(2-hydroxyethyl)-2-nitrophenylsulfonamido)ethyl)phenyl 2-nitrobenzenesulfonate Sodium hydride (0.31 g, 7.0 mmol) was added to a solution of 3.0 g (5.82 mmol) of the title compound produced in step (i) of Reference Example 12 in N,N-dimethylformamide (19.1 ml), and the mixture was stirred at room temperature for 30 min. Thereafter, 1.65 g (5.82 mmol) of tert-butyl(2-iodoethoxy)dimethylsilane was added thereto, and the mixture was stirred at 100° C. for 21 hr. The reaction was stopped by adding sodium hydrogencarbonate, and the mixture was extracted with ethyl acetate. The organic layer was washed with water and saturated brine in that order, was dried over anhydrous sodium sulfate and was then filtered. The filtrate was concentrated under the reduced pressure. Methanol (48 ml) was added to the concentrate, 11.6 ml (11.6 mmol) of 1 N hydrochloric acid was added thereto, and the mixture was stirred at room temperature for 30 min. Sodium hydrogencarbonate was added to stop the reaction, and methanol as the solvent was removed under the reduced pressure, followed by extraction with ethyl acetate. The organic layer was washed with water and saturated brine in that order, was dried over anhydrous sodium sulfate and was then filtered. The filtrate was concentrated under the reduced pressure, and the residue was purified by column chromatography on silica gel (chloroform:methanol=100:1) to give 2.22 g (yield 68%) of the title compound.

(iii) 4-(4-(2-Nitrobenzenesulfonyl)morpholin-2-yl) phenyl 2-nitrobenzenesulfonate A 1 M toluene solution of 5.87 ml (5.87 mmol) of (cyanomethylene)tributylphosphorane was added to a solution of 2.22 g (3.91 mmol) of the title compound produced in step (ii) of Reference Example 12 in toluene (55.0 ml), and the mixture was stirred with heating under reflux for 1 hr 20 min. The reaction solution was then cooled to room temperature, and the solvent was removed under the reduced pressure. The residue was purified by column chromatography on silica gel (hexane:ethyl acetate=2:1) to give 1.16 g (yield 54%) of the title compound.

(iv) 4-(Morpholin-2-yl)phenol

Potassium carbonate (0.88 g, 6.33 mmol) was added to a solution of 1.16 g (2.11 mmol) of the title compound produced in step (iii) of Reference Example 12 in N,N-dimethylformamide (8.5 ml), and the mixture was stirred at room temperature for 5 min. Next, 1.20 g (6.33 mmol) of 4-bromobenzenethiol was added thereto, and the mixture was stirred at room temperature for 3.5 hr. The reaction was stopped by adding 1 N hydrochloric acid, and the reaction solution was adjusted to pH=3. The aqueous layer was washed with ethyl acetate and was concentrated to dryness under the reduced pressure. Methanol was added to the residue, and the mixture was filtered, The filtrate was concentrated under the reduced pressure, and the residue was purified by column chromatography on silica gel (chloroform:methanol=20:1, chloroform:methanol:28% aqueous ammonia=9:2:0.2) to give 240 mg (yield 63%) of the title compound.

(v) 4-(4-Methylmorpholin-2-yl)phenol

A 36% aqueous formaldehyde solution (20.1 mg, 2.51 mmol), 0.029 ml (0.502 mmol) of acetic acid, and 53.2 mg (0.251 mmol) of triacetoxysodium borohydride were successively added to a solution of 15 mg (0.084 mmol) of the title compound produced in step (iv) of Reference Example 12 in methanol (0.7 ml), and the mixture was stirred at room temperature for 15 min. Thereafter, the reaction solution was purified by preparative thin layer chromatography (chloroform:methanol:28% aqueous ammonia=9:2:0.2) to give 15 mg (yield 93%) of the title compound.

$^1$H-NMR (400 MHz, CD$_3$OD: CDCl$_3$=1:1) δ: 2.15 (1H, dd, J=10.7, 11.7 Hz), 2.30 (1H, dt, J=3.4, 11.7 Hz), 2.79 (1H, d, J=11.7 Hz), 2.86 (1H, d, J=11.9 Hz), 3.82 (1H, dt, J=2.2, 11.7 Hz), 7.02 (1H, dd, J=2.2, 11.7 Hz), 4.46 (1H, dd, J=3.2, 10.4 Hz), 6.80 (2H, ddd, J=2.0, 2.7, 8.5 Hz), 7.20 (2H, ddd, J=2.0, 2.7, 8.8 Hz).

MS (ESI$^+$) m/z: 194 (M$^+$+1).

The following compounds were synthesized in the same manner as in Reference Example 12 and were used in the Examples.

4-(4-Propylmorpholin-2-yl)phenol.

Reference Example 13

4-(4-(2-Methoxyethyl)morpholin-2-yl)phenol

Triethylamine (0.12 ml, 0.835 mmol) was added to a solution of 30.0 mg (0.167 mmol) of the title compound produced in step (iv) of Reference Example 12 in tetrahydrofuran-methylene chloride (1 ml:1 ml), and the mixture was stirred at room temperature for 10 min. Thereafter, 0.023 ml (0.251 mmol) of 1-bromo-2-methoxyethane was added thereto, N,N-dimethylformamide (1 ml) was further added, and the mixture was stirred at room temperature for 5 days. A saturated aqueous sodium hydrogencarbonate solution was added to stop the reaction, and the reaction solution was extracted with ethyl acetate. The extract was dried over anhydrous sodium sulfate and was then filtered. The filtrate was concentrated under the reduced pressure and was purified by preparative thin layer chromatography (chloroform:methanol:28% aqueous ammonia=9:2:0.2) to give 20 mg (yield 50%) of the title compound.

Reference Example 14

(i) 4-Bromo-3'-aminobiphenyl 1,4-Dibromobenzene (311 mg, 1.3 mmol) and 201 mg (1.3 mmol) of 3-aminophenylboronic acid were dissolved in 17 ml of N,N-dimethylformamide and 4.2 ml of water. Tetrakistriphenylphosphine palladium (154 mg, 0.13 mmol) and 211 mg (2.0 mmol) of sodium carbonate were added to the solution, and the mixture was stirred at 80° C. for 3 hr. Ethyl acetate (60 ml) and 8.5 ml of water were added to the reaction solution, and the mixture was filtered through Celite. The organic layer as the filtrate was washed five times with 30 ml of water. The organic layer was dried over anhydrous sodium sulfate and was filtered. The solvent was then removed by distillation. The residue was purified by column chromatography on silica gel (n-hexane:ethyl acetate=5:1) to give 182 mg (yield 57%) of the title compound.

$^1$H-NMR (300 MHz, CDCl$_3$) δ: 3.75 (2H, s), 6.68 (1H, ddd, J=1.2, 2.4, 7.8 Hz), 6.85 (1H, t, J=2.1 Hz), 6.93 (1H, ddd, J=0.9, 1.8, 7.5 Hz), 7.21 (1H, t, J=8.1 Hz), 7.41 (2H, ddd, J=2.1, 2.4, 8.7 Hz), 7.53 (2H, ddd, J=2.1, 2.4, 8.7 Hz).

MS (FAB) m/z: 247 (M$^+$+1).

The following compounds were synthesized in the same manner as in step (i) of Reference Example 14 and were used in the Examples.

4-Bromo-3'-methylthiobiphenyl,
3-(4-bromophenyl)-5-methoxypyridine,
5-(4-bromophenyl)-2-methoxypyridine,
4-(4-bromophenyl)isoquinoline,
5-bromo-2-(3-aminophenyl)pyridine,
3-(4-bromophenyl)-2-fluoropyridine,
3-(4-bromophenyl)-5-fluoropyridine,
3-(4-bromophenyl)-6-fluoropyridine,
3-(4-bromophenyl)-5-cyanopyridine,
5-(4-bromophenyl)pyridine-2-amine,
4-(4-bromophenyl)-1-methyl-1H-pyrazole,
6-(4-bromophenyl)imidazo[2,1-b]thiazole,
1-(4-bromo-3,5-difluorophenyl)-1H-tetrazole,
2-bromoimidazo[2,1-b]thiazole-6-carboxamide,
2-bromo-N,N-dimethylimidazo[2,1-b]thiazole-6-carboxamide,
6-bromo-2-(4-(trifluoromethoxy)phenyl)imidazo[1,2-a]pyridine,
and 3-(4-bromophenyl)-2-methoxypyridine.

(ii) 4-Bromo-3'-N,N-dimethylaminobiphenyl

Acetic acid (125 μl, 2.2 mmol), 0.32 ml (4.3 mmol) of a 37% aqueous formaldehyde solution, and 941 mg (4.4 mmol) of sodium triacetoxyboron were added to a solution of 105 mg (0.42 mmol) of the title compound produced in step (i) of Reference Example 14 in methanol (3 ml), and the mixture was stirred at room temperature for 24 hr. The solvent was removed by distillation, and the residue was purified by column chromatography on silica gel (n-hexane:ethyl acetate=10:1) to give 71 mg (yield 61%) of the title compound.

$^1$H-NMR (300 MHz, CDCl$_3$) δ: 3.00 (6H, s), 6.73-6.76 (1H, m), 6.85-6.91 (2H, m), 7.30 (1H, t, J=7.8 Hz), 7.45 (2H, d, J=8.7 Hz), 7.54 (2H, d, J=8.7 Hz).

(iii) 4-Bromo-3'-N-acetylaminobiphenyl

Triethylamine (88 μl, 0.62 mmol) and 23 μl (0.31 mmol) of acetyl chloride were added under ice cooling to a solution of 51 mg (0.21 mmol) of the title compound produced in step (i) of Reference Example 14 in tetrahydrofuran (2 ml), and the mixture was stirred for 1.5 hr. The reaction solution was diluted with 20 ml of ethyl acetate and was washed with a saturated aqueous ammonium chloride solution. The aqueous layer was extracted twice with 2 ml of ethyl acetate, and the organic layers were combined and were washed with 25% brine. The organic layer was dried over anhydrous sodium sulfate and was filtered, and the filtrate was concentrated under the reduced pressure, and the residue was purified by preparative thin layer chromatography (n-hexane:ethyl acetate=1:2) to give 91 mg (yield 96%) of the title compound.

$^1$H-NMR (300 MHz, CDCl$_3$) δ: 2.20 (3H, s), 7.27-7.48 (3H, m), 7.43 (2H, d, J=8.7 Hz), 7.54 (2H, d, J=8.4 Hz), 7.75 (1H, s).

MS (FAB) m/z: 290 (M$^+$+1).

Reference Example 15

(i) 4-(N-Pyridin-3-yl)aminophenyl Bromide

A solution of 3-aminopyridine (200 mg, 2.1 mmol) and 304 mg (3.2 mmol) of sodium tert-butoxide were added to 502 mg (2.1 mmol) of 1,4-dibromobenzene, 127 mg (0.21 mmol) of 4,5-bis(diphenylphosphino)-9,9-dimethylxantene, and 97 mg (0.11 mmol) of tris(dibenzylideneacetone)dipalladium in toluene (15 ml), and the mixture was stirred at 100° C. for 3 hr. The reaction solution was diluted with 20 ml of ethyl acetate, and the insolubles were filtered through a chromato-disk. The filtrate was concentrated under the reduced pressure, and the residue was purified by column chromatography on silica gel (n-hexane:ethyl acetate=2:1) to give 312 mg (yield 50%) of a mixture of the title compound with a debromination product thereof (about 3.5:1).

$^1$H-NMR (300 MHz, CDCl$_3$) δ: 5.96 (1H, d, J=28.8 Hz), 6.92-6.97 (2H, m), 7.19 (1H, t, J=5.1 Hz), 7.35-7.41 (3H, m), 8.19 (1H, dd, J=0.9, 4.8 Hz), 8.37 (1H, m).

MS (API) m/z: 249 (M$^+$+1).

(ii) 4-(N-Methyl)(N-pyridin-3-yl)aminophenyl Bromide

Sodium hydride (51 mg, 1.3 mmol) and 73 μl (1.2 mmol) of methyl iodide were added to a solution of 193 mg (0.78 mmol) of the title compound produced in step (i) of Reference Example 15 in N,N-dimethylformamide (4 ml), and the mixture was stirred at room temperature for 1 hr. The reaction solution was diluted with 20 ml of ethyl acetate and was washed with a saturated aqueous ammonium chloride solution. The aqueous layer was extracted twice with 2 ml of ethyl acetate, and the organic layers were combined and were washed with 25% brine. The organic layer was dried over anhydrous sodium sulfate and was filtered. The filtrate was concentrated under the reduced pressure, and the residue was purified by column chromatography on silica gel (n-hexane: ethyl acetate=3:1) to give 163 mg (yield 80%) of the title compound.

$^1$H-NMR (300 MHz, CDCl$_3$) δ: 3.31 (3H, s), 6.89-6.95 (2H, m), 7.13-7.31 (2H, m), 7.37-7.42 (2H, m), 8.20 (1H, d, J=4.2 Hz), 8.34 (1H, d, J=2.7 Hz).

Example 1

(i) 2,3,4-Tri-o-trimethylsilyl Lincomycin

Trimethylsilyl chloride (90 ml, 71 mmol) and 65 ml (60 mmol) of hexamethyldisilazane were added under ice cooling to a solution of 50 g (122 mmol) of lincomycin in pyridine (200 ml), and the mixture was stirred at room temperature for 2 hr. The solvent was removed by distillation, and the residue was diluted with hexane and was washed twice with water. The solvent was removed by distillation. An 80% aqueous acetic acid solution (22.5 ml) was added to a solution of the residue in methanol (150 ml), and the mixture was stirred at room temperature for 16 hr. A saturated aqueous sodium hydrogencarbonate solution (30 ml) was added to the reaction solution, and the solvent was removed by distillation. The residue was diluted with hexane and was washed twice with water. The solvent was removed by distillation to give 69.5 g (yield 91%) of the title compound.

$^1$H-NMR (300 MHz, CDCl$_3$) δ: 0.25-0.45 (27H, m).

(ii) 7-(6-Aminobenzo[d]thiazol-2-ylthio)-7-deoxy-7-epilincomycin

Compound 1

Triphenylphosphine (197 mg, 0.75 mmol), 0.12 ml (0.75 mmol) of diethyl azodicarboxylate, and 137 mg (0.75 mmol) of 6-aminobenzo[d]thiazole-2-thiol were successively added under ice cooling to a solution of 312 mg (0.5 mmol) of the title compound produced in step (i) of Example 1 in tetrahydrofuran (6 ml), and the mixture was stirred at room temperature for 16 hr. 1 N hydrochloric acid (1 ml, 1 mmol) was added thereto, and the solvent was removed by distillation, and the residue was diluted with water and was then washed with diethyl ether. Sodium hydrogencarbonate (150 mg) was added to the aqueous layer, and the mixture was extracted with ethyl acetate. The organic layer was dried over anhydrous sodium sulfate. The dried organic layer was filtered, and the solvent was removed by distillation. The residue was purified by preparative thin layer chromatography (chloroform:methanol:28% aqueous ammonia=20:1:0.1) to give 185 mg (yield 65%) of the title compound.

Compound 114 was produced by using diethyl azodicarboxylate (1.0 mmol) and using 4-nitrophenyldisulfide (0.75 mmol), tri-n-butylphosphine (1.5 mmol), and 2 N hydrochloric acid-methanol instead of 6-aminobenzo[d]thiazole-2-thiol, triphenylphosphine, and 1 N hydrochloric acid in step (ii) of Example 1.

Compound 115 was produced by using diethyl azodicarboxylate (1.0 mmol) and using 2-nitrophenyldisulfide (0.75 mmol), tri-n-butylphosphine (1.5 mmol), and 2 N hydrochloric acid-methanol instead of 6-aminobenzo[d]thiazole-2-thiol, triphenylphosphine, and 1 N hydrochloric acid in step (ii) of Example 1.

Compound 116 was produced by using diethyl azodicarboxylate (1.0 mmol) and using 3-nitrophenyldisulfide (0.75 mmol), tri-n-butylphosphine (1.5 mmol), and 2 N hydrochloric acid-methanol instead of 6-aminobenzo[d]thiazole-2-thiol, triphenylphosphine, and 1 N hydrochloric acid in step (ii) of Example 1.

Compounds produced in the same manner as in step (ii) of Example 1 (compounds 1 to 119, 416, and 428) and $^1$H-NMR data and MS data for these compounds are shown in Tables 2 to 7 and Table 21b.

Example 2

(i) 7-o-Methylsulfonyl-2,3,4-tri-o-trimethylsilyl Lincomycin

Triethylamine (2.45 ml, 16.1 mmol) and 0.99 ml (12.8 mmol) of methanesulfonyl chloride were added under ice cooling to a solution of 4.0 g (6.42 mmol) of the title compound produced in step (i) of Example 1 in chloroform (20 ml). The mixture was stirred at room temperature for 3 hr. The reaction solution was diluted with 150 ml of chloroform, 150 ml of a 10% aqueous sodium hydrogencarbonate solution was added thereto for washing, and the organic layer was dried over anhydrous sodium sulfate. The dried organic layer was filtered, and the filtrate was concentrated. The residue was purified by column chromatography on silica gel (hexane:ethyl acetate=100:0 to 75:25) to give 4.2 g (yield 93%) of the title compound.

$^1$H-NMR (400 MHz, CDCl$_3$) δ: 0.13-0.17 (27H, m), 2.10 (3H, s), 2.39 (3H, s), 3.08 (3H, s).

(ii) 7-Deoxy-7-epi-7-(5-(thiazol-4-yl)-1,3,4-thiadiazol-2-ylthio)-2,3,4-tri-o-trimethylsilyl Lincomycin Potassium carbonate (88.7 mg, 0.642 mmol) and 86.2 mg (0.428 mmol) of 5-(thiazol-4-yl)-1,3,4-thiadiazole-2-thiol were added to a solution of 150 g (0.214 mmol) of the title compound produced in step (i) of Example 2 in N,N-dimethylformamide (1.5 ml), and the mixture was stirred at 80° C. for 8 hr. The reaction solution was diluted with 15 ml of ethyl acetate and was washed with 15 ml of 10% brine, and the organic layer was dried over anhydrous sodium sulfate. The dried organic layer was filtered, and the filtrate was concentrated. The residue was purified by column chromatography on silica gel (hexane:ethyl acetate=100:0 to 75:25) to give 29 mg (yield 17%) of the title compound.

$^1$H-NMR (400 MHz, CDCl$_3$) δ: 0.11-0.18 (27H, m), 1.56 (1H, d, J=6.8 Hz), 5.20 (1H, d, J=5.3 Hz), 8.18 (1H, m), 8.86 (1H, m).

(iii) 7-Deoxy-7-epi-7-(5-(thiazol-4-yl)-1,3,4-thiadiazol-2-ylthio)lincomycin Compound 120

1 N hydrochloric acid (0.179 ml) was added to a solution of 29 mg (0.0359 mmol) of the title compound produced in step (ii) of Example 2 in methanol (1.5 ml), and the mixture was stirred at room temperature for 5 min. The reaction solution was diluted with 15 ml of ethyl acetate. The diluted solution was washed with 15 ml of a 10% aqueous sodium hydrogencarbonate solution, and the organic layer was dried over anhydrous sodium sulfate. The dried organic layer was filtered, and the filtrate was concentrated. The residue was purified by preparative thin layer chromatography (chloroform:methanol:28% aqueous ammonia=9:1:0.1) to give 9 mg (yield 43%) of the title compound.

Compounds produced in the same manner as in steps (ii) and (iii) of Example 2 (compounds 120 to 134) and $^1$H-NMR data and MS data for these compounds are shown in Tables 7 and 8.

Example 3

(i) 7-Acetylthio-7-deoxy-7-epi-2,3,4-tri-o-trimethylsilyl Lincomycin

Potassium thioacetate (163 mg, 1.43 mmol) was added to a solution of 200 mg (0.285 mmol) of the title compound produced in step (i) of Example 2 in N,N-dimethylformamide (0.65 ml), and the mixture was stirred at 60° C. for 4 hr. The reaction solution was diluted with 50 ml of ethyl acetate and was washed with 50 ml of a 10% aqueous sodium hydrogencarbonate solution. The organic layer was dried over anhydrous sodium sulfate. The dried organic layer was filtered, and the filtrate was concentrated. The residue was purified by column chromatography on silica gel (hexane:ethyl acetate=100:0 to 75:25) to give 170 mg (yield 88%) of the title compound.

$^1$H-NMR (400 MHz, CDCl$_3$) δ: 0.12-0.17 (27H, m), 2.31 (3H, s), 2.40 (3H, s), 5.18 (1H, d, J=5.6 Hz).

MS (API) m/z: 422 (M$^+$+1).

(ii) 7-Acetylthio-7-deoxy-7-epilincomycin

2 N hydrochloric acid (38.9 ml) was added to a solution of 10.6 g (15.6 mmol) of the title compound produced in step (i) of Example 3 in methanol (50 ml), and the mixture was stirred at room temperature for 10 min. A 10% aqueous sodium hydrogencarbonate solution (30 ml) was added to the reaction solution, and methanol was removed by distillation under the reduced pressure. Ethyl acetate (250 ml) and 250 ml of 10% brine were added to the residue, followed by extraction. The organic layer was dried over anhydrous sodium sulfate. The dried organic layer was filtered, and the filtrate was concentrated. The residue was purified by column chromatography on silica gel (ethyl acetate:methanol=100:0 to 95:5) to give 7.05 g (yield 97%) of the title compound.

$^1$H-NMR (400 MHz, CDCl$_3$) δ: 2.38 (3H, s), 2.41 (3H, s), 5.31 (1H, d, J=5.6 Hz).

(iii) 7-Deoxy-7-epi-7-mercaptolincomycin

Sodium methoxide (2.46 g, 45.5 mmol) was added to a solution of 7.05 g (15.2 mmol) of the title compound produced in step (ii) of Example 3 in methanol (50 ml), and the mixture was stirred at room temperature for 20 min. The reaction solution was neutralized by adding a saturated aqueous ammonium chloride solution, and methanol was removed by distillation under the reduced pressure. A 10% aqueous sodium hydrogencarbonate solution (300 ml) was added to the concentrate, and the mixture was extracted with 300 ml of ethyl acetate. The organic layer was dried over anhydrous sodium sulfate, and the dried organic layer was filtered. The filtrate was concentrated, and the residue was purified by column chromatography on silica gel (chloroform:methanol: 28% aqueous ammonia=95:5:0.1) to give 6.06 g (yield 94%) of the title compound.

$^1$H-NMR (400 MHz, CDCl$_3$) δ: 2.23 (3H, s), 2.42 (3H, s), 5.34 (1H, d, J=5.6 Hz).

MS (EI) m/z: 422 (M$^+$).

(iv) 7-(5-(4,5-Dimethoxy-2-nitrophenyl)-1,3,4-thiadiazol-2-ylthio)-7-deoxy-7-epilincomycin Compound 135

A 1 M sodium hexamethyldisilazide tetrahydrofuran solution (0.332 ml) and 35 mg (0.105 mmol) of 2-(4,5-dimethoxy-2-nitrophenyl)-5-methylsulfonyl-1,3,4-thiadiazole were added to a solution of 74 mg (0.166 mmol) of the title compound produced in step (iii) of Example 3 in N,N-dimethylformamide (0.55 ml), and the mixture was stirred at room temperature for 15 min. The reaction solution was diluted with 15 ml of ethyl acetate, and the diluted solution was neutralized with a saturated aqueous ammonium chloride solution. Thereafter, the neutralized solution was washed with 15 ml of a 10% aqueous sodium hydrogencarbonate solution. The organic layer was dried over anhydrous sodium sulfate. The dried organic layer was filtered, and the filtrate was concentrated. The residue was purified by preparative thin layer chromatography (chloroform:methanol:28% aqueous ammonia=9:1:0.1) to give 75 mg (yield 67%) of the title compound.

Compound 136 was produced in the same manner as in step (iv) of Example 3, except that 2-chloro-(5-(2-methoxycarbonylphenyl))-1,3,4-thiadiazole was used instead of 2-(4,5-dimethoxy-2-nitrophenyl)-5-methylsulfonyl-1,3,4-thiadiazole.

(v) 7-Deoxy-7-epi-7-(4-(N-methylacetamido)phenylthio)lincomycin

Compound 169

N-(4-Bromophenyl)-N-methylacetamide (75.6 mg, 0.33 mmol) and 0.058 ml (0.33 mmol) of diisopropylethylamine were added to a solution of 70 mg (0.17 mmol) of the title compound produced in step (iii) of Example 3, 9.7 mg (0.017 mmol) of 4,5-bis(diphenylphosphino)-9,9-dimethylsantene, and 7.6 mg (0.0084 mmol) of tris(dibenzylideneacetone)dipalladium in dioxane (1 ml), and the mixture was heated under reflux for 6 hr. The reaction was stopped by adding a saturated aqueous sodium hydrogencarbonate solution (15 ml), and the insolubles were then filtered through Celite. The residue was extracted with ethyl acetate (30 ml). The organic layer was washed with water and saturated brine and was dried over anhydrous sodium sulfate, and the filtrate was concentrated. The residue was purified by preparative thin layer chromatography (chloroform:methanol:28% aqueous ammonia=9:2:0.2) to give 87 mg (yield 92%) of the title compound.

(vi) 7-Deoxy-7-epi-7-(4-(4-methylmorpholin-2-yl) phenylthio)lincomycin 2,6-Lutidine (0.011 ml, 0.093 mmol) was added to a solution of 15 mg (0.078 mmol) of the title compound produced in step (v) of Reference Example 12 in methylene chloride (1 ml), and the mixture was stirred at 0° C. for 10 min. Trifluoromethanesulfonic anhydride (0.019 ml, 0.116 mmol) was added thereto, and the mixture was stirred for 15 min. The reaction was stopped by adding a saturated aqueous sodium hydrogencarbonate solution, and the reaction solution was extracted with methylene chloride. The organic layer was washed with water and saturated brine and was then dried over anhydrous sodium sulfate. The dried organic layer was filtered, and the filtrate was concentrated under the reduced pressure, and the residue was dried. 4,5-Bis(diphenylphosphino)-9,9-dimethylsantene (4.5 mg, 0.0078 mmol), 3.6 mg (0.0039 mmol) of tris(dibenzylideneacetone)dipalladium, 39.4 mg (0.0931 mmol) of the title compound produced in step (iii) of Example 3, and 0.027 ml (0.155 mmol) of diisopropylethylamine were successively added to a solution of this crude product in dioxane (0.7 ml), and the mixture was heated under reflux for 5 hr. The reaction was stopped by adding a saturated aqueous sodium hydrogencarbonate solution (15 ml), and the insolubles were filtered through Celite, followed by extraction with ethyl acetate (30 ml). The organic layer was washed with water and saturated brine and was then dried over anhydrous sodium sulfate. The filtrate was concentrated, and the residue was purified by preparative thin layer chromatography (chloroform:methanol:28% aqueous ammonia=9:2:0.2) to give 32 mg (yield 69%) of the title compound.

Compounds produced in the same manner as in steps (iv), (v), and (vi) of Example 3 (compounds 135 to 179 and 429 to 489) and $^1$H-NMR data and MS data for these compounds are shown in tables which will be described later (Tables 8 to 10 and 21c to 21f).

Example 4

(i) 7-(5-Aminobenzo[d]thiazol-2-ylthio)-7-deoxy-7-epilincomycin

Compound 180

Stannic chloride dihydrate (140 mg, 0.5 mmol) and 4.6 mg (0.13 mmol) of sodium borohydride were successively added to a solution of 75 mg (0.125 mmol) of compound 4 in ethanol (3 ml). The mixture was stirred at room temperature for 3 hr. The solvent was removed by distillation, and the residue was diluted with ethyl acetate, and the diluted solution was washed with water. The solvent was removed by distillation, and the residue was purified by preparative thin layer chromatography (chloroform:methanol:28% aqueous ammonia=20:1:0.1) to give 32 mg (yield 45%) of the title compound.

(ii) 7-(5-Aminopyridin-2-ylthio)-7-deoxy-7-epilincomycin

Compound 186

Stannic chloride dihydrate (170 mg, 0.6 mmol) and 330 mg of tetra-n-butylammonium bromide were added to 108 mg (0.2 mmol) of compound 85, and the mixture was stirred at 80° C. for 2 hr. The reaction solution was diluted with ethyl acetate and was washed with water. The solvent was removed by distillation, and the residue was purified by preparative thin layer chromatography (chloroform:methanol:28% aqueous ammonia=20:1:0.1) to give 56.2 mg (yield 55%) of the title compound.

Compounds (180 to 189) produced in the same manner as in Example 4 and $^1$H-NMR data and MS data for these compounds are shown in Table 10.

Example 5

(i) 7-(4-Aminophenylthio)-7-deoxy-7-epi-2,3,4-tri-o-trimethylsilyl Lincomycin Compound 187 was provided, and hydroxyl groups at the 2-, 3-, and 4-positions of the compound were trimethylsilylated by the method described in U.S. Pat. No. 3,418,414 to give 2.8 g (yield 97%) of the title compound.

$^1$H-NMR (400 MHz, CDCl$_3$) δ: 0.11-0.17 (27H, m), 2.20 (3H, s), 2.42 (3H, s), 5.27 (1H, d, J=5.6 Hz), 6.55-6.57 (2H, m), 7.13-7.16 (2H, m).

(ii) 7-Deoxy-7-epi-7-(4-(propionamido)phenylthio) lincomycin

Compound 204

Triethylamine (0.046 ml, 0.33 mmol) was added to a solution of 80 mg (0.11 mmol) of the title compound produced in step (i) of Example 5 in N,N-dimethylformamide (1 ml). Propionyl chloride (0.014 ml, 0.17 mmol) was then added thereto, and the mixture was stirred at room temperature for 3 hr. Thereafter, methanol (1 ml)-1 N hydrochloric acid (2 ml) was added thereto, and the mixture was stirred for 30 min. The reaction was stopped by adding a saturated aqueous sodium hydrogencarbonate solution, and the mixture was extracted with ethyl acetate. The extract was dried over anhydrous sodium sulfate. The dried solution was filtered, and the filtrate was concentrated. The residue was purified by preparative thin layer chromatography (chloroform:methanol:28% aqueous ammonia=9:2:0.2) to give 47 mg (yield 75%) of the title compound.

(iii) 7-(6-Aminobenzo[d]thiazol-2-ylthio)-7-deoxy-7-epi-2,3,4-tri-o-trimethylsilyl Lincomycin The title compound (1.7 g, yield 87%) was produced in the same manner as in step (ii) of Example 1, except that the compound produced in step (i) of Example 1 was used and 1 N hydrochloric acid was not used.

(iv) 7-(6-(Acetamido)benzo[d]thiazol-2-ylthio)-7-deoxy-7-epilincomycin

Compound 197

4-Dimethylaminopyridine (3.1 mg, 0.025 mmol) was added to a solution of 100 mg (0.13 mmol) of the title compound produced in step (iii) of Example 5 in pyridine (1 ml). Acetic anhydride (0.018 ml, 0.19 mmol) was then added thereto, and the mixture was stirred at room temperature for 5 hr. The reaction was stopped by adding a saturated aqueous sodium hydrogencarbonate solution, and the reaction solution was extracted with ethyl acetate. The extract was dried over anhydrous sodium sulfate and was filtered. The filtrate was then concentrated, methanol (1 ml)-2 N hydrochloric acid (2 ml) was added to the residue, and the mixture was stirred for 30 min. The reaction was stopped by adding a saturated aqueous sodium hydrogencarbonate solution. The reaction solution was then extracted with ethyl acetate and was dried over anhydrous sodium sulfate. The filtrate was concentrated, and the residue was purified by preparative thin layer chromatography (chloroform:methanol:28% aqueous ammonia=9:2:0.2) to give 74 mg (yield 95%) of the title compound.

(v) 7-Deoxy-7-epi-7-(6-((4R)-1-methyl-4-propylpyrrolidine-2-carboxamido)benzo[d]thiazol-2-ylthio) lincomycin

Compound 196

1-Hydroxybenzotriazole (25.5 mg, 0.019 mmol) and 36.2 mg (0.19 mmol) of 1-ethyl-3-(3-dimethylaminopropyl)carbodiimide hydrochloride were added to a solution of 100 mg (0.13 mmol) of the title compound produced in step (iii) of Example 5 in N,N-dimethylformamide (1 ml). Thereafter, 32.4 mg (0.19 mmol) of (2S,4R)-1-methyl-4-propylpyrrolidine-2-carboxylic acid was added thereto, and the mixture was stirred at room temperature for 3.5 hr. Methanol (4 ml)-2 N hydrochloric acid (1 ml) was added thereto, and the mixture was stirred for 30 min. The reaction was stopped by adding a saturated aqueous sodium hydrogencarbonate solution, and the reaction solution was extracted with ethyl acetate. The extract was dried over anhydrous sodium sulfate and was filtered. The filtrate was then concentrated, and the residue was purified by preparative thin layer chromatography (chloroform:methanol:28% aqueous ammonia=9:2:0.2) to give 41.9 mg (2 steps, yield 46%) of the title compound.

Compound 200 was produced in the same manner as in step (v) of Example 5, except that dicyclohexylcarbodiimide was used instead of 1-ethyl-3-(3-dimethylaminopropyl)carbodiimide hydrochloride, and 2-(dimethylamino)acetic acid was further used.

(vi) 7-(6-((S)-2-Amino-3-methylbutanamido)benzo[d]thiazol-2-ylthio)-7-deoxy-7-epilincomycin Compound 198

1-Hydroxybenzotriazole (25.5 mg, 0.019 mmol) and 39.0 mg (0.19 mmol) of dicyclohexylcarbodiimide were added to a solution of 100 mg (0.13 mmol) of the title compound produced in step (iii) of Example 5 in N,N-dimethylformamide (1 ml). (S)-2-Tert-butoxycarbonylamino-3-methylbutane carboxylic acid (41.1 mg, 0.19 mmol) was then added thereto, and the mixture was stirred at room temperature for 3.5 hr. The reaction was stopped by adding a saturated aqueous sodium hydrogencarbonate solution, and the reaction solution was extracted with ethyl acetate. The extract was dried over anhydrous sodium sulfate and was filtered. The filtrate was then concentrated, and the residue was dried. Trifluoroacetic acid (1 ml) was added thereto, and the mixture was stirred for 30 min. The reaction was stopped by adding a saturated aqueous sodium hydrogencarbonate solution, and the reaction solution was extracted with ethyl acetate. The extract was dried over anhydrous sodium sulfate and was filtered. The filtrate was then concentrated, and the residue was purified by preparative thin layer chromatography (chloroform:methanol:28% aqueous ammonia=9:2:0.2) to give 30.3 mg (3 steps, yield 36%) of the title compound.

(vii) 7-Deoxy-7-epi-7-(6-(2-methylaminoacetamido)benzo[d]thiazol-2-ylthio)lincomycin Compound 201

The procedure of step (iv) of Example 5 was repeated for condensation, except that 100 mg (0.13 mmol) of the title compound in step (iii) of Example 5 and 35.8 mg (0.19 mmol) of 2-(N-methyl-N-tert-butoxycarbonylamino)acetic acid were used. Methanol (4 ml)-2 N hydrochloric acid (1 ml) was added thereto, and the mixture was stirred for 30 min. The reaction was stopped by adding a saturated aqueous sodium hydrogencarbonate solution, and the reaction solution was then extracted with ethyl acetate. The extract was dried over anhydrous sodium sulfate and was filtered. The filtrate was then concentrated, and the residue was dried. Trifluoroacetic acid (1 ml) was added thereto, and the mixture was stirred for 30 min. The reaction was stopped by adding a saturated aqueous sodium hydrogencarbonate solution, and the reaction solution was then extracted with ethyl acetate. The extract was dried over anhydrous sodium sulfate and was filtered. The filtrate was then concentrated, and the residue was purified by preparative thin layer chromatography (chloroform:methanol:28% aqueous ammonia=9:2:0.2) to give 55.0 mg (3 steps, yield 68%) of the title compound.

Compounds (190 to 210) produced in the same manner as in Example 5 and $^1$H-NMR data and MS data for these compounds are shown in Tables 10 and 11.

Example 6

7-Deoxy-7-epi-7-(4-(methylsulfonamido)phenylthio)lincomycin

Compound 211

Triethylamine (0.027 ml, 0.20 mmol) was added to a solution of 83.8 mg (0.16 mmol) of compound 187 in N,N-dimethylformamide (1 ml). Methanesulfonyl chloride (0.02 ml, 0.2 mmol) was then added thereto, and the mixture was stirred at room temperature for 30 min. The reaction was stopped by adding a saturated aqueous sodium hydrogencarbonate solution. The reaction solution was then extracted with ethyl acetate. The extract was dried over anhydrous sodium sulfate and was filtered. The filtrate was then concentrated, and the residue was purified by preparative thin layer chromatography (chloroform:methanol:28% aqueous ammonia=9:2:0.2) to give 28.0 mg (yield 29%) of the title compound.

$^1$H-NMR data and MS data on compound (211) produced in Example 6 are shown in Table 11.

Example 7

(i) 7-(6-(Tert-butoxycarbonylamino)benzo[d]thiazol-2-ylthio)-7-deoxy-7-epi-2,3,4-tri-o-trimethylsilyl Lincomycin Triethylamine (3.2 ml, 22.7 mmol) was added to a solution of 12.0 g (15.1 mmol) of the title compound produced in step (iii) of Example 5 in N,N-dimethylformamide (120 ml). Tert-butyl dicarbonate (8.3 ml, 36.3 mmol) was then added thereto, and the mixture was stirred at room temperature for 18 hr. The reaction was stopped by adding a saturated aqueous sodium hydrogencarbonate solution, and the reaction solution was extracted with ethyl acetate. The extract was dried over anhydrous sodium sulfate and was filtered. The filtrate was concentrated, and the residue was purified by column chromatography on silica gel (hexane:ethyl acetate=2:1) to give 12.1 g (yield 91%) of the title compound.

$^1$H-NMR (400 MHz, CDCl$_3$) δ: 1.54 (9H, s), 2.01 (3H, s), 2.31 (3H, s), 5.34 (1H, d, J=5.6 Hz), 6.65 (1H, s), 7.16 (1H, dd, J=8.8, 2.2 Hz), 7.79 (1H, d, J=8.8 Hz), 8.16 (1H, brs), 8.46 (1H, brd, J=9.3 Hz).

(ii) 7-(6-(Tert-butoxycarbonylamino)benzo[d]thiazol-2-ylthio)-7-deoxy-7-epilincomycin 1 N hydrochloric acid (30 ml) was added to a solution of 12.1 g (13.7 mmol) of the title compound produced in step (i) of Example 7 in methanol (300 ml), and the mixture was stirred at room temperature for 30 min. The reaction was stopped by adding a saturated aqueous sodium hydrogencarbonate solution, and methanol was removed by distillation under the reduced pressure. The reaction solution was extracted with ethyl acetate. The extract was dried over anhydrous sodium sulfate and was filtered. The filtrate was concentrated, and the residue was purified by column chromatography on silica gel (chloroform:methanol:28% aqueous ammonia=9:1:0.1) to give 4.7 g (yield 53%) of the title compound.

(iii) 7-(6-(Tert-butoxycarbonylamino)benzo[d]thiazol-2-ylthio)-7-deoxy-7-epi-3,4-o-isopropylidene Lincomycin p-Toluenesulfonic acid monohydrate (1.2 g, 7.1 mmol) was added to a solution of 4.4 g (6.5 mmol) of the title compound produced in step (ii) of Example 7 in N,N-dimethylformamide (17 ml). Acetone dimethyl acetal (3.2 ml, 26.1 mmol) was then added thereto, and the mixture was stirred at 40° C. for 24 hr. The reaction was stopped by adding a saturated aqueous sodium hydrogencarbonate solution, and the reaction solution was extracted with ethyl acetate. The extract was dried over anhydrous sodium sulfate and was filtered. The filtrate was concentrated, and the residue was purified by column chromatography on silica gel (chloroform:methanol=50:1) to give 4.61 g (yield 99%) of the title compound.

$^1$H-NMR (400 MHz, CDCl$_3$) δ: 1.53 (9H, s), 1.62 (3H, s), 1.69 (3H, s), 1.90 (3H, s), 2.35 (3H, s), 5.18 (1H, brd, J=4.8 Hz), 6.67 (1H, brs), 7.11 (1H, dd, J=8.8, 2.2 Hz), 7.73 (1H, d, J=8.8 Hz), 7.77 (1H, brd, J=10.0 Hz), 8.13 (1H, brs).

(iv) 7-(6-(N-Allyl-N-tert-butoxycarbonyl)aminobenzo[d]thiazol-2-ylthio)-7-deoxy-7-epi-3,4-isopropylidene Lincomycin Sodium hydride (9.2 mg, 0.21 mmol) (55% in oil) was added to a solution of 100 mg (0.14 mmol) of the title compound produced in step (iii) of Example 7 in N,N-dimethylformamide (1 ml), and the mixture was stirred at room temperature for 30 min. Thereafter, 0.015 ml (0.17 mmol) of allyl iodide was added thereto, and the mixture was stirred at room temperature for 5 hr. The reaction was stopped by adding a saturated aqueous sodium hydrogencarbonate solution, and the reaction solution was then extracted with ethyl acetate. The extract was dried over anhydrous sodium sulfate and was filtered. The filtrate was then concentrated, and the residue was purified by column chromatography on silica gel (chloroform:methanol=20:1) to give 31.2 mg (yield 30%) of the title compound.

$^1$H-NMR (400 MHz, CDCl$_3$) δ: 1.30 (6H, s), 1.44 (9H, s), 1.91 (3H, s), 2.36 (3H, s), 5.13-5.17 (2H, m), 5.20 (1H, d, J=4.8 Hz), 5.87-5.97 (1H, m), 7.28 (1H, brs), 7.62 (1H, s), 7.78 (1H, d, J=8.8 Hz), 7.80-7.84 (1H, m).

MS (FAB$^+$): 751 (M$^+$+1).

(v) 7-(6-Allylaminobenzo[d]thiazol-2-ylthio)-7-deoxy-7-epilincomycin

Compound 212

Trifluoroacetic acid was added to 31.2 mg (0.042 mmol) of the title compound produced in step (iv) of Example 7, and the mixture was stirred at room temperature for 30 min. The reaction was stopped by adding a saturated aqueous sodium hydrogencarbonate solution, and the reaction solution was then extracted with ethyl acetate. The extract was dried over anhydrous sodium sulfate and was filtered. The filtrate was then concentrated, and the residue was purified by preparative thin layer chromatography (chloroform:methanol:28% aqueous ammonia=9:1:0.1) to give 20.0 mg (yield 79%) of the title compound.

$^1$H-NMR data and MS data on compound (212) produced in Example 7 are shown in Table 11.

Example 8

7-(6-Carbamoylbenzo[d]thiazol-2-ylthio)-7-deoxy-7-epilincomycin

Compound 213

Compound 6 (100 mg, 0.13 mmol) was dissolved in a 7 N ammonia methanol solution (3 ml), and the solution was stirred in a sealed tube at 80° C. for 16 hr. The solvent was removed by distillation, and the residue was purified by preparative thin layer chromatography (chloroform:methanol:28% aqueous ammonia=20:1:0.1) to give 63 mg (yield 81%) of the title compound.

Compounds (213 to 233, 490, and 491) produced in the same manner as in Example 8 and $^1$H-NMR data and MS data on these compounds are shown in Tables 11, 12, and 21f.

Example 9

7-Deoxy-7-epi-7-(4-hydroxymethylphenylthio)lincomycin

Compound 234

A solution of 200 mg (0.36 mmol) of compound 113 in tetrahydrofuran (2 ml) was cooled to −78° C., 1.1 ml of a 1 M lithium aluminum hydridetetrahydrofuran solution was added thereto, and the mixture was stirred for 20 min. The temperature of the reaction system was raised to 0° C. over a period of 3 hr. A saturated potassium sodium tartrate solution was added to stop the reaction, and the reaction solution was extracted with ethyl acetate. The extract was dried over anhydrous sodium sulfate and was filtered. The filtrate was concentrated, and the residue was purified by preparative thin layer chromatography (chloroform:methanol:28% aqueous ammonia=9:1:0.1) to give 114 mg (yield 60%) of the title compound.

$^1$H-NMR data and MS data on compound (234) produced in Example 9 are shown in Table 12.

Example 10

(i)
7-(4-Carboxyphenylthio)-7-deoxy-7-epilincomycin

A 1 N aqueous sodium hydroxide solution (5 ml) was added to a solution of 1.84 g (3.31 mmol) of compound 113 in methanol (20 ml), and the mixture was stirred at room temperature for 19 hr. The reaction solution was acidified by the addition of 1 N hydrochloric acid, and the weakly acidified solution was concentrated to dryness. The residue was purified by Diaion High Porous Polymer 20 to give 1.61 g (yield 90%) of the title compound.

$^1$H-NMR (400 MHz, CD$_3$OD) δ: 1.83 (3H, s), 2.97 (3H, s), 3.99 (1H, dq, J=2.4, 6.8 Hz), 5.26 (1H, d, J=5.6 Hz), 7.42 (2H, d, J=8.5 Hz), 7.93 (2H, d, J=8.6 Hz).

(ii) 7-Deoxy-7-epi-7-(4-(morpholinocarbonyl)phenylthio)lincomycin

Compound 246

1-Hydroxybenzotriazole (74.7 mg, 0.55 mmol) and 106.0 mg (0.55 mmol) of 1-ethyl-3-(3-dimethylaminopropyl)carbodiimide hydrochloride were added to a solution of 200 mg (0.37 mmol) of the title compound in step (i) of Example 10 in N,N-dimethylformamide (2 ml), 0.048 ml (0.55 mmol) of morpholine was added thereto, and the mixture was stirred at room temperature for 4 hr. The reaction was stopped by adding a saturated aqueous sodium hydrogencarbonate solution, and the reaction solution was extracted with ethyl acetate. The extract was dried over anhydrous sodium sulfate and was filtered. The filtrate was then concentrated, and the residue was purified by preparative thin layer chromatography (chloroform:methanol:28% aqueous ammonia=9:2:0.2) to give 142.0 mg (yield 63%) of the title compound.

Compound 251 was produced in the same manner as in step (ii) of Example 10, except that 4-oxopiperidine monohydrochloride monohydrate was used instead of morpholine, and triethylamine was used as a base.

(iii) 7-(4-(N-Tert-butoxycarbonylpiperazino)phenylthio)-7-deoxy-7-epilincomycin 1-Hydroxybenzotriazole (52.6 mg, 0.39 mmol) and 74.7 mg (0.39 mmol) of 1-ethyl-3-(3-dimethylaminopropyl)carbodiimide hydrochloride were added to a solution of 140.9 mg (0.26 mmol) of the title compound produced in step (i) of Example 10 in N,N-dimethylformamide (1.4 ml), 72.5 mg (0.39 mmol) of N-tert-butoxycarbonyl piperazine was added thereto, and the mixture was stirred at room temperature for 8 hr. The reaction was stopped by adding a saturated aqueous sodium hydrogencarbonate solution, and the reaction solution was then extracted with ethyl acetate. The extract was dried over anhydrous sodium sulfate and was filtered. Thereafter, the filtrate was concentrated, and the residue was purified by preparative thin layer chromatography (chloroform:methanol:28% aqueous ammonia=9:2:0.2) to give 115 mg (yield 62%) of the title compound.

$^1$H-NMR (400 MHz, CD$_3$OD) δ: 1.46 (9H, s), 1.91 (3H, s), 2.42 (3H, s), 3.46 (6H, br), 3.68 (2H, br), 3.97 (1H, dq, J=2.7, 6.8 Hz), 5.27 (1H, d, J=5.6 Hz), 7.40 (2H, d, J=8.5 Hz), 7.47 (2H, d, J=8.3 Hz).

(iv) 7-Deoxy-7-epi-7-(4-(piperazinocarbonyl)phenylthio)lincomycin

Compound 252

Trifluoroacetic acid which had previously been ice cooled was added to 115 mg (0.16 mmol) of the title compound produced in step (iii) of Example 10, and the mixture was stirred at room temperature for 1 hr. Trifluoroacetic acid was removed by distillation under the reduced pressure. The residue was purified by preparative thin layer chromatography (chloroform:methanol:28% aqueous ammonia=9:2:0.2) to give 29 mg (yield 29%) of the title compound.

Compounds (235 to 262, 492 to 495) produced in the same manner as in Example 10 and $^1$H-NMR data and MS data on these compounds are shown in Tables 12, 13, and 21g.

Example 11

(i) 7-Deoxy-7-epi-7-(5-(2-nitrophenyl)thiazol-2-ylthio)lincomycin

Compound 263

2-Nitrophenylboronic acid (29.2 mg, 0.17 mmol), 12.3 mg (0.01 mmol) of tetrakistriphenylphosphine palladium, and 31.1 mg (0.22 mmol) of potassium carbonate were added to a solution of 56.8 mg (0.1 mmol) of 7-(5-bromothiazol-2-ylthio)-7-deoxy-7-epilincomycin, produced in the same manner as in step (v) of Example 3, in isopropanol/water (1 ml, 40:1), and the mixture was stirred at 80° C. for 24 hr. The reaction solution was filtered through Celite, and the filtrate was then concentrated. The residue was purified by preparative thin layer chromatography (chloroform:methanol:28% aqueous ammonia=10:1:0.1) to give 33.0 mg (yield 53%) of the title compound.

(ii) 7-Deoxy-7-epi-7-(5-(pyridin-2-yl)azol-2-ylthio)lincomycin

Compound 264

Tri-n-butyl(2-pyridyl)tin (44.0 ml, 0.12 mmol) and 12.5 mg (0.01 mmol) of tetrakistriphenylphosphine palladium were added to a solution of 57.8 mg (0.1 mmol) of 7-(5-bromothiazol-2-ylthio)-7-deoxy-7-epilincomycin, produced in the same manner as in step (v) of Example 3, in toluene (1 ml), and the mixture was stirred at 100° C. for 8 hr. The solvent was removed by distillation, and the residue was purified by preparative thin layer chromatography (chloroform:acetone:28% aqueous ammonia=10:4:0.1) to give 12.8 mg (yield 22%) of the title compound.

Compounds (263 to 266 and 496 to 508) produced in the same manner as in Example 11 and $^1$H-NMR data and MS data on these compounds are shown in Tables 13, 14, 21g, and 21h.

Example 12

7-Deoxy-7-(5-(5-dimethylamino-4-fluoro-2-nitrophenyl)-1,3,4-thiadiazol-2-ylthio)-7-epilincomycin

Compound 273

To a solution of 25 mg (0.035 mmol) of hydrochloride as compound 53 was added 1 ml of a 2 M dimethylamine methanol solution. The mixture was sealed and was stirred at 50° C. for 4 hr. The reaction solution was concentrated under the reduced pressure, and the residue was purified by preparative thin layer chromatography (chloroform:methanol:28% aqueous ammonia=9:2:0.2) to give 20 mg (yield 83%) of the title compound.

Compounds (267 to 274) produced in the same manner as in Example 12 and $^1$H-NMR data and MS data on these compounds are shown in Table 14.

Example 13

7-Deoxy-7-epi-7-(5-(4-fluoro-5-methoxy-2-nitrophenyl)-1,3,4-thiadiazol-2-ylthio)lincomycin

Compound 276

Sodium methoxide (3.7 mg, 0.0678 mmol) was added to a solution of 15 mg (0.0204 mmol) of hydrochloride as compound 53 in methanol (0.4 ml), and the mixture was stirred at room temperature for 15 min. The reaction solution was diluted with 15 ml of ethyl acetate. The diluted solution was neutralized by adding a saturated aqueous ammonium chloride solution, and the mixture was then washed with 15 ml of a 10% aqueous sodium hydrogencarbonate solution. The organic layer was dried over anhydrous sodium sulfate and was filtered. The filtrate was concentrated, and the residue was purified by preparative thin layer chromatography (chloroform:methanol:28% aqueous ammonia=9:1:0.1) to give 10 mg (yield 69%) of the title compound.

Compounds (275 and 276) produced in the same manner as in Example 13 and $^1$H-NMR data and MS data on these compounds are shown in Table 14.

Example 14

(i) 7-(Azetidin-3-ylthio)-7-deoxy-7-epilincomycin

Ice cooled trifluoroacetic acid (3 ml) was added to 280 mg (0.352 mmol) of 7-(1-(tert-butoxycarbonyl)azetidin-3-ylthio)-7-deoxy-7-epi-2,3,4-tri-o-trimethylsilyl lincomycin produced in the same manner as in step (ii) of Example 2 except that tert-butyl 3-mercaptoazetidine-1-carboxylate was used, and the mixture was stirred under ice cooling for 20 min. The reaction solution was concentrated under the reduced pressure, and the residue was purified by preparative thin layer chromatography (chloroform:methanol:28% aqueous ammonia=9:2:0.2) to give 99 mg (yield 73%) of the title compound.

$^1$H-NMR (400 MHz, CDCl$_3$) δ: 1.31 (3H, d, J=6.9 Hz), 2.18 (3H, s), 2.61 (3H, s), 5.26 (1H, d, J=5.6 Hz).

MS (EI) m/z: 447 (M$^+$).

(ii) 7-(Azetidin-3-ylthio)-7-deoxy-7-epi-2,3,4-tri-o-trimethylsilyl Lincomycin

Trimethylsilyl chloride (4.59 ml, 35.9 mmol) and 7.5 ml (35.9 mmol) of hexamethyldisilazane were added under ice cooling to a solution of 3.43 g (7.18 mmol) of the title compound produced in step (i) of Example 14 in pyridine (20 ml), and the mixture was stirred at room temperature for 1 hr. The reaction solution was transferred to 200 ml of a 10% aqueous hydrogencarbonate solution, and the mixture was extracted with 200 ml of ethyl acetate. The organic layer was dried over anhydrous sodium sulfate and was filtered. The filtrate was concentrated, and the residue was dissolved in 30 ml of methanol. Acetic acid (6 N, 3.59 ml) was added to the solution, and the mixture was stirred at room temperature for 3.5 hr. The reaction solution was transferred to 200 ml of a 10% aqueous hydrogencarbonate solution, and the mixture was extracted with 200 ml of ethyl acetate. The organic layer was then dried over anhydrous sodium sulfate and was filtered. The filtrate was then concentrated. The residue was purified by column chromatography on silica gel (amino silica gel, hexane:ethyl acetate=1:1) to give 3.0 g (yield 60%) of the title compound.

$^1$H-NMR (400 MHz, CDCl$_3$) δ: 0.12-0.19 (27H, m), 2.18 (3H, s), 2.43 (3H, s), 5.23 (1H, d, J=5.6 Hz).

MS (API) m/z: 694 (M$^+$+1).

(iii) 7-Deoxy-7-(1-(dimethylaminocarbamoyl)azetidin-3-ylthio)-7-epilincomycin

Compound 277

Triethylamine (0.0202 ml, 0.144 mmol), 17.6 mg (0.144 mmol) of dimethylaminopyridine, and 0.0132 ml (0.144 mmol) of dimethylcarbamic chloride were added to a solution of 100 mg (0.144 mmol) of the title compound produced in step (ii) of Example 14 in chloroform (0.7 ml), and the mixture was stirred at room temperature for 1 hr. The reaction solution was diluted with 20 ml of ethyl acetate, and 20 ml of a 10% aqueous sodium hydrogencarbonate solution was added to the diluted solution to wash the organic layer and was dried over anhydrous sodium sulfate. The dried solution was filtered, and the filtrate was concentrated, and the residue was purified by column chromatography on silica gel (hexane:ethyl acetate=50:50 to 0:100) to give 95 mg of a protected product. Next, the protected product was dissolved in 1 ml of methanol, 1 ml of 1 N hydrochloric acid was added to the solution, and the mixture was stirred at room temperature for 10 min. The reaction solution was diluted with 15 ml of ethyl acetate and was washed with 15 ml of a 10% aqueous sodium hydrogencarbonate solution. The organic layer was then dried over anhydrous sodium sulfate and was filtered. The filtrate was then concentrated under the reduced pressure to give 55 mg (yield 68%) of the title compound.

(iv) 7-Deoxy-7-epi-7-(1-(2-nitrophenyl)azetidin-3-ylthio)lincomycin

Compound 290

Triethylamine (0.0202 ml, 0.144 mmol) and 0.0052 ml (0.144 mmol) of 1-fluoro-2-nitrobenzene were added to a solution of 100 mg (0.144 mmol) of the title compound produced in step (ii) of Example 14 in N,N-dimethylformamide (0.5 ml), and the mixture was stirred at room temperature for 1 hr. The reaction solution was diluted with 20 ml of ethyl acetate, 20 ml of a 10% aqueous sodium hydrogencarbonate solution was added thereto to wash the organic layer, followed by drying over anhydrous sodium sulfate. The dried solution was filtered, and the filtrate was concentrated under the reduced pressure. The residue was purified by column chromatography on silica gel (hexane:ethyl acetate=100:0 to 85:15) to give 67 mg of a protective product. The product was then dissolved in 1 ml of methanol, 1 ml of 1 N hydrochloric acid was added thereto, and the mixture was stirred at room temperature for 10 min. The reaction solution was diluted with 15 ml of ethyl acetate, and the organic layer was washed with 15 ml of a 10% aqueous sodium hydrogencarbonate solution, was then dried over anhydrous sodium sulfate, and was filtered. The filtrate was concentrated under the reduced pressure to give 49 mg (yield 57%) of the title compound.

(v) 7-(1-(4-Aminophenyl)azetidin-3-ylthio)-7-deoxy-7-epilincomycin

Compound 295

Platinum oxide (77.2 mg, 0.318 mmol) was added to a solution of 127 mg (0.212 mmol) of compound 291 in methanol (4 ml), and the mixture was stirred under hydrogen atmosphere for one hr. The reaction solution was filtered through Celite, and the filtrate was concentrated under the reduced pressure. The residue was purified by column chromatography on silica gel (ethyl acetate:methanol=100:0 to 95:5) to give 77 mg (yield 64%) of the title compound.

(vi) 7-Deoxy-7-epi-7-(1-(2-morpholino-2-oxoethyl)azetidin-3-ylthio)lincomycin

Compound 289

Triethylamine (0.0202 ml, 0.144 mmol) and 17.7 mg (0.108 mmol) of 2-chloro-1-morpholinoethanone were added to a solution of 50 mg (0.072 mmol) of the title compound in step (ii) of Example 14 in chloroform (0.3 ml), and the mixture was stirred at room temperature for 12 hr. The reaction solution was diluted with 20 ml of ethyl acetate, and 20 ml of a 10% aqueous sodium hydrogencarbonate solution was added thereto to wash the organic layer which was then dried over anhydrous sodium sulfate. The dried solution was filtered, and the filtrate was concentrated under the reduced pressure. The residue was purified by column chromatography on silica gel (hexane:ethyl acetate=50:50 to 0:100) to give 34 mg of a protective product. Next, the product was dissolved in 1 ml of methanol, 1 ml of 1 N hydrochloric acid was added to the solution, and the mixture was stirred at room temperature for 10 min. The reaction solution was diluted with 15 ml of ethyl acetate and was washed with 15 ml of a 10% aqueous sodium hydrogencarbonate solution. The organic layer was dried over anhydrous sodium sulfate and was filtered. The filtrate was concentrated under the reduced pressure to give 9 mg (yield 21%) of the title compound.

(vii) 7-(1-(2-Cyanoethyl)azetidin-3-ylthio)-7-deoxy-7-epilincomycin

Compound 285

Acrylonitrile (0.0051 ml, 0.077 mmol) was added to a solution of 60 mg (0.077 mmol) of the title compound produced in step (ii) of Example 14 in ethanol (0.5 ml), and the mixture was stirred at room temperature for 3 hr. The reaction solution was concentrated under the reduced pressure. The residue was purified by chromatography on silica gel (hexane:ethyl acetate=50:50 to 0:100) to give 53 mg of a protective product. Next, the product was dissolved in 1 ml of methanol, 1 ml of 1 N hydrochloric acid was added to the solution, and the mixture was stirred at room temperature for 10 min. The reaction solution was diluted with 15 ml of ethyl acetate and was washed with 15 ml of a 10% aqueous sodium hydrogencarbonate solution. The organic layer was dried over anhydrous sodium sulfate and was filtered. The filtrate was concentrated under the reduced pressure to give 40 mg (yield 98%) of the title compound.

(viii) 7-Deoxy-7-epi-7-(1-(piperidinocarbonyl)azetidin-3-ylthio)lincomycin

Compound 293

Pyridine (0.0205 ml, 0.254 mmol), 0.0125 ml (0.127 mmol) of piperidine, 12.6 mg (0.0423 mmol) of triphosgene, and 80 mg (0.115 mmol) of the title compound produced in step (ii) of Example 14 were added under ice cooling to dichloromethane (0.5 ml), and the mixture was stirred at room temperature for 1 hr. The reaction solution was diluted with 20 ml of ethyl acetate, and 20 ml of a 10% aqueous sodium hydrogencarbonate solution was added to wash the organic layer which was then dried over anhydrous sodium sulfate. The dried solution was filtered, and the filtrate was concentrated under the reduced pressure. The residue was purified by column chromatography on silica gel (hexane:ethyl acetate=100:0 to 50:50) to give 22 mg of a protective product. Next, the product was dissolved in 1 ml of methanol, 1 ml of 1 N hydrochloric acid was added thereto, and the mixture was stirred at room temperature for 10 min. The reaction solution was diluted with 15 ml of ethyl acetate, and the diluted solution was washed with 15 ml of a 10% aqueous sodium hydrogencarbonate solution. The organic layer was dried over anhydrous sodium sulfate and was then filtered. The filtrate was concentrated under the reduced pressure to give 16 mg (yield 23%) of the title compound.

Compounds (277 to 295) produced in the same manner as in steps (iii) to (viii) of Example 14 and $^1$H-NMR data and MS data on these compounds are shown in Tables 14 and 15.

Example 15

(i) Benzyl (S)-1-N-tert-butoxycarbonyl-5-oxopyrrolidine-2-carboxylate

The title compound (200 g, two steps, yield 94%) was produced from (S)-5-oxopyrrolidine-2-carboxylic acid in the same manner as in the method described in Tetrahedron Lett., 43, (2002), 3499.

(ii) Benzyl (2S,4R)-4-allyl-1-N-tert-butoxycarbonylpyrrolidine-2-carboxylate The title compound (95.1 g, three steps, yield 51%) was produced using the title e compound in step (i) of Example 15 in the same manner as in the method described in Tetrahedron Lett., 35, (1994), 2053 and J. Am. Chem. Soc., 110, (1998), 3894.

(iii) 1'-Tert-butoxycarbonyl-1'-demethyl-2,3,4-tri-o-trimethylsilyl Lincomycin Pd—C (5 g) was added under argon atmosphere to a solution of 30.2 g (87.4 mmol) of the title compound produced in step (ii) of Example 15 in methanol (350 ml), and the mixture was stirred under hydrogen atmosphere at room temperature for 7.5 hr. The unnecessary matter was removed by filtration through Celite, and the filtrate was concentrated under the reduced pressure. 1-Hydroxybenzotriazole (17.7 g, 131.1 mmol), 27.1 g (131.1 mmol) of dicyclohexylcarbodiimide, and 33.2 g (131.1 mmol) of methyl 1-thio-α-lincosamide were successively added to a solution of the residue in pyridine (207 ml), and the mixture was stirred at room temperature for 16 hr. Water was added, and the precipitate was filtered. The filtrate was concentrated to dryness. The title compound (18.2 g, four steps) was produced in the same manner as in step (i) of Example 1, except that the half amount of the residue was used.

$^1$H-NMR (400 MHz, CDCl$_3$) δ: 0.12 (9H, s), 0.12 (9H, s), 0.15 (9H, s), 1.34 (9H, s), 1.92 (3H, s), 5.05 (1H, brd, J=5.4 Hz).

(iv) 7-(6-Aminobenzo[d]thiazol-2-ylthio)-1'-demethyl-7-deoxy-7-epilincomycin

Compound 297

7-(6-Aminobenzo[d]thiazol-2-ylthio)-1'-tert-butoxycarbonyl-1'-demethyl-7-deoxy-7-epilincomycin was produced in the same manner as in step (ii) of Example 1, except that 200 mg (0.28 mmol) of the title compound in step (iii) of Example 15 and 79.7 mg (0.44 mmol) of 6-aminobenzo[d]thiazole-2-thiol were used. 4 N Ethyl acetate hydrochloride (2.5 ml) was added to a solution of this compound in methanol (2 ml), and the mixture was stirred at room temperature for 1.5 hr. The reaction solution was diluted with methanol, and the solvent was removed by distillation under the reduced pressure. The residue was purified by preparative thin layer chromatography (chloroform:methanol:28% aqueous ammonia=9:2:0.2) to give 96.4 g (three steps, yield 58%) of the title compound.

Compounds (296 to 311) produced in the same manner as in Example 15 and $^1$H-NMR data and MS data on these compounds are shown in Tables 15 and 16.

Example 16

(i) 1'-Tert-butoxycarbonyl-1'-demethyl-7-o-methylsulfonyl-2,3,4-tri-o-trimethylsilyl Lincomycin The title compound was produced as a crude product in the same manner as in step (i) of Example 2, except that 5 g (7.1 mmol) of the title compound in step (iii) of Example 15, chloroform (22 ml), 2.5 ml (17.6 mmol) of triethylamine, and 1.1 ml (14.1 mmol) of methanesulfonyl chloride were used.

(ii) 1'-Tert-butoxycarbonyl-1'-demethyl-7-deoxy-7-epi-7-(4-methoxylcarbonylphenylthio)lincomycin The title compound (1.25 g, three steps, yield 28%) was produced in the same manner as in steps (ii) and (iii) of Example 2, except that the title compound in step (i) of Example 16 and 2.4 g (14.1 mmol) of 4-methoxyphenylthiol were used and the temperature was 100° C.

$^1$H-NMR (400 MHz, CD$_3$OD) δ: 1.48 (9H, s), 1.79 (3H, s), 3.88 (3H, s), 5.23 (1H, d, J=5.3 Hz), 7.41 (2H, d, J=8.5 Hz), 7.91 (2H, d, J=8.5 Hz).

(iii) 1'-Tert-butoxycarbonyl-7-(4-carboxyphenylthio)-1'-demethyl-7-deoxy-7-epilincomycin The title compound (761 mg, yield 95%) was produced in the same manner as in step (i) of Example 10, except that 761 mg (1.2 mmol) of the title compound in step (ii) of Example 16 was used.
$^1$H-NMR (400 MHz, CD$_3$OD) δ: 1.48 (9H, s), 1.81 (3H, s), 5.24 (1H, d, J=5.6 Hz), 7.41 (2H, d, J=8.6 Hz), 7.92 (2H, d, J=8.3 Hz).

(iv) 1'-Tert-butoxycarbonyl-1'-demethyl-7-deoxy-7-epi-7-(4-morpholinocarbonylphenylthio)lincomycin The title compound (215 mg, yield 97%) was produced in the same manner as in step (ii) of Example 10, except that 200 mg (0.32 mmol) of the title compound produced in step (iii) of Example 16 was used.

(v) 1'-Demethyl-7-deoxy-7-epi-7-(4-morpholinocarbonylphenylthio)lincomycin

Compound 312

Ice cooled trifluoroacetic acid was added to 215 mg (0.31 mmol) of the title compound produced in step (iv) of Example 16. The mixture was stirred at room temperature for 40 min. Trifluoroacetic acid was removed by distillation under the reduced pressure, and the residue was purified by preparative thin layer chromatography (chloroform:methanol:28% aqueous ammonia=9:2:0.2) to give 104 mg (yield 57%) of the title compound.
Compounds (312 to 315) produced in the same manner as in Example 16 and $^1$H-NMR data and MS data on these compounds are shown in Table 16.

Example 17

(i) 7-Acetylthio-1'-N-tert-butoxycarbonyl-1'-demethyl-7-deoxy-7-epi-2,3,4-tri-o-trimethylsilyl Lincomycin The title compound (218 mg, yield 40%) was produced in the same manner as in step (i) of Example 3, except that 555 mg (0.705 mmol) of the title compound produced in step (i) of Example 16 was used.
$^1$H-NMR (300 MHz, CDCl$_3$) δ: 0.13-0.16 (27H, m), 1.51 (9H, s), 1.99 (3H, s), 2.29 (3H, s), 4.02 (1H, dq, J=2.4, 6.9 Hz), 5.16 (1H, d, J=5.4 Hz).
MS (API) m/z: 767 (M$^+$+1).

(ii) 7-Acetylthio-1'-N-tert-butoxycarbonyl-1'-demethyl-7-deoxy-7-epilincomycin

The title compound (137 mg, yield 88%) was produced in the same manner as in step (ii) of Example 3, except that 218 mg (0.284 mmol) of the title compound produced in step (i) of Example 17 was used.
$^1$H-NMR (300 MHz, CD$_3$OD) δ: 1.47 (9H, s), 2.01 (3H, s), 2.32 (3H, s), 3.96 (1H, dq, J=2.4, 6.9 Hz), 5.21 (1H, d, J=5.7 Hz).
MS (API) m/z: 551 (M$^+$+1).

(iii) 1'-N-Tert-butoxycarbonyl-1'-demethyl-7-deoxy-7-epi-7-mercaptolincomycin

The title compound (120 mg, yield 95%) was produced in the same manner as in step (iii) of Example 3, except that 137 mg (0.249 mmol) of the title compound produced in step (ii) of Example 17 was used.

$^1$H-NMR (300 MHz, CD$_3$OD) δ: 1.47 (9H, s), 2.15 (3H, s), 3.40-3.52 (1H, m), 5.25 (1H, d, J=5.7 Hz).
MS (FAB$^+$) m/z: 509 (M$^+$+1).

(iv) 1'-N-Tert-butoxycarbonyl-1'-demethyl-7-deoxy-7-epi-7-(4-(pyridin-3-yl)phenylthio)lincomycin The title compound (126 mg, yield 80%) was produced in the same manner as in step (v) of Example 3, except that 120 mg (0.236 mmol) of the title compound produced in step (iii) of Example 17 was used.
$^1$H-NMR (300 MHz, CD$_3$OD) δ: 1.48 (9H, s), 1.94 (3H, s), 3.86-3.94 (1H, m), 5.27 (1H, d, J=5.7 Hz), 7.50 (1H, d, J=7.2 Hz), 7.52 (2H, d, J=8.1 Hz), 7.63 (2H, d, J=8.1 Hz), 8.09 (1H, ddd, J=1.5, 2.1, 7.8 Hz), 8.66 (1H, dd, J=1.5, 4.8 Hz), 8.80 (1H, d, J=1.8 Hz).
MS (FAB$^+$) m/z: 662 (M$^+$+1).

(v) 1'-Demethyl-7-deoxy-7-epi-7-(4-(pyridin-3-yl)phenylthio)lincomycin

Compound 316

The title compound (99.1 mg, yield 93%) was produced in the same manner as in step (v) of Example 16, except that 126 mg (0.190 mmol) of the title compound in step (iv) of Example 17 was used.
$^1$H-NMR data and MS data on the compound (316) produced in Example 17 are shown in Table 16.

Example 18

(i) 1'-Tert-butoxycarbonyl-1'-demethyl-7-deoxy-7-epi-7-(5-(2-nitro phenyl)-1,3,4-thiadiazol-2-ylthio)lincomycin The title compound (235.3 mg, two steps, yield 58%) was produced in the same manner as in step (ii) of Example 1, except that 400 mg (0.56 mmol) of the title compound produced in step (iii) of Example 15 and 209.2 mg (0.87 mmol) of 5-(2-nitrophenyl)-1,3,4-thiadiazole-2-thiol were used.

(ii) 1'-Demethyl-7-deoxy-7-epi-7-(5-(2-nitrophenyl)-1,3,4-thiadiazol-2-ylthio)lincomycin Compound 298

The title compound (62.5 mg, yield 31%) was produced in the same manner as in step (v) of Example 16, except that 235.3 mg (0.33 mmol) of the title compound produced in step (i) of Example 18 was used.

(iii) 7-(5-(2-Aminophenyl)-1,3,4-thiadiazol-2-ylthio)-1'-demethyl-7-deoxy-7-epilincomycin Compound 317

The title compound (10.8 mg, yield 21%) was produced in the same manner as in step (i) of Example 4, except that 62.5 mg (0.088 mmol) of the title compound produced in step (ii) of Example 18 was used.
$^1$H-NMR data and MS data on the compound (317) produced in Example 18 are shown in Table 16.

Example 19

(i) 7-(5-Aminopyridin-2-ylthio)-1'-N-tert-butoxycarbonyl-1'-demethyl-7-deoxy-7-epilincomycin The title compound (285 mg, yield 45%) was produced in the same manner as in step (ii) of Example 4, except that 667 mg (1.06 mmol) of 1'-N-tert-butoxycarbonyl-7-deoxy-7-epi-7-(5-nitropyridin-2-ylthio)lincomycin, which had been produced from the title compound in step (iii) of Example 15 and 2-mercapto-5-nitropyridine in the same manner as in step (ii) of Example 1 except that toluene was used instead of tetrahydrofuran, was used.

$^1$H-NMR (300 MHz, CD$_3$OD) δ: 1.49 (9H, s), 1.99 (3H, d, J=20.1 Hz), 5.29 (1H, d, J=5.1 Hz), 7.05 (1H, ddd, J=2.7, 3.0, 8.1 Hz), 7.28 (1H, t, J=8.1 Hz), 8.04 (1H, dd, J=2.4, 9.3 Hz).

MS (EI) m/z: 600 (M$^+$).

(ii) 7-(5-Aminopyridin-2-ylthio)-1'-N-tert-butoxycarbonyl-1'-demethyl-7-deoxy-7-epi-2,3,4-tri-o-trimethylsilyl Lincomycin The title compound (296 mg, yield 76%) was produced in the same manner as in step (i) of Example 5, except that 285 mg (0.474 mmol) of the title compound produced in step (i) of Example 19 was used.

$^1$H-NMR (300 MHz, CDCl$_3$) δ: 0.13-0.19 (27H, m), 1.45 (9H, d, J=23.1 Hz), 1.95 (3H, s), 5.19 (1H, d, J=5.7 Hz), 6.86 (1H, dd, J=3.0, 8.1 Hz), 7.04-7.08 (1H, m), 7.95-7.99 (1H, m).

MS (FAB$^+$) m/z: 817 (M$^+$+1).

(iii) 7-(5-Acetamidopyridin-2-ylthio)-1'-N-tert-butoxycarbonyl-1'-demethyl-7-deoxy-7-epi-2,3,4-tri-o-trimethylsilyl Lincomycin The title compound (332 mg, yield 100%) was produced in the same manner as in step (ii) of Example 5, except that 296 mg (0.362 mmol) of the title compound produced in step (ii) of Example 19 was used and acetyl chloride was used instead of propionyl chloride.

$^1$H-NMR (300 MHz, CDCl$_3$) δ: 0.12-0.18 (27H, m), 1.46 (9H, d, J=25.2 Hz), 1.80 (3H, d, J=17.4 Hz), 2.18 (3H, s), 5.16 (1H, d, J=5.4 Hz), 7.81-7.95 (1H, m), 7.95 (1H, br), 8.39 (1H, d, J=2.1 Hz).

MS (API) m/z: 859 (M$^+$+1).

(iv) 7-(5-Acetamidopyridin-2-ylthio)-1'-N-tert-butoxycarbonyl-1'-demethyl-7-deoxy-7-epilincomycin The title compound (177 mg, yield 76%) was produced in the same manner as in step (ii) of Example 3, except that 332 mg (0.387 mmol) of the title compound produced in step (iii) of Example 19 was used.

$^1$H-NMR (300 MHz, CD$_3$OD) δ: 1.37 (9H, d, J=7.2 Hz), 2.08 (3H, s), 5.17 (1H, d, J=4.8 Hz), 7.26 (1H, dd, J=9.0, 11.7 Hz), 7.83 (1H, d, J=8.4 Hz), 8.63 (1H, d, J=15.9 Hz).

MS (API) m/z: 643 (M$^+$+1).

(v) 7-(5-Acetamidopyridin-2-ylthio)-1'-demethyl-7-deoxy-7-epilincomycin

Compound 318

The title compound (113 mg, yield 100%) was produced in the same manner as in step (v) of Example 16, except that 128 mg (0.198 mmol) of the title compound produced in step (iv) of Example 19 was used.

Compounds (318 and 319) produced in the same manner as in Example 19 and $^1$H-NMR data and MS data on these compounds are shown in Table 16.

Example 20

1'-Demethyl-7-deoxy-7-epi-7-(5-(4-fluoro-5-methoxy-2-nitrophenyl)-1,3,4-thiadiazol-2-ylthio)lincomycin

Compound 320

The title compound (14 mg, yield 36%) was produced in the same manner as in Example 13, except that 40 mg (0.0583 mmol) of a hydrochloride of compound 307 was used.

$^1$H-NMR data and MS data on compound (320) produced in Example 20 are shown in Table 16.

Example 21

(i) 1'-Demethyl-7-deoxy-7-epi-1'-isopropyl-7-(5-(2-nitrophenyl)-1,3,4-thiadiazol-2-ylthio)lincomycin

Compound 321

Acetone (40.0 ml, 0.5 mmol), 21.7 mg (0.1 mmol) of sodium triacetoxyboron, and a catalytic amount of acetic acid were added to a solution of 30.5 mg (0.05 mmol) of compound 298 in 1,2-dichloroethane (1 ml), and the mixture was stirred at room temperature for 24 hr. The solvent was removed by distillation, and the residue was purified by preparative thin layer chromatography (chloroform:methanol:28% aqueous ammonia=10:1:0.1) to give 20.1 mg (yield 61%) of the title compound.

(ii) 7-((4-Amino-5-ethoxycarbonyl)pyrimidin-2-ylthio)-1'-demethyl-7-deoxy-7-epi-1'-ethyllincomycin

Compound 331

Iodoethane (24.0 ml, 0.3 mmol) and 42.0 ml (0.3 mmol) of triethylamine were added to a solution of 116.0 mg (0.2 mmol) of compound 310 in acetonitrile (1 ml), and the mixture was stirred at room temperature for 24 hr. The solvent was removed by distillation, and the residue was purified by preparative thin layer chromatography (chloroform:methanol:28% aqueous ammonia=10:1:0.1) to give 43.5 mg (yield 36%) of the title compound.

Compounds (321 to 333) produced in the same manner as in Example 21 and $^1$H-NMR data and MS data on these compounds are shown in Tables 16 and 17.

Example 22

7-((4-Amino-5-ethoxycarbonyl)pyrimidin-2-ylthio)-1'-demethyl-7-deoxy-7-epi-1'-(2-hydroxyacetyl)lincomycin

Compound 337

Hydroxyacetic acid (32.0 mg, 0.42 mmol), 86.3 mg (0.42 mmol) of dicyclohexylcarbodiimide, and 56.0 mg (0.42 mmol) of 1-hydroxybenzotriazole were added to a solution of 155.1 mg (0.27 mmol) of compound 310 in N,N-dimethylformamide (2 ml), and the mixture was stirred at room temperature for 24 hr. The solvent was removed by distillation, and the residue was purified by preparative thin layer chromatography (chloroform:methanol:28% aqueous ammonia=10:1:0.1) to give 70.4 mg (yield 41%) of the title compound.

Compounds (334 to 338) produced in the same manner as in Example 22 and $^1$H-NMR data and MS data on these compounds are shown in Table 17.

Example 23

(i) Benzyl(2S,4R)-4-((E)-but-2-enyl)-1-N-tert-butoxycarbonylpyrrolidine-2-carboxylate The title compound (5.08 g, yield 58%) was produced in the same manner as in step (ii) of Example 15, except that 7.5 g (23.5 mmol) of the title compound produced in step (i) of Example 15 and 2.42 ml (23.5 mmol) of (E)-1-bromo-2-butene were used.

$^1$H-NMR (400 MHz, CDCl$_3$) δ: 1.40-1.44 (9H, m), 1.61-1.67 (3H, m), 1.94-2.28 (5H, m), 4.45-4.52 (1H, m), 5.15-5.24 (2H, m), 5.27-5.38 (1H, m), 5.40-5.56 (1H, m), 7.32-7.40 (5H, m).

MS (FAB$^+$) m/z: 374 (M$^+$+1).

(ii) (2S,4R)-4-((E)-But-2-enyl)-1-N-(tert-butoxycarbonyl)piperidine-2-carboxylic acid A 1 N aqueous sodium hydroxide solution (25 ml) was added to a solution of 2.45 g (6.82 mmol) of the title compound in step (i) of Example 23 in methanol (25 ml), and the mixture was stirred at room temperature for 4.5 hr. Methanol was removed by distillation under the reduced pressure. The residue was adjusted to pH 3 by the addition of citric acid and was extracted with ethyl acetate. The organic layer was dried over anhydrous sodium sulfate and was then filtered. The filtrate was concentrated under the reduced pressure to give 1.80 g (yield 98%) of the title compound.

$^1$H-NMR (400 MHz, CDCl$_3$) δ: 1.47-1.53 (9H, br), 2.90-3.19 (1H, m), 3.48-3.75 (1H, m), 4.27-4.43 (1H, m), 5.30-5.50 (2H, m).

MS (FAB$^+$) m/z: 270 (M$^+$+1).

(iii) 4'-((E)-But-2-enyl)-1'-N-tert-butoxycarbonyl-1'-demethyl-4'-depropyl-2,3,4-tri-o-trimethylsilyl Lincomycin The title compound (3.94 g, three steps, yield 85%) was produced by applying a corresponding method described in step (iii) of Example 15 to 1.80 g (6.68 mmol) of the title compound produced in step (ii) of Example 23.

$^1$H-NMR (400 MHz, CDCl$_3$) δ: 0.12-0.19 (27H, m), 2.18 (3H, s), 2.43 (3H, s), 5.23 (1H, d, J=5.6 Hz).

MS (API) m/z: 694 (M$^+$+1).

(iv) 7-(5-Amino-1,3,4-thiadiazol-2-ylthio)-4'-((E)-but-2-enyl)-1'-demethyl-7-deoxy-4'-depropyl-7-epilincomycin Compound 339

The title compound (93 mg, yield 43%) was produced in the same manner as in step (iv) of Example 15, except that 300 mg (0.416 mmol) of the title compound produced in step (iii) of Example 23 and 144 mg (0.645 mmol) of tert-butyl 5-mercapto-1,3,4-thiadiazol-2-ylcarbamate were used.

Compound (339 and 340) produced in the same manner as in Example 23 and $^1$H-NMR data and MS data on these compounds are shown in Table 17.

Example 24

7-(5-Amino-1,3,4-thiadiazol-2-ylthio)-4'-((E)-but-2-enyl)-7-deoxy-4'-depropyl-7-epilincomycin Compound 341

The title compound (23 mg, yield 45%) was produced in the same manner as in step (i) of Example 21, except that 50 mg (0.0962 mmol) of the title compound produced in step (iv) of Example 23 and 24 mg (0.289 mmol) of aqueous formaldehyde were used.

Compounds (341 and 342) produced in the same manner as in Example 23 and $^1$H-NMR data and MS data on these compounds are shown in Table 17.

Example 25

(i) 1'-Tert-butoxycarbonyl-4'-butyl-1'-demethyl-4-depropyl-2,3,4-tri-o-trimethylsilyl Lincomycin The title compound (3.02 g, three steps, yield 86%) was produced in the same manner as in step (iii) of Example 15, except that 1.80 g (5.01 mmol) of the title compound produced in step (i) of Example 23 was used.

$^1$H-NMR (400 MHz, CDCl$_3$) δ: 0.13-0.17 (27H, m), 0.88 (3H, t, J=7.1 Hz), 1.48 (9H, s), 2.06 (3H, s), 5.19 (1H, d, J=5.4 Hz).

MS (FAB$^+$) m/z: 723 (M$^+$+1).

(ii) 7-(5-Amino-1,3,4-thiadiazol-2-ylthio)-4'-butyl-1'-demethyl-7-deoxy-4'-depropyl-7-epilincomycin Compound 343

The title compound (72 mg, yield 33%) was produced in the same manner as in step (iv) of Example 15, except that 300 mg (0.416 mmol) of the title compound produced in step (i) of Example 25 and 144 mg (0.645 mmol) of tert-butyl 5-mercapto-1,3,4-thiadiazol-2-ylcarbamate were used.

Compounds (343 and 344) produced in the same manner as in step (ii) of Example 25 and $^1$H-NMR data and MS data on these compounds are shown in Table 17.

Example 26

7-(5-Amino-1,3,4-thiadiazol-2-ylthio)-4'-butyl-7-deoxy-4'-depropyl-7-epilincomycin Compound 345

The title compound (19 mg, yield 39%) produced in the same manner as in step (i) of Example 21, except that 47 mg (0.0901 mmol) of the title compound produced in step (ii) of Example 25 and 22.5 mg (0.270 mmol) of aqueous formaldehyde were used.

Compounds (345 and 346) produced in the same manner as in Example 26 and $^1$H-NMR data and MS data on these compounds are shown in Table 17.

Example 27

(i) Benzyl (2S,4R)-4-((E)-pent-2-enyl)-1-N-tert-butoxycarbonylpyrrolidine-2-carboxylate The title compound (2.01 g, yield 34%) was produced in the same manner as in step (ii) of Example 15, except that 5 g (15.7 mmol) of the title compound produced in step (i) of Example 15 and 1.9 ml (15.7 mmol) of (E)-1-bromo-2-pentene were used.

$^1$H-NMR (400 MHz, CDCl$_3$) δ: 0.95 (3H, t, J=7.6 Hz), 1.33 (9H, s), 1.80-2.05 (6H, m), 2.27-2.32 (1H, m), 3.04 (1H, dd, J=10.5, 8.3 Hz), 3.70 (1H, dd, J=10.5, 7.7 Hz), 4.29 (1H, dd, J=9.0, 2.7 Hz), 5.07-5.50 (4H, m), 7.34-7.35 (5H, m).

(ii) 1'-Tert-butoxycarbonyl-1'-demethyl-4'-depropyl-4'-((E)-pent-2-enyl)-2,3,4-tri-o-trimethylsilyl Lincomycin The title compound (3.29 g, four steps, yield 77%) was produced in the same manner as in steps (ii) and (iii) of Example 23, except that 2.0 g (5.8 mmol) of the title compound produced in step (i) of Example 27 was used.

$^1$H-NMR (400 MHz, CDCl$_3$) δ: 0.15-0.18 (27H, m), 0.97 (3H, t, J=7.3 Hz), 1.49 (9H, s), 2.01 (2H, dq, 17.1, 14.1 Hz), 2.07 (3H, s), 5.20 (1H, d, J=5.1 Hz), 5.33 (1H, dt, J=6.8, 14.1 Hz), 5.50 (1H, dt, J=6.4, 15.1 Hz).

(iii) 1'-Demethyl-7-deoxy-4'-depropyl-7-epi-7-(5-(2-nitrophenyl)-1,3,4-thiadiazol-2-ylthio)-4'-((E)-pent-2-enyl)lincomycin Compound 347

The title compound (112.8 mg, three steps, yield 32%) was produced in the same manner as in step (iv) of Example 15, except that 400 mg (0.54 mmol) of the title compound produced in step (ii) of Example 27 and 201.8 mg (0.84 mmol) of 5-(2-nitrophenyl)-1,3,4-thiadiazole-2-thiol were used.

Compounds (347 to 350) produced in the same manner as in Example 27 and $^1$H-NMR data and MS data on these compounds are shown in Table 17.

Example 28

7-Deoxy-4'-depropyl-7-epi-7-(5-(2-nitrophenyl)-1,3,4-thiadiazol-2-ylthio)-4'-((E)-pent-2-enyl)lincomycin Compound 351

The title compound (48 mg, yield 87%) was produced in the same manner as in step (i) of Example 21, except that 54 mg (0.084 mmol) of the title compound produced in step (iii) of Example 27 and aqueous formaldehyde were used.

Compounds (351 and 352) produced in the same manner as in Example 28 and $^1$H-NMR data and MS data on these compounds are shown in Table 18.

Example 29

(i) 1'-Tert-butoxycarbonyl-1'-demethyl-4'-depropyl-4'-pentyl-2,3,4-tri-o-trimethylsilyl Lincomycin The title compound (2.21 g, four steps, yield 67%) was produced in the same manner as in step (iii) of Example 15, except that 1.7 g (4.5 mmol) of the title compound produced in step (i) of Example 27 was used.

$^1$H-NMR (400 MHz, CDCl$_3$) δ: 0.14-0.17 (27H, m), 0.86-0.90 (3H, m), 1.16 (2H, br), 1.24-1.39 (9H, m), 1.48 (9H, s), 2.07 (3H, s), 5.19 (1H, d, J=5.4 Hz).

(ii) 1'-Demethyl-7-deoxy-4'-depropyl-7-epi-7-(5-(2-nitrophenyl)-1,3,4-thiadiazol-2-ylthio)-4'-pentyllincomycin Compound 353

The title compound (72.6 mg, yield 21%) was produced in the same manner as in step (iv) of Example 15, except that 400 mg (0.54 mmol) of the title compound produced in step (i) of Example 29 and 201.4 mg (0.84 mmol) of 5-(2-nitrophenyl)-1,3,4-thiadiazole-2-thiol were used. Compounds (353 to 355) produced in the same manner as in Example 29 and $^1$H-NMR data and MS data on these compounds are shown in Table 18.

Example 30

7-Deoxy-4'-depropyl-7-epi-7-(5-(2-nitrophenyl)-1,3,4-thiadiazol-2-ylthio)-4'-pentyllincomycin Compound 357

The title compound (49.1 mg, yield 86%) was produced in the same manner as in step (i) of Example 21, except that 56.1 mg (0.087 mmol) of the title compound produced in step (ii) of Example 29 and aqueous formaldehyde were used.

Compounds (356 to 358) produced in the same manner as in Example 30 and $^1$H-NMR data and MS data on these compounds are shown in Table 18.

Example 31

(i) Methyl 6-N-((2S,4R)-1-tert-butoxycarbonyl-4-propyl)pipecoloyl-2,3,4-tri-o-trimethylsilyl-1-thio-α-lincosamide Platinum oxide (IV) (79.8 mg, 0.35 mmol) was added to a solution of 1.05 g (5.22 mmol) of 4-propyl pyridine-2-carboxylate hydrochloride produced according to the method described in a document (J. Med. Chem., 27, (1984), 216) in acetic acid (8 ml), and the mixture was stirred under a hydrogen atmosphere at the atmospheric pressure for 24 hr. The reaction solution was filtered through Celite, and the solvent was then removed by distillation to give 9.9 g of 4-propylpiperidine-2-carboxylic acid acetate as a crude crystal. Di-tert-butyl dicarbonate (11.9 ml, 52 mmol) and 43 ml of a 2 N aqueous sodium hydroxide solution were successively added to a solution of the crude crystal in tert-butanol (40 ml), and the mixture was stirred at room temperature for 24 hr. The solvent was removed by distillation. Water and diethyl ether were then added to the residue. Ethyl acetate and 2 N hydrochloric acid were added to the aqueous layer, and the mixture was extracted with ethyl acetate. The organic layer was washed with saturated brine and was then dried over anhydrous sodium sulfate. The dried organic layer was filtered, and the filtrate was then removed by distillation to give 7.9 g (yield 68%) of 1-N-(tert-butoxycarbonyl)-4-propylpiperidine-2-carboxylic acid. Methyl 6-N-((2S,4R)-4-propyl)pipecoloyl-1-thio-α-lincosamide (14.5 g, yield 99%) was produced in the same manner as in step (iii) of Example 15, except that 7.9 g of 1-N-(tert-butoxycarbonyl)-4-propylpiperidine-2-carboxylic acid, 10.96 g (43.5 mmol) of methyl 1-thio-α-lincosamide, 8.95 g (43.4 mmol) of dicyclohexylcarbodiimide, 5.86 g (43.4 mmol) of 1-hydroxybenzotriazole, and 85 ml of N,N-dimethylformamide were used.

The title compound (0.8 g, yield 41%) was produced in the same manner as in step (i) of Experiment Example 1, except that 1.35 g (2.68 mmol) of methyl 6-N-((2S,4R)-4-propyl)pipecoloyl-1-thio-α-lincosamide was used.

$^1$H-NMR (400 MHz, CDCl$_3$) d: 0.11 (18H, s), 0.16 (9H, s), 1.33 (9H, s), 5.14 (1H, d, J=5.4 Hz), 6.32 (1H, brd, J=8.7 Hz).

MS (FAB$^+$) m/z: 724 (M$^+$+1).

(ii) Methyl 7-deoxy-7-epi-7-(4-fluoro-2-nitrophenyl-1,3,4-thiadiazol-2-ylthio)-6-N-((2S,4R)-4-propyl)pipecoloyl-1-thio-α-lincosamide Compound 366

The title compound (46.2 mg, yield 14%) was produced in the same manner as in step (iv) of Example 15, except that 358.1 mg (0.5 mmol) of the title compound in step (i) of Example 31, 153.3 mg (0.6 mmol), 120 ml (0.76 mmol) of diethylazocarboxylate, 195.8 mg (0.75 mmol) of triphenylphosphine, and 3 ml of tetrahydrofuran were used.

Compounds (359 to 367 and 509 to 512) produced in the same manner as in Example 31 and $^1$H-NMR data and MS data on these compounds are shown in Tables 18 and 21h.

Example 32

(i) Methyl 6-N-((2S,4R)-1-N-tert-butoxycarbonyl-4-propyl)pipecoloyl-7-o-methanesulfonyl-2,3,4-tri-o-trimethylsilyl-1-thio-α-lincosamide The title compound (530 mg, yield 95%) was produced in the same manner as in step (i) of Example 2, except that 500 mg (0.693 mmol) of the title compound in step (i) of Example 31 was used.

$^1$H-NMR (400 MHz, CDCl$_3$) δ: 0.13-0.18 (27H, m), 0.88 (3H, t, J=7.1 Hz), 1.43 (3H, d, J=6.3 Hz), 1.47 (9H, s), 2.06 (3H, s), 3.06 (3H, s), 5.12 (1H, d, J=5.4 Hz).

(ii) Methyl 7-deoxy-7-(1-(4,5-dihydrothiazol-2-yl)azetidin-3-ylthio)-7-epi-6-N-((2S,4R)-4-propyl)pipecoloyl-1-thio-α-lincosamide Compound 368

The title compound (46 mg, yield 39%) was produced in the same manner as in step (ii) of Example 2 and step (v) of Example 16, except that 152 mg (0.210 mmol) of the title compound in step (i) of Example 32 was used.

$^1$H-NMR data and MS data on compound (368) produced in Example 32 are shown in Tables 18 and 21h.

Example 33

(i) Methyl 7-acetylthio-6-N-((2S,4R)-1-N-tert-butoxycarbonyl-4-propyl)pipecolyl-7-deoxy-7-epi-1-thio-2,3,4-tri-o-trimethylsilyl-α-lincosamide The title compound (357 mg, yield 69%) was produced in the same manner as in step (i) of Example 3, except that 530 mg (0.662 mmol) of the title compound in step (i) of Example 32 was used.

$^1$H-NMR (400 MHz, CDCl$_3$) δ: 0.13 (18H, m), 0.18 (9H, s), 0.88 (3H, t, J=6.6 Hz), 1.35 (3H, d, J=6.2 Hz), 1.49 (9H, s), 1.99 (3H, s), 2.29 (3H, s), 5.15 (1H, d, J=5.6 Hz).
MS (FAB$^+$) m/z: 781 (M$^+$+1).

(ii) Methyl 7-acetylthio-6-N-((2S,4R)-1-N-tert-butoxycarbonyl-4-propyl)pipecoloyl-7-deoxy-7-epi-1-thio-α-lincosamide The title compound (250 mg) was produced in the same manner as in step (ii) of Example 3, except that 341 mg (0.436 mmol) of the title compound in step (i) of Example 33 was used.

$^1$H-NMR (400 MHz, CDCl$_3$) δ: 0.90 (3H, t, J=7.3 Hz), 1.43 (3H, d, J=7.3 Hz), 1.46 (9H, s), 2.15 (3H, s), 2.36 (3H, s), 5.29 (1H, d, J=5.6 Hz).
MS (FAB$^+$) m/z: 565 (M$^+$+1).

(iii) Methyl 6-N-((2S,4R)-1-N-tert-butoxycarbonyl-4-propyl)pipecoloyl-7-deoxy-7-epi-7-mercapto-1-thio-α-lincosamide The title compound (234 mg, yield 96%) was produced in the same manner as in step (iii) of Example 3, except that 244 mg (0.432 mmol) of the title compound in step (ii) of Example 33 was used.

$^1$H-NMR (400 MHz, CDCl$_3$) δ: 0.90 (3H, t, J=7.1 Hz), 1.47 (9H, s), 2.22 (3H, s), 5.33 (1H, d, J=5.6 Hz).
MS (FAB$^+$) m/z: 523 (M$^+$+1).

(iv) Methyl 7-deoxy-7-epi-7-(5-(4-fluoro-5-methoxy-2-nitrophenyl)-1,3,4-thiadiazol-2-ylthio)-6-N-((2S,4R)-4-propyl)pipecoloyl-1-thio-α-lincosamide Compound 369

The title compound (30 mg, yield 26%) was produced in the same manner as in step (iv) of Example 3 and step (v) of Example 16, except that 90 mg (0.172 mmol) of the title compound produced in step (iii) of Example 33 and 52.4 mg (0.181 mmol) of 2-chloro-5-(4-fluoro-5-methoxy-2-nitrophenyl)-1,3,4-thiadiazole were used.

(v) Methyl 1-N-tert-butoxycarbonyl-7-deoxy-7-epi-6-N-((2S,4R)-4-propyl)pipecoloyl-7-(4-(pyridin-3-yl)phenylthio)-1-thio-α-lincosamide The title compound (141 mg, yield 88%) was produced in the same manner as in step (v) of Example 3, except that 123 mg (0.236 mmol) of the title compound produced in step (iii) of Example 33 was used.

$^1$H-NMR (300 MHz, CD$_3$OD) δ: 1.46 (9H, s), 1.95 (3H, s), 3.88 (1H, dq, J=2.7, 6.6 Hz), 5.28 (1H, d, J=5.4 Hz), 7.53 (2H, d, J=8.4 Hz), 7.63 (2H, d, J=8.4 Hz), 8.09 (1H, ddd, J=1.5, 2.1, 8.1 Hz), 8.51 (1H, dd, J=1.5, 5.1 Hz), 8.80 (1H, d, J=2.1 Hz).
MS (API) m/z: 676 (M$^+$+1).

(vi) Methyl 7-deoxy-7-epi-6-N-((2S,4R)-4-propyl)pipecoloyl-7-(4-(pyridin-3-yl)phenylthio)-1-thio-α-lincosamide Compound 370

The title compound (94.7 mg, yield 79%) was produced in the same manner as in step (v) of Example 16, except that 141 mg (0.209 mmol) of the title compound produced in step (v) of Example 33 was used.

Compounds (369, 370, and 513 to 516) produced in steps (iv) and (vi) of Example 33 and $^1$H-NMR data and MS data on these compounds are shown in Tables 19 and 21h.

Example 34

(i) Methyl 7-(5-aminopyridin-2-ylthio)-7-deoxy-7-epi-6-N-((2S,4R)-1-N-tert-butoxycarbonyl-4-propyl)pipecoloyl-1-thio-α-lincosamide The title compound (522 mg, yield 46%) was produced in the same manner as in step (ii) of Example 4, except that 1.20 g (1.86 mmol) of 7-deoxy-7-epi-7-(5-nitropyridin-2-ylthio)-6-N-((2S,4R)-1-N-tert-butoxycarbonyl-4-propyl)pipecoloyl-1-thio-α-lincosamide, which had been produced in the same manner as in step (ii) of Example 1 except that the title compound produced in step (i) of Example 31, 2-mercapto-5-nitropyridine, and toluene instead of tetrahydrofuran were used, was used.

$^1$H-NMR (300 MHz, CD$_3$OD) δ: 1.48 (9H, s), 2.12 (3H, s), 3.77 (1H, dq, J=2.4, 6.9 Hz), 5.31 (1H, d, J=5.7 Hz), 7.05 (1H, dd, J=2.7, 8.4 Hz), 7.30 (1H, d, J=8.7 Hz), 8.02 (1H, d, J=2.7 Hz).

MS (FAB$^+$) m/z: 615 (M$^+$+1).

(ii) Methyl 7-5-aminopyridin-2-ylthio)-7-deoxy-7-epi-6-N-((2'S, 4'R)-1'-N-tert-butoxycarbonyl-4'-propyl)pipecoloyl-1-thio-2,3,4-tri-o-trimethylsilyl-α-lincosamide The title compound (692 mg, yield 98%) was produced in the same manner as in step (i) of Example 5, except that 522 mg (0.849 mmol) of the title compound produced in step (i) of Example 34 was used.

$^1$H-NMR (300 MHz, CDCl$_3$) δ: 0.13-0.19 (27H, m), 1.44 (9H, s), 1.99 (3H, s), 3.98 (1H, dq, J=2.4, 6.9 Hz), 5.19 (1H, d, J=5.4 Hz), 6.86 (1H, dd, J=3.0, 8.4 Hz), 7.97 (1H, d, J=3.0 Hz).

MS (FAB$^+$) m/z: 831 (M$^+$+1).

(iii) Methyl 7-(5-acetamidopyridin-2-ylthio)-7-deoxy-7-epi-6-N-((2'S,4'R)-1'-N-tert-butoxycarbonyl-4'-propyl)pipecoloyl-1-thio-2,3,4-tri-o-trimethylsilyl-α-lincosamide The title compound (242 mg, yield 99%) was produced in the same manner as in step (iii) of Example 19, except that 232 mg (0.278 mmol) of the title compound produced in step (ii) of Example 34 was used.

$^1$H-NMR (300 MHz, CDCl$_3$) δ: 0.12-0.19 (27H, m), 1.45 (9H, s), 1.84 (3H, s), 2.18 (3H, s), 4.24 (1H, dq, J=3.0, 6.9 Hz), 5.16 (1H, d, J=5.7 Hz), 6.74 (1H, d, J=9.6 Hz), 7.92 (1H, dd, J=2.4, 8.7 Hz), 8.46 (1H, d, J=1.5 Hz).

MS (API) m/z: 873 (M$^+$+1).

(iv) Methyl 7-(5-acetamidopyridin-2-ylthio)-7-deoxy-7-epi-6-N-((2S,4R)-1-N-tert-butoxycarbonyl-4-propyl)pipecoloyl-1-thio-α-lincosamide The title compound (115 mg, yield 63%) was produced in the same manner as in step (iv) of Example 19, except that 242 mg (0.278 mmol) of the title compound in step (iii) of Example 34 was used.

$^1$H-NMR (300 MHz, CD$_3$OD) δ: 1.42 (9H, s), 1.95 (3H, s), 2.14 (3H, s), 5.24 (1H, d, J=5.7 Hz), 7.35 (1H, d, J=8.7 Hz), 7.86 (1H, dd, J=2.4, 8.4 Hz), 8.75 (1H, d, J=2.1 Hz).

MS (FAB$^+$) m/z: 657 (M$^+$+1).

(v) Methyl 7-(5-acetamidopyridin-2-ylthio)-7-deoxy-7-epi-6-N-((2S,4R)-4-propyl)pipecoloyl-1-thio-α-lincosamide Compound 371

The title compound (92.3 mg, yield 94%) was produced in the same manner as in step (v) of Example 16, except that 115 mg (0.176 mmol) of the title compound in step (iv) of Example 34 was used.

Compounds (371 and 372) produced in the same manner as in steps (iii), (iv), and (v) of Example 34 and $^1$H-NMR data and MS data on these compounds are shown in Table 19.

Example 35

Methyl 7-deoxy-7-epi-7-(5-(piperidinocarbonyl)-1,3,4-thiadiazol-2-ylthio)-6-N-((2S,4R)-4-propyl)pipecoloyl-1-thio-α-lincosamide Compound 373

The title compound (38.5 mg, yield 69%) was produced in the same manner as in Example 8, except that 50.6 mg of methyl 6-N-((2S,4R)-4-propyl)pipecoloyl-7-deoxy-7-epi-7-(5-ethoxycarbonyl)-1,3,4-thiadiazol-2-ylthio)-1-thio-α-lincosamide and 1 ml of ethanol, and 0.2 ml of piperidine were used.

Compounds (373 and 374) produced in the same manner as in Example 35 and $^1$H-NMR data and MS data on these compounds are shown in Table 19.

Example 36

(i) Methyl 7-(5-carboxypyridin-2-ylthio)-7-deoxy-7-epi-6-N-((2S,4R)-1-N-tert-butoxycarbonyl-4-propyl)pipecoloyl-1-thio-α-lincosamide The title compound (374 mg, yield 93%) was produced in the same manner as in step (i) of Example 10, except that 412 mg (0.627 mmol) of methyl 7-deoxy-7-epi-7-(5-methoxycarbonylpyridin-2-ylthio)-6-N-((2S,4R)-1-N-tert-butoxycarbonyl-4-propyl)pipecoloyl-1-thio-α-lincosamide, which had been produced in the same manner as in step (ii) of Example 1 except that the title compound produced in step (i) of Example 31, 4-methoxycarbonylpyridine-2-thiol, and toluene as a solvent were used, was used.

$^1$H-NMR (300 MHz, CD$_3$OD) δ: 1.43 (9H, s), 1.85 (3H, s), 4.28 (1H, dq, J=3.0, 6.9 Hz), 5.23 (1H, d, J=5.7 Hz), 7.32 (1H, d, J=8.4 Hz), 8.09 (1H, dd, J=2.1, 8.4 Hz), 8.94 (1H, d, J=2.1 Hz).

MS (FAB$^+$) m/z: 644 (M$^+$+1).

(ii) Methyl 7-deoxy-7-epi-7-(5-(piperidinocarbonyl)pyridin-2-ylthio)-6-N-((2S,4R)-1-N-tert-butoxycarbonyl-4-propyl)pipecoloyl-1-thio-α-lincosamide The title compound (19.4 mg, yield 18%) was produced in the same manner as in step (iv) of Example 16, except that 100 mg (0.156 mmol) of the title compound produced in step (i) of Example 36 was used and piperidine was used instead of morpholine.

$^1$H-NMR (300 MHz, CD$_3$OD) δ: 1.44 (9H, s), 1.80 (3H, s), 5.22 (1H, d, J=5.7 Hz), 7.36 (1H, d, J=8.4 Hz), 7.92 (1H, dd, J=2.4, 8.4 Hz), 8.45 (1H, d, J=2.4 Hz).

MS (FAB$^+$) m/z: 711 (M$^+$+1).

(iii) Methyl 7-deoxy-7-epi-7-(5-(piperidinocarbonyl)pyridin-2-ylthio)-6-N-((2S,4R)-4-propyl)pipecoloyl-1-thio-α-lincosamide Compound 376

The title compound (13.1 mg, yield 79%) was produced in the same manner as in step (v) of Example 16, except that 19.4 mg (0.0273 mmol) of the title compound produced in step (ii) of Example 36 was used.

Compounds (375 to 379) produced in the same manner as in steps (ii) and (iii) of Example 36 and ¹H-NMR data and MS data on these compounds are shown in Table 19.

Example 37

(i) Methyl 6-N-((2S,4R)-1-N-tert-butoxycarbonyl-4-propyl)pipecoloyl-7-deoxy-7-epi-7-(5-(5-fluoro-2-nitrophenyl)-1,3,4-thiadiazol-2-ylthio)-1-thio-α-lincosamide Triphenylphosphine (100 mg, 0.38 mmol), 0.06 ml (0.38 mmol) of diethyl azodicarboxylate, and 97 mg (0.38 mmol) of 5-(5-fluoro-2-nitrophenyl)-1,3,4-thiadiazole-2-thiol were successively added under ice cooling to a solution of 180 mg (0.25 mmol) of the title compound in step (i) of Example 31 in tetrahydrofuran (6 ml), and the mixture was stirred at room temperature for 16 hr. The solvent was removed by distillation, and the residue was purified by gel filtration column chromatography (CM-Sephadex LH-20). To a solution of the residue in methanol (3 ml) was added 0.1 ml of 1 N hydrochloric acid. The solvent was removed by distillation, and the residue was purified by preparative thin layer chromatography (chloroform:methanol=30:1) to give 81 mg (yield 44%) of the title compound.

(ii) Methyl 7-deoxy-7-epi-7-(5-(5-methylamino-2-nitrophenyl)-1,3,4-thiadiazol-2-ylthio)-6-N-((2S,4R)-4-propyl)pipecoloyl-1-thio-α-lincosamide Compound 380

A 40% methylamine methanol solution (10.2 ml) was added to a solution of 81 mg (0.11 mmol) of the title compound produced in step (i) of Example 37 in methanol (1 ml), and the mixture was stirred at room temperature for 16 hr. The solvent was removed by distillation, 0.5 ml of trifluoroacetic acid was added to the residue, and the mixture was stirred at room temperature for 1 hr. Isopropyl ether (5 ml) was added to the reaction solution, and the resultant precipitate was collected by filtration and was purified by preparative thin layer chromatography (chloroform:methanol:28% aqueous ammonia=20:1:0.1) to give 48 mg (yield 58%) of the title compound.

Compounds (380 and 381) produced in the same manner as in Example 37 and ¹H-NMR data and MS data on these compounds are shown in Table 19.

Example 38

Methyl 7-deoxy-7-epi-7-(5-(5-methoxy-2-nitrophenyl)-1,3,4-thiadiazol-2-ylthio)-6-N-((2S,4R)-4-propyl)pipecoloyl-1-thio-α-lincosamide Compound 382

A 28% sodium methylate methanol solution (0.1 ml) was added to a solution of 30 mg (0.04 mmol) of the title compound produced in the same manner as in step (i) of Example 37 in methanol (0.5 ml), and the mixture was stirred at room temperature for 3 hr. To the reaction solution was added 1 N hydrochloric acid. The solvent was removed by distillation, 0.2 ml of trifluoroacetic acid was added to the residue, and the mixture was stirred at room temperature for 1 hr. Isopropyl ether (5 ml) was added to the reaction solution, and the resultant precipitate was collected by filtration and was purified by preparative thin layer chromatography (chloroform:methanol:28% aqueous ammonia=20:1:0.1) to give 21.7 mg (yield 83%) of the title compound.

Compound (382) produced in the same manner as in Example 38 and ¹H-NMR data and MS data on these compounds are shown in Table 19.

Example 39

Methyl 7-deoxy-7-epi-7-(5-(4-fluoro-2-nitrophenyl)-1,3,4-thiadiazol-2-ylthio)-6-N-((2S,4R)-1-methyl-4-propyl)pipecoloyl-1-thio-α-lincosamide Compound 389

The title compound (22.2 mg, yield 37%) was produced in the same manner as in step (i) of Example 21, except that 55.4 g (0.09 mmol) of compound 366, 38 ml (0.46 mmol) of aqueous formaldehyde, 58.3 mg (0.27 mmol) of sodium triacetoxyboron, a catalytic amount of acetic acid, and 1 ml of and methanol were used.

Compounds (383 to 393) produced in the same manner as in Example 39 and ¹H-NMR data and MS data on these compounds are shown in Table 20.

Example 40

(i) Methyl 6-N-((2S,4R)-1-N-tert-butoxycarbonyl-4-ethyl)pipecoloyl-1-thio-2,3,4-tri-o-trimethylsilyl-α-lincosamide The title compound (10.9 g, five steps, yield 38%) was produced in the same manner as in step (i) of Example 31, except that 7.65 g (40.7 mmol) of 4-ethyl pyridine-2-carboxylate hydrochloride was used.

¹H-NMR (300 MHz, CDCl₃) δ: 0.15 (18H, m), 0.20 (9H, s), 0.86 (3H, t, J=7.1 Hz), 1.13 (3H, d, J=6.6 Hz), 1.42 (9H, s), 2.01 (3H, s), 5.12 (1H, d, J=5.4 Hz).

MS (FAB⁺) m/z: 709 (M⁺+1).

(ii) Methyl 7-deoxy-7-epi-7-(5-(4-fluoro-2-nitrophenyl)-1,3,4-thiadiazol-2-ylthio)-6-N-((2S,4R)-4-ethyl)pipecoloyl-1-thio-α-lincosamide Compound 394

The title compound (107 mg, yield 45%) was produced in the same manner as in step (iv) of Example 15, except that 180 mg (0.25 mmol) of the title compound produced in the same manner as in step (i) of Example 40 and 80 mg (0.31 mmol) of 4-fluoro-2-nitrophenyl)-1,3,4-thiadiazole-2-thiol were used.

Compounds (394, 395, and 517) produced in the same manner as in Example 40 and ¹H-NMR data and MS data on these compounds are shown in Tables 20 and 21h.

Example 41

Methyl 7-deoxy-7-epi-7-(5-(4-fluoro-2-nitrophenyl)-1,3,4-thiadiazol-2-ylthio)-6-N-((2S,4R)-1-N-methyl-4-ethyl)pipecoloyl-1-thio-α-lincosamide Compound 396

The title compound (33.2 mg, yield 84%) was produced in the same manner as in step (i) of Example 21, except that 40 mg (0.16 mmol) of the title compound produced in the same manner as in step (ii) of Example 40 and aqueous formaldehyde were used.

Compound (396) produced in the same manner as in Example 41 and $^1$H-NMR data and MS data on these compounds are shown in Table 20.

Example 42

(i) Methyl 6-N-((2S,4R)-1-N-tert-butoxycarbonyl-4-butyl)pipecoloyl-2,3,4-tri-o-trimethylsilyl-1-thio-α-lincosamide The title compound (11.4 g, five steps, yield 31%) was produced in the same manner as in step (i) of Example 31, except that 10.8 g (50 mmol) of 4-butyl pyridine-2-carboxylate hydrochloride was used.

$^1$H-NMR (400 MHz, CDCl$_3$) δ: 0.14 (18H, m), 0.19 (9H, s), 0.88 (3H, m), 1.15 (3H, d, J=6.6 Hz), 5.17 (1H, d, J=5.4 Hz).

MS (FAB$^+$) m/z: 737 (M$^+$+1).

(ii) Methyl 6-N-((2S,4R)-4-butyl)pipecoloyl-7-deoxy-7-epi-7-(5-(2-nitrophenyl)-1,3,4-thiadiazol-2-ylthio)-1-thio-α-lincosamide Compound 400

The title compound (93 mg, yield 21%) was produced in the same manner as in step (iv) of Example 15, except that 500 mg (0.678 mmol) of the title compound produced in the same manner as in step (i) of Example 42 and 211 mg (0.882 mmol) of 5-(2-nitrophenyl)-1,3,4-thiadiazole-2-thiol were used.

Compounds (397 to 402, and 518) produced in the same manner as in step (ii) of Example 42 and $^1$H-NMR data and MS data on these compounds are sown in Tables 21a and 21h.

Example 43

(i) Methyl 6-N-((2S,4R)-1-N-tert-butoxycarbonyl-4-butyl)pipecoloyl-7-deoxy-7-epi-7-(5-nitropyridin-2-ylthio)-1-thio-2,3,4-tri-o-trimethylsilyl-α-lincosamide Triphenylphosphine (1.13 g, 4.10 mmol), 0.66 ml (4.07 mmol) of diethyl azodicarboxylate, and 651 mg (4.09 mmol) of 2-mercapto-5-nitropyridine were successively added under ice cooling to a solution of 2.00 g (2.71 mmol) of the title compound produced in step (i) of Example 42 in 40 ml of toluene, and the mixture was stirred at room temperature for 7 hr. The solvent was removed by distillation, and the residue was purified by column chromatography on silica gel (hexane:ethyl acetate=8:1 to 6:1) to give 2.07 g (yield 87%) of the title compound.

$^1$H-NMR (300 MHz, CDCl$_3$) δ: 0.12-0.19 (27H, m), 1.48 (9H, s), 2.05 (3H, s), 4.55 (1H, dq, J=3.3, 6.9 Hz), 5.14 (1H, d, J=5.4 Hz), 7.24 (1H, d, J=8.7 Hz), 8.20 (1H, dd, J=2.7, 8.7 Hz), 9.21 (1H, dd, J=0.3, 3.3 Hz).

MS (FAB$^+$) m/z: 875 (M$^+$+1).

(ii) Methyl 7-(5-aminopyridin-2-ylthio)-6-N-((2S,4R)-1-N-tert-butoxycarbonyl-4-butyl)pipecoloyl-7-deoxy-7-epi-1-thio-2,3,4-tri-o-trimethylsilyl-α-lincosamide The title compound (365 mg, yield 18%) was produced in the same manner as in step (ii) of Example 4, except that 2.07 g (2.37 mmol) of the title compound produced in step (i) of Example 43 was used.

$^1$H-NMR (300 MHz, CDCl$_3$) δ: 0.13-0.19 (27H, m), 1.44 (9H, s), 2.05 (3H, s), 3.99 (1H, dq, J=2.4, 6.9 Hz), 5.19 (1H, d, J=5.7 Hz), 6.86 (1H, dd, J=3.0, 8.4 Hz), 7.11 (1H, d, J=8.4 Hz), 7.98 (1H, d, J=3.0 Hz).

MS (API) m/z: 845 (M$^+$+1).

(iii) Methyl 7-(5-acetamidopyridin-2-ylthio)-6-N-((2S,4R)-1-N-tert-butoxycarbonyl-4-butyl)pipecoloyl-7-deoxy-7-epi-1-thio-2,3,4-tri-o-trimethylsilyl-α-lincosamide The title compound (409 mg, yield 100%) was produced in the same manner as in step (iii) of Example 19, except that 365 mg (0.432 mmol) of the title compound produced in step (ii) of Example 43 was used.

$^1$H-NMR (300 MHz, CDCl$_3$) δ: 0.12-0.19 (27H, m), 1.45 (9H, s), 1.84 (3H, s), 2.18 (3H, s), 4.23 (1H, dq, J=3.0, 6.9 Hz), 5.16 (1H, d, J=5.7 Hz), 7.14 (1H, d, J=8.4 Hz), 7.92 (1H, dd, J=2.4, 8.4 Hz), 8.45 (1H, d, J=2.4 Hz).

MS (API) m/z: 887 (M$^+$+1).

(iv) Methyl 7-(5-acetamidopyridin-2-ylthio)-6-N-((2S,4R)-1-N-tert-butoxycarbonyl-4-butyl)pipecoloyl-7-deoxy-7-epi-1-thio-α-lincosamide The title compound (252 mg, yield 82%) was produced in the same manner as in step (ii) of Example 3, except that 409 mg (0.461 mmol) of the title compound produced in step (iii) of Example 43 was used.

$^1$H-NMR (300 MHz, CD$_3$OD) δ: 1.44 (9H, s), 1.97 (3H, s), 2.17 (3H, s), 5.27 (1H, d, J=5.4 Hz), 7.29 (1H, d, J=8.7 Hz), 7.80 (1H, d, J=10.2 Hz), 8.80 (1H, s).

MS (FAB) m/z: 671 (M$^+$+1).

(v) Methyl 7-(5-acetamidopyridin-2-ylthio)-6-N-((2S,4R)-4-butyl)pipecoloyl-7-deoxy-7-epi-1-thio-α-lincosamide Compound 403

The title compound (194 mg, yield 91%) was produced in the same manner as in step (v) of Example 16, except that 252 mg (0.376 mmol) of the title compound produced in step (iv) of Example 43 was used.

$^1$H-NMR data and MS data on compound (403) produced in Example 43 are shown in Table 21a.

Example 44

Methyl 6-N-((2S,4R)-4-butyl-1-methyl)pipecoloyl-7-deoxy-7-epi-7-(5-(2-nitrophenyl)-1,3,4-thiadiazo-2-ylthio)-1-thio-α-lincosamide Compound 406

The title compound (51 mg, yield 88%) was produced in the same manner as in step (i) of Example 21, except that 57 mg (0.0888 mmol) of the title compound produced in step (ii) of Example 42 and 74 μl (0.888 mmol) of aqueous formaldehyde were used.

Compounds (404 to 408) produced in the same manner as in Example 44 and $^1$H-NMR data and MS data on these compounds are shown in Table 21a.

Example 45

7-(6-Aminobenzo[d]thiazol-2-ylthio)-7-deoxylincomycin

Compound 409

Potassium carbonate (138 mg, 1 mmol) and 137 mg (0.75 mmol) of 6-aminobenzo[d]thiazole-2-thiol were successively added to a solution of 231 mg (0.5 mmol) of clindamycin hydrochloride in N,N-dimethylformamide (1 ml), and the mixture was stirred at 90° C. for 16 hr. The reaction solution was diluted with ethyl acetate and was washed twice with water. The solvent was removed by distillation, and the residue was purified by preparative thin layer chromatography (chloroform:methanol:28% aqueous ammonia=20:1:0.1) to give 113 mg (yield 40%) of the title compound.

Compound (409) produced in Example 45 and $^1$H-NMR data and MS data on these compounds are shown in Table 21a.

Example 46

(i) 3,4-o-Isopropylidene Lincomycin

The title compound was produced by the method described in Journal of Medicinal Chemistry, 13, 616, (1970) using LCM.

(ii) 2-o-(2,6-Dichlorobenzyl)-3,4-o-isopropylidene Lincomycin

Potassium tert-butoxide (18.9 mg, 0.17 mmol) was added to a solution of 50 mg (0.11 mmol) of the title compound produced in step (i) of Example 46 in benzene (1 ml), and the mixture was stirred at room temperature for 30 min. 2,6-Dichlorobenzyl bromide (32.1 mg, 0.13 mmol) was added thereto, and the mixture was stirred at room temperature for 19 hr. A saturated aqueous ammonium chloride solution was added to stop the reaction. The reaction solution was extracted with ethyl acetate, and the extract was dried over anhydrous sodium sulfate. The filtrate was concentrated, and the residue was purified by column chromatography on silica gel (chloroform:methanol:28% aqueous ammonia=20:1:0.1) to give 31.9 mg (yield 47%) of the title compound.

$^1$H-NMR (400 MHz, CDCl$_3$) δ: 1.32 (3H, s), 1.44 (3H, s), 2.09 (3H, s), 2.36 (3H, s), 4.93 (2H, s), 5.32 (1H, d, J=5.1 Hz), 7.17-7.21 (1H, m), 7.32 (2H, d, J=8.0 Hz).

(iii) 7-(5-(Tert-butoxycarbonylamino)-1,3,4-thiadiazol-2-ylthio)-7-deoxy-2-o-(2,6-dichlorobenzyl)-7-epi-3,4-o-isopropylidene lincomycin The title compound (71.8 mg, yield 67%) was produced in the same manner as in step (ii) of Example 1, except that 79.5 mg (0.13 mmol) of the title compound produced in step (ii) of Example 46 and 47.5 mg (0.2 mmol) of 5-(tert-butoxycarbonylamino)-1,3,4-thiadiazole-2-thiol were used.

$^1$H-NMR (400 MHz, CDCl$_3$) δ: 1.26 (3H, s), 1.40 (3H, s), 1.55 (9H, s), 2.00 (3H, s), 2.38 (3H, s), 4.91 (1H, d, J=10.8 Hz), 4.95 (1H, d, J=10.8 Hz), 5.31 (1H, d, J=5.1 Hz), 7.18 (1H, dd, J=7.7, 7.7 Hz), 7.31 (1H, d, J=5.1 Hz), 7.31 (1H, d, J=5.1 Hz), 7.77 (1H, d, J=10.2 Hz).

(iv) 7-(5-Amino-1,3,4-thiadiazol-2-ylthio)-7-deoxy-2-o-(2,6-dichloro benzyl)-7-epilincomycin Compound 410

Ice cooled trifluoroacetic acid (1 ml) was added to 71.8 mg (0.088 mmol) of the title compound produced in step (iii) of Example 46. The mixture was then stirred at room temperature for 3 hr. Methanol was added to the reaction solution, and the mixture was evaporated under the reduced pressure to dryness. The residue was purified by preparative thin layer chromatography (chloroform:methanol:28% aqueous ammonia=9:1:0.1) to give 32.7 mg (yield 55%) of the title compound.

Compounds (410 to 412) produced in the same manner as in Example 46 and $^1$H-NMR data and MS data on these compounds are shown in Table 21a.

Example 47

(i) (S)-Methyl 2-(2-nitrophenylsulfonamido)pent-4-enoate

L-2-Amino-4-pentenoic acid was added to a solution of 3.18 ml (43.5 mmol) of thionyl chloride in methanol (40 ml) which had been cooled to 0° C., and the mixture was stirred at room temperature for 24 hr. The reaction solution was concentrated under the reduced pressure and was then dried. A solution of this crude product thus obtained in diethyl ether (26 ml) was cooled to 0° C., and a saturated aqueous sodium hydrogencarbonate solution (26 ml) was added thereto. 2-Nitrobenzenesulfonyl chloride (4.24 g, 19.14 mmol) was added thereto, and the mixture was stirred at room temperature for 7 hr. Thereafter, the reaction solution was cooled to 0° C., N,N-dimethylethylenediamine (2 ml) was added thereto, and the mixture was stirred at room temperature for 30 min. The organic layer was separated. The aqueous layer was adjusted to pH 3 by the addition of citric acid and was extracted with diethyl ether. The combined organic layer was washed with a 3% aqueous citric acid solution, a saturated aqueous sodium hydrogencarbonate solution, and saturated brine in that order, was dried over anhydrous sodium sulfate and was then filtered. The filtrate was concentrated under the reduced pressure, and the residue was then purified by column chromatography on silica gel (hexane:ethyl acetate=5:1) to give 4.52 g (yield 83%) of the title compound.

$^1$H-NMR (400 MHz, CDCl$_3$) δ: 2.58 (2H, dd, 15.9, 6.8 Hz), 3.52 (3H, s), 4.30 (1H, dt, J=5.8, 8.8 Hz), 5.12-5.15 (1H, m), 5.17 (1H, s), 5.62-5.72 (1H, m), 6.09 (1H, d, J=8.7 Hz), 7.72-7.76 (2H, m), 7.91-7.96 (1H, m), 8.06-8.10 (1H, m).

MS (FAB$^+$) m/z: 315 (M$^+$+1).

(ii) 3-Methylene hexan-1-ol

Butyllithium (2.66 M toluene solution) (82 ml, 218.2 mmol) was added to a solution of 39 ml (258 mmol) of N,N,N',N'-tetramethylethylenediamine in diethyl ether (148 ml) which had been cooled to 0° C., and the mixture was stirred at room temperature for 1 hr. The reaction solution was cooled to 0° C., 10.1 ml (99.2 mmol) of 3-methyl-3-buten-1-ol was added thereto, and the mixture was stirred at room temperature for 6 hr. The reaction solution was cooled to −78° C., a solution of 8.9 ml (119 mmol) of bromoethane in diethyl ether (29.2 ml) was added to the cooled solution. The temperature of the mixture was gradually raised to room temperature before the mixture was stirred for 15 hr. A saturated aqueous ammonium chloride solution was added thereto, and the mixture was extracted with diethyl ether. The organic layer was washed with a 3% aqueous citric acid solution, a saturated aqueous sodium hydrogencarbonate solution, and saturated brine in that order, was dried over anhydrous magnesium sulfate, and was then filtered. The filtrate was concentrated under the reduced pressure, and the residue was then purified by distillation under the reduced pressure to give 1.4 g (yield 12%) of the title compound.

$^1$H-NMR (400 MHz, CDCl$_3$) δ: 0.80 (3H, t, J=7.3 Hz), 1.35 (2H, tq, J=7.3. 7.5 Hz), 1.89 (2H, t, J=7.5 Hz), 2.17 (2H, t, J=6.3 Hz), 3.59 (2H, dt, J=5.3, 6.1 Hz), 4.70 (1H, dd, J=0.7, 1.2 Hz), 4.74 (1H, d, J=1.5 Hz).

MS (GC) m/z: 114 (M$^+$).

(iii) (S)-Methyl 2-(N-(3-methylenehexyl)-2-nitrophenylsulfonamido)pent-4-enoate Tetrahydrofuran (30.2 ml) was added to 2.27 g (7.22 mmol) of the title compound produced in step (i) of Example 47 and 1.07 g (9.39 mmol) of the title compound produced in step (ii) of Example 47. The mixture was cooled to 0° C., 2.84 g (10.8 mmol) of triphenylphosphine was added thereto, and the mixture was stirred for 10 min. Diisopropyl azodicarboxylate (2.1 ml, 10.8 mmol) was added thereto. The temperature of the mixture was raised over a period of 2 hr before it was stirred for 19 hr. The solvent was removed under the reduced pressure, and the residue was purified by column chromatography on silica gel (hexane:ethyl acetate=20:1) to give 2.42 g (yield 82%) of the title compound.

$^1$H-NMR (400 MHz, CDCl$_3$) δ: 0.90 (3H, t, J=7.3 Hz), 1.45 (2H, tq, J=7.3. 7.6 Hz), 1.99 (2H, t, J=7.5 Hz), 2.32 (1H, dt, J=5.1, 12.9 Hz), 2.44-2.55 (2H, m), 2.83 (1H, dtt, J=1.5, 6.0, 15.1 Hz), 3.25 (1H, ddd, J=5.1, 12.2, 15.4 Hz), 3.53 (1H, ddd, J=5.1, 12.0, 15.3 Hz), 3.58 (3H, s), 4.71-4.75 (2H, m), 4.79 (1H, d, J=1.4 Hz), 5.14 (1H, dq, J=1.5, 10.2 Hz), 5.20 (1H, dq, J=1.5, 17.1 Hz), 5.82 (ddt, J=6.8, 10.5, 17.0 Hz), 7.56-7.60 (1H, m), 7.67-7.74 (2H, m), 8.02-8.06 (1H, m).

MS (FAB$^+$) m/z: 411 (M$^+$+1).

(iv) (S,Z)-Methyl 1-(2-nitrophenylsulfonyl)-5-propyl-2,3,6,7-tetrahydro-1H-azepine-2-carboxylate Benzylidene[1,3-bis(2,4,6-trimethylphenyl)-2-imidazolidinylidene]dichloro(tricyclohexylphosphine)ruthenium (250 mg, 0.295 mmol) was added to a solution of 2.42 g (5.89 mmol) of the title compound produced in step (iii) of Example 47 in methylene chloride (295 ml), and the mixture was heated under reflux for one hr. The reaction solution was cooled to room temperature, and the solvent was removed under the reduced pressure. The residue was purified by column chromatography on silica gel (hexane:ethyl acetate=10:1) to give 1.84 g (yield 82%) of the title compound.

$^1$H-NMR (400 MHz, CDCl$_3$) δ: 0.82 (3H, t, J=7.3 Hz), 1.22-1.42 (2H, m), 1.91 (3H, t, J=7.3 Hz), 2.28 (1H, ddd, J=1.9, 6.1, 16.3 Hz), 2.38-2.47 (1H, m), 2.56-2.64 (1H, m), 2.79 (1H, dt, J=7.3, 14.9 Hz), 3.45 (1H, ddd, J=2.2, 10.5, 14.4 Hz), 3.62 (3H, s), 3.83 (1H, ddd, J=3.2, 6.3, 14.4 Hz), 4.90 (1H, dd, J=3.4, 6.8 Hz), 5.45 (1H, ddd, J=1.0, 5.3, 7.3 Hz), 7.61-7.65 (1H, m), 7.66-7.71 (2H, m), 8.05-8.10 (1H, m).

MS (ESI$^+$) m/z: 383 (M$^+$+1).

(v) Methyl 6-N-((2S,Z)-1-(2-nitrophenylsulfonyl)-5-propyl-2-(2,3,6,7-tetrahydroazepine)carbonyl)-1-thio-α-lincosamide Lithium hydroxide monohydrate (164.6 mg, 3.92 mmol) was added to a solution of 500 mg (1.31 mmol) of the title compound produced in step (iv) of Example 47 in 1,4-dioxane:water=4:1 (7 ml), and the mixture was stirred at room temperature for 4 hr. Water and diethyl ether were added to the reaction solution for dilution. The diluted solution was then filtered through Celite to separate the organic layer. A 3% aqueous citric acid solution was added to the aqueous layer, and the mixture was extracted with ethyl acetate, and the combined organic layer was dried over anhydrous sodium sulfate and was then filtered. The filtrate was concentrated under the reduced pressure, and the concentrate was dried. 1-Hydroxybenzotriazole (265.0 mg, 1.96 mmol), 375.8 mg (1.96 mmol) of 1-ethyl-3-(3-dimethylaminopropyl)carbodiimide hydrochloride, and N,N-dimethylformamide (5.0 ml) were successively added to the crude product, and the mixture was stirred at room temperature for 20 min. Thereafter, 496.8 mg (1.96 mmol) of methyl 1-thio-α-lincosamide was added thereto, and the mixture was stirred at room temperature for 13 hr. A saturated aqueous sodium hydrogencarbonate solution was added thereto, and the mixture was extracted with ethyl acetate, and the extract was dried over anhydrous sodium sulfate and was then filtered. The filtrate was concentrated under the reduced pressure, and the residue was purified by column chromatography on silica gel (chloroform:methanol=50:1) to give 660 mg (yield 84%) of the title compound.

$^1$H-NMR (400 MHz, CD$_3$OD) δ: 0.83 (3H, t, J=7.3 Hz), 1.15 (3H, d, J=6.3 Hz), 1.26-1.34 (2H, m), 1.80 (2H, t, J=7.3 Hz), 2.05 (3H, s), 2.25-2.55 (3H, m), 2.75 (1H, dt, J=7.5, 15.8 Hz), 3.58 (1H, dd, J=3.4, 10.2 Hz), 3.75-3.83 (3H, m), 4.03-4.11 (3H, m), 4.38 (1H, d, J=5.8 Hz), 5.22 (1H, d, J=5.6 Hz), 5.37-5.42 (1H, m), 7.74-7.78 (1H, m), 7.79-7.86 (2H, m), 8.09-8.14 (1H, m).

MS (FAB$^+$) m/z: 604 (M$^+$+1).

(vi) Methyl 6-N-((2S,5S)-5-propyl-2-azepanecarbonyl)-1-thio-α-lincosamide

4-Bromobenzenethiol (413.4 mg, 2.19 mmol) was added to a solution of 660 mg (1.09 mmol) of the title compound produced in step (v) of Example 47 in N,N-dimethylformamide (5 ml), and the mixture was cooled to 0° C. 1,3,4,6,7,8-Hexahydro-1-methyl-2H-pyrimido[1,2-a]pyrimidine was added thereto, and the mixture was stirred for 6 hr. The solvent was removed under the reduced pressure, and the residue was purified by column chromatography (hexane:ethyl acetate=1:1, chloroform:methanol=10:1). Raney nickel (1 g) was added to a solution of 475 mg of the crude product in methanol (5 ml), and the mixture was stirred under a hydrogen atmosphere for 37 hr. The reaction solution was filtered through Celite, and the filtrate was concentrated under the reduced pressure, and the residue was purified by column chromatography on silica gel (chloroform:methanol:28% aqueous ammonia=20:1:0.1) to give 130 mg (yield 28%) of the title compound.

$^1$H-NMR (400 MHz, CD$_3$OD) δ: 0.90 (3H, t, J=7.3 Hz), 1.18 (3H, d, J=6.6 Hz), 1.19-1.42 (7H, m), 1.61-1.71 (1H, m), 1.80-1.86 (1H, m), 1.95-2.03 (2H, m), 2.08 (3H, s), 2.74-2.82 (1H, m), 3.03 (1H, ddd, J=2.4, 5.6, 14.2 Hz), 3.57 (1H, dd, J=3.4, 10.2 Hz), 3.59 (1H, t, J=5.6 Hz), 3.96 (1H, d, J=2.7 Hz), 4.06 (1H, q, J=6.4 Hz), 4.10 (1H, dd, J=5.6, 10.2 Hz), 4.18 (1H, dd, J=6.3, 7.8 Hz), 4.24 (1H, d, J=7.8 Hz), 5.24 (1H, d, J=5.4 Hz).

MS (FAB$^+$) m/z: 421 (M$^+$+1).

(vii) Methyl 7-acetylthio-7-deoxy-7-epi-6-N-((2S,5S)-1-N-tert-butoxycarbonyl-5-propyl-2-azepanecarbonyl)-2,3,4-tri-o-trimethylsilyl-1-thio-α-lincosamide Lithium hydroxide monohydrate (16.5 mg, 0.393 mmol) was added to a solution of 110 mg (0.262 mmol) of the title compound produced in step (vi) of Example 47 in 1,4-dioxane:water=4:1 (5.5 ml), and the mixture was stirred at room temperature for 5 min. Tert-butyl dicarbonate was added thereto, and the mixture was stirred at room temperature for 1 hr. A saturated aqueous sodium hydrogencarbonate solution was added thereto, and the mixture was extracted with ethyl acetate. The extract was dried over anhydrous sodium sulfate and was then filtered. The filtrate was concentrated under the reduced pressure, and the residue was dried to give methyl 6-N-((2S,5S)-1-N-tert-butoxycarbonyl-5-propyl-2-azepanecarbonyl)-1-thio-α-lincosamide as a crude product. Methyl 6-N-((2S,5S)-1-N-tert butoxycarbonyl-5-propyl-2-azepanecarbonyl)-2,3,4-tri-o-trimethylsilyl-1-thio-α-lincosamide was produced in the same manner as in step (i) of Example 1, except that this crude product, 0.166 ml (1.31 mmol) of trimethylsilyl chloride, 0.275 mol (1.31 mmol) of hexamethyldisilazane, pyridine (5.5 ml), methanol (5.5 ml), and 0.171 ml (0.341 mmol) of a 2 N aqueous acetic acid solution were used. Methyl 6-N-((2S,5S)-1-N-tert-butoxycarbonyl-5-propyl-2-azepanecarbonyl)-7-o-methylsulfonyl-2,3,4-tri-o-trimethylsilyl-1-thio-α-lincosamide was produced in the same manner as in step (i) of Example 2, except that this crude product, 0.182 ml (1.31 mmol) of triethylamine, 0.082 ml (1.05 mmol) of methanesulfonyl chloride, and chloroform (3.0 ml) were used. The title compound (96 mg, 46%) was produced in the same manner as in step (i) of Example 3, except that this crude product, 181.3 mg (1.59 mmol) of potassium thioacetate, and N,N-dimethylformamide (1.5 ml) were used.

$^1$H-NMR (400 MHz, CDCl$_3$) δ: −0.0043 (9H, s), 0.00 (9H, s), 0.042 (9H, s), 0.76 (3H, t, J=6.9 Hz), 1.06-1.23 (9H, m), 1.35-1.38 (1H, m), 1.38 (9H, s), 1.50-1.80 (4H, m), 1.85 (3H, s), 2.16 (3H, s), 2.70-2.95 (1H, m), 3.35-3.45 (2H, m), 3.58-4.20 (4H, m), 4.25-4.50 (2H, m), 5.02 (1H, d, J=5.6 Hz), 6.16 (1H, brd).

MS (FAB$^+$) m/z: 795 (M$^+$+1).

(viii) Methyl 6-N-((2S,5S)-1-N-tertbutoxycarbonyl-5-propyl-2-azepanecarbonyl)-7-deoxy-7-epi-7-mercapto-1-thio-α-lincosamide 1 N hydrochloric acid (0.424 ml, 0.424 mmol) was added to a solution of 96 mg (0.121 mmol) of the title compound produced in step (vii) of Example 47 in methanol (2.0 ml), and the mixture was stirred at room temperature for 40 min. The reaction solution was concentrated under the reduced pressure, and the residue was dried. A solution (0.03 ml) of 4.1 N sodium methoxide in methanol was added to a solution of the crude product in methanol (2 ml), and the mixture was stirred at room temperature for 30 min. A saturated aqueous sodium hydrogencarbonate solution was added thereto, and the mixture was extracted with ethyl acetate. The extract was dried over anhydrous sodium sulfate and was then filtered. The filtrate was concentrated under the reduced pressure, and the residue was purified by column chromatography on silica gel (chloroform:methanol:28% aqueous ammonia=20:1:0.1) to give 40 mg (yield 62%) of the title compound.

$^1$H-NMR (400 MHz, CD$_3$OD) δ: 0.91 (3H, t, J=6.8 Hz), 1.24-1.35 (8H, m), 1.45-1.50 (1H, m), 1.48 (9H, s), 1.60-1.75 (3H, m), 1.90-2.05 (2H, m), 2.15 (3H, s), 3.45-3.59 (3H, m), 3.80-3.90 (1H, m), 4.02-4.15 (2H, m), 4.24-4.34 (1H, m), 4.36-4.32 (2H, m), 5.24 (1H, d, J=5.6 Hz).

MS (ESI$^+$) m/z: 537 (M$^+$+1).

(ix) Methyl 6-N-((2S,5S)-1-N-tert-butoxycarbonyl-5-propyl-2-azepanecarbonyl)-7-deoxy-7-epi-7-(4-(morpholinocarbonyl)phenylthio)-1-thio-α-lincosamide The title compound (6.1 mg, yield 45%) was produced in the same manner as in step (v) of Example 3, except that 10 mg (0.0186 mmol) of the title compound produced in step (viii) of Example 47, 7.5 mg (0.0279 mmol) of the title compound produced in step (i) of Reference Example 8, 2.2 mg (0.00372 mmol) of 4,5-bis(diphenylphosphino)-9,9-dimethylsantene, 1.7 mg (0.00186 mmol) of tris(dibenzylideneacetone)dipalladium, 0.0065 ml (0.037 mmol) of diisopropylethylamine, and 1,4-dioxane (0.2 ml) were used.

$^1$H-NMR (400 MHz, CD$_3$OD) δ: 0.91 (3H, t, J=6.8 Hz), 1.28-1.39 (9H, m), 1.49 (9H, s), 1.59-1.75 (2H, m), 1.86-2.04 (5H, s), 3.45-3.80 (9H, m), 3.80-4.12 (3H, m), 4.35-4.56 (3H, m), 5.24 (1H, d, J=5.3 Hz), 7.38 (2H, d, J=8.3 Hz), 7.46 (2H, d, J=8.3 Hz).

MS (ESI$^+$) m/z: 726 (M$^+$+1).

(x) Methyl 7-deoxy-7-epi-7-(4-(morpholinocarbonyl)phenylthio)-6-N-((2S,5S)-5-propyl-2-azepanecarbonyl)-1-thio-α-lincosamide Compound 519

The title compound (5.2 mg, yield 99%) was produced in the same manner as in step (v) of Example 16, except that 6.1 mg (0.0084 mmol) of the title compound produced in step (ix) of Example 47 and 0.1 ml of trifluoroacetic acid were used.

$^1$H-NMR (400 MHz, CD$_3$OD) δ: 0.90 (3H, t, J=7.2 Hz), 1.20-1.40 (9H, m), 1.43-1.53 (1H, m), 1.63-1.77 (1H, m), 1.85-1.89 (1H, m), 1.90 (3H, s), 1.97-2.05 (2H, m), 2.71-2.82 (1H, m), 3.05-3.15 (1H, m), 3.40-3.80 (10H, m), 3.82-3.85 (1H, m), 3.91-3.99 (1H, qd, J=7.0, 2.7 Hz), 4.08 (1H, q, J=5.6 Hz), 4.36 (1H, d, J=9.8 Hz), 4.52 (1H, dd, J=9.8, 2.7 Hz), 5.25 (1H, d, J=5.6 Hz), 7.38 (2H, ddd, J=8.6, 1.9, 1.9 Hz), 7.46 (2H, ddd, J=8.6, 1.9, 1.9 Hz).

MS (FAB$^+$) m/z: 626 (M$^+$+1).

(xi) Methyl 7-deoxy-7-epi-7-(4-(morpholinocarbonyl)phenylthio)-6-N-((2S,5S)—N-methyl-5-propyl-2-azepanecarbonyl)-1-thio-α-lincosamide Compound 520

The title compound (2.3 mg, yield 43%) was produced in the same manner as in step (i) of Example 21, except that 5.2 mg (0.00831 mmol) of the title compound produced in step (x) of Example 47, 2.1 mg (0.0249 mmol) of a 36% aqueous formaldehyde solution, 10.6 mg (0.0498 mmol) of sodium boron triacetoxyhydride, 0.00142 ml (0.0249 mmol) of acetic acid, and methanol (0.1 ml) were used.

$^1$H-NMR (400 MHz, CD$_3$OD) δ: 0.90 (3H, t, J=7.1 Hz), 1.19-1.50 (11H, m), 1.63-1.76 (1H, m), 1.86-2.05 (4H, m), 2.05-2.2 (1H, m), 2.42-2.58 (3H, brs), 2.80-3.05 (2H, m), 3.29-3.32 (1H, m), 3.40-3.80 (9H, m), 3.85-3.90 (1H, m), 3.94-4.10 (1H, m), 4.1 (1H, dd, J=5.6 Hz, J=10.3 Hz), 4.32-4.39 (1H, m), 4.42-4.54 (1H, m), 5.25 (1H, d, J=5.6 Hz), 7.40 (2H, d, J=8.5, Hz), 7.50 (2H, d, J=8.5 Hz).

MS (ESI$^+$) m/z: 640 (M$^+$+1).

Compounds shown in Tables 22 to 53 may be mentioned as specific examples of compounds according to the present invention.

Test Example 1

Antimicrobial Activity

For representative compounds among lincomycin derivatives according to the present invention, the minimal inhibitory concentration (MIC, μg/ml) against various pneumococci was measured according to the method described in CHEMOTHERAPY, vol. 16, No. 1, 99, 1968. The results are shown in Table 1. Sensitivity disk agar-N+5% horse blood was used as the medium for the measurement. The amount of bacteria inoculated was 10$^6$ CFU/ml. In Table 1, CLDM represents clindamycin.

TABLE 1

| | Example No. | | | | | | | | | |
|---|---|---|---|---|---|---|---|---|---|---|
| | 170 | 191 | 195 | 228 | 235 | 304 | 364 | 396 | 446 | CLDM |
| S. pneumoniae DPI Type | 0.13 | 0.015 | 0.06 | 0.13 | 0.015 | 0.13 | 0.13 | 0.015 | 0.03 | 0.13 |
| S. pneumoniae IP692 | 0.13 | 0.015 | 0.03 | 0.06 | 0.015 | 0.13 | 0.13 | 0.008 | 0.03 | 0.13 |
| S. pneumoniae 1913 | 0.13 | 0.015 | 0.13 | 0.13 | 0.03 | 0.13 | 0.13 | 0.008 | 0.03 | 256 |
| S. pneumoniae 1820 | 8 | 4 | 16 | 4 | 8 | 4 | 4 | 16 | 4 | 256 |
| S. pneumoniae 225 | 128 | 32 | 64 | 16 | 32 | 16 | 4 | >128 | 64 | 256 |
| S. pneumoniae PRC-206 | 16 | 8 | 64 | 4 | 4 | 4 | 4 | 64 | 8 | 256 |
| S. pneumoniae TH-662 | 8 | ND | 8 | 2 | 1 | 2 | 2 | 8 | 2 | 256 |
| S. pneumoniae PRC0-91 | 8 | 2 | 8 | 2 | ND | 2 | ND | 4 | 4 | 256 |
| S. pneumoniae PRC-53 | 0.13 | 0.03 | 0.06 | 0.06 | 0.03 | 0.13 | 0.03 | 0.015 | 0.015 | 0.13 |
| S. pneumoniae TH-96 | 0.13 | 0.03 | 0.06 | ND | 0.03 | 0.13 | 0.06 | 0.015 | 0.015 | 0.13 |

The lincomycin derivatives of general formula (I) according to the present invention demonstrated potent antimicrobial activity against resistant pneumococci.

TABLE 2

| Compound No. | Compound name | NMR data δ (ppm) from TMS | Solvent/Hz | MS (FAB+) |
|---|---|---|---|---|
| 1 | 7-(6-Aminobenzo[d]thiazol-2-ylthio)-7-deoxy-7-epilincomycin | 2.04 (3H, s), 2.17 (3H, s), 5.34 (1H, d, J=5.4 Hz), 6.81 (1H, dd, J=2.4, 8.7 Hz), 7.02 (1H, d, J=2.4 Hz), 7.70 (1H, d, J=8.7 Hz) | CDCl$_3$ (300 MHz) | 571 (M$^+$ + 1) |
| 2 | 7-(5-Chlorobenzo[d]thiazol-2-ylthio)-7-deoxy-7-epilincomycin | 2.02 (3H, s), 2.33 (3H, s), 5.34 (1H, d, J=5.4 Hz), 7.25 (1H, dd, J=2.4, 8.7 Hz), 7.68 (1H, d, J=8.7 Hz), 7.93 (1H, d, J=2.4 Hz) | CDCl$_3$ (300 MHz) | 591 (M$^+$ + 1) |
| 3 | 7-Deoxy-7-epi-7-(6-fluorobenzo-[d]thiazol-2-ylthio)-lincomycin | 2.17 (3H, s), 2.33 (3H, s), 5.33 (1H, d, J=5.4 Hz), 7.09 (1H, dt, J=2.4, 8.7 Hz), 7.43 (1H, dd, J=5.1, 8.7 Hz), 7.84 (1H, dd, J=2.4, 8.7 Hz) | CDCl$_3$ (300 MHz) | 574 (M$^+$ + 1) |
| 4 | 7-Deoxy-7-epi-7-(5-nitrobenzo-[d]thiazol-2-ylthio)lincomycin | 1.99 (3H, s), 2.39 (3H, s), 5.34 (1H, d, J=5.7 Hz), 7.91 (1H, d, J=9.0 Hz), 8.24 (1H, dd, J=2.4, 9.0 Hz), 8.76 (1H, d, J=2.4 Hz) | CDCl$_3$ (300 MHz) | 601 (M$^+$ + 1) |
| 5 | 7-(6-Cyanobenzo[d]thiazol-2-ylthio)-7-deoxy-7-epilincomycin | 1.92 (3H, s), 2.38 (3H, s), 5.34 (1H, d, J=5.4 Hz), 7.71 (1H, dd, J=2.4, 8.4 Hz), 7.96 (1H, d, J=8.4 Hz), 8.10 (1H, d, J=2.4 Hz) | CDCl$_3$ (300 MHz) | 601 (M$^+$ + 1) |
| 6 | 7-(6-(Benzhydryloxycarbonyl)-benzo[d]thiazol-2-ylthio)-7-deoxy-7-epilincomycin | 1.98 (3H, s), 2.37 (3H, s), 5.34 (1H, d, J=5.7 Hz), 7.18 (1H, s), 7.25-7.45 (8H, m), 7.84 (1H, d, J=9.0 Hz), 8.11 (1H, d, J=9.0 Hz), 8.66 (1H, s) | CDCl$_3$ (300 MHz) | 767 (M$^+$ + 1) |
| 7 | 7-Deoxy-7-epi-7-(6-(ethylamino)-benzo[d]thiazol-2-ylthio)-lincomycin | 1.29 (1H, t, J=7.2 Hz), 2.04 (3H, s), 2.31 (3H, s), 3.63 (2H, q, J=7.1 Hz), 5.29 (1H, d, J=5.6 Hz), 6.82 (1H, dd, J=2.3, 8.9 Hz), 6.95 (1H, d, J=2.5 Hz), 7.65 (1H, t, J=5.0 Hz) | CDCl$_3$ (300 MHz) | 599 (M$^+$ + 1) |
| 8 | 7-Deoxy-7-epi-7-(6-nitrobenzo-[d]thiazol-2-ylthio)lincomycin | 1.91 (3H, s), 2.39 (3H, s), 5.33 (1H, d, J=5.4 Hz), 7.97 (1H, d, J=9.0 Hz), 8.34 (1H, dd, J=2.4, 9.0 Hz), 8.71 (1H, d, J=2.4 Hz) | CDCl$_3$ (300 MHz) | 601 (M$^+$ + 1) |
| 9 | 7-Deoxy-7-epi-7-(5-nitrobenzo-[d]oxazol-2-ylthio)lincomycin | 2.00 (3H, s), 2.43 (3H, s), 5.33 (1H, d, J=5.4 Hz), 7.67 (1H, d, J=8.7 Hz), 8.30 (1H, dd, J=1.8, 9.0 Hz), 8.36 (1H, d, J=1.8 Hz) | CDCl$_3$ (300 MHz) | 585 (M$^+$ + 1) |

TABLE 2-continued

| Compound No. | Compound name | NMR data δ (ppm) from TMS | Solvent/Hz | MS (FAB+) |
|---|---|---|---|---|
| 10 | 7-Deoxy-7-epi-7-(6-nitrobenzo-[d]thiazol-2-ylthio)lincomycin | 2.01 (3H, s), 2.43 (3H, s), 5.33 (1H, d, J=5.4 Hz), 7.67 (1H, d, J=8.7 Hz), 8.30 (1H, dd, J=2.1, 8.7 Hz), 8.37 (1H, d, J=2.1 Hz) | CDCl₃ (300 MHz) | 585 (M⁺ + 1) |
| 11 | 7-(5-Amino-1,3,4-thiadiazol-2-ylthio)-7-deoxy-7-epilincomycin | 2.10 (3H, s), 2.95 (3H, s), 5.35 (1H, d, J=5.7 Hz) | CDCl₃ (300 MHz) | 522 (M⁺ + 1) |
| 12 | 7-Deoxy-7-epi-7-(5-methylamino-1,3,4-thiadiazol-2-ylthio)-lincomycin | 2.18 (3H, s), 2.32 (3H, s), 3.03 (3H, s), 5.35 (1H, d, J=5.4 Hz) | CDCl₃ (300 MHz) | 536 (M⁺ + 1) |
| 13 | 7-Deoxy-7-epi-7-(5-methyl-carbamoyl-1,3,4-thiadiazol-2-ylthio)lincomycin | 2.07 (3H, s), 2.47 (3H, s), 3.06 (3H, d, J=5.4 Hz), 5.33 (1H, d, J=5.4 Hz), 7.24 (1H, d, J=5.4 Hz) | CDCl₃ (300 MHz) | 564 (M⁺ + 1) |
| 14 | 7-(5-Carbamoyl-1,3,4-thiadiazol-2-ylthio)-7-deoxy-7-epilincomycin | 2.10 (3H, s), 2.41 (3H, s), 5.34 (1H, d, J=5.4 Hz) | CDCl₃ (300 MHz) | 550 (M⁺ + 1) |
| 15 | 7-Deoxy-7-(5-(dimethylcarbamoyl)-1,3,4-thiadiazol-2-ylthio)-7-epilincomycin | 2.12 (3H, s), 2.18 (3H, s), 3.18 (3H, s), 3.59 (3H, s), 5.33 (1H, d, J=5.4 Hz) | CDCl₃ (300 MHz) | 578 (M⁺ + 1) |
| 16 | 7-Deoxy-7-epi-7-(5-(4-nitrophenyl)-1,3,4-thiadiazol-2-ylthio)lincomycin | 2.05 (3H, s), 2.33 (3H, s), 5.26 (1H, d, J=5.4 Hz), 7.99 (2H, d, J=9.0 Hz), 8.27 (2H, d, J=9.0 Hz) | CDCl₃ (300 MHz) | 628 (M⁺ + 1) |
| 17 | 7-Deoxy-7-epi-7-(5-phenyl-1,3,4-thiadiazol-2-ylthio)lincomycin | 2.13 (3H, s), 2.39 (3H, s), 5.34 (1H, d, J=5.4 Hz), 7.45-7.60 (3H, m), 7.85-7.80 (2H, m) | CDCl₃ (300 MHz) | 583 (M⁺ + 1) |
| 18 | 7-(5-(2-Aminoethylthio)-1,3,4-thiadiazol-2-ylthio)-7-deoxy-7-epilincomycin | 2.00 (3H, s) 2.96 (3H, s), 5.37 (1H, d, J=5.4 Hz) | CDCl₃ (300 MHz) | 581 (M⁺ + 1) |
| 19 | 7-Deoxy-7-epi-7-(5-(quinolin-3-yl)-1,3,4-thiadiazol-2-ylthio)-lincomycin | 2.20 (3H, s), 2.43 (3H, s), 5.36 (1H, d, J=5.4 Hz), 7.67 (1H, t, J=8.7 Hz), 7.84 (1H, t, J=8.7 Hz), 7.98 (1H, d, J=8.7 Hz), 8.19 (1H, d, J=8.7 Hz), 8.60 (1H, s), 9.47 (1H, s) | CDCl₃ (300 MHz) | 634 (M⁺ + 1) |
| 20 | 7-Deoxy-7-epi-7-(5-(pyridin-2-yl)-1,3,4-thiadiazol-2-ylthio)-lincomycin | 2.15 (3H, s), 2.40 (3H, s), 5.35 (1H, d, J=5.4 Hz), 7.40 (1H, t, J=5.7 Hz), 7.87 (1H, t, J=8.1 Hz), 8.28 (1H, d, J=8.1 Hz), 8.64 (1H, s) | CDCl₃ (300 MHz) | 584 (M⁺ + 1) |
| 21 | 7-Deoxy-7-epi-7-(5-(pyridin-4-yl)-1,3,4-thiadiazol-2-ylthio)-lincomycin | 2.15 (3H, s), 2.50 (3H, s), 5.36 (1H, d, J=5.4 Hz), 7.76 (2H, d, J=5.1 Hz), 7.58 (2H, d, J=5.1 Hz) | CDCl₃ (300 MHz) | 584 (M⁺ + 1) |
| 22 | 7-Deoxy-7-epi-7-(5-(pyridin-3-yl)-1,3,4-thiadiazol-2-ylthio)lincomycin | 2.10 (3H, s), 2.33 (3H, s), 5.38 (1H, d, J=5.7 Hz), 7.40 (1H, t, J=5.1 Hz), 8.16 (1H, d, J=8.1 Hz), 8.67 (1H, d, J=5.1 Hz), 8.98 (1H, d, J=8.1 Hz) | CDCl₃ (300 MHz) | 584 (M⁺ + 1) |

TABLE 3

| Compound No. | Compound name | NMR data δ (ppm) from TMS | Solvent/Hz | MS (FAB+) |
|---|---|---|---|---|
| 23 | 7-Deoxy-7-epi-7-(5-(2-nitrophenyl)-1,3,4-thiadiazol-2-ylthio)lincomycin | 2.19 (3H, s), 2.39 (3H, s), 5.35 (1H, d, J=5.4 Hz), 7.65-7.80 (3H, m), 8.02 (1H, d, J=5.7 Hz) | CDCl₃ (300 MHz) | 628 (M⁺ + 1) |
| 24 | 7-Deoxy-7-epi-7-(5-(3-nitrophenyl)-1,3,4-thiadiazol-2-yl thio)lincomycin | 2.17 (3H, s), 2.42 (3H, s), 5.36 (1H, d, J=5.1 Hz), 7.72 (1H, t, J=8.1 Hz), 8.26 (1H, d, J=8.1 Hz), 8.38 (1H, d, J=8.1 Hz), 8.71 (1H, s) | CDCl₃ (300 MHz) | 628 (M⁺ + 1) |
| 25 | 7-Deoxy-7-epi-7-(5-(naphthalen-2-yl)-1,3,4-thiadiazol-2-ylthio)-lincomycin | 2.19 (3H, s), 2.41 (3H, s), 5.37 (1H, d, J=5.4 Hz), 7.55-7.65 (2H, m), 7.85-8.10 (4H, m), 8.31 (1H, s) | CDCl₃ (300 MHz) | 633 (M⁺ + 1) |
| 26 | 7-Deoxy-7-epi-7-(5-(thiophen-2-yl)-1,3,4-thiadiazol-2-ylthio)lincomycin | 2.17 (3H, s), 2.37 (3H, s), 5.35 (1H, d, J=5.4 Hz), 7.15-7.20 (1H, m), 7.50-7.55 (2H, m) | CDCl₃ (300 MHz) | 589 (M⁺ + 1) |
| 27 | 7-Deoxy-7-(5-(3,5-diaminophenyl)-1,3,4-thiadiazol-2-ylthio)-7-epilincomycin | 2.15 (3H, s), 2.73 (3H, s), 5.34 (1H, d, J=5.1 Hz), 6.13 (1H, s), 6.63 (1H, s) | CDCl₃ (300 MHz) | 613 (M⁺ + 1) |
| 28 | 7-Deoxy-7-(5-(3,4-diaminophenyl)-1,3,4-thiadiazol-2-ylthio)-7-epilincomycin | 2.12 (3H, s), 2.36 (3H, s), 5.33 (1H, d, J=5.7 Hz), 6.73 (1H, d, J=8.1 Hz), 7.17 (1H, d, J=8.1 Hz), 7.32 (1H, s) | CDCl₃ (300 MHz) | 613 (M⁺ + 1) |

TABLE 3-continued

| | | | | |
|---|---|---|---|---|
| 29 | 7-Deoxy-7-epi-7-(5-(5-nitrofuran-2-yl)-1,3,4-thiadiazol-2-ylthio)-lincomycin | 2.14 (3H, s), 2.41 (3H, s), 5.35 (1H, d, J=5.1 Hz), 7.29 (1H, t, J=3.9 Hz), 7.48 (1H, d, J=3.9 Hz) | $CDCl_3$ (300 MHz) | 618 ($M^+$ + 1) |
| 30 | 7-Deoxy-7-epi-7-(5-(5-methyl-aminothiazol-4-yl)-1,3,4-thiadiazol-2-ylthio)lincomycin | 2.13 (3H, s), 2.35 (3H, s), 3.17 (3H, d, J=5.1 Hz), 5.35 (1H, d, J=5.7 Hz), 7.56 (1H, d, J=5.1 Hz), 8.03 (1H, s) | $CDCl_3$ (300 MHz) | 619 ($M^+$ + 1) |
| 31 | 7-Deoxy-7-epi-7-(5-(furan-2-yl)-1,3,4-thiadiazol-2-ylthio)-lincomycin | 2.06 (3H, s), 2.27 (3H, s), 5.25 (1H, d, J=5.4 Hz), 6.50 (1H, d, J=3.3 Hz), 7.06 (1H, d, J=3.3 Hz), 7.51 (1H, s) | $CDCl_3$ (300 MHz) | 753 ($M^+$ + 1) |
| 32 | 7-(5-(2-Aminothiazol-4-yl)-1,3,4-thiadiazol-2-ylthio)-7-deoxy-7-epilincomycin | 2.03 (3H, s), 2.27 (3H, s), 5.24 (1H, d, J=5.4 Hz), 7.28 (1H, s) | $CDCl_3$ (300 MHz) | 605 ($M^+$ + 1) |
| 33 | 7-(5-(5-Amino-1-methyl-1H-pyrazol-4-yl)-1,3,4-thiadiazol-2-ylthio)-7-deoxy-7-epilincomycin | 2.07 (3H, s), 2.22 (3H, s), 3.62 (3H, s), 5.26 (1H, d, J=5.4 Hz), 7.38 (1H, s) | $CDCl_3$ (300 MHz) | 602 ($M^+$ + 1) |
| 34 | 7-(5-(2-Cyanophenyl)-1,3,4-thiadiazol-2-ylthio)-7-deoxy-7-epilincomycin | 1.98 (3H, s), 2.20 (3H, s), 3.62 (3H, s), 5.14 (1H, d, J=5.4 Hz), 7.60-7.75 (2H, m), 7.75-7.85 (2H, m) | $CDCl_3$ (300 MHz) | 608 ($M^+$ + 1) |
| 35 | 7-(5-(3-Aminothiophen-2-yl)-1,3,4-thiodiazol-2-ylthio)-7-deoxy-7-epilincomycin | 2.03 (3H, s), 2.98 (3H, s), 5.38 (1H, d, J=5.4 Hz), 6.78 (1H, d, J=5.4 Hz), 7.45 (1H, d, J=5.4 Hz) | DCl (300 MHz) | 604 ($M^+$ + 1) |
| 36 | 7-Deoxy-7-epi-7-(5-(1,2,3-thiadiazol-4-yl)-1,3,4-thiadiazol-2-ylthio)lincomycin | 2.01 (3H, s), 3.01 (3H, s), 5.36 (1H, d, J=5.7 Hz), 9.66 (1H, s) | DCl (300 MHz) | 591 ($M^+$ + 1) |
| 37 | 7-(5-(2-Chlorophenyl)-1,3,4-thiadiazol-2-ylthio)-7-deoxy-7-epilincomycin | 2.08 (3H, s), 2.39 (3H, s), 5.27 (1H, d, J=5.4 Hz), 7.25-7.55 (4H, m) | $CDCl_3$ (300 MHz) | 618 ($M^+$ + 1) |
| 38 | 7-Deoxy-7-epi-7-(5-(2-methyl-thiophenyl)-1,3,4-thiadiazol-2-ylthio)lincomycin | 2.00 (3H, s), 2.23 (3H, s), 3.03 (3H, s), 5.42 (1H, d, J=5.1 Hz), 7.10-7.40 (4H, m) | DCl (300 MHz) | 629 ($M^+$ + 1) |
| 39 | 7-Deoxy-7-epi-7-(5-(2-methyl-sulfonylphenyl)-1,3,4-thiadiazol-2-ylthio)lincomycin | 2.00 (3H, s), 2.84 (3H, s), 3.02 (3H, s), 5.41 (1H, d, J=5.1 Hz), 7.40-7.85 (4H, m) | DCl (300 MHz) | 661 ($M^+$ + 1) |
| 40 | 7-Deoxy-7-epi-7-(5-(2-methoxy-phenyl)-1,3,4-thiadiazol-2-ylthio)-lincomycin | 1.99 (3H, s), 3.01 (3H, s), 3.73 (3H, s), 5.41 (1H, d, J=5.1 Hz), 6.85-7.30 (4H, m) | $CDCl_3$ (300 MHz) | 613 ($M^+$ + 1) |
| 41 | 7-Deoxy-7-epi-7-(5-(pyrazin-2-yl)-1,3,4-thiadiazol-2-ylthio)lincomycin | 2.15 (3H, s), 2.42 (3H, s), 5.35 (1H, d, J=5.4 Hz), 7.96 (1H, d, J=2.4 Hz), 9.00 (1H, d, J=2.4 Hz), 9.52 (1H, s) | $CDCl_3$ (300 MHz) | 585 ($M^+$ + 1) |
| 42 | 7-(5-(3-Aminopyrazin-2-yl)-1,3,4-thiadiazol-2-ylthio)-7-deoxy-7-epilincomycin | 2.12 (3H, s), 2.41 (3H, s), 5.35 (1H, d, J=5.4 Hz), 7.96 (1H, d, J=2.4 Hz), 8.14 (1H, d, J=2.4 Hz) | $CDCl_3$ (300 MHz) | 600 ($M^+$ + 1) |
| 43 | 7-Deoxy-7-epi-7-(5-(2-fluoro-phenyl)-1,3,4-thiadiazol-2-ylthio)lincomycin | 2.17 (3H, s), 2.32 (3H, s), 5.35 (1H, d, J=5.7 Hz), 7.20-7.40 (2H, m), 7.45-7.60 (1H, m), 8.30-8.40 (1H, m) | $CDCl_3$ (300 MHz) | 600 ($M^+$ + 1) |
| 44 | 7-Deoxy-7-epi-7-(5-(4-methyl-1,2,3-thiadiazol-5-yl)-1,3,4-thiadiazol-2-ylthio)lincomycin | 2.13 (3H, s) 2.18 (3H, s), 2.99 (3H, s), 5.35 (1H, d, J=5.4 Hz) | $CDCl_3$ (300 MHz) | 605 ($M^+$ + 1) |

TABLE 4

| | | | | |
|---|---|---|---|---|
| 45 | 7-Deoxy-7-epi-7-(5-(2-(pyrrolidin-1-yl)ethylcarbamoyl)-1,3,4-thiadiazol-2-ylthio)lincomycin | 2.10 (3H, s), 2.40 (3H, s), 5.35 (1H, d, J=5.7 Hz) | $CDCl_3$ (300 MHz) | 647 ($M^+$ + 1) |
| 46 | 7-(5-(4-Chlorophenyl)-1,3,4-thiadiazol-2-ylthio)-7-deoxy-7-epilincomycin | 2.08 (3H, s), 2.37 (3H, s), 5.30 (1H, d, J=5.4 Hz), 7.52 (2H, d, J=8.7 Hz), 7.61 (2H, d, J=8.7 Hz) | $CDCl_3$ (300 MHz) | 618 ($M^+$ + 1) |
| 47 | 7-(5-(4-Chloro-2-nitrophenyl)-1,3,4-thiadiazol-2-ylthio)-7-deoxy-7-epilincomycin | 2.13 (3H, s), 2.39 (3H, s), 5.34 (1H, d, J=5.4 Hz), 7.45-7.55 (2H, m), 8.03 (1H, s) | $CDCl_3$ (300 MHz) | 663 ($M^+$ + 1) |
| 48 | 7-Deoxy-7-epi-7-(5-(2-methyl-phenyl)-1,3,4-thiadiazol-2-ylthio)-lincomycin | 2.10 (3H, s), 2.39 (3H, s), 2.42 (3H, s), 5.35 (1H, d, J=5.4 Hz), 7.15-7.35 (4H, m) | $CDCl_3$ (300 MHz) | 597 ($M^+$ + 1) |
| 49 | 7-Deoxy-7-(5-(4-difluoromethyl-thiophenyl)amino-1,3,4-thiadiazol-2-ylthio)-7-epilincomycin | 2.08 (3H, s), 2.34 (3H, s), 5.35 (1H, d, J=5.4 Hz), 5.36 (1H, d, J=5.4 Hz), 6.80 (1H, t, J=5.7 Hz), 7.46 (2H, d, J=8.4 Hz), 7.60 (2H, d, J=8.4 Hz) | $CDCl_3$ (300 MHz) | 597 ($M^+$ + 1) |
| 50 | 7-(5-(Carbamoylmethylthio)-1,3,4-thiadiazol-2-ylthio)-7-deoxy-7-epilincomycin | 2.18 (3H, s), 2.41 (3H, s), 5.31 (1H, d, J=5.4 Hz), 6.05-6.10 (1H, m), 6.45-6.50 (1H, m) | $CDCl_3$ (300 MHz) | 596 ($M^+$ + 1) |

TABLE 4-continued

| | | | | |
|---|---|---|---|---|
| 51 | 7-Deoxy-7-epi-7-(5-(4-fluoro-2-nitrophenyl)-1,3,4-thiadiazol-2-ylthio)-lincomycin | 2.18 (3H, s), 2.41 (3H, s), 5.35 (1H, d, J=6.0 Hz), 7.40-7.50 (1H, m), 7.70-7.80 (2H, m) | CDCl$_3$ (300 MHz) | 646 (M$^+$ + 1) |
| 52 | 7-Deoxy-7-epi-7-(5-ethoxy-carbonyl)-1,3,4-thiadiazol-2-ylthio)-lincomycin | 1.45 (3H, t, J=7.1 Hz), 2.10 (3H, s), 2.41 (3H, s), 4.45 (2H, q, J=7.1 Hz), 5.33 (1H, d, J=5.7 Hz) | CDCl$_3$ (300 MHz) | 579 (M$^+$ + 1) |
| 53 | 7-Deoxy-7-(5-(4,5-difluoro-2-nitro-phenyl)-1,3,4-thiadiazol-2-ylthio)-7-epilincomycin | 2.17 (3H, s), 2.40 (3H, s), 5.35 (1H, d, J=5.7 Hz), 7.63 (1H, t, J=8.4 Hz), 7.99 (1H, t, J=8.4 Hz) | CDCl$_3$ (300 MHz) | 597 (M$^+$ + 1) |
| 54 | 7-Deoxy-7-(5-(2,4-dinitrophenyl)-1,3,4-thiadiazol-2-ylthio)-7-epilincomycin | 2.16 (3H, s), 2.41 (3H, s), 5.35 (1H, d, J=5.4 Hz), 8.02 (1H, t, J=8.4 Hz), 8.58 (1H, t, J=8.4 Hz), 8.81 (1H, s) | CDCl$_3$ (300 MHz) | 673 (M$^+$ + 1) |
| 55 | 7-Deoxy-7-epi-7-(5-(2-methyl-aminophenyl)-1,3,4-thiadiazol-2-ylthio)lincomycin | 2.10 (3H, s), 2.17 (3H, s), 3.00 (3H, d, J=5.1 Hz), 5.35 (1H, d, J=5.4 Hz), 6.60-6.80 (2H, m), 7.25-7.45 (2H, m), 7.50 (1H, d, J=5.1 Hz) | CDCl$_3$ (300 MHz) | 612 (M$^+$ + 1) |
| 56 | 7-Deoxy-7-epi-7-(5-(5-fluoro-2-nitrophenyl)-1,3,4-thiadiazol-2-ylthio)lincomycin | 2.17 (3H, s), 2.41 (3H, s), 5.35 (1H, d, J=5.7 Hz), 7.40-7.50 (2H, m), 8.05-8.20 (1H, m) | CDCl$_3$ (300 MHz) | 646 (M$^+$ + 1) |
| 57 | 7-(5-(6-Cyano-2-nitrophenyl)-1,3,4-thiadiazol-2-ylthio)-7-deoxy-7-epilincomycin | 2.17 (3H, s), 2.44 (3H, s), 5.35 (1H, d, J=5.4 Hz), 7.97 (1H, t, J=5.0 Hz), 8.42 (1H, d, J=5.0 Hz), 8.53 (1H, d, J=5.0 Hz) | CDCl$_3$ (300 MHz) | 653 (M$^+$ + 1) |
| 58 | 7-Deoxy-7-epi-7-(5-(2-(methyl-sulfinyl)phenyl)-1,3,4-thiadiazol-2-ylthio)lincomycin | 1.55-1.62 (3H, m), 2.11-2.17 (3H, m), 2.42-2.48 (3H, m), 2.95-2.99 (3H, m), 5.31-5.34 (1H, m), 7.58-7.68 (2H, m), 7.75-7.82 (1H, m), 8.38-8.42 (1H, m) | CDCl$_3$ (300 MHz) | 645 (M$^+$ + 1) |
| 59 | 7-Deoxy-7-epi-7-(5-(5-methyl-2-nitrophenyl)-1,3,4-thiadiazol-2-ylthio)lincomycin | 2.17 (3H, s), 2.41 (3H, s), 2.51 (1H, s), 5.35 (1H, d, J=5.4 Hz), 7.40-7.55 (2H, m), 8.00-8.10 (1H, m) | CDCl$_3$ (300 MHz) | 612 (M$^+$ + 1) |
| 60 | 7-Deoxy-7-epi-7-(4-phenylthiazol-2-ylthio)lincomycin | 2.07 (3H, s), 2.25 (3H, s), 5.36 (1H, d, J=5.4 Hz), 7.30-7.45 (4H, m), 7.80-7.90 (2H, m) | CDCl$_3$ (300 MHz) | 582 (M$^+$ + 1) |
| 61 | 7-Deoxy-7-epi-7-(5-nitrothiazol-2-ylthio)lincomycin | 2.11 (3H, s), 2.40 (3H, s), 5.32 (1H, d, J=5.4 Hz), 8.31 (1H, s) | CDCl$_3$ (300 MHz) | 551 (M$^+$ + 1) |
| 62 | 7-Deoxy-7-epi-7-(4-ethoxy-carbonylthiazol-2-ylthio)lincomycin | 1.33 (3H, t, J=6.9 Hz), 2.01 (3H, s), 2.28 (3H, s), 4.33 (2H, q, J=6.9 Hz), 5.27 (1H, d, J=5.7 Hz), 8.03 (1H, s) | CDCl$_3$ (300 MHz) | 578 (M$^+$ + 1) |
| 63 | 7-Deoxy-7-epi-7-(5-ethoxy-carbonylthiazol-2-ylthio)lincomycin | 1.30 (3H, t, J=6.9 Hz), 2.07 (3H, s), 2.29 (3H, s), 4.29 (2H, q, J=6.9 Hz), 5.25 (1H, d, J=5.4 Hz), 8.10 (1H, s) | CDCl$_3$ (300 MHz) | 578 (M$^+$ + 1) |
| 64 | 7-Deoxy-7-epi-7-(5-(pyridin-2-ylthio)thiazol-2-ylthio)lincomycin | 2.19 (3H, s), 2.34 (3H, s), 5.35 (1H, d, J=5.4 Hz), 7.00-7.15 (2H, m), 7.50-7.60 (1H, m), 7.76 (1H, s), 8.40-8.50 (1H, m) | CDCl$_3$ (300 MHz) | 615 (M$^+$ + 1) |
| 65 | 7-(4-Carbamoylthiazol-5-ylthio)-7-deoxy-7-epilincomycin | 1.91 (3H, s), 2.92 (3H, s), 5.31 (1H, d, J=5.4 Hz), 8.63 (1H, s) | CDCl$_3$ (300 MHz) | 549 (M$^+$ + 1) |
| 66 | 7-Deoxy-7-(4-(dimethylcarbamoyl)-thiazol-5-ylthio)-7-epilincomycin | 2.15 (3H, s), 2.31 (3H, s), 2.92 (3H, s), 5.35 (1H, d, J=5.4 Hz), 8.63 (1H, s) | CDCl$_3$ (300 MHz) | 576 (M$^+$ + 1) |

TABLE 5

| | | | | |
|---|---|---|---|---|
| 67 | 7-Deoxy-7-epi-7-(5-phenyl-1,3,4-oxadiazol-2-ylthio)lincomycin | 2.04 (3H, s), 2.93 (3H, s), 5.38 (1H, d, J=6.0 Hz), 7.45-7.65 (3H, m), 7.85-8.00 (2H, m) | CDCl$_3$ (300 MHz) | 567 (M$^+$ + 1) |
| 68 | 7-Deoxy-7-epi-7-(5-(pyridin-3-yl)-1,3,4-oxadiazol-2-ylthio)lincomycin | 2.19 (3H, s), 2.43 (3H, s), 5.35 (1H, d, J=5.4 Hz), 7.45 (1H, dd, J=5.7, 8.1 Hz), 8.31 (1H, d, J=8.1 Hz), 8.83 (2H, d, J=5.7 Hz) | CDCl$_3$ (300 MHz) | 568 (M$^+$ + 1) |
| 69 | 7-Deoxy-7-epi-7-(5-(pyridin-4-yl)-1,3,4-oxadiazol-2-ylthio)lincomycin | 2.18 (3H, s), 2.43 (3H, s), 5.35 (1H, d, J=5.4 Hz), 7.88 (2H, d, J=6.0 Hz), 8.83 (2H, t, J=6.0 Hz) | CDCl$_3$ (300 MHz) | 568 (M$^+$ + 1) |
| 70 | 7-Deoxy-7-epi-7-(5-(2,6-dichloropyridin-4-yl)-1,3,4-oxadiazol-2-ylthio)-7-epilincomycin | 2.23 (3H, s), 2.48 (3H, s), 5.40 (1H, d, J=5.4 Hz), 7.78 (2H, s) | CDCl$_3$ (300 MHz) | 637 (M$^+$ + 1) |
| 71 | 7-Deoxy-7-epi-7-(5-(5-methyl amino-thiazol-4-yl)-1,3,4-oxa diazol-2-ylthio)lincomycin | 2.14 (3H, s), 2.38 (3H, s), 3.25 (3H, d, J=5.1 Hz), 5.34 (1H, d, J=5.4 Hz), 7.00 (d, 1H, J=5.1 Hz), 8.03 (1H, s) | CDCl$_3$ (300 MHz) | 603 (M$^+$ + 1) |

TABLE 5-continued

| | | | | |
|---|---|---|---|---|
| 72 | 7-(5-(5-Amino-1-methyl-1H-pyrazol-4-yl)-1,3,4-oxadiazol-2-ylthio)-7-deoxy-7-epilincomycin | 2.06 (3H, s), 2.29 (3H, s), 3.62 (3H, s), 5.25 (1H, d, J=5.1 Hz), 7.52 (1H, s) | CDCl$_3$ (300 MHz) | 586 (M$^+$ + 1) |
| 73 | 7-(5-(3-Aminothiophen-2-yl)-1,3,4-oxadiazol-2-ylthio)-7-deoxy-7-epilincomycin | 2.09 (3H, s), 2.97 (3H, s), 5.37 (1H, d, J=5.7 Hz), 6.80 (1H, d, J=5.4 Hz), 7.57 (1H, d, J=5.4 Hz) | CDCl$_3$ (300 MHz) | 588 (M$^+$ + 1) |
| 74 | 7-(5-(3-Aminopyrazin-2-yl)-1,3,4-oxadiazol-2-ylthio)-7-deoxy-7-epilincomycin | 2.17 (3H, s), 2.43 (3H, s), 5.34 (1H, d, J=5.4 Hz), 8.06 (1H, d, J=2.4 Hz), 8.21 (1H, d, J=2.4 Hz) | CDCl$_3$ (300 MHz) | 584 (M$^+$ + 1) |
| 75 | 7-Deoxy-7-epi-7-(5-ethoxycarbonyl-4-methyl-4H-1,2,4-triazol-3-ylthio)lincomycin | 1.89 (3H, s), 2.26 (3H, s), 3.79 (3H, s), 3.84 (3H, s), 5.14 (1H, d, J=5.6 Hz) | CDCl$_3$ (300 MHz) | 582 (M$^+$ + 1) |
| 76 | 7-(5-(4-Chlorophenyl)-4-methyl-4H-1,2,4-triazol-3-ylthio)-7-deoxy-7-epilincomycin | 2.23 (3H, s), 2.35 (3H, s), 3.68 (3H, s), 5.35 (1H, d, J=5.4 Hz), 7.51 (2H, d, J=8.4 Hz), 7.60 (2H, d, J=8.4 Hz) | CDCl$_3$ (300 MHz) | 615 (M$^+$ + 1) |
| 77 | 7-Deoxy-7-epi-7-(4-ethyl-5-phenyl-4H-1,2,4-triazol-3-ylthio)-lincomycin | 1.33 (3H, t, J=6.9 Hz), 2.23 (3H, s), 2.39 (3H, s), 4.07 (2H, q, J=6.9 Hz), 5.35 (1H, d, J=5.4 Hz), 7.45-7.60 (5H, m) | CDCl$_3$ (300 MHz) | 594 (M$^+$ + 1) |
| 78 | 7-Deoxy-7-(4,5-diphenyl-4H-1,2,4-triazol-3-ylthio)-7-epilincomycin | 1.33 (3H, t, J=6.9 Hz), 2.23 (3H, s), 2.39 (3H, s), 4.07 (2H, q, J=6.9 Hz), 5.35 (1H, d, J=5.4 Hz), 7.45-7.60 (5H, m) | CDCl$_3$ (300 MHz) | 642 (M$^+$ + 1) |
| 79 | 7-Deoxy-7-epi-7-(4-ethyl-5-(4-fluoro-phenyl)-4H-1,2,4-triazol-3-ylthio)-lincomycin | 1.33 (3H, t, J=6.9 Hz), 2.24 (3H, s), 2.39 (3H, s), 4.07 (2H, q, J=6.9 Hz), 5.36 (1H, d, J=5.4 Hz), 7.20-7.35 (2H, m), 7.60-7.75 (2H, m) | CDCl$_3$ (300 MHz) | 612 (M$^+$ + 1) |
| 80 | 7-(5-(3-Chlorophenyl)-4-phenyl-4H-1,2,4-triazol-3-ylthio)-7-deoxy-7-epilincomycin | 2.09 (3H, s), 2.41 (3H, s), 5.28 (1H, d, J=5.4 Hz), 7.15-7.40 (5H, m), 7.51 (2H, d, J=8.4 Hz), 7.60 (2H, d, J=8.4 Hz) | CDCl$_3$ (300 MHz) | 676 (M$^+$ + 1) |
| 81 | 7-Deoxy-7-epi-7-(5-phenyl-4H-1,2,4-triazol-3-ylthio)lincomycin | 2.23 (3H, s), 2.39 (3H, s), 5.35 (1H, d, J=5.4 Hz), 7.45-7.60 (5H, m) | CDCl$_3$ (300 MHz) | 566 (M$^+$ + 1) |
| 82 | 7-(4-Amino-5-phenyl-4H-1,2,4-triazol-3-ylthio)-7-deoxy-7-epilincomycin | 2.23 (3H, s), 2.39 (3H, s), 5.35 (1H, d, J=5.4 Hz), 7.35-7.45 (3H, m), 7.50-7.60 (2H, s) | CDCl$_3$ (300 MHz) | 581 (M$^+$ + 1) |
| 83 | 7-(4-Amino-5-(pyridin-4-yl)-4H-1,2,4-triazol-3-ylthio)-7-deoxy-7-epilincomycin | 2.22 (3H, s), 2.40 (3H, s), 5.35 (1H, d, J=5.4 Hz), 7.68 (2H, d, J=6.0 Hz), 8.73 (2H, t, J=6.0 Hz) | CDCl$_3$ (300 MHz) | 582 (M$^+$ + 1) |
| 84 | 7-Deoxy-7-epi-7-(3-phenyl-1,2,4-thiadiazol-5-ylthio)lincomycin | 2.19 (3H, s), 2.38 (3H, s), 5.34 (1H, d, J=5.7 Hz), 7.40-7.50 (3H, m), 8.20-8.30 (2H, m) | CDCl$_3$ (300 MHz) | 583 (M$^+$ + 1) |
| 85 | 7-Deoxy-7-epi-7-(5-nitropyridin-2-ylthio)lincomycin | 2.03 (3H, s), 2.39 (3H, s), 5.32 (1H, d, J=5.1 Hz), 7.39 (1H, d, J=7.8 Hz), 8.28 (1H, d, J=7.8 Hz), 9.23 (1H, s) | CDCl$_3$ (300 MHz) | 545 (M$^+$ + 1) |
| 86 | 7-Deoxy-7-epi-7-(5-methoxy-carbonylpyridin-2-ylthio)lincomycin | 1.98 (3H, s), 2.41 (3H, s), 3.65 (3H, s), 5.32 (1H, d, J=5.4 Hz), 7.33 (1H, d, J=8.7 Hz), 8.09 (1H, d, J=8.7 Hz), 9.01 (1H, s) | CDCl$_3$ (300 MHz) | 545 (M$^+$ + 1) |
| 87 | 7-(5-(4-Chlorophenyl)pyrimidin-2-ylthio)-7-deoxy-7-epilincomycin | 1.95 (3H, s), 2.43 (3H, s), 5.34 (1H, d, J=5.4 Hz), 7.45-7.55 (4H, m), 7.65-7.75 (2H, m) | CDCl$_3$ (300 MHz) | 545 (M$^+$ + 1) |
| 88 | 7-(6-Chlorothiazolo[5,4-b]pyridin-2-ylthio)-7-deoxy-7-epilincomycin | 1.98 (3H, s), 2.39 (3H, s), 5.33 (1H, d, J=5.4 Hz), 8.11 (1H, d, J=1.5 Hz), 8.45 (1H, d, J=1.5 Hz) | CDCl$_3$ (300 MHz) | 592 (M$^+$ + 1) |

TABLE 6

| | | | | |
|---|---|---|---|---|
| 89 | 7-(7-Chlorothiazolo[5,4-d]-pyrimidin-2-ylthio)-7-deoxy-7-epilincomycin | 1.93 (3H, s), 2.40 (3H, s), 5.36 (1H, d, J=5.4 Hz), 8.78 (1H, s) | CDCl$_3$ (300 MHz) | 593 (M$^+$ + 1) |
| 90 | 7-Deoxy-7-(2-difluoromethyl-imidazo[5,1-b]thiazol-5-ylthio)-7-epilincomycin | 2.18 (3H, s), 2.25 (3H, s), 5.32 (1H, d, J=5.7 Hz), 6.77 (1H, t, J=54.8 Hz), 7.23 (1H, s), 7.90 (1H, s) | CDCl$_3$ (300 MHz) | 595 (M$^+$ + 1) |
| 91 | 7-Deoxy-7-epi-7-(4-(ethoxy-carbonyl)-1H-imidazol-2-ylthio)-lincomycin | 2.09 (3H, s), 2.30 (3H, s), 5.25 (1H, d, J=5.6 Hz), 7.79 (1H, s) | CDCl$_3$ (300 MHz) | 561 (M$^+$ + 1) |
| 92 | 7-Deoxy-7-epi-7-(4-phenyl-1H-imidazol-2-ylthio)-lincomycin | 2.18 (3H, s), 2.24 (3H, s), 5.31 (1H, d, J=5.6 Hz), 7.26-7.44 (5H, m), 7.60-7.61 (1H, m) | CDCl$_3$ (300 MHz) | 565 (M$^+$ + 1) |

TABLE 6-continued

| | | | | |
|---|---|---|---|---|
| 93 | 7-Deoxy-7-epi-7-(4-ethyl-5-(4-fluorophenyl)-4H-1,2,4-triazol-3-ylthio)lincomycin | 1.34 (3H, t, J=6.9 Hz), 2.20 (3H, s), 2.37 (3H, s), 4.08 (2H, q, J=6.9 Hz), 7.45-7.65 (4H, m) | CDCl$_3$ (300 MHz) | 612 (M$^+$ + 1) |
| 94 | 7-((5-Carbamoyl-4-methyl)-4H-1,2,4-triazol-5-ylthio)-7-deoxy-7-epilincomycin | 1.89 (3H, s), 2.25 (3H, s), 3.77 (3H, s), 5.13 (1H, d, J=5.6 Hz) | CD$_3$OD (400 MHz) | 547 (M$^+$ + 1) |
| 95 | 7-Deoxy-7-epi-7-(5-(trifluoromethyl)-pyridin-2-ylthio)-lincomycin | 1.76 (3H, s), 2.35 (3H, s), 5.21 (1H, d, J=5.6 Hz), 7.45 (1H, d, J=8.6 Hz), 7.83-7.85 (1H, m), 8.68-8.69 (1H, m) | CD$_3$OD (400 MHz) | 568 (M$^+$ + 1) |
| 96 | 7-((3-Cyano-4-ethoxycarbonyl-6-methyl)pyridin-2-ylthio)-7-deoxy-7-epilincomycin | 1.33 (3H, t, J=7.2 Hz), 1.65 (3H, s), 2.27 (3H, s), 2.54 (3H, s), 4.35 (2H, q, J=7.2 Hz), 5.14 (1H, d, J=5.8 Hz), 7.45 (1H, s) | CD$_3$OD (400 MHz) | 611 (M$^+$ + 1) |
| 97 | 7-((3-Cyano-6-phenyl-4-trifluoromethyl)-pyridin-2-ylthio)-7-deoxy-7-epilincomycin | 1.64 (3H, s), 2.26 (3H, s), 5.11 (1H, d, J=10.0 Hz), 7.47-7.49 (3H, m), 7.95 (1H, s), 8.11-8.13 (2H, m) | CD$_3$OD (400 MHz) | 669 (M$^+$ + 1) |
| 98 | 7-Deoxy-7-epi-(4-(furan-2-yl)-pyrimidin-2-ylthio)lincomycin | 1.72 (3H, s), 2.28 (3H, s), 5.19 (1H, d, J=5.6 Hz), 6.60-6.64 (1H, m), 7.30-7.37 (2H, m), 7.71-7.74 (1H, m), 8.47-8.49 (1H, m) | CD$_3$OD (400 MHz) | 567 (M$^+$ + 1) |
| 99 | 7-Deoxy-7-epi-7-(4-(thiophen-2-yl)pyrimidin-2-ylthio)-lincomycin | 2.17 (3H, s), 2.68 (3H, s), 5.62 (1H, d, J=5.6 Hz), 7.59 (1H, dd, J=4.9, 3.9 Hz), 7.90 (1H, d, J=5.4 Hz), 8.10 (1H, dd, J=4.9, 1.1 Hz), 8.32 (1H, dd, J=3.9, 1.1 Hz), 8.85 (1H, d, J=5.4 Hz) | CD$_3$OD (400 MHz) | 583 (M$^+$ + 1) |
| 100 | 7-Deoxy-7-epi-7-(4-(4-methoxy-phenyl)pyrimidin-2-ylthio)lincomycin | 1.97 (3H, s), 2.51 (3H, s), 4.09 (3H, s), 5.44 (1H, d, J=5.6 Hz), 7.28 (2H, ddd, J=9.0, 2.2, 2.2 Hz), 7.78 (1H, d, J=5.4 Hz), 8.35 (2H, ddd, J=9.0, 2.2, 2.2 Hz), 8.69 (1H, d, J=5.4 Hz) | CD$_3$OD (400 MHz) | 607 (M$^+$ + 1) |
| 101 | 7-((4-Amino-5-ethoxycarbonyl)-pyrimidin-2-ylthio)-7-deoxy-7-epilincomycin | 1.36 (3H, t, J=7.3 Hz), 1.86 (3H, s), 2.35 (3H, s), 4.33 (2H, q, J=7.3 Hz), 5.22 (1H, d, J=5.7 Hz), 8.57 (1H, s) | CD$_3$OD (400 MHz) | 588 (M$^+$ + 1) |
| 102 | 7-(4-(4-Chlorophenyl)pyrimidin-2-ylthio)-7-deoxy-7-epilincomycin | 1.74 (3H, s), 2.31 (3H, s), 5.22 (1H, d, J=5.6 Hz), 7.28 (2H, ddd, J=8.8, 2.1, 2.1 Hz), 7.64 (1H, d, J=5.4 Hz), 8.35 (2H, ddd, J=8.8, 2.1, 2.1 Hz), 8.58 (1H, d, J=5.4 Hz) | CD$_3$OD (400 MHz) | 611 (M$^+$ + 1) |
| 103 | 7-Deoxy-7-epi-7-(5-phenylthiazol-2-ylthio)lincomycin | 2.04 (3H, s), 2.35 (3H, s), 5.26 (1H, d, J=5.6 Hz), 7.33-7.36 (1H, m), 7.40-7.46 (2H, m), 7.58 (2H, d, J=7.4, 1.7 Hz), 7.97 (1H, s) | CD$_3$OD (400 MHz) | 582 (M$^+$ + 1) |
| 104 | 7-Deoxy-7-epi-7-(5-(2-nitrophenyl)-oxazol-2-ylthio)lincomycin | 1.99 (3H, s), 2.37 (3H, s), 5.26 (1H, d, J=5.6 Hz), 7.46 (1H, s), 7.59-7.64 (1H, m), 7.71-7.78 (2H, m), 7.89 (1H, d, J=8.2, 0.8 Hz) | CD$_3$OD (400 MHz) | 611 (M$^+$ + 1) |
| 105 | 7-Deoxy-7-epi-7-(5-(4-methoxy-phenyl)oxazol-2-ylthio)lincomycin | 2.02 (3H, s), 2.36 (3H, s), 5.26 (1H, d, J=5.6 Hz), 6.99 (1H, ddd, J=8.8, 2.0, 2.0 Hz), 7.36 (1H, s), 7.57 (1H, ddd, J=8.8, 2.0, 2.0 Hz) | CD$_3$OD (400 MHz) | 596 (M$^+$ + 1) |
| 106 | 7-(5-(4-Chlorophenyl)oxazol-2-ylthio)-7-deoxy-7-epilincomycin | 2.00 (3H, s), 2.37 (3H, s), 5.26 (1H, d, J=5.6 Hz), 7.45 (1H, ddd, J=9.2, 2.4, 2.4 Hz), 7.53 (1H, s), 7.64 (1H, ddd, J=9.5, 2.4, 2.4 Hz) | CD$_3$OD (400 MHz) | 600 (M$^+$ + 1) |
| 107 | 7-Deoxy-7-epi-7-(4-ethoxycarbonyl-1-methyl-1H-imidazol-2-ylthio)-lincomycin | 2.09 (3H, s), 2.30 (3H, s), 3.72 (3H, s), 5.25 (1H, d, J=5.6 Hz), 7.79 (1H, s) | CD$_3$OD (400 MHz) | 575 (M$^+$ + 1) |
| 108 | 7-Deoxy-7-epi-7-(4-phenyl-1-methyl-1H-imidazol-2-ylthio)lincomycin | 2.18 (3H, s), 2.24 (3H, s), 3.70 (1H, s), 5.31 (1H, d, J=5.6 Hz), 7.26-7.44 (5H, m), 7.60-7.61 (1H, m) | CD$_3$OD (400 MHz) | 579 (M$^+$ + 1) |
| 109 | 7-(4-(4-Chlorophenyl)-1-methyl-1H-imidazol-2-ylthio)-7-deoxy-7-epilincomycin | 2.11 (3H, s), 2.31 (3H, s), 3.72 (3H, s), 5.26 (1H, d, J=6.0 Hz), 7.17 (1H, s), 5.42-7.51 (1H, m) | CD$_3$OD (400 MHz) | 613 (M$^+$ + 1) |
| 110 | 7-Deoxy-7-epi-7-(5-ethoxycarbonyl-methyl-4-methylthiazol-2-ylthio)lincomycin | 1.16 (3H, t, J=6.1 Hz), 1.89 (3H, s), 2.21 (3H, s), 2.27 (3H, s), 4.07 (2H, q, J=6.1 Hz), 5.15 (1H, d, J=5.8 Hz) | CD$_3$OD (400 MHz) | 606 (M$^+$ + 1) |

TABLE 7

| | | | | |
|---|---|---|---|---|
| 111 | 7-(5-(Carbamoylmethyl)-4-methyl-thiazol-2-ylthio)-7-deoxy-7-epilincomycin | 2.00 (3H, s), 2.33 (3H, s), 2.36 (3H, s), 5.25 (1H, d, J=5.6 Hz) | CD$_3$OD (400 MHz) | 577 (M$^+$ + 1) |
| 112 | 7-(5-Chloro-7-methylbenzo[d]-oxazol-2-ylthio)-7-deoxy-7-epilincomycin | 1.76 (3H, s), 2.32 (3H, s), 2.36 (3H, s), 5.15 (1H, d, J=5.6 Hz), 7.03 (1H, s), 7.28 (1H, s) | CD$_3$OD (400 MHz) | 588 (M$^+$ + 1) |
| 113 | 7-Deoxy-7-epi-7-(4-methoxy-carbonyl)phenylthiolincomycin | 1.70 (3H, s), 2.32 (3H, s), 3.70 (3H, s), 5.11 (1H, d, J=5.6 Hz), 7.31 (2H, d, J=8.5 Hz), 7.80 (2H, d, J=8.3 Hz) | CD$_3$OD (400 MHz) | 557 (M$^+$ + 1) |
| 114 | 7-Deoxy-7-epi-7-(4-nitrophenylthio)-lincomycin | 1.80 (3H, s), 2.40 (3H, s), 5.23 (1H, d, J=5.6 Hz), 7.53 (2H, d, J=9.0 Hz), 8.15 (2H, d, J=9.0 Hz) | CD$_3$OD (400 MHz) | 544 (M$^+$ + 1) |
| 115 | 7-Deoxy-7-epi-7-(2-nitrophenylthio)-lincomycin | 1.78 (3H, s), 2.42 (3H, s), 5.21 (1H, d, J=5.6 Hz), 7.37 (1H, dt, J=1.5, 7.7 Hz), 7.63 (2H, dt, J=1.5, 7.2 Hz), 7.70 (1H, dd, J=1.5, 7.1 Hz), 8.05 (1H, dd, J=1.4, 8.3 Hz) | CD$_3$OD (400 MHz) | 544 (M$^+$ + 1) |
| 116 | 7-Deoxy-7-epi-7-(3-nitrophenylthio)-lincomycin | 1.92 (3H, s), 2.39 (3H, s), 5.25 (1H, d, J=5.6 Hz), 7.15 (1H, t, J=8.1 Hz), 7.78 (1H, d, J=5.0 Hz), 8.07 (1H, dd, J=2.0 Hz), 8.20 (1H, t, J=2.0 Hz) | CD$_3$OD (400 MHz) | 544 (M$^+$ + 1) |
| 117 | 7-(4-(2-Carbamoylethyl)thiazol-2-ylthio)-7-deoxy-7-epilincomycin | 1.96 (3H, s), 2.37 (3H, s), 5.34 (1H, d, J=5.4 Hz), 5.91 (1H, s), 6.13 (1H, s), 6.95 (1H, s) | CDCl$_3$ (300 MHz) | 577 (M$^+$ + 1) |
| 118 | 7-(5-(2-Aminoacetamido)-1,3,4-thiadiazol-2-ylthio)-7-deoxy-7-epilincomycin | 1.94 (3H, s), 2.91 (3H, s), 5.29 (1H, d, J=6.0 Hz) | D$_2$O (300 MHz) | 579 (M$^+$ + 1) |
| 119 | 7-(5-(2-Amino-N-methylacetamido)-1,3,4-thiadiazol-2-ylthio)-7-deoxy-7-epilincomycin | 1.96 (3H, s), 2.91 (3H, s), 3.05 (3H, s), 5.29 (1H, d, J=6.0 Hz) | D$_2$O (300 MHz) | 593 (M$^+$ + 1) |
| 120 | 7-Deoxy-7-epi-7-(5-(thiazol-4-yl)-1,3,4-thiadiazol-2-ylthio)lincomycin | 1.56 (3H, d, J=7.1 Hz), 1.99 (3H, s), 2.38 (3H, s), 5.26 (1H, d, J=5.6 Hz), 8.37 (1H, d, J=1.9 Hz), 9.12 (1H, d, J=1.9 Hz) | CD$_3$OD (400 MHz) | 590 (M$^+$ + 1) |
| 121 | 7-Deoxy-7-(1-(4,5-dihydrothiazol-2-yl)-azetidin-3-ylthio)-7-epilincomycin | 1.29 (3H, d, J=7.1 Hz), 2.18 (3H, s), 2.42 (3H, s), 3.38 (2H, t, J=7.5 Hz), 3.94 (2H, t, J=7.5 Hz), 5.26 (1H, d, J=5.6 Hz) | CD$_3$OD (400 MHz) | 563 (M$^+$ + 1) |
| 122 | 7-(5-(5-Aminothiazol-4-yl)-1,3,4-thiadiazol-2-ylthio)-7-deoxy-7-epilincomycin | 1.53 (3H, d, J=7.1 Hz), 2.04 (3H, s), 2.39 (3H, s), 5.27 (1H, d, J=5.6 Hz), 8.08 (1H, s) | CD$_3$OD (400 MHz) | 605 (M$^+$ + 1) |
| 123 | 7-(5-(2-Amino-1,3,4-thiadiazol-5-yl)-1,3,4-thiadiazol-2-ylthio)-7-deoxy-7-epilincomycin | 1.54 (3H, m), 2.04 (3H, m), 2.36 (3H, s), 5.26 (1H, d, J=5.6 Hz) | CD$_3$OD (400 MHz) | 605 (M$^+$ + 1) |
| 124 | 7-(5-(2-Aminopyridin-3-yl)-1,3,4-thiadiazol-2-ylthio)-7-deoxy-7-epilincomycin | 1.57 (3H, d, J=6.8 Hz), 2.01 (3H, s), 2.37 (3H, s), 5.27 (1H, d, J=5.6 Hz), 6.73-6.78 (1H, m), 7.86-7.88 (1H, m), 8.09-8.11 (1H, m) | CD$_3$OD (400 MHz) | 599 (M$^+$ + 1) |
| 125 | 7-(5-(2-Aminopyridin-5-yl)-1,3,4-thiadiazol-2-ylthio)-7-deoxy-7-epilincomycin | 1.53 (3H, d, J=6.8 Hz), 2.02 (3H, s), 2.35 (3H, s), 5.27 (1H, d, J=5.6 Hz), 6.63-6.67 (1H, m), 7.93-7.97 (1H, m), 8.41-8.44 (1H, m) | CD$_3$OD (400 MHz) | 599 (M$^+$ + 1) |
| 126 | 7-(4-Aminopyrimidin-2-ylthio)-7-deoxy-7-epilincomycin | 2.08 (3H, s), 2.38 (3H, s), 5.33 (1H, d, J=6.0 Hz), 6.32 (2H, d, J=5.7 Hz), 8.00 (2H, t, J=5.7 Hz) | CD$_3$OD (400 MHz) | 516 (M$^+$ + 1) |
| 127 | 7-Deoxy-7-epi-7-(2-fluorophenylthio)-lincomycin | 2.03 (3H, s), 2.45 (3H, s), 5.26 (1H, d, J=5.6 Hz), 7.11-7.18 (2H, m), 7.31-7.38 (1H, m), 7.50 (1H, dt, J=1.7, 7.8 Hz) | CD$_3$OD (400 MHz) | 517 (M$^+$ + 1) |
| 128 | 7-Deoxy-7-epi-7-(4-fluorophenylthio)-lincomycin | 2.06 (3H, s), 2.40 (3H, s), 5.27 (1H, d, J=5.6 Hz), 7.53 (2H, t, J=8.8 Hz), 7.59 (2H, dd, J=5.3, 8.7 Hz) | CD$_3$OD (400 MHz) | 517 (M$^+$ + 1) |
| 129 | 7-Deoxy-7-epi-7-(4-trifluoromethyl-phenylthio)lincomycin | 1.87 (3H, s), 2.44 (3H, s), 5.26 (1H, d, J=5.6 Hz), 7.53 (2H, d, J=8.3 Hz), 7.59 (2H, d, J=8.5 Hz) | CD$_3$OD (400 MHz) | 567 (M$^+$ + 1) |
| 130 | 7-(4-Chlorophenylthio)-7-deoxy-7-epilincomycin | 2.00 (3H, s), 2.40 (3H, s), 5.28 (1H, d, J=5.6 Hz), 7.33 (2H, d, J=8.5 Hz), 7.41 (2H, d, J=8.5 Hz) | CD$_3$OD (400 MHz) | 533 (M$^+$ + 1) |
| 131 | 7-(4-(Acetamido)phenylthio)-7-deoxy-7-epilincomycin | 2.06 (3H, s), 2.12 (3H, s), 2.40 (3H, s), 5.28 (1H, d, J=5.6 Hz), 7.40 (2H, d, J=8.5 Hz), 7.55 (2H, d, J=8.5 Hz) | CD$_3$OD (400 MHz) | 556 (M$^+$ + 1) |

TABLE 7-continued

| 132 | 7-(3-Chlorophenylthio)-7-deoxy-7-epilincomycin | 1.96 (3H, s), 2.42 (3H, s), 5.27 (1H, d, J=5.4 Hz), 7.24 (1H, dt, J=1.7, 7.7 Hz), 7.30 (1H, t, J=7.7 Hz), 7.36 (1H, dt, J=1.7, 7.7 Hz),, 7.41 (1H, t, J=1.6 Hz) | $CD_3OD$ (400 MHz) | 532 ($M^+ + 1$) |

TABLE 8

| 133 | 7-(2-Chlorophenylthio)-7-deoxy-7-epilincomycin | 1.91 (3H, s), 2.42 (3H, s), 5.25 (1H, d, J=5.6 Hz), 7.22 (1H, dt, J=1.7, 7.5 Hz), 7.29 (1H, dt, J=1.7, 7.6 Hz), 7.42 (1H, dd, J=1.5, 7.8 Hz), 7.49 (1H, dd, J=1.4, 7.8 Hz) | $CD_3OD$ (400 MHz) | 532 ($M^+ + 1$) |
| 134 | 7-Deoxy-7-epi-7-(3-(methoxy-carbonyl)phenylthio)lincomycin | 1.97 (3H, s), 2.40 (3H, s), 3.90 (3H, s), 5.29 (1H, d, J=5.6 Hz), 7.45 (1H, t, J=7.8 Hz), 7.66 (1H, d, J=7.8 Hz), 7.88 (1H, d, J=7.8 Hz), 8.03 (1H, s) | $CD_3OD$ (400 MHz) | 557 ($M^+ + 1$) |
| 135 | 7-Deoxy-7-(5-(4,5-dimethoxy-2-nitrophenyl)-1,3,4-thiadiazol-2-ylthio)-7-epilincomycin | 1.57 (3H, d, J=6.8 Hz), 2.18 (3H, s), 2.40 (3H, s), 4.00 (3H, s), 4.03 (3H, s), 5.36 (1H, d, J=5.6 Hz), 7.14 (1H, s), 7.67 (1H, s) | $CD_3OD$ (400 MHz) | 688 ($M^+ + 1$) |
| 136 | 7-Deoxy-7-epi-7-(5-(2-(methoxy-carbonyl)phenyl)-1,3,4-thiadiazol-2-ylthio)lincomycin | 1.82 (3H, d, J=6.8 Hz), 2.18 (3H, s), 2.40 (3H, s), 3.81 (3H, s), 5.36 (1H, d, J=5.6 Hz), 7.58-7.64 (3H, m), 7.92-7.95 (1H, m) | $CD_3OD$ (400 MHz) | 641 ($M^+ + 1$) |
| 137 | 7-Deoxy-7-epi-7-(4-(methoxy-carbonyl)benzylthio)-lincomycin | 1.33 (3H, d, J=6.8 Hz), 2.08 (3H, s), 2.40 (3H, s), 3.89 (2H, s), 5.23 (1H, d, J=5.2 Hz), 7.44-7.49 (2H, m), 7.94-7.98 (2H, m) | $CD_3OD$ (400 MHz) | 571 ($M^+ + 1$) |
| 138 | 7-Deoxy-7-epi-7-(3-(methoxy-carbonyl)benzylthio)-lincomycin | 2.10 (3H, s), 2.40 (3H, s), 3.91 (2H, s), 5.24 (1H, d, J=5.6 Hz), 7.42-7.45 (1H, m), 7.57-7.62 (1H, m), 7.87-7.92 (1H, m), 8.03 (1H, br) | $CD_3OD$ (400 MHz) | 571 ($M^+ + 1$) |
| 139 | 7-Deoxy-7-epi-7-(4-(methyl-sulfonyl)benzylthio)lincomycin | 2.08 (3H, s), 2.39 (3H, s), 3.11 (3H, s), 3.94-4.04 (2H, m), 5.24 (1H, d, J=5.5 Hz), 7.59-7.64 (2H, m), 7.88-7.92 (2H, m) | $CD_3OD$ (400 MHz) | 591 ($M^+ + 1$) |
| 140 | 7-Deoxy-7-epi-7-(5-(pyridin-3-yl)pyridin-3-ylthio)-lincomycin | 1.95 (3H, s), 2.39 (3H, s), 3.98 (1H, dq, J=3.0, 6.9 Hz), 5.25 (1H, d, J=5.4 Hz), 7.58 (1H, dd, J=4.8, 7.8 Hz), 8.15-8.19 (2H, m), 8.60-8.63 (2H, m), 8.67 (1H, d, J=1.8 Hz), 8.87 (1H, d, J=2.1 Hz) | $CD_3OD$ (300 MHz) | 577 ($M^+ + 1$) |
| 141 | 7-Deoxy-7-epi-7-(3-(pyridin-3-yl)phenylthio)-lincomycin | 1.91 (3H, s), 2.37 (3H, s), 3.91 (1H, dq, J=2.7, 6.9 Hz), 5.25 (1H, d, J=5.7 Hz), 7.41-7.52 (4H, m), 7.65 (1H, s), 8.04 (1H, d, J=7.8 Hz), 8.53 (1H, d, J=4.2 Hz), 8.74 (1H, s) | $CD_3OD$ (300 MHz) | 576 ($M^+ + 1$) |
| 142 | 7-Deoxy-7-epi-7-(3-(1H-1,2,4-triazol-1-yl)-phenylthio)lincomycin | 1.94 (3H, s), 2.43 (3H, s), 3.98 (1H, dq, J=2.7, 7.2 Hz), 5.28 (1H, d, J=5.7 Hz), 7.45-7.53 (2H, m), 7.68-7.72 (1H, m), 7.90 (1H, s), 8.17 (1H, s), 9.15 (1H, s) | $CD_3OD$ (300 MHz) | 566 ($M^+ + 1$) |
| 143 | 7-Deoxy-7-epi-7-(3-(1H-imidazol-1-yl)phenylthio)-lincomycin | 1.92 (3H, s), 2.40 (3H, s), 3.97 (1H, dq, J=3.0, 6.9 Hz), 5.26 (1H, d, J=5.4 Hz), 7.15 (1H, s), 7.41-7.51 (3H, m), 7.59 (1H, s), 7.60 (1H, s), 8.17 (1H, s) | $CD_3OD$ (300 MHz) | 565 ($M^+ + 1$) |
| 144 | 7-(5-Benzoylpyridin-3-ylthio)-7-deoxy-7-epilincomycin | 1.95 (3H, s), 2.40 (3H, s), 5.22 (1H, d, J=5.7 Hz), 7.53-7.58 (1H, m), 7.67-7.71 (2H, m), 7.77-7.80 (1H, m), 8.15 (1H, t, J=2.1 Hz), 8.71 (1H, d, J=1.5 Hz), 8.79 (1H, d, J=2.4 Hz) | $CD_3OD$ (300 MHz) | 604 ($M^+ + 1$) |
| 145 | 7-Deoxy-7-epi-7-(4-(pyridin-3-yl)-phenylthio)lincomycin | 1.96 (3H, s), 2.39 (3H, s), 3.93 (1H, dq, J=2.7, 6.6 Hz), 5.27 (1H, d, J=5.7 Hz), 7.47-7.51 (1H, m), 7.52 (2H, d, J=8.4 Hz), 7.63 (2H, d, J=8.4 Hz), 8.07 (1H, ddd, J=1.5, 2.4, 8.1 Hz), 8.49 (1H, dd, J=1.5, 4.8 Hz), 8.78 (1H, dd, J=0.9, 2.7 Hz) | $CD_3OD$ (300 MHz) | 576 ($M^+ + 1$) |

TABLE 8-continued

| | | | | |
|---|---|---|---|---|
| 146 | 7-Deoxy-7-epi-7-(4-(1H-1,2,4-triazol-1-yl)phenylthio)-lincomycin | 1.99 (3H, s), 2.41 (3H, s), 3.93 (1H, dq, J=2.7, 6.9 Hz), 5.27 (1H, d, J=5.4 Hz), 7.59 (2H, d, J=9.0 Hz), 7.80 (2H, d, J=9.3 Hz), 8.16 (1H, s), 9.09 (1H, s) | CD$_3$OD (300 MHz) | 566 (M$^+$ + 1) |
| 147 | 7-Deoxy-7-epi-7-(4-(pyridin-3-yloxy)phenylthio)lincomycin | 2.06 (3H, s), 2.42 (3H, s), 3.81 (1H, dq, J=2.7, 6.9 Hz), 5.28 (1H, d, J=5.7 Hz), 7.04 (2H, d, J=8.7 Hz), 7.41-7.47 (2H, m), 7.50 (2H, d, J=8.7 Hz), 8.30-8.22 (2H, m) | CD$_3$OD (300 MHz) | 592 (M$^+$ + 1) |
| 148 | 7-Deoxy-7-epi-7-(4-(1H-1,2,3-triazol-1-yl)-phenylthio)lincomycin | 1.98 (3H, s), 2.42 (3H, s), 3.96 (1H, dq, J=2.7, 6.9 Hz), 5.28 (1H, d, J=5.7 Hz), 7.62 (2H, d, J=9.0 Hz), 7.83 (2H, d, J=8.7 Hz), 7.90 (1H, d, J=1.2 Hz), 8.54 (1H, d, J=1.2 Hz) | CD$_3$OD (300 MHz) | 566 (M$^+$ + 1) |
| 149 | 7-Deoxy-7-epi-7-(4-(2H-1,2,3-triazol-2-yl)phenylthio)lincomycin | 2.01 (3H, s), 2.42 (3H, s), 3.90 (1H, dq, J=2.7, 6.9 Hz), 5.28 (1H, d, J=5.4 Hz), 7.58 (2H, d, J=9.3 Hz), 7.92 (2H, s), 8.04 (2H, d, J=8.7 Hz) | CD$_3$OD (300 MHz) | 566 (M$^+$ + 1) |
| 150 | 7-Deoxy-7-epi-7-(4-(1-methyl-1H-tetrazol-5-yl)phenylthio)-lincomycin | 1.92 (3H, s), 2.43 (3H, s), 3.97 (1H, dq, J=2.7, 6.9 Hz), 4.41 (3H, s), 5.27 (1H, d, J=6.0 Hz), 7.53 (2H, d, J=8.4 Hz), 8.03 (2H, d, J=8.7 Hz) | CD$_3$OD (300 MHz) | 581 (M$^+$ + 1) |
| 151 | 7-Deoxy-7-epi-7-(4-(piperidino-sulfonyl)phenylthio)-lincomycin | 1.58-1.65 (4H, m), 1.81 (3H, s), 2.43 (3H, s), 2.95 (4H, t, J=5.4 Hz), 4.05 (1H, dq, J=2.7, 6.9 Hz), 5.25 (1H, d, J=5.4 Hz), 7.47 (2H, d, J=8.4 Hz), 7.67 (2H, d, J=8.7 Hz) | CD$_3$OD (300 MHz) | 646 (M$^+$ + 1) |
| 152 | 7-Deoxy-7-epi-7-(4-(1H-tetrazol-5-(4H)-on-1-yl)phenylthio)lincomycin | 2.01 (3H, s), 2.61 (3H, s), 3.86 (1H, dq, J=2.4, 6.9 Hz), 5.29 (1H, d, J=5.7 Hz), 7.54 (2H, d, J=8.4 Hz), 7.89 (2H, d, J=8.4 Hz) | CD$_3$OD (300 MHz) | 583 (M$^+$ + 1) |
| 153 | 7-Deoxy-7-epi-7-(4-(2H-1,2,4-triazol-3(4H)-on-2-yl)phenylthio)-lincomycin | 2.05 (3H, s), 2.36 (3H, s), 3.82 (1H, dq, J=1.4, 6.6 Hz), 5.28 (1H, d, J=5.7 Hz), 7.52 (2H, d, J=8.7 Hz), 7.88 (1H, s), 7.91 (2H, d, J=8.7 Hz) | CD$_3$OD (300 MHz) | 582 (M$^+$ + 1) |
| 154 | 7-Deoxy-7-epi-7-(4-((N-methoxy-N-methyl)-carbamoyl)phenylthio)-lincomycin | 1.87 (3H, s), 2.44 (3H, s), 3.34 (3H, s), 3.58 (3H, s), 3.99 (1H, dq, J=2.7, 6.9 Hz), 5.26 (1H, d, J=5.4 Hz), 7.44 (2H, d, J=8.4 Hz), 7.61 (2H, d, J=8.7 Hz) | CD$_3$OD (300 MHz) | 586 (M$^+$ + 1) |

TABLE 9

| | | | | |
|---|---|---|---|---|
| 155 | 7-Deoxy-7-epi-7-(4-(pyridin-2-yl)phenylthio)lincomycin | 1.95 (3H, s), 2.40 (3H, s), 3.94 (1H, dq, J=2.4, 6.9 Hz), 5.27 (1H, d, J=5.4 Hz), 7.31-7.36 (1H, m), 7.51 (2H, d, J=8.1 Hz), 7.82-7.87 (2H, m), 7.91 (2H, d, J=8.1 Hz), 8.59 (1H, d, J=5.1 Hz) | CD$_3$OD (300 MHz) | 576 (M$^+$ + 1) |
| 156 | 7-Deoxy-7-epi-7-(4-(pyridin-4-yl)phenylthio)lincomycin | 1.95 (3H, s), 2.44 (3H, s), 3.98 (1H, dq, J=2.7, 6.9 Hz), 5.28 (1H, d, J=5.7 Hz), 7.54 (2H, d, J=8.7 Hz), 7.71 (2H, dd, J=1.8, 4.5 Hz), 7.74 (2H, d, J=8.4 Hz), 8.57 (2H, dd, J=1.8, 4.5 Hz) | CD$_3$OD (300 MHz) | 576 (M$^+$ + 1) |
| 157 | 7-Deoxy-7-epi-7-(4-(pentan-1-oyl)-phenylthio)lincomycin | 0.95 (3H, t, J=7.2 Hz), 1.66 (2H, tt, J=7.2, 7.5 Hz), 1.83 (3H, s), 2.42 (3H, s), 2.98 (2H, t, J=7.2 Hz), 5.25 (1H, d, J=5.7 Hz), 7.45 (2H, d, J=8.7 Hz), 7.91 (2H, d, J=8.4 Hz) | CD$_3$OD (300 MHz) | 583 (M$^+$ + 1) |
| 158 | 7-Deoxy-7-epi-7-(4-(4-methyl-2H-1,2,4-triazol-3(4H)-on-2-yl)-phenylthio)-lincomycin | 2.03 (3H, s), 2.38 (3H, s), 3.35 (3H, s), 3.82 (1H, dq, J=1.8, 6.9 Hz), 5.27 (1H, d, J=5.7 Hz), 7.52 (2H, d, J=9.0 Hz), 7.91 (2H, d, J=8.7 Hz), 7.95 (1H, s) | CD$_3$OD (300 MHz) | 596 (M$^+$ + 1) |
| 159 | 7-Deoxy-7-epi-7-(4-(1-methyl-1H-tetrazol-5(4H)-on-4-yl)phenylthio)-lincomycin | 1.97 (3H, s), 2.42 (3H, s), 3.67 (3H, s), 3.91 (1H, dq, J=2.7, 6.9 Hz), 5.27 (1H, d, J=5.7 Hz), 7.56 (2H, d, J=8.7 Hz), 7.87 (2H, d, J=8.7 Hz) | CD$_3$OD (300 MHz) | 597 (M$^+$ + 1) |
| 160 | 7-Deoxy-7-epi-7-(5-(methoxy-carbonyl)thiophen-2-ylthio)-lincomycin | 2.15 (3H, s), 2.35 (3H, s), 3.87 (2H, s), 5.32 (1H, d, J=5.6 Hz), 7.21 (2H, d, J=3.8 Hz), 7.68 (2H, d, J=3.8 Hz) | CD$_3$OD (400 MHz) | 563 (M$^+$ + 1) |
| 161 | 7-Deoxy-7-epi-7-(5-(morpholino-carbonyl)thiophen-2-ylthio)-lincomycin | 2.17 (3H, s), 2.38 (3H, s), 5.29 (1H, d, J=5.6 Hz), 7.18 (2H, d, J=3.9 Hz), 7.33 (2H, d, J=3.9 Hz) | CD$_3$OD (400 MHz) | 617 (M$^+$ + 1) |

TABLE 9-continued

| | | | | |
|---|---|---|---|---|
| 162 | 7-(4-Cyanophenylthio)-7-deoxy-7-epilincomycin | 1.83 (3H, s), 2.41 (3H, s), 4.06 (1H, dq, J=2.9, 6.8 Hz), 5.26 (1H, d, J=5.6 Hz), 7.21 (2H, ddd, J=8.6, 1.7, 1.7 Hz), 7.68 (2H, ddd, J=8.6, 1.7, 1.7 Hz) | $CD_3OD$ (400 MHz) | 524 ($M^+ + 1$) |
| 163 | 7-(4-Cyano-3-fluorophenylthio)-7-deoxy-7-epilincomycin | 1.84 (3H, s), 2.41 (3H, s), 5.26 (1H, d, J=5.6 Hz), 7.30 (1H, dd, J=8.3, 1.7 Hz), 7.35 (2H, dd, J=10.2, 1.7 Hz), 7.65 (2H, dd, J=10.2, 8.3 Hz) | $CD_3OD$ (400 MHz) | 542 ($M^+ + 1$) |
| 164 | 7-(4-Acetylphenylthio)-7-deoxy-7-epilincomycin | 1.84 (3H, s), 2.41 (3H, s), 2.57 (3H, s), 4.06 (1H, dq, J=2.6, 6.8 Hz), 5.27 (1H, d, J=5.6 Hz), 7.45 (2H, d, J=8.5 Hz), 7.92 (2H, d, J=8.5 Hz) | $CD_3OD$ (400 MHz) | 541 ($M^+ + 1$) |
| 165 | 7-Deoxy-7-epi-7-(3-fluoro-4-(morpholinocarbonyl)phenylthio)-lincomycin | 1.91 (3H, s), 2.41 (3H, s), 3.99 (1H, dq, J=2.8, 6.8 Hz), 5.26 (1H, d, J=5.4 Hz), 7.24-7.30 (2H, m), 7.36 (1H, dd, J=7.6, 7.6 Hz) | $CD_3OD$ (400 MHz) | 630 ($M^+ + 1$) |
| 166 | 7-Deoxy-7-epi-7-(3-fluoro-4-(piperidinocarbonyl)phenylthio)-lincomycin | 1.91 (3H, s), 2.41 (3H, s), 3.98 (1H, dq, J=2.7, 6.7 Hz), 5.26 (1H, d, J=5.7 Hz), 7.23-7.33 (3H, m) | $CD_3OD$ (400 MHz) | 628 ($M^+ + 1$) |
| 167 | 7-Deoxy-7-epi-7-(2-fluoro-4-(morpholinocarbonyl)phenylthio)-lincomycin | 1.98 (3H, s), 2.41 (3H, s), 4.01 (1H, dq, J=2.7, 6.8 Hz), 5.25 (1H, d, J=5.6 Hz), 7.23-7.26 (2H, m), 7.57 (1H, dd, J=7.4, 7.4 Hz) | $CD_3OD$ (400 MHz) | 630 ($M^+ + 1$) |
| 168 | 7-Deoxy-7-epi-7-(2-fluoro-4-(piperidinocarbonyl)phenylthio)-lincomycin | 1.98 (3H, s), 2.42 (3H, s), 4.00 (1H, dq, J=2.7, 7.0 Hz), 5.26 (1H, d, J=5.7 Hz), 7.19-7.22 (2H, m), 7.57 (1H, dd, J=7.3, 7.3 Hz) | $CD_3OD$ (400 MHz) | 628 ($M^+ + 1$) |
| 169 | 7-Deoxy-7-epi-7-(4-(N-methyl-acetamido)phenylthio)lincomycin | 1.85 (3H, s), 1.95 (3H, s), 2.44 (3H, s), 3.22 (3H, s), 3.89-3.97 (1H, m), 5.28 (1H, d, J=5.6 Hz), 7.26 (2H, d, J=8.3 Hz), 7.49 (2H, d, J=8.3 Hz) | $CD_3OD$ (400 MHz) | 570 ($M^+ + 1$) |
| 170 | 7-Deoxy-7-epi-7-(4-(methoxy-N-methylacetamido)phenylthio)-lincomycin | 1.95 (3H, s), 2.44 (3H, s), 3.24 (3H, s), 3.81 (2H, br), 3.90-3.97 (1H, m), 5.28 (1H, d, J=5.3 Hz), 7.28 (2H, d, J=8.5 Hz), 7.49 (2H, d, J=8.3 Hz) | $CD_3OD$ (400 MHz) | 600 ($M^+ + 1$) |
| 171 | 7-Deoxy-7-epi-7-(4-(methoxy-N-propylacetamido)phenylthio)-lincomycin | 0.88 (3H, t, J=7.3 Hz), 1.52 (2H, tq, J=7.3, 7.3 Hz), 1.93 (3H, s), 2.45 (3H, s), 3.27 (3H, s), 3.65 (2H, t, J=7.3 Hz), 3.76 (2H, s), 3.91-3.98 (1H, m), 5.28 (1H, d, J=5.6 Hz), 7.24 (2H, d, J=8.3 Hz), 7.49 (2H, d, J=8.5 Hz) | $CD_3OD$ (400 MHz) | 628 ($M^+ + 1$) |
| 172 | 7-Deoxy-7-epi-7-(4-(morpholinomethyl)-phenylthio)-lincomycin | 1.98 (3H, s), 2.41 (3H, s), 2.42-2.46 (4H, m), 3.49 (2H, s), 3.67 (4H, t, J=4.6 Hz), 3.86 (1H, dq, J=2.6, 6.9 Hz), 5.27 (1H, d, J=5.6 Hz), 7.30 (2H, d, J=8.3 Hz), 7.39 (2H, d, J=8.3 Hz) | $CD_3OD$ (400 MHz) | 598 ($M^+ + 1$) |
| 173 | 7-Deoxy-7-epi-7-(4-(morpholino-carbonyl)-3-nitrophenylthio)-lincomycin | 1.92 (3H, s), 2.41 (3H, s), 3.28 (2H, br), 3.60-3.63 (2H, m), 3.78 (4H, br), 4.05 (1H, dq, J=2.9, 6.8 Hz), 5.27 (1H, d, J=5.6 Hz), 7.46 (1H, d, J=8.0 Hz), 7.82 (1H, dd, J=1.7, 8.0 Hz), 8.16 (1H, d, J=1.9 Hz) | $CD_3OD$ (400 MHz) | 657 ($M^+ + 1$) |
| 174 | 7-Deoxy-7-epi-7-(4-(morpholino-sulfonyl)phenylthio)lincomycin | 1.81 (3H, s), 2.41 (3H, s), 2.94 (4H, t, J=4.6 Hz), 3.70 (4H, t, J=4.6 Hz), 4.07 (1H, dq, J=2.7, 6.8 Hz), 5.25 (1H, d, J=5.6 Hz), 7.57 (1H, d, J=8.5 Hz), 7.69 (1H, d, J=8.5 Hz) | $CD_3OD$ (400 MHz) | 648 ($M^+ + 1$) |
| 175 | 7-Deoxy-7-epi-7-(3-methyl-4-(morpholinocarbonyl)phenylthio)-lincomycin | 1.95 (3H, s), 2.27 (3H, s), 2.42 (3H, s), 3.22-3.29 (3H, m), 3.55-3.62 (2H, m), 3.76 (5H, br), 3.93 (1H, dq, J=2.7, 6.8 Hz), 5.27 (1H, d, J=5.6 Hz), 7.16 (1H, d, J=7.8 Hz), 7.29-7.32 (2H, m) | $CD_3OD$ (400 MHz) | 626 ($M^+ + 1$) |
| 176 | 7-Deoxy-7-epi-7-(4-fluoro-3-morpholinophenylthio)lincomycin | 1.89 (3H, s), 2.26 (3H, s), 2.90-2.93 (4H, m), 3.61 (1H, dq, J=2.7, 6.8 Hz), 3.67-3.70 (4H, m), 5.13 (1H, d, J=5.6 Hz), 6.87-6.96 (3H, m) | $CD_3OD$ (400 MHz) | 602 ($M^+ + 1$) |

TABLE 10

| | | | | |
|---|---|---|---|---|
| 177 | 7-Deoxy-7-epi-7-(4-morpholinophenylthio)-lincomycin | 2.13 (3H, s), 2.35 (3H, s), 5.28 (1H, d, J=5.4 Hz), 6.92 (2H, ddd, J=8.9, 2.1, 2.1 Hz), 7.37 (2H, ddd, J=8.9, 2.1, 2.1 Hz) | $CD_3OD$ (400 MHz) | 584 ($M^+ + 1$) |
| 178 | 7-Deoxy-7-epi-7-(4-(((S)-2-(hydroxymethyl)pyrrolidino-carbonyl)-phenylthio)lincomycin | 1.91 (3H, s), 2.42 (3H, s), 3.38-3.46 (1H, m), 3.48-3.56 (1H, m), 3.74 (1H, dd, J=3.7, 11.0 Hz), 3.81 (1H, dd, J=5.1, 11.0 Hz), 3.98 (1H, dq, J=2.7, 6.6 Hz), 4.26-4.31 (1H, m), 5.27 (1H, d, J=5.6 Hz), 7.45 (2H, d, J=7.8 Hz), 7.50 (2H, d, J=8.3 H) | $CD_3OD$ (400 MHz) | 625 ($M^+ + 1$) |
| 179 | 7-Deoxy-7-epi-7-(4-(((S)-2-(methoxymethyl)pyrrolidino-carbonyl)-phenylthio)lincomycin | 1.92 (3H, s), 2.42 (3H, s), 3.08 (1H, br), 3.38 (3H, s), 3.47-3.56 (1H, m), 3.60-3.64 (1H, m), 3.98 (1H, dq, J=2.6, 6.8 Hz), 5.27 (1H, d, J=5.6 Hz), 7.46 (4H, s) | $CD_3OD$ (400 MHz) | 640 ($M^+ + 1$) |
| 180 | 7-(5-Aminobenzo[d]thiazol-2-ylthio)-7-deoxy-7-epilincomycin | 2.01 (3H, s), 2.33 (3H, s), 5.34 (1H, d, J=5.7 Hz), 6.76 (1H, dd, J=2.4 Hz, 8.7 Hz), 7.22 (1H, d, J=1.5, 2.4 Hz), 7.52 (1H, d, J=8.7 Hz) | $CDCl_3$ (300 MHz) | 571 ($M^+ + 1$) |
| 181 | 7-(5-Aminobenzo[d]oxazol-2-ylthio)-7-deoxy-7-epilincomycin | 1.81 (3H, s), 2.25 (3H, s), 5.15 (1H, d, J=5.7 Hz), 6.60 (1H, dd, J=2.0, 8.5 Hz), 6.72 (1H, d, J=1.9 Hz), 7.17 (1H, d, J=8.5 Hz) | $CD_3OD$ (400 MHz) | 555 ($M^+ + 1$) |
| 182 | 7-(6-Aminobenzo[d]oxazol-2-ylthio)-7-deoxy-7-epilincomycin | 1.81 (3H, s), 2.26 (3H, s), 5.14 (1H, d, J=5.7 Hz), 6.60 (1H, dd, J=2.1, 8.5 Hz), 6.72 (1H, d, J=1.9 Hz), 7.17 (1H, d, J=8.5 Hz) | $CD_3OD$ (400 MHz) | 555 ($M^+ + 1$) |
| 183 | 7-(5-(4-Aminophenyl)-1,3,4-thiadiazol-2-ylthio)-7-deoxy-7-epilincomycin | 2.01 (3H, s), 2.99 (3H, s), 5.38 (1H, d, J=5.7 Hz), 7.25 (2H, d, J=8.4 Hz), 7.84 (2H, d, J=8.4 Hz) | $CDCl_3$ (300 MHz) | 598 ($M^+ + 1$) |
| 184 | 7-(5-(2-Aminophenyl)-1,3,4-thiadiazol-2-ylthio)-7-deoxy-7-epilincomycin | 2.17 (3H, s), 2.38 (3H, s), 5.35 (1H, d, J=5.4 Hz), 7.20-7.60 (4H, m) | $CDCl_3$ (300 MHz) | 598 ($M^+ + 1$) |
| 185 | 7-(5-(3-Aminophenyl)-1,3,4-thiadiazol-2-ylthio)-7-deoxy-7-epilincomycin | 2.11 (3H, s), 2.38 (3H, s), 5.35 (1H, d, J=5.4 Hz), 6.72 (1H, t, J=7.5 Hz), 6.80 (1H, d, J=7.5 Hz), 7.22 (1H, d, J=7.5 Hz), 7.35 (1H, d, J=7.5 Hz) | $CDCl_3$ (300 MHz) | 598 ($M^+ + 1$) |
| 186 | 7-(5-Aminopyridin-2-ylthio)-7-deoxy-7-epilincomycin | 2.12 (3H, s), 2.31 (3H, s), 5.39 (1H, d, J=5.1 Hz), 6.92 (1H, d, J=8.4 Hz), 8.28 (1H, d, J=8.4 Hz), 7.96 (1H, s) | $CDCl_3$ (300 MHz) | 515 ($M^+ + 1$) |
| 187 | 7-(4-Aminophenylthio)-7-deoxy-7-epilincomycin | 2.16 (3H, s), 2.39 (3H, s), 5.27 (1H, d, J=5.6 Hz), 6.64 (2H, d, J=8.5 Hz), 7.22 (2H, d, J=8.8 Hz) | $CD_3OD$ (400 MHz) | 514 ($M^+ + 1$) |
| 188 | 7-(2-Aminophenylthio)-7-deoxy-7-epilincomycin | 2.19 (3H, s), 2.27 (3H, s), 5.26 (1H, d, J=5.6 Hz), 6.63 (1H, dt, J=1.0, 7.7 Hz), 6.80 (1H, dd, J=1.0, 8.0 Hz), 7.12 (1H, dt, J=1.5, 7.7 Hz), 7.32 (1H, dd, J=1.4, 7.8 Hz) | $CD_3OD$ (400 MHz) | 514 ($M^+ + 1$) |
| 189 | 7-(3-Aminophenylthio)-7-deoxy-7-epilincomycin | 1.92 (3H, s), 2.29 (3H, s), 5.17 (1H, d, J=5.6 Hz), 6.49 (1H, d, J=8.0 Hz), 6.61 (1H, d, J=7.6 Hz), 6.70 (1H, d, J=2.0 Hz), 6.92 (1H, t, J=7.8 Hz) | $CD_3OD$ (400 MHz) | 514 ($M^+ + 1$) |
| 190 | 7-(5-(Acetamido)pyridin-2-ylthio)-7-deoxy-7-epilincomycin | 1.91 (3H, s), 2.15 (3H, s), 2.38 (3H, s), 4.18 (1H, dq, J=3.0, 6.9 Hz), 5.25 (1H, d, J=5.4 Hz), 7.31 (1H, d, J=8.4 Hz), 7.85 (1H, dd, J=2.4, 8.4 Hz), 8.72 (1H, d, J=2.4 Hz) | $CD_3OD$ (300 MHz) | 557 ($M^+ + 1$) |
| 191 | 7-Deoxy-7-epi-7-(5-(propionamido)pyridin-2-ylthio)-lincomycin | 1.20 (3H, t, J=7.5 Hz), 1.90 (3H, s), 2.37 (3H, s), 2.42 (2H, q, J=7.5 Hz), 5.25 (1H, d, J=5.7 Hz), 7.31 (1H, d, J=8.7 Hz), 7.86 (1H, dd, J=2.4, 8.7 Hz), 8.73 (1H, d, J=2.1 Hz) | $CD_3OD$ (300 MHz) | 571 ($M^+ + 1$) |
| 192 | 7-Deoxy-7-epi-7-(5-(pentanamido)pyridin-2-ylthio)-lincomycin | 0.95 (3H, t, J=7.2 Hz), 1.67 (2H, tt, J=7.2, 7.2 Hz), 1.90 (3H, s), 2.36 (3H, s), 2.39 (2H, t, J=7.2 Hz), 4.16 (1H, dq, J=3.0, 7.2 Hz), 5.24 (1H, d, J=5.7 Hz), 7.30 (1H, dd, J=0.6, 8.7 Hz), 7.84 (1H, dd, J=2.7, 8.7 Hz), 8.72 (1H, d, J=2.7 Hz) | $CD_3OD$ (300 MHz) | 599 ($M^+ + 1$) |

TABLE 10-continued

| | | | | |
|---|---|---|---|---|
| 193 | 7-Deoxy-7-epi-7-(5-(2-methoxyacetamido)pyridin-2-ylthio)lincomycin | 1.91 (3H, s), 2.39 (3H, s), 3.50 (3H, s), 4.08 (2H, s), 4.21 (1H, dq, J=3.0, 6.9 Hz), 5.26 (1H, d, J=5.7 Hz), 7.34 (1H, dd, J=0.6, 8.4 Hz), 7.91 (1H, dd, J=2.7, 8.7 Hz), 8.81 (1H, dd, J=0.6, 2.7 Hz) | CD$_3$OD (300 MHz) | 587 (M$^+$ + 1) |
| 194 | 7-(5-Acetamido-1,3,4-thiadiazol-2-ylthio)-7-deoxy-7-epilincomycin | 2.04 (3H, s), 2.23 (1H, s), 2.36 (3H, s), 4.14-4.42 (1H, m), 5.23 (1H, d, J=5.6 Hz) | CD$_3$OD (300 MHz) | 564 (M$^+$ + 1) |
| 195 | 7-Deoxy-7-epi-7-(5-(2-methoxyacetamido)-1,3,4-thiadiazol-2-ylthio)lincomycin | 2.04 (3H, s), 2.38 (3H, s), 3.48 (3H, s), 4.20 (1H, dq, J=3.0, 6.9 Hz), 4.21 (2H, s), 5.26 (1H, d, J=5.4 Hz) | CD$_3$OD (300 MHz) | 594 (M$^+$ + 1) |
| 196 | 7-Deoxy-7-epi-7-(6-((2S,4R)-1-methyl-4-propylpyrrolidine-2-carboxamido)benzo[d]thiazol-2-ylthio)lincomycin | 1.91 (3H, s), 2.36 (3H, s), 2.47 (3H, s), 5.27 (1H, d, J=5.6 Hz), 7.52 (1H, dd, J=2.2, 8.7 Hz), 7.81 (1H, d, J=8.8 Hz), 8.37 (1H, d, J=1.9 Hz) | CD$_3$OD (400 MHz) | 724 (M$^+$ + 1) |
| 197 | 7-(6-(Acetamido)benzo[d]-thiazol-2-ylthio)-7-deoxy-7-epi lincomycin | 1.76 (3H, s), 2.06 (3H, s), 2.23 (6H, s), 5.16 (1H, d, J=5.6 Hz), 7.35 (1H, d, J=2.1, 8.9 Hz), 7.65 (1H, d, J=8.8 Hz), 8.21 (1H, d, J=2.0 Hz) | CD$_3$OD (400 MHz) | 613 (M$^+$ + 1) |
| 198 | 7-(6-((S)-2-Amino-3-methyl-butanamido)benzo[d]thiazol-2-ylthio)-7-deoxy-7-epilincomycin | 0.90 (3H, d, J=6.8 Hz), 0.95 (3H, d, J=7.0 Hz), 1.75 (3H, s), 2.25 (3H, s), 5.15 (1H, d, J=5.6 Hz), 7.41 (1H, dd, J=2.1, 8.9 Hz), 7.68 (1H, d, J=8.8 Hz), 8.25 (1H, d, J=2.2 Hz) | CD$_3$OD (400 MHz) | 670 (M$^+$ + 1) |

TABLE 11

| | | | | |
|---|---|---|---|---|
| 199 | 7-(6-((S)-2-Amino-3-hydroxy-propanamido)benzo[d]thiazol-2-ylthio)-7-deoxy-7-epilincomycin | 1.75 (3H, s), 2.25 (3H, s), 5.15 (1H, d, J=5.6 Hz), 7.43 (1H, dd, J=2.2, 8.8 Hz), 7.68 (1H, d, J=8.8 Hz), 8.26 (1H, d, J=2.2 Hz) | CD$_3$OD (400 MHz) | 658 (M$^+$ + 1) |
| 200 | 7-Deoxy-7-(6-(2-dimethylamino-acetamido)-benzo[d]thiazol-2-ylthio)-7-epilincomycin | 1.75 (3H, s), 2.23 (3H, s), 2.28 (6H, s), 5.16 (1H, d, J=5.6 Hz), 7.43 (1H, dd, J=2.2, 8.8 Hz), 7.67 (1H, d, J=8.9 Hz), 8.24 (1H, d, J=1.9 Hz) | CD$_3$OD (400 MHz) | 656 (M$^+$ + 1) |
| 201 | 7-Deoxy-7-epi-7-(6-(2-methyl-aminoacetamido)benzo[d]-thiazol-2-ylthio)lincomycin | 1.80 (3H, s), 2.26 (3H, s), 2.41 (3H, s), 5.20 (1H, d, J=5.6 Hz), 7.45 (1H, dd, J=2.2, 8.8 Hz), 7.72 (1H, d, J=8.8 Hz), 8.30 (1H, d, J=2.0 Hz) | CD$_3$OD (400 MHz) | 642 (M$^+$ + 1) |
| 202 | 7-(6-((S)-2-Aminosuccinamide)-benzo[d]thiazol-2-ylthio)-7-deoxy-7-epilincomycin | 1.84 (3H, s), 2.35 (3H, s), 5.23 (1H, d, J=5.6 Hz), 7.51 (1H, d, J=2.2, 8.8 Hz), 7.77 (1H, d, J=8.8 Hz), 8.33 (1H, d, J=2.0 Hz) | CD$_3$OD (400 MHz) | 685 (M$^+$ + 1) |
| 203 | 7-(6-(Aminoacetamido)benzo-[d]thiazol-2-ylthio)-7-deoxy-7-epilincomycin | 1.76 (3H, s), 2.25 (3H, s), 5.20 (1H, d, J=5.6 Hz), 7.44 (1H, dd, J=2.2, 8.7 Hz), 7.72 (1H, d, J=8.7 Hz), 8.30 (1H, d, J=2.1 Hz) | CD$_3$OD (400 MHz) | 628 (M$^+$ + 1) |
| 204 | 7-Deoxy-7-epi-7-(4-(propionamido)-phenylthio)-lincomycin | 2.07 (3H, s), 2.35 (3H, s), 5.27 (1H, d, J=5.6 Hz), 7.41 (2H, d, J=8.6 Hz), 7.56 (2H, d, J=8.5 Hz) | CD$_3$OD (400 MHz) | 570 (M$^+$ + 1) |
| 205 | 7-Deoxy-7-epi-7-(4-(pentanamido)-phenylthio)lincomycin | 2.07 (3H, s), 2.35 (3H, s), 5.27 (1H, d, J=5.6 Hz), 7.42 (2H, d, J=8.8 Hz), 7.56 (2H, d, J=8.8 Hz) | CD$_3$OD (400 MHz) | 598 (M$^+$ + 1) |
| 206 | 7-Deoxy-7-epi-7-(4-(methoxy-acetamido)phenylthio)lincomycin | 2.02 (3H, s), 2.36 (3H, s), 3.47 (3H, s), 5.28 (1H, d, J=5.6 Hz), 7.42 (2H, d, J=8.7 Hz), 7.62 (2H, d, J=8.6 Hz) | CD$_3$OD (400 MHz) | 586 (M$^+$ + 1) |
| 207 | 7-(4-(Acrylamido)phenylthio)-7-deoxy-7-epilincomycin | 2.06 (3H, s), 2.36 (3H, s), 5.28 (1H, d, J=5.6 Hz), 5.77 (1H, dd, J=2.4, 9.5 Hz), 6.36 (1H, dd, J=2.4, 17.1 Hz), 6.43 (1H, dd, J=9.5, 17.1 Hz), 7.44 (1H, d, J=8.7 Hz), 7.64 (1H, d, J=8.7 Hz) | CD$_3$OD (400 MHz) | 568 (M$^+$ + 1) |
| 208 | 7-Deoxy-7-epi-7-(4-(methylamino-acetamido)phenylthio)lincomycin | 2.05 (3H, s), 2.36 (3H, s), 2.48 (3H, s), 5.27 (1H, d, J=5.6 Hz), 7.44 (2H, d, J=8.8 Hz), 7.59 (2H, d, J=8.8 Hz) | CD$_3$OD (400 MHz) | 585 (M$^+$ + 1) |
| 209 | 7-Deoxy-7-epi-7-(4-(morpholino-carbonylamino)phenylthio)-lincomycin | 2.09 (3H, s), 2.37 (3H, s), 5.28 (1H, d, J=5.6 Hz), 7.90 (4H, s) | CD$_3$OD (400 MHz) | 627 (M$^+$ + 1) |

TABLE 11-continued

| | | | | |
|---|---|---|---|---|
| 210 | 7-(6-(Acetamido)benzo[d]oxazol-2-ylthio)-7-deoxy-7-epilincomycin | 1.88 (3H, s), 2.14 (3H, s), 2.45 (3H, s), 5.25 (1H, d, J=5.6 Hz), 7.28 (1H, dd, J=1.9, 8.5 Hz), 7.48 (1H, d, J=8.5 Hz), 8.07 (1H, d, J=1.7 Hz) | $CD_3OD$ (400 MHz) | 597 ($M^+ + 1$) |
| 211 | 7-Deoxy-7-epi-7-(4-(methyl-sulfonamido)-phenylthio)lincomycin | 2.04 (3H, s), 2.40 (3H, s), 2.97 (3H, s), 5.27 (1H, d, J=5.6 Hz), 7.22 (2H, d, J=8.8 Hz), 7.43 (2H, d, J=8.5 Hz) | $CD_3OD$ (400 MHz) | 592 ($M^+ + 1$) |
| 212 | 7-(6-Allylaminobenzo[d]thiazol-2-ylthio)-7-deoxy-7-epilincomycin | 1.94 (3H, s), 2.26 (3H, s), 5.13 (1H, dq, J=1.6, 10.2 Hz), 5.24 (1H, d, J=6.0 Hz), 5.27 (1H, dq, J=1.7, 17.1 Hz), 5.88-5.98 (1H, m), 6.82 (1H, dd, J=2.2, 8.8 Hz), 6.95 (1H, d, J=2.2 Hz), 7.59 (1H, d, J=8.7 Hz) | $CD_3OD$ (400 MHz) | 611 ($M^+ + 1$) |
| 213 | 7-(6-Carbamoylbenzo[d]thiazol-2-ylthio)-7-deoxy-7-epilincomycin | 1.94 (3H, s), 2.35 (3H, s), 5.33 (1H, d, J=5.4 Hz), 7.83 (2H, s), 8.36 (1H, s) | $CDCl_3$ (300 MHz) | 599 ($M^+ + 1$) |
| 214 | 7-Deoxy-7-(6-(dimethylcarbamoyl)-benzo[d]thiazol-2-ylthio)-7-epilincomycin | 1.99 (3H, s), 2.36 (3H, s), 3.03 (6H, s), 5.34 (1H, d, J=5.4 Hz), 7.41 (1H, d, J=8.1 Hz), 7.80 (1H, d, J=8.1 Hz), 7.97 (1H, s) | $CDCl_3$ (300 MHz) | 627 ($M^+ + 1$) |
| 215 | 7-(6-(Azetidinocarbonyl)benzo-[d]thiazol-2-ylthio)-7-deoxy-7-epilincomycin | 1.96 (3H, s), 2.36 (3H, s), 5.34 (1H, d, J=5.4 Hz), 7.65 (1H, d, J=8.1 Hz), 7.81 (1H, d, J=8.1 Hz), 8.14 (1H, s) | $CDCl_3$ (300 MHz) | 639 ($M^+ + 1$) |
| 216 | 7-Deoxy-7-epi7-(6-(methyl-carbamoyl)-benzo[d]thiazol-2-ylthio)-lincomycin | 1.93 (3H, s), 2.36 (3H, s), 3.05 (3H, d, J=4.5 Hz), 5.34 (1H, d, J=5.1 Hz), 6.56 (1H, d, J=4.5 Hz), 7.80 (2H, s), 7.30 (1H, s) | $CDCl_3$ (300 MHz) | 613 ($M^+ + 1$) |
| 217 | 7-Deoxy-7-epi-7-(5-(morpholino-carbonyl)-1,3,4-thiadiazol-2-ylthio)lincomycin | 2.12 (3H, s), 2.35 (3H, s), 3.60-3.80 (8H, m), 5.34 (1H, d, J=5.4 Hz) | $CDCl_3$ (300 MHz) | 620 ($M^+ + 1$) |
| 218 | 7-Deoxy-7-epi-7-(5-piperidino-carbonyl-1,3,4-thiadiazol-2-ylthio)-lincomycin | 2.13 (3H, s), 2.39 (3H, s), 1.65-1.80 (6H, m), 3.50-3.65 (4H, m), 5.34 (1H, d, J=5.4 Hz) | $CDCl_3$ (300 MHz) | 618 ($M^+ + 1$) |
| 219 | 7-Deoxy-7-(5-((2S,6R)-(2,6-dimethylmorpholino))-Carbonyl-1,3,4-thiadiazol-2-ylthio)-7-epilincomycin | 1.25-1.40 (6H, m), 2.12 (3H, s), 2.40 (3H, s), 3.55-3.70 (6H, m), 5.32 (1H, d, J=5.4 Hz) | $CDCl_3$ (300 MHz) | 648 ($M^+ + 1$) |
| 220 | 7-Deoxy-7-epi-7-(5-(pyrrolidino-carbonyl)-1,3,4-thiadiazol-2-ylthio)lincomycin | 1.15-1.25 (4H, m), 2.12 (3H, s), 2.40 (3H, s), 3.60-3.70 (4H, m), 5.32 (1H, d, J=5.4 Hz) | $CDCl_3$ (300 MHz) | 604 ($M^+ + 1$) |

TABLE 12

| | | | | |
|---|---|---|---|---|
| 221 | 7-Deoxy-7-epi-7-(4-(piperidino-carbonyl)thiazol-2-ylthio)lincomycin | 1.50-1.70 (6H, m), 1.93 (3H, s), 2.34 (3H, s), 3.55-3.65 (4H, m), 5.34 (1H, d, J=5.4 Hz), 7.70 (1H, s) | $CDCl_3$ (300 MHz) | 617 ($M^+ + 1$) |
| 222 | 7-Deoxy-7-epi-7-(5-(piperidino-carbonyl)thiazol-2-ylthio)-lincomycin | 1.50-1.70 (6H, m), 2.09 (3H, s), 2.25 (3H, s), 3.55-3.65 (4H, m), 5.25 (1H, d, J=5.4 Hz), 7.67 (1H, s) | $CDCl_3$ (300 MHz) | 617 ($M^+ + 1$) |
| 223 | 7-Deoxy-7-epi-7-(5-(pyrrolidino-carbonyl)thiazol-2-ylthio)-lincomycin | 1.80-2.00 (4H, m), 2.12 (3H, s), 2.40 (3H, s), 3.60-3.75 (4H, m), 5.33 (1H, d, J=5.4 Hz), 7.98 (1H, s) | $CDCl_3$ (300 MHz) | 603 ($M^+ + 1$) |
| 224 | 7-Deoxy-7-epi-7-(5-(4-methyl-piperidinocarbonyl)thiazol-2-ylthio)-lincomycin | 1.00 (3H, d, J=6.9 Hz), 1.20-1.35 (5H, m), 2.13 (3H, s), 2.38 (3H, s), 3.50-3.75 (4H, m), 5.33 (1H, d, J=5.4 Hz), 7.75 (1H, s) | $CDCl_3$ (300 MHz) | 631 ($M^+ + 1$) |
| 225 | 7-Deoxy-7-(5-(2S,6R)-(2,6-di methylmorpholino)carbonyl-thiazol-2-ylthio)-7-epilincomycin | 1.25-1.40 (6H, m), 2.12 (3H, s), 2.40 (3H, s), 3.45-3.65 (6H, m), 5.32 (1H, d, J=5.4 Hz), 7.96 (1H, s) | $CDCl_3$ (300 MHz) | 649 ($M^+ + 1$) |
| 226 | 7-Deoxy-7-epi-7-(5-(morpholinocarbonyl)-thiazol-2-ylthio)lincomycin | 1.84 (3H, s), 2.38 (3H, s), 3.40-3.55 (8H, m), 5.25 (1H, d, J=6.0 Hz), 7.89 (1H, s) | $CDCl_3$ (300 MHz) | 619 ($M^+ + 1$) |
| 227 | 7-Deoxy-7-(4-(dimethylcarbamoyl)-phenylthio)-7-epilincomycin | 1.90 (3H, s), 2.64 (3H, s), 3.00 (3H, s), 3.08 (3H, s), 5.26 (1H, d, J=5.6 Hz), 7.38 (2H, d, J=8.3 Hz), 7.45 (2H, d, J=8.5 Hz) | $CD_3OD$ (400 MHz) | 570 ($M^+ + 1$) |
| 228 | 7-Deoxy-7-epi-7-(4-(pyrrolidino-carbonyl)phenylthio)lincomycin | 1.91 (3H, s), 2.42 (3H, s), 5.26 (1H, d, J=5.6 Hz), 7.45 (2H, d, J=8.6 Hz), 7.49 (2H, d, J=8.5 Hz) | $CD_3OD$ (400 MHz) | 596 ($M^+ + 1$) |

TABLE 12-continued

| | | | | |
|---|---|---|---|---|
| 229 | 7-Deoxy-7-epi-7-(4-(propyl-carbamoyl)-phenylthio)lincomycin | 1.88 (3H, s), 2.40 (3H, s), 5.26 (1H, d, J=5.6 Hz), 7.45 (2H, d, J=8.5 Hz), 7.76 (2H, d, J=8.5 Hz) | CD$_3$OD (400 MHz) | 624 (M$^+$ + 1) |
| 230 | 7-Deoxy-7-epi-7-(4-(2-hydroxy-ethylcarbamoyl)phenylthio)-lincomycin | 1.87 (3H, s), 2.40 (3H, s), 5.27 (1H, d, J=5.4 Hz), 7.44 (2H, d, J=8.8 Hz), 7.80 (2H, d, J=8.3 Hz) | CD$_3$OD (400 MHz) | 586 (M$^+$ + 1) |
| 231 | 7-Deoxy-7-epi-7-(3-(methyl-carbamoyl)-phenylthio)lincomycin | 1.94 (3H, s), 2.38 (3H, s), 2.91 (3H, s), 5.26 (1H, d, J=5.6 Hz), 7.41 (1H, t, J=7.8 Hz), 7.57 (1H, dt, J=1.5, 7.8 Hz), 7.68 (1H, dt, J=1.5, 7.8 Hz), 7.88 (1H, t, J=1.7 Hz) | CD$_3$OD (400 MHz) | 556 (M$^+$ + 1) |
| 232 | 7-(4-Carbamoylphenylthio)-7-deoxy-7-epilincomycin | 1.88 (3H, s), 2.44 (3H, s), 2.90 (3H, s), 5.25 (1H, d, J=5.4 Hz), 7.45 (2H, d, J=8.5 Hz), 7.81 (2H, d, J=8.6 Hz) | CD$_3$OD (400 MHz) | 542 (M$^+$ + 1) |
| 233 | 7-Deoxy-7-epi-7-(4-(methyl-carbamoyl)-phenylthio)lincomycin | 1.86 (3H, s), 2.43 (3H, s), 2.90 (3H, s), 5.25 (1H, d, J=5.6 Hz), 7.44 (2H, d, J=8.6 Hz), 7.75 (2H, d, J=8.3 Hz) | CD$_3$OD (400 MHz) | 556 (M$^+$ + 1) |
| 234 | 7-Deoxy-7-epi-7-(4-hydroxy-methylphenylthio)lincomycin | 2.00 (3H, s), 2.40 (3H, s), 4.58 (2H, s), 5.28 (1H, d, J=5.4 Hz), 7.31 (2H, d, J=8.3 Hz), 7.40 (2H, d, J=8.3 Hz) | CD$_3$OD (400 MHz) | 529 (M$^+$ + 1) |
| 235 | 7-Deoxy-7-epi-7-(4-(piperidino-carbonyl)benzyl thio)lincomycin | 2.42 (3H, s), 5.24 (1H, d, J=5.7 Hz), 7.31-7.48 (4H, m) | CD$_3$OD (400 MHz) | 624 (M$^+$ + 1) |
| 236 | 7-Deoxy-7-epi-7-(4-(morpholino-carbonyl)benzylthio)lincomycin | 2.11 (3H, s), 2.40 (3H, s), 3.89-3.98 (2H, m), 5.24 (1H, d, J=5.6 Hz), 7.36-7.47 (4H, m) | CD$_3$OD (400 MHz) | 626 (M$^+$ + 1) |
| 237 | 7-Deoxy-7-epi-7-(3-(morpholino-carbonyl)benzylthio)-lincomycin | 2.40 (3H, s), 5.24 (1H, d, J=5.4 Hz), 7.29-7.33 (1H, m), 7.38-7.49 (3H, m) | CD$_3$OD (400 MHz) | 626 (M$^+$ + 1) |
| 238 | 7-((4-Amino-5-morpholinocarbonyl)-pyrimidin-2-ylthio)-7-deoxy-7-epilincomycin | 1.71 (3H, s), 2.22 (3H, s), 5.07 (1H d, J=5.6 Hz), 7.81 (1H, s) | CD$_3$OD (400 MHz) | 629 (M$^+$ + 1) |
| 239 | 7-(4-(N-(1-Adamantyl)-aminocarbonyl)-phenylthio)-7-deoxy-7-epilincomycin | 1.90 (3H, s), 2.41 (3H, s), 3.97 (1H, dq, J=2.7, 6.9 Hz), 5.24 (1H, d, J=5.4 Hz), 7.41 (2H, d, J=8.4 Hz), 7.69 (2H, d, J=8.1 Hz) | CD$_3$OD (300 MHz) | 676 (M$^+$ + 1) |
| 240 | 7-Deoxy-7-epi-7-(5-(pyrrolidinocarbonyl)pyridin-2-ylthio)lincomycin | 1.80 (3H, s), 1.93-2.09 (4H, m), 2.42 (3H, s), 3.44 (2H, t, J=6.9 Hz), 3.52 (2H, t, J=6.9 Hz), 5.25 (1H, d, J=5.4 Hz), 7.38 (1H, dd, J=0.6, 8.4 Hz), 7.79 (1H, dd, J=2.4, 8.4 Hz), 8.61 (1H, dd, J=0.6, 2.4 Hz) | CD$_3$OD (300 MHz) | 597 (M$^+$ + 1) |
| 241 | 7-Deoxy-7-epi-7-(5-(piperidinocarbonyl)-pyridin-2-ylthio)lincomycin | 1.67 (6H, br), 1.81 (3H, s), 2.42 (3H, s), 3.44 (2H, br), 3.72 (2H, br), 5.27 (1H, d, J=6.0 Hz), 7.40 (1H, dd, J=0.9, 8.1 Hz), 7.67 (1H, dd, J=2.1, 8.1 Hz), 8.48 (1H, dd, J=0.9, 2.1 Hz) | CD$_3$OD (300 MHz) | 611 (M$^+$ + 1) |
| 242 | 7-Deoxy-7-epi-7-(5-morpholinocarbonylpyridin-2-ylthio)lincomycin | 1.81 (3H, s), 2.42 (3H, s), 3.72 (8H, br), 4.46 (1H, dq, J=3.0, 6.9 Hz), 5.27 (1H, d, J=5.7 Hz), 7.41 (1H, dd, J=0.9, 8.1 Hz), 7.71 (1H, dd, J=2.4, 8.1 Hz), 8.52 (1H, dd, J=0.9, 2.1 Hz) | CD$_3$OD (300 MHz) | 613 (M$^+$ + 1) |

TABLE 13

| | | | | |
|---|---|---|---|---|
| 243 | 7-Deoxy-7-epi-7-(2-(pyrrolidino-carbonyl)phenylthio)-lincomycin | 1.42-1.52 (1H, m), 1.70-1.79 (1H, m), 2.08 (3H, s), 2.25 (3H, s), 4.47 (2H, s), 5.29 (1H, d, J=5.7 Hz), 7.30-7.34 (1H, m), 7.40-7.46 (2H, m), 7.58-7.62 (1H, m) | CD$_3$OD (300 MHz) | 596 (M$^+$ + 1) |
| 244 | 7-Deoxy-7-epi-7-(4-(pyridino-3-ylcarbamoyl)phenylthio)-lincomycin | 1.88 (3H, s), 2.50 (3H, s), 5.26 (1H, d, J=5.4 Hz), 7.45 (1H, dq, J=0.7, 4.9 Hz), 7.50 (2H, d, J=8.8 Hz), 7.91 (2H, d, J=8.5 Hz), 8.25 (1H, dq, J=1.6, 8.5 Hz), 8.30 (1H, dd, J=1.5, 4.9 Hz), 8.88 (1H, d, J=2.7 Hz) | CD$_3$OD (400 MHz) | 619 (M$^+$ + 1) |
| 245 | 7-Deoxy-7-epi-7-(4-(piperidino-carbonyl)phenylthio)lincomycin | 1.91 (3H, s), 2.44 (3H, s), 5.26 (1H, d, J=5.4 Hz), 7.35 (2H, d, J=8.3 Hz), 7.47 (2H, d, J=8.2 Hz) | CD$_3$OD (400 MHz) | 610 (M$^+$ + 1) |

TABLE 13-continued

| | | | | |
|---|---|---|---|---|
| 246 | 7-Deoxy-7-epi-7-(4-(morpholino-carbonyl)phenylthio)lincomycin | 1.91 (3H, s), 2.45 (3H, s), 5.26 (1H, d, J=5.4 Hz), 7.39 (2H, d, J=8.6 Hz), 7.47 (2H, d, J=8.5 Hz) | $CD_3OD$ (400 MHz) | 612 ($M^+$ + 1) |
| 247 | 7-(4-(Cyclohexylcarbamoyl)-phenylthio)-7-deoxy-7-epilincomycin | 1.93 (3H, s), 2.46 (3H, s), 5.29 (1H, d, J=5.6 Hz), 7.56 (2H, d, J=8.5 Hz), 7.97 (2H, d, J=8.0 Hz) | $CD_3OD$ (400 MHz) | 624 ($M^+$ + 1) |
| 248 | 7-(4-(Cyclopropylcarbamoyl)-phenylthio)-7-deoxy-7-epilincomycin | 0.60-0.65 (2H, m), 0.90-0.96 (1H, m), 1.87 (3H, s), 2.44 (3H, s), 5.25 (1H, d, J=5.7 Hz), 7.43 (2H, d, J=8.8 Hz), 7.74 (2H, d, J=8.5 Hz) | $CD_3OD$ (400 MHz) | 582 ($M^+$ + 1) |
| 249 | 7-Deoxy-7-epi-7-(4-(N-methylpiperazinocarbonyl)-phenylthio)lincomycin | 1.91 (3H, s), 2.33 (3H, s), 2.46 (3H, s), 5.25 (1H, d, J=5.7 Hz), 7.38 (2H, d, J=8.5 Hz), 7.47 (2H, d, J=8.5 Hz) | $CD_3OD$ (400 MHz) | 625 ($M^+$ + 1) |
| 250 | 7-Deoxy-7-epi-7-(4-(thiomorpholinocarbonyl)-phenylthio)-lincomycin | 1.91 (3H, s), 2.42 (3H, s), 5.25 (1H, d, J=5.7 Hz), 7.36 (2H, d, J=8.5 Hz), 7.47 (2H, d, J=8.6 Hz) | $CD_3OD$ (400 MHz) | 628 ($M^+$ + 1) |
| 251 | 7-Deoxy-7-epi-7-(4-(4-oxopiperidinocarbonyl)-phenylthio)-lincomycin | 1.91 (3H, s), 2.43 (3H, s), 5.26 (1H, d, J=5.7 Hz), 7.37 (1H, d, J=8.5 Hz), 7.46 (1H, d, J=8.6 Hz), 7.48 (1H, d, J=8.5 Hz), 7.97 (1H, s) | $CD_3OD$ (400 MHz) | 624 ($M^+$ + 1) |
| 252 | 7-Deoxy-7-epi-7-(4-(piperazino-carbonyl)phenylthio)lincomycin | 1.91 (3H, s), 2.50 (3H, s), 5.26 (1H, d, J=5.7 Hz), 7.42 (2H, d, J=8.5 Hz), 7.48 (2H, d, J=8.6 Hz) | $CD_3OD$ (400 MHz) | 610 ($M^+$ + 1) |
| 253 | 7-Deoxy-7-epi-7-(4-(1,3,4-thiadiazol-2-ylcarbamoyl)-phenylthio)-lincomycin | 1.86 (3H, s), 2.41 (3H, s), 5.25 (1H, d, J=5.3 Hz), 7.53 (2H, d, J=8.5 Hz), 8.00 (1H, d, J=8.7 Hz), 9.08 (1H, s) | $CD_3OD$ (400 MHz) | 626 ($M^+$ + 1) |
| 254 | 7-Deoxy-7-epi-7-(4-(thiazol-2-ylcarbamoyl)phenylthio)-lincomycin | 1.91 (3H, s), 2.49 (3H, s), 5.31 (1H, d, J=5.6 Hz), 7.10 (1H, d, J=3.4 Hz), 7.48 (1H, d, J=3.4 Hz), 7.50 (2H, d, J=8.8 Hz), 8.00 (1H, d, J=8.5 Hz) | $CD_3OD$ (400 MHz) | 625 ($M^+$ + 1) |
| 255 | 7-Deoxy-7-(4-((2S,6R)-(2,6-dimethylmorpholino))phenylthio)-7-epilincomycin | 1.90 (3H, s), 2.43 (3H, s), 5.26 (1H, d, J=5.7 Hz), 7.37 (2H, d, J=8.5 Hz), 7.47 (2H, d, J=8.5 Hz) | $CD_3OD$ (400 MHz) | 640 ($M^+$ + 1) |
| 256 | 7-Deoxy-7-epi-7-(3-(morpholino-carbonyl)phenylthio)lincomycin | 1.95 (3H, s), 2.42 (3H, s), 5.26 (1H, d, J=5.7 Hz), 7.28 (1H, d, J=7.8 Hz), 7.40-7.46 (1H, m), 7.52 (1H, d, J=7.8 Hz), 7.98 (1H, s) | $CD_3OD$ (400 MHz) | 612 ($M^+$ + 1) |
| 257 | 7-Deoxy-7-epi-7-(3-(piperidino-carbonyl)phenylthio)lincomycin | 1.95 (3H, s), 2.43 (3H, s), 5.26 (1H, d, J=5.6 Hz), 7.24 (1H, d, J=7.8 Hz), 7.38-7.44 (1H, m), 7.50 (1H, d, J=7.8 Hz), 7.97 (1H, s) | $CD_3OD$ (400 MHz) | 610 ($M^+$ + 1) |
| 258 | 7-Deoxy-7-epi-7-(3-(pyrrolidino-carbonyl)phenylthio)lincomycin | 1.96 (3H, s), 2.43 (3H, s), 5.26 (1H, d, J=5.6 Hz), 7.35-7.45 (1H, m), 7.50-7.55 (2H, m), 7.98 (1H, s) | $CD_3OD$ (400 MHz) | 596 ($M^+$ + 1) |
| 259 | 7-Deoxy-7-epi-7-(4-((R)-2-(hydroxymethyl)pyrrolidino-carbonyl)phenylthio)-lincomycin | 1.90 (3H, s), 2.44 (3H, s), 3.38-3.44 (1H, m), 3.48-3.55 (1H, m), 3.74 (1H, dd, J=3.7, 11.0 Hz), 3.81 (1H, dd, J=5.1, 11.2 Hz), 3.97 (1H, dd, J=2.4, 6.8 Hz), 4.23-4.31 (1H, m), 5.25 (1H, d, J=5.6 Hz), 7.45 (2H, d, J=7.8 Hz), 7.50 (2H, d, J=8.3 H) | $CD_3OD$ (400 MHz) | 626 ($M^+$ + 1) |
| 260 | 7-((4-Amino-5-carbamoyl)pyrimidin-2-ylthio)-7-deoxy-7-epilincomycin | 1.76 (3H, s), 2.25 (3H, s), 5.13 (1H, d, J=5.6 Hz), 8.33 (1H, s) | $CD_3OD$ (400 MHz) | 559 ($M^+$ + 1) |
| 261 | 7-((4-Amino-5-(pyrrolidinocarbonyl)pyrimidin-2-ylthio)-7-deoxy-7-epilincomycin | 1.87 (3H, s), 2.37 (3H, s), 5.23 (1H, d, J=5.6 Hz), 8.08 (1H, s) | $CD_3OD$ (400 MHz) | 613 ($M^+$ + 1) |
| 262 | 7-((4-Amino-5-(piperidinocarbonyl)pyrimidin-2-ylthio)-7-deoxy-7-epilincomycin | 1.86 (3H, s), 2.37 (3H, s), 5.23 (1H, d, J=5.8 Hz), 7.92 (1H, s) | $CD_3OD$ (400 MHz) | 627 ($M^+$ + 1) |
| 263 | 7-Deoxy-7-epi-7-(5-(2-nitro phenyl)thiazol-2-ylthio)lincomycin | 2.03 (3H, s), 2.36 (3H, s), 5.26 (1H, d, J=5.6 Hz), 7.60-7.66 (2H, m), 7.66 (1H, s), 7.70-7.74 (1H, m), 7.90-7.95 (1H, m) | $CD_3OD$ (400 MHz) | 627 ($M^+$ + 1) |
| 264 | 7-Deoxy-7-epi-7-(5-(pyridin-2-yl)thiazol-2-ylthio)lincomycin | 2.01 (3H, s), 2.36 (3H, s), 5.26 (1H, d, J=5.6 Hz), 7.27-7.33 (1H, m), 7.81-7.85 (2H, m), 8.24 (1H, s), 8.50-8.51 (1H, m) | $CD_3OD$ (400 MHz) | 583 ($M^+$ + 1) |

TABLE 14

| | | | | |
|---|---|---|---|---|
| 265 | 7-Deoxy-7-epi-7-(6-(pyridin-3-yl)pyridin-3-ylthio)lincomycin | 2.01 (3H, s), 2.39 (3H, s), 5.26 (1H, d, J=5.6 Hz), 7.56 (1H, ddd, J=8.0, 4.9, 0.7 Hz), 7.93 (1H, dd, J=8.3, 0.7 Hz), 8.00 (1H, dd, J=8.3, 2.2 Hz), 8.45 (1H, ddd, J=8.1, 2.2, 0.7 Hz), 8.59 (1H, dd, J=4.9, 1.7 Hz), 8.70 (1H, dd, J=2.2, 0.7 Hz), 9.18 (1H, dd, J=2.2, 0.7 Hz) | $CD_3OD$ (400 MHz) | 577 ($M^+ + 1$) |
| 266 | 7-Deoxy-7-epi-7-(5-(pyridin-3-yl)pyridin-2-ylthio)lincomycin | 1.84 (3H, s), 2.38 (3H, s), 5.24 (1H, d, J=5.9 Hz), 7.43 (1H, d, J=8.4 Hz), 7.54 (1H, ddd, J=8.0, 2.4, 2.4 Hz), 7.94 (1H, dd, J=8.4, 2.4 Hz), 8.12 (1H, ddd, J=8.0, 2.2, 2.2 Hz), 8.57 (1H, dd, J=8.4, 1.8 Hz), 8.73 (1H, d, J=2.2 Hz), 8.82 (1H, d, J=1.8 Hz) | $CD_3OD$ (400 MHz) | 577 ($M^+ + 1$) |
| 267 | 7-Deoxy-7-(5-(4-dimethylamino-2-nitrophenyl)-1,3,4-thiadiazol-2-ylthio)-7-epilincomycin | 2.19 (3H, s), 2.41 (3H, s), 3.12 (6H, s), 5.35 (1H, d, J=5.7 Hz), 6.86 (1H, dd, J=2.5, 9.0 Hz), 7.10 (1H, d, J=2.5 Hz), 7.55 (1H, d, J=9.0 Hz) | $CDCl_3$ (300 MHz) | 671 ($M^+ + 1$) |
| 268 | 7-Deoxy-7-epi-7-(5-(5-dimethylamino-2-nitrophenyl)-1,3,4-thiadiazol-2-ylthio)-7-epilincomycin | 2.18 (3H, s), 2.40 (3H, s), 3.15 (6H, s), 5.36 (1H, d, J=5.4 Hz), 6.73 (1H, s), 6.74 (1H, d, J=9.0 Hz), 8.18 (1H, d, J=9.0 Hz) | $CDCl_3$ (300 MHz) | 671 ($M^+ + 1$) |
| 269 | 7-Deoxy-7-epi-7-(5-(5-methylamino-2-nitrophenyl)-1,3,4-thiadiazol-2-ylthio)lincomycin | 2.16 (3H, s), 2.40 (3H, s), 2.95 (3H, d, J=4.8 Hz), 5.36 (1H, d, J=5.1 Hz), 6.67 (1H, s), 6.68 (1H, d, J=9.0 Hz), 8.13 (1H, d, J=9.0 Hz) | $CDCl_3$ (300 MHz) | 657 ($M^+ + 1$) |
| 270 | 7-(5-(5-Amino-2-nitrophenyl)-1,3,4-thiadiazol-2-ylthio)-7-deoxy-7-epilincomycin | 2.12 (3H, s), 2.39 (3H, s), 5.36 (1H, d, J=5.4 Hz), 6.75-6.80 (2H, m), 8.08 (1H, d, J=9.0 Hz) | $CDCl_3$ (300 MHz) | 643 ($M^+ + 1$) |
| 271 | 7-Deoxy-7-epi-7-(5-(4-(2-hydroxyethylamino)-2-nitrophenyl)-1,3,4-thiadiazol-2-ylthio)lincomycin | 1.55 (3H, d, J=6.8 Hz), 2.37 (3H, s), 5.27 (1H, d, J=5.6 Hz), 6.89-6.95 (1H, m), 7.13-7.17 (1H, m), 7.43-7.48 (1H, m) | $CDCl_3$ (400 MHz) | 687 ($M^+ + 1$) |
| 272 | 7-Deoxy-7-epi-7-(5-(4-fluoro-5-(2-hydroxyethylamino)-2-nitrophenyl)-1,3,4-thiadiazol-2-ylthio)lincomycin | 1.58 (3H, d, J=7.1 Hz), 2.40 (3H, s), 3.41 (2H, t, J=5.6 Hz), 3.73 (2H, t, J=5.6 Hz), 5.28 (1H, d, J=5.6 Hz), 6.90-6.96 (1H, m), 7.95-8.02 (1H, m) | $CDCl_3$ (300 MHz) | 705 API ($M^+ + 1$) |
| 273 | 7-Deoxy-7-(5-(5-dimethylamino-4-fluoro-2-nitrophenyl)-1,3,4-thiadiazol-2-ylthio)-7-epilincomycin | 1.57 (3H, d, J=7.1 Hz), 2.40 (3H, s), 5.36 (1H, d, J=5.6 Hz), 6.82-6.89 (1H, m), 7.90-7.98 (1H, m) | $CDCl_3$ (300 MHz) | 689 API ($M^+ + 1$) |
| 274 | 7-Deoxy-7-epi-7-(5-(4-fluoro-5-methylamino-2-nitrophenyl)-1,3,4-thiadiazol-2-ylthio)lincomycin | 2.40 (3H, s), 3.00 (3H, d, J=5.4 Hz), 5.38 (1H, d, J=5.4 Hz), 6.74-6.80 (1H, m), 7.91-7.98 (1H, m) | $CDCl_3$ (300 MHz) | 675 ($M^+ + 1$) |
| 275 | 7-Deoxy-7-epi-7-(5-(5-methoxy-2-nitrophenyl)-1,3,4-thiadiazol-2-ylthio)lincomycin | 2.14 (3H, s), 2.40 (3H, s), 3.94 (3H, s), 5.36 (1H, d, J=5.4 Hz), 7.05-7.20 (2H, m), 8.16 (1H, d, J=8.4 Hz) | $CDCl_3$ (300 MHz) | 658 ($M^+ + 1$) |
| 276 | 7-Deoxy-7-epi-7-(5-(4-fluoro-5-methoxy-2-nitrophenyl)-1,3,4-thiadiazol-2-ylthio)lincomycin | 1.58 (3H, d, J=6.82 Hz), 2.17 (3H, s), 2.40 (3H, s), 5.36 (1H, d, J=5.4 Hz), 7.23-7.26 (1H, m), 7.94-7.99 (1H, m) | $CDCl_3$ (300 MHz) | 676 ($M^+ + 1$) |
| 277 | 7-Deoxy-7-(1-(dimethylamino-carbamoyl)azetidin-3-ylthio)-7-epilincomycin | 0.85-0.95 (3H, m), 2.42 (3H, s), 2.84 (6H, s), 5.26 (1H, d, J=5.6 Hz) | $CD_3OD$ (400 MHz) | 549 ($M^+ + 1$) |
| 278 | 7-Deoxy-7-epi-7-(1-(morpholino-carbonyl)azetidin-3-ylthio)-lincomycin | 0.87-0.95 (3H, m), 2.18 (3H, s), 2.42 (3H, s), 3.59-3.64 (4H, m), 5.26 (1H, d, J=5.7 Hz) | $CD_3OD$ (400 MHz) | 591 ($M^+ + 1$) |
| 279 | 7-Deoxy-7-epi-7-(1-(4-ethyl-2,3-dioxopiperazin-1-yl-carbamoyl)-azetidin-3-ylthio)lincomycin | 0.79-0.93 (3H, m), 2.18 (3H, br), 2.42 (3H, s), 5.26 (1H, d, J=5.7 Hz) | $CD_3OD$ (400 MHz) | 646 ($M^+ + 1$) |
| 280 | 7-(1-Benzoylazetidin-3-ylthio)-7-deoxy-7-epilincomycin | 0.87-0.94 (3H, m), 2.35-2.43 (3H, m), 5.18-5.29 (1H, m), 7.43-7.55 (3H, m), 7.60-7.65 (2H, m) | $CD_3OD$ 400 MHz) | 582 ($M^+ + 1$) |
| 281 | 7-Deoxy-7-epi-7-(1-(2-nitrobenzoyl)azetidin-3-ylthio)lincomycin | 0.86-0.94 (3H, m), 2.35-2.44 (3H, m), 5.14-5.27 (1H, m), 7.50-7.56 (1H, m), 7.67-7.73 (1H, m), 7.77-7.84 (1H, m), 8.15-8.21 (1H, m) | $CD_3OD$ (400 MHz) | 627 ($M^+ + 1$) |
| 282 | 7-Deoxy-7-epi-7-(1-(5-(methyl-amino)thiazol-4-yl-carbonyl)-azetidin-3-ylthio)lincomycin | 0.87-0.94 (3H, m), 2.42 (3H, s), 5.25 (1H, d, J=5.3 Hz), 7.90 (1H, s) | $CD_3OD$ (400 MHz) | 618 ($M^+ + 1$) |
| 283 | 7-Deoxy-7-epi-7-(1-(2-morpholinoacetyl)-azetidin-3-ylthio)-lincomycin | 0.85-0.94 (3H, m), 2.42 (3H, s), 2.46-2.53 (4H, m), 3.03-3.08 (2H, m), 5.24-5.29 (1H, m) | $CD_3OD$ (400 MHz) | 605 ($M^+ + 1$) |

TABLE 14-continued

| | | | | |
|---|---|---|---|---|
| 284 | 7-Deoxy-7-epi-7-(1-phenylsulfonylazetidin-3-ylthio)lincomycin | 0.88-0.94 (3H, m), 2.34 (3H, m), 5.21 (1H, d, J=5.6 Hz), 7.65-7.78 (3H, m), 7.33-7.89 (2H, m) | CD₃OD (400 MHz) | 618 (M⁺ + 1) |
| 285 | 7-(1-(2-Cyanoethyl)azetidin-3-ylthio)-7-deoxy-7-epilincomycin | 0.88-0.95 (3H, m), 2.05 (3H, s), 2.42 (3H, s), 2.48 (2H, t, J=6.3 Hz), 2.72 (2H, t, J=6.3 Hz), 5.26 (1H, d, J=5.6 Hz) | CD₃OD (400 MHz) | 531 (M⁺ + 1) |
| 286 | 7-Deoxy-7-(1-(2-dimethylcarbamoylethyl)-azetidin-3-ylthio)-7-epilincomycin | 0.88-0.95 (3H, m), 2.18 (3H, s), 2.38-2.44 (3H, m), 2.64-2.77 (2H, m), 2.91 (3H, s), 5.26 (1H, d, J=5.6 Hz) | CD₃OD (400 MHz) | 577 (M⁺ + 1) |

TABLE 15

| | | | | |
|---|---|---|---|---|
| 287 | 7-Deoxy-7-epi-7-(1-(2-methoxycarbonylethyl)-azetidin-3-ylthio)lincomycin | 0.88-0.96 (3H, m), 2.36 (2H, t, J=7.1 Hz), 2.42 (3H, s), 2.75 (2H, t, J=7.1 Hz), 5.25 (1H, d, J=5.5 Hz) | CD₃OD (400 MHz) | 564 (M⁺ + 1) |
| 288 | 7-Deoxy-7-epi-7-(1-(2-(morpholinocarbonyl)ethyl)azetidin-3-ylthio)lincomycin | 0.88-0.94 (3H, m), 1.28 (3H, d, J=7.1 Hz), 2.18 (3H, s), 2.39-2.44 (5H, m), 2.72-2.78 (3H, m), 3.49-3.58 (4H, m), 5.25 (1H, d, J=5.6 Hz) | CD₃OD (400 MHz) | 619 (M⁺ + 1) |
| 289 | 7-Deoxy-7-epi-7-(1-(morpholino-carbonylmethyl)azetidin-3-ylthio)lincomycin | 0.88-0.95 (3H, m), 2.42 (3H, s), 5.25 (1H, d, J=5.6 Hz) | CD₃OD (400 MHz) | 605 (M⁺ + 1) |
| 290 | 7-Deoxy-7-epi-7-(1-(2-nitro phenyl)azetidin-3-ylthio)lincomycin | 0.87-0.94 (3H, m), 2.15 (3H, s), 2.42 (3H, s), 5.26 (1H, d, J=5.6 Hz), 6.69-6.74 (1H, m), 6.77-6.83 (1H, m), 7.42-7.48 (1H, m), 7.76-7.80 (1H, m) | CD₃OD (400 MHz) | 599 (M⁺ + 1) |
| 291 | 7-Deoxy-7-epi-7-(1-(4-nitro phenyl)azetidin-3-ylthio)lincomycin | 0.86-0.94 (3H, m), 2.41 (3H, s), 5.26 (1H, d, J=5.4 Hz), 6.39-6.44 (2H, m), 8.04-8.10 (2H, m) | CD₃OD (400 MHz) | 599 (M⁺ + 1) |
| 292 | 7-(1-(Benzo[d]oxazol-2-yl)azetidin-3-ylthio)-7-deoxy-7-epilincomycin | 0.86-0.95 (3H, m), 2.41 (3H, s), 5.25 (1H, d, J=5.6 Hz), 7.04-7.10 (1H, m), 7.15-7.21 (1H, m), 7.26-7.34 (2H, m) | CD₃OD (400 MHz) | 595 (M⁺ + 1) |
| 293 | 7-Deoxy-7-epi-7-(1-(piperidino-carbonyl)azetidin-3-ylthio)-lincomycin | 0.88-0.96 (3H, m), 1.49-1.58 (4H, m), 1.59-1.67 (2H, m), 2.42 (3H, s), 5.26 (1H, d, J=5.6 Hz) | CD₃OD (400 MHz) | EI 588 (M⁺) |
| 294 | 7-Deoxy-7-(1-(diethylcarbamoyl)-azetidin-3-ylthio)-7-epilincomycin | 0.88-0.95 (3H, m), 1.12 (6H, t, J=7.0 Hz), 2.19 (3H, s), 2.42 (3H, s), 5.26 (1H, d, J=5.7 Hz) | CD₃OD (400 MHz) | EI 576 (M⁺) |
| 295 | 7-(1-(4-Aminophenyl)azetidin-3-ylthio)-7-deoxy-7-epilincomycin | 0.86-0.96 (3H, m), 2.41 (3H, s), 5.26 (1H, d, J=5.6 Hz), 6.30-6.44 (2H, m), 6.60-6.75 (2H, m) | CD₃OD (400 MHz) | 569 (M⁺ + 1) |
| 296 | 1'-Demethyl-7-deoxy-7-epi-7-(5-(pyridin-2-yl)-1,3,4-thiadiazol-2-ylthio)lincomycin | 1.87 (3H, s), 5.18 (1H, d, J=5.6 Hz), 7.40 (1H, ddd, J=1.0, 4.9, 7.6 Hz), 7.87 (1H, dt, J=1.7, 7.8 Hz), 8.13 (1H, d, J=8.0 Hz), 8.56 (1H, d, J=4.4 Hz) | CD₃OD (400 MHz) | 570 (M⁺ + 1) |
| 297 | 7-(6-Aminobenzo[d]thiazol-2-ylthio)-1'-demethyl-7-deoxy-7-epilincomycin | 1.82 (3H, s), 5.16 (1H, d, J=5.6 Hz), 6.75 (1H, dd, J=2.2, 8.6 Hz), 6.97 (1H, d, J=2.2 Hz), 7.48 (1H, d, J=8.8 Hz) | CD₃OD (400 MHz) | 557 (M⁺ + 1) |
| 298 | 1'-Demethyl-7-deoxy-7-epi-7-(5-(2-nitrophenyl)-1,3,4-thiadiazol-2-ylthio)lincomycin | 2.00 (3H, s), 5.27 (1H, d, J=5.6 Hz), 7.75-7.85 (3H, m), 8.07-8.12 (1H, m) | CD₃OD (400 MHz) | 614 (M⁺ + 1) |
| 299 | 7-(5-Amino-1,3,4-thiadiazol-2-ylthio)-1'-demethyl-7-deoxy-7-epilincomycin | 2.10 (3H, s), 5.27 (1H, d, J=6.0 Hz) | CD₃OD (400 MHz) | 508 (M⁺ + 1) |
| 300 | 1'-Demethyl-7-deoxy-7-epi-7-(5-(5-(methylamino)thiazol-4-yl)-1,3,4-thiadiazol-2-ylthio)lincomycin | 2.01 (3H, s), 3.12 (3H, s), 5.27 (1H, d, J=5.8 Hz), 8.12 (1H, s) | CD₃OD (400 MHz) | 605 (M⁺ + 1) |
| 301 | 1'-Demethyl-7-deoxy-7-epi-7-(5-(5-nitrofuran-2-yl)-1,3,4-thiadiazol-2-ylthio)lincomycin | 1.97 (3H, s), 5.27 (1H, d, J=5.6 Hz), 7.43 (1H, d, J=4.1 Hz), 7.64 (1H, d, J=3.9 Hz) | CD₃OD (400 MHz) | 604 (M⁺ + 1) |
| 302 | 7-(5-(5-Amino-1-methyl-1H-pyrazol-4-yl)-1,3,4-thiadiazol-2-ylthio)-1'-demethyl-7-deoxy-7-epilincomycin | 1.99 (3H, s), 3.64 (3H, s), 5.34 (1H, d, J=5.4 Hz), 7.76 (1H, s) | DCl (300 MHz) | 588 (M⁺ + 1) |
| 303 | 7-(5-(2-Cyanophenyl)-1,3,4-thiadiazol-2-ylthio)-1'-demethyl-7-deoxy-7-epilincomycin | 2.00 (3H, s), 5.29 (1H, d, J=5.6 Hz), 7.73 (1H, t, J=7.8 Hz), 7.78 (1H, t, J=7.8 Hz), 7.96 (1H, d, J=7.8 Hz), 8.04 (1H, d, J=7.8 Hz) | DCl (300 MHz) | 594 (M⁺ + 1) |

TABLE 15-continued

| | | | | |
|---|---|---|---|---|
| 304 | 7-(5-(3-Aminothiophen-2-yl)-1,3,4-thiadiazol-2-ylthio)-1'-demethyl-7-deoxy-7-epilincomycin | 2.03 (3H, s), 2.98 (3H, s), 5.38 (1H, d, J=5.4 Hz), 6.78 (1H, d, J=5.4 Hz), 7.45 (1H, d, J=5.4 Hz) | DCl (300 MHz) | 590 (M$^+$ + 1) |
| 305 | 7-(5-(3-Aminopyrazin-2-yl)-1,3,4-thiadiazol-2-ylthio)-1'-demethyl-7-deoxy-7-epilincomycin | 1.93 (3H, s), 5.38 (1H, d, J=5.4 Hz), 7.77 (1H, d, J=2.4 Hz), 8.01 (1H, d, J=2.4 Hz) | DCl (300 MHz) | 584 (M$^+$ + 1) |
| 306 | 1'-Demethyl-7-deoxy-7-epi-7-(5-(4-fluoro-2-nitrophenyl)-1,3,4-thiadiazol-2-ylthio)lincomycin | 2.18 (3H, s), 5.35 (1H, d, J=6.0 Hz), 7.40-7.50 (1H, m), 7.70-7.80 (2H, m) | CDCl$_3$ (300 MHz) | 632 (M$^+$ + 1) |
| 307 | 1'-Demethyl-7-deoxy-7-(5-(4,5-difluoro-2-nitrophenyl)-1,3,4-thiadiazol-2-ylthio)-7-epilincomycin | 2.17 (3H, s), 5.34 (1H, d, J=5.7 Hz), 7.52 (1H, t, J=8.4 Hz), 8.00 (1H, t, J=8.4 Hz) | CDCl$_3$ (300 MHz) | 650 (M$^+$ + 1) |
| 308 | 1'-Demethyl-7-deoxy-7-epi-7-(5-nitrothiazol-2-ylthio)lincomycin | 2.04 (3H, s), 5.33 (1H, d, J=5.1 Hz), 8.35 (1H, s) | CDCl$_3$ (300 MHz) | 537 (M$^+$ + 1) |

TABLE 16

| | | | | |
|---|---|---|---|---|
| 309 | 1'-Demethyl-7-deoxy-7-epi-7-(5-(5-(methylamino)thiazol-4-yl)-1,3,4-oxadiazol-2-ylthio)lincomycin | 2.02 (3H, s), 3.11 (3H, s), 5.26 (1H, d, J=5.6 Hz), 8.19 (1H, s) | CD$_3$OD (400 MHz) | 589 (M$^+$ + 1) |
| 310 | 7-((4-Amino-5-ethoxycarbonyl)-pyrimidin-2-ylthio)-1'-demethyl-7-deoxy-7-epilincomycin | 1.36 (3H, t, J=7.3 Hz), 1.82 (3H, s), 4.34 (2H, q, J=7.3 Hz), 5.21 (1H, d, J=5.9 Hz), 8.60 (1H, s) | CD$_3$OD (400 MHz) | 574 (M$^+$ + 1) |
| 311 | 1'-Demethyl-7-deoxy-7-epi-7-(5-(2-nitrophenyl)oxazol-2-ylthio)lincomycin | 1.99 (3H, s), 5.28 (1H, d, J=5.6 Hz), 7.50 (1H, s), 7.63-7.65 (1H, m), 7.74-7.77 (1H, m), 7.90 (1H, d, J=7.8 Hz) | CD$_3$OD (400 MHz) | 597 (M$^+$ + 1) |
| 312 | 1'-Demethyl-7-deoxy-7-epi-7-(4-(morpholinocarbonyl)-phenylthio)-lincomycin | 1.81 (3H, s), 5.18 (1H, d, J=5.6 Hz), 7.28 (2H, d, J=8.6 Hz), 7.36 (2H, d, J=8.6 Hz) | CD$_3$OD (400 MHz) | 598 (M$^+$ + 1) |
| 313 | 1'-Demethyl-7-deoxy-7-epi-7-(4-(piperidinocarbonyl)phenylthio)-lincomycin | 1.91 (3H, s), 5.29 (1H, d, J=5.6 Hz), 7.34 (2H, d, J=8.0 Hz), 7.46 (2H, d, J=8.0 Hz) | CD$_3$OD (400 MHz) | 596 (M$^+$ + 1) |
| 314 | 7-(4-(Cyclohexylcarbamoyl)-phenylthio)-1'-demethyl-7-deoxy-7-epilincomycin | 1.94 (3H, s), 5.29 (1H, d, J=5.6 Hz), 7.42 (2H, d, J=8.3 Hz), 7.75 (2H, d, J=8.0 Hz) | CD$_3$OD (400 MHz) | 610 (M$^+$ + 1) |
| 315 | 1'-Demethyl-7-deoxy-7-epi-7-(4-(propylcarbamoyl)phenylthio)-lincomycin | 1.87 (3H, s), 5.29 (1H, d, J=5.6 Hz), 7.42 (2H, d, J=8.6 Hz), 7.76 (2H, d, J=8.5 Hz) | CD$_3$OD (400 MHz) | 570 (M$^+$ + 1) |
| 316 | 1'-Demethyl-7-deoxy-7-epi-7-(4-(pyridin-3-yl)phenylthio)-lincomycin | 1.98 (3H, s), 5.29 (1H, d, J=5.7 Hz), 7.53 (2H, d, J=8.4 Hz), 7.64 (2H, d, J=8.7 Hz), 8.09 (1H, ddd, J=1.8, 2.4, 7.2 Hz), 8.51 (1H, dd, J=1.5, 4.8 Hz), 8.80 (1H, dd, J=1.6, 2.4 Hz) | CD$_3$OD (300 MHz) | 562 (M$^+$ + 1) |
| 317 | 7-(5-(2-Aminophenyl)-1,3,4-thiadiazol-2-ylthio)-1'-demethyl-7-deoxy-7-epilincomycin | 0.91 (3H, t, J=7.1 Hz), 1.54 (3H, d, J=7.0 Hz), 2.0 (3H, s), 5.28 (1H, d, J=5.6 Hz), 6.66 (1H, ddd, J=0.9, 8.0, 8.0 Hz), 6.87 (1H, d, J=8.5 Hz), 7.19 (1H, ddd, J=1.5, 7.0, 8.4 Hz), 7.39 (1H, dd, J=1.2, 8.0 Hz) | CD$_3$OD (400 MHz) | 584 (M$^+$ + 1) |
| 318 | 7-(5-Acetamidopyridin-2-ylthio)-1'-demethyl-7-deoxy-7-epilincomycin | 1.84 (3H, s), 2.13 (3H, s), 4.20 (1H, dq, J=2.7, 6.9 Hz), 5.25 (1H, d, J=5.4 Hz), 7.29 (1H, dd, J=0.6, 8.7 Hz), 7.88 (1H, dd, J=2.7, 8.7 Hz), 8.65 (1H, dd, J=0.6, 2.7 Hz) | CD$_3$OD (300 MHz) | 543 (M$^+$ + 1) |
| 319 | 1'-Demethyl-7-deoxy-7-epi-7-(4-(2-methoxyacetamido)-phenylthio)lincomycin | 2.05 (3H, s), 3.48 (3H, s), 4.03 (2H, s), 5.27 (1H, d, J=5.6 Hz), 7.41 (2H, ddd, J=8.8, 2.2, 2.2 Hz), 7.58 (2H, ddd, J=8.8, 2.2, 2.2 Hz) | CD$_3$OD (400 MHz) | 572 (M$^+$ + 1) |
| 320 | 1'-Demethyl-7-deoxy-7-epi-7-(5-(4-fluoro-5-methoxy-2-nitrophenyl)-1,3,4-thiadiazol-2-ylthio)lincomycin | 0.90-0.94 (3H, m), 1.58 (3H, d, J=7.0 Hz), 4.05 (3H, s), 5.31 (1H, d, J=5.6 Hz), 7.31-7.36 (1H, m), 8.03-8.08 (1H, m) | CD$_3$OD (400 MHz) | 622 (M$^+$ + 1) |
| 321 | 1'-Demethyl-7-deoxy-7-epi-1'-isopropyl-7-(5-(2-nitrophenyl)-1,3,4-thiadiazol-2-yl thio)lincomycin | 1.12-1.19 (6H, m), 2.00 (3H, s), 3.54-3.61 (1H, m), 5.26 (1H, d, J=5.6 Hz), 7.77-7.85 (3H, m), 8.09-8.11 (1H, m) | CD$_3$OD (400 MHz) | 656 (M$^+$ + 1) |
| 322 | 7-(5-Amino-1,3,4-thiadiazol-2-ylthio)-1'-demethyl-7-deoxy-7-epi-1'-isopropyllincomycin | 1.09 (3H, d, J=6.5 Hz), 1.12 (3H, d, J=6.5 Hz), 2.08 (3H, s), 5.25 (1H, d, J=5.6 Hz) | CD$_3$OD (400 MHz) | 550 (M$^+$ + 1) |

TABLE 16-continued

| | | | | |
|---|---|---|---|---|
| 323 | 1'-Demethyl-7-deoxy-7-epi-1'-(2-hydroxyethyl)-7-(5-(5-(methyl-amino)thiazol-4-yl)-1,3,4-thiadiazol-2-ylthio)lincomycin | 1.99 (3H, s), 3.12 (3H, s), 5.25 (1H, d, J=5.6 Hz), 8.12 (1H, s) | CD$_3$OD (400 MHz) | 649 (M$^+$ + 1) |
| 324 | 1'-Demethyl-7-deoxy-7-epi-1'-(2-hydroxyethyl)-7-(5-(2-nitrophenyl)-1,3,4-thiadiazol-2-ylthio)lincomycin | 1.89 (3H, s), 5.17 (1H, d, J=5.6 Hz), 7.67-7.75 (3H, m), 7.99-8.01 (1H, m) | CD$_3$OD (400 MHz) | 658 (M$^+$ + 1) |
| 325 | 1'-(2-Aminoethyl)-1'-demethyl-7-deoxy-7-epi-7-(5-(5-(methylamino)thiazol-4-yl)-1,3,4-thiadiazol-2-ylthio)lincomycin | 1.93 (3H, s), 3.02 (3H, s), 5.18 (1H, d, J=5.6 Hz), 8.03 (1H, s) | CD$_3$OD (400 MHz) | 648 (M$^+$ + 1) |
| 326 | 7-(5-Amino-1,3,4-thiadiazol-2-ylthio)-1'-demethyl-7-deoxy-7-epi-1'-(2-hydroxyethyl)lincomycin | 1.90 (3H, s), 5.06 (1H, d, J=5.9 Hz) | CD$_3$OD (400 MHz) | 552 (M$^+$ + 1) |
| 327 | 1'-(2-Aminoethyl)-7-(5-amino-1,3,4-thiadiazol-2-ylthio)-1'-demethyl-7-deoxy-7-epilincomycin | 2.12 (3H, s), 5.27 (1H, d, J=5.6 Hz) | CD$_3$OD (400 MHz) | 551 (M$^+$ + 1) |
| 328 | 1'-Demethyl-7-deoxy-7-epi-1'-((R)-2-hydroxypropyl)-7-(5-(5-(methylamino)thiazol-4-yl)-1,3,4-thiadiazol-2-ylthio)lincomycin | 1.14 (3H, d, J=6.1 Hz), 1.99 (3H, s), 3.11 (3H, s), 5.25 (1H, d, J=5.6 Hz), 8.11 (1H, s) | CD$_3$OD (400 MHz) | 663 (M$^+$ + 1) |
| 329 | 1'-Demethyl-7-deoxy-7-epi-1'-(4-methylthiazol-5-yl)methyl-7-(5-(5-(methylamino)-thiazol-4-yl)-1,3,4-thiadiazol-2-ylthio)lincomycin | 1.94 (3H, s), 2.27 (2H, s), 3.00 (3H, s), 5.16 (1H, d, J=5.3 Hz), 8.02 (1H, s), 8.69 (1H, s) | CD$_3$OD (400 MHz) | 716 (M$^+$ + 1) |
| 330 | 7-(4-Amino-5-ethoxycarbonyl-pyrimidin-2-ylthio)-1'-demethyl-7-deoxy-7-epi-1'-pentyllincomycin | 1.35 (3H, t, J=7.1 Hz), 1.82 (3H, s), 1.95-2.11 (2H, m), 4.36 (2H, q, J=7.1 Hz), 5.20 (1H, d, J=5.6 Hz), 8.58 (1H, s) | CD$_3$OD (400 MHz) | 644 (M$^+$ + 1) |

TABLE 17

| | | | | |
|---|---|---|---|---|
| 331 | 7-(4-Amino-5-ethoxycarbonyl-pyrimidin-2-ylthio)-1'-demethyl-7-deoxy-7-epi-1'-ethyllincomycin | 1.15 (3H, t, J=7.1 Hz), 1.36 (3H, t, J=7.1 Hz), 1.82 (3H, s), 4.33 (2H, q, J=7.1 Hz), 5.21 (1H, d, J=5.6 Hz), 8.57 (1H, s) | CD$_3$OD (400 MHz) | 602 (M$^+$ + 1) |
| 332 | 1'-Allyl-7-(4-amino-5-ethoxycarbonylpyrimidin-2-ylthio)-1'-demethyl-7-deoxy-7-epilincomycin | 1.36 (3H, t, J=7.1 Hz), 1.83 (3H, s), 4.33 (2H, q, J=7.1 Hz), 5.10 (1H, dd, J=10.0, 1.5 Hz), 5.21 (1H, d, J=5.6 Hz), 5.22 (1H, dd, J=17.1, 1.5 Hz), 5.94-6.04 (1H, m), 8.57 (1H, s) | CD$_3$OD (400 MHz) | 614 (M$^+$ + 1) |
| 333 | 7-((4-Amino-5-ethoxycarbonyl)-pyrimidin-2-ylthio)-1'-cyanomethyl-1'-demethyl-7-deoxy-7-epilincomycin | 1.36 (3H, t, J=7.1 Hz), 1.83 (3H, s), 3.69 (1H, s), 3.78 (1H, s), 4.33 (2H, q, J=7.1 Hz), 5.22 (1H, d, J=5.6 Hz), 8.56 (1H, s) | CD$_3$OD (400 MHz) | 613 (M$^+$ + 1) |
| 334 | 1'-Aminoacetyl-7-(5-amino-1,3,4-thiadiazol-2-ylthio)-1'-demethyl-7-deoxy-7-epilincomycin | 2.11 (3H, s), 5.26 (1H, d, J=5.6 Hz) | CD$_3$OD (400 MHz) | 565 (M$^+$ + 1) |
| 335 | 1'-Acetyl-1'-demethyl-7-deoxy-7-epi-7-(5-(5-(methylamino)-thiazol-4-yl)-1,3,4-thiadiazol-2-ylthio)lincomycin | 1.99 (3H, s), 2.09 (3H, s), 3.12 (3H, s), 5.25 (1H, d, J=5.4 Hz), 8.11 (1H, s) | CD$_3$OD (400 MHz) | 647 (M$^+$ + 1) |
| 336 | 1'-Demethyl-7-deoxy-7-epi-1'-hydroxyacetyl-7-(5-(5-(methylamino)-thiazol-4-yl)-1,3,4-thiadiazol-2-ylthio)lincomycin | 1.99 (3H, s), 3.12 (3H, s), 4.20 (1H, s), 4.22 (1H, s), 5.25 (1H, d, J=5.4 Hz), 8.12 (1H, s) | CD$_3$OD (400 MHz) | 663 (M$^+$ + 1) |
| 337 | 7-(4-Amino-5-ethoxycarbonyl-pyrimidin-2-ylthio)-1'-demethyl-7-deoxy-7-epi-1'-(2-hydroxyacetyl-lincomycin | 1.36 (3H, t, J=7.1 Hz), 1.80 (3H, s), 4.19 (1H, s), 4.21 (1H, s), 4.33 (2H, q, J=7.1 Hz), 5.20 (1H, d, J=5.6 Hz), 8.56 (1H, s) | CD$_3$OD (400 MHz) | 632 (M$^+$ + 1) |
| 338 | 7-(4-Amino-5-ethoxycarbonyl-pyrimidin-2-ylthio)-1'-demethyl-7-deoxy-7-epi-1'-(2-(thiophen-2-yl)acetyllincomycin | 1.57 (3H, t, J=7.1 Hz), 2.01 (3H, s), 4.18 (2H, s), 4.54 (2H, q, J=7.1 Hz), 5.41 (1H, d, J=5.6 Hz), 7.16-7.19 (2H, m), 7.49 (1H, dd, J=5.0, 1.4 Hz), 8.77 (1H, s) | CD$_3$OD (400 MHz) | 698 (M$^+$ + 1) |
| 339 | 7-(5-Amino-1,3,4-thiadiazol-2-ylthio)-4'-((E)-but-2-enyl)-1'-demethyl-7-deoxy-4'-de propyl-7-epilincomycin | 1.34-1.40 (3H, m), 1.60-1.66 (3H, m), 5.26 (1H, d, J=5.6 Hz), 5.35-5.54 (2H, m) | CD$_3$OD (400 MHz) | 520 (M$^+$ + 1) |

TABLE 17-continued

| | | | | |
|---|---|---|---|---|
| 340 | 4'-((E)-But-2-enyl)-1'-demethyl-7-deoxy-4'-depropyl-7-epi-7-(5-(2-nitrophenyl)-1,3,4-thiadiazol-2-ylthio)lincomycin | 1.55 (3H, d, J=7.1 Hz), 1.63-1.67 (3H, m), 5.30 (1H, d, J=5.6 Hz), 5.34-5.53 (2H, m), 7.76-7.86 (3H, m), 8.08-8.13 (1H, m) | $CD_3OD$ (400 MHz) | 626 ($M^+ + 1$) |
| 341 | 7-(5-Amino-1,3,4-thiadiazol-2-ylthio)-4'-((E)-but-2-enyl)-7-deoxy-4'-depropyl-7-epilincomycin | 1.41 (3H, d, J=6.8 Hz), 1.61-1.66 (3H, m), 2.11 (3H, s), 2.34 (3H, s), 5.26 (1H, d, J=5.8 Hz), 5.35-5.52 (2H, m) | $CD_3OD$ (400 MHz) | 534 ($M^+ + 1$) |
| 342 | 4'-((E)-But-2-enyl)-7-deoxy-4'-depropyl-7-epi-7-(5-(2-nitrophenyl)-1,3,4-thiadiazol-2-ylthio)lincomycin | 1.58 (3H, d, J=7.1 Hz), 1.63 (3H, d, J=5.4 Hz), 2.39 (3H, s), 5.28 (1H, d, J=5.6 Hz), 5.34-5.52 (2H, m), 7.76-7.87 (3H, m), 8.06-8.12 (1H, m) | $CD_3OD$ (400 MHz) | 640 ($M^+ + 1$) |
| 343 | 7-(5-Amino-1,3,4-thiadiazol-2-ylthio)-4'-butyl-1'-demethyl-7-deoxy-4'-depropyl-7-epilincomycin | 0.80-0.94 (3H, m), 2.11 (3H, s), 5.26 (1H, d, J=5.6 Hz) | $CD_3OD$ (400 MHz) | 522 ($M^+ + 1$) |
| 344 | 4'-Butyl-1'-demethyl-7-deoxy-4'-depropyl-7-epi-7-(5-(2-nitrophenyl)-1,3,4-thiadiazol-2-ylthio)lincomycin | 0.86-0.93 (3H, m), 1.56 (3H, d, J=6.8 Hz), 2.00 (3H, s), 5.28 (1H, d, J=5.6 Hz), 7.76-7.86 (3H, m), 8.08-8.12 (1H, m) | $CD_3OD$ (400 MHz) | 628 ($M^+ + 1$) |
| 345 | 7-(5-Amino-1,3,4-thiadiazol-2-ylthio)-4'-butyl-7-deoxy-4'-depropyl-7-epilincomycin | 0.88-0.94 (3H, m), 2.11 (3H, s), 2.34 (3H, s), 5.26 (1H, d, J=5.7 Hz) | $CD_3OD$ (400 MHz) | 536 ($M^+ + 1$) |
| 346 | 4'-Butyl-7-deoxy-4'-depropyl-7-epi-7-(5-(2-nitrophenyl)-1,3,4-thiadiazol-2-ylthio)lincomycin | 0.87-0.92 (3H, m), 1.58 (3H, d, J=7.1 Hz), 2.39 (3H, s), 5.27 (1H, d, J=5.6 Hz), 7.76-7.86 (3H, m), 8.06-8.11 (1H, m) | $CD_3OD$ (400 MHz) | 642 ($M^+ + 1$) |
| 347 | 1'-Demethyl-7-deoxy-4'-depropyl-7-epi-7-(5-(2-nitrophenyl)-1,3,4-thiadiazol-2-ylthio)-4'-((E)-pent-2-enyl)lincomycin | 1.99 (3H, s), 5.27 (1H, d, J=5.6 Hz), 5.33-5.56 (2H, m), 7.76-7.86 (3H, m), 8.06-8.10 (1H, m) | $CD_3OD$ (400 MHz) | 640 ($M^+ + 1$) |
| 348 | 7-(5-Amino-1,3,4-thiadiazol-2-ylthio)-1'-demethyl-7-deoxy-4'-depropyl-7-epi-4'-((E)-pent-2-enyl)lincomycin | 2.10 (3H, s), 5.27 (1H, d, J=6.1 Hz), 5.33-5.56 (2H, m) | $CD_3OD$ (400 MHz) | 647 ($M^+ + 1$) |
| 349 | 1'-Demethyl-7-deoxy-4'-depropyl-7-epi-7-(5-(5-(methylamino)thiazol-4-yl)-1,3,4-thiadiazol-2-ylthio)-4'-((E)-pent-2-enyl)-lincomycin | 2.02 (3H, s), 3.11 (3H, s), 5.28 (1H, d, J=5.6 Hz), 5.33-5.56 (2H, m), 8.12 (1H, s) | $CD_3OD$ (400 MHz) | 631 ($M^+ + 1$) |
| 350 | 1'-Demethyl-7-deoxy-4'-depropyl-7-epi-7-(5-(5-(methylamino)thiazol-4-yl)-1,3,4-oxadiazol-2-ylthio)-4'-((E)-pent-2-enyl)lincomycin | 2.03 (3H, s), 3.11 (3H, s), 5.27 (1H, d, J=5.6 Hz), 5.33-5.56 (2H, m), 8.18 (1H, s) | $CD_3OD$ (400 MHz) | 615 ($M^+ + 1$) |

TABLE 18

| | | | | |
|---|---|---|---|---|
| 351 | 7-Deoxy-4'-depropyl-7-epi-7-(5-(2-nitrophenyl)-1,3,4-thiadiazol-2-ylthio)-4'-((E)-pent-2-enyl)lincomycin | 2.01 (3H, s), 2.41 (3H, s), 5.27 (1H, d, J=5.7 Hz), 5.33-5.56 (2H, m), 7.76-5.86 (3H, m), 8.06-8.10 (1H, m) | $CD_3OD$ (400 MHz) | 654 ($M^+ + 1$) |
| 352 | 7-(5-Amino-1,3,4-thiadiazol-2-ylthio)-7-deoxy-4'-depropyl-7-epi-4'-((E)-pent-2-enyl)lincomycin | 2.12 (3H, s), 2.36 (3H, s), 5.26 (1H, d, J=5.8 Hz), 5.33-5.56 (2H, m) | $CD_3OD$ (400 MHz) | 548 ($M^+ + 1$) |
| 353 | 1'-Demethyl-7-deoxy-4'-depropyl-7-epi-7-(5-(2-nitrophenyl)-1,3,4-thiadiazol-2-ylthio)-4'-pentyllincomycin | 2.09 (3H, s), 5.31 (1H, d, J=5.6 Hz), 7.73-7.85 (3H, m), 8.09-8.12 (1H, m) | $CD_3OD$ (400 MHz) | 642 ($M^+ + 1$) |
| 354 | 1'-Demethyl-7-deoxy-4'-depropyl-7-epi-7-(5-(5-(methylamino)thiazol-4-yl)-1,3,4-thiadiazol-2-ylthio)-4'-pentyllincomycin | 2.10 (3H, s), 5.27 (1H, d, J=5.6 Hz) | $CD_3OD$ (400 MHz) | 633 ($M^+ + 1$) |
| 355 | 7-(5-Amino-1,3,4-thiadiazol-2-ylthio)-1'-demethyl-7-deoxy-4'-depropyl-7-epi-4'-pentyllincomycin | 0.88-0.92 (3H, m), 1.27-1.40 (8H, m), 2.11 (3H, s), 3.96 (1H, dq, J=2.4, 6.8 Hz), 5.27 (1H, d, J=5.6 Hz) | $CD_3OD$ (400 MHz) | 536 ($M^+ + 1$) |
| 356 | 7-(5-Amino-1,3,4-thiadiazol-2-ylthio)-7-deoxy-4'-depropyl-7-epi-4'-pentyllincomycin | 2.11 (3H, s), 2.38 (3H, s), 5.26 (1H, d, J=5.6 Hz) | $CD_3OD$ (400 MHz) | 550 ($M^+ + 1$) |

TABLE 18-continued

| | | | | |
|---|---|---|---|---|
| 357 | 7-Deoxy-4'-depropyl-7-epi-7-(5-(2-nitrophenyl)-1,3,4-thiadiazol-2-ylthio)-4'-pentyllincomycin | 2.01 (3H, s), 2.41 (3H, s), 5.29 (1H, d, J=5.6 Hz), 7.77-7.85 (3H, m), 8.08-8.10 (1H, m) | CD$_3$OD (400 MHz) | 656 (M$^+$ + 1) |
| 358 | 7-Deoxy-4'-depropyl-7-epi-7-(5-(5-(methylamino)-thiazol-4-yl)-1,3,4-thiadiazol-2-ylthio)-4'-pentyllincomycin | 0.89 (3H, t, J=6.8 Hz), 1.22-1.36 (8H, m), 2.10 (3H, s), 2.39 (3H, s), 3.12 (3H, s), 4.27 (1H, dq, J=2.9, 7.1 Hz), 5.27 (1H, d, J=5.6 Hz), 8.13 (1H, s) | CD$_3$OD (400 MHz) | 647 (M$^+$ + 1) |
| 359 | Methyl 7-deoxy-7-epi-7-(5-(5-(methylamino)-thiazol-4-yl)-1,3,4-thiadiazol-2-ylthio)-6-N-((2S,4R)-4-propyl)pipecoloyl-1-thio-α-lincosamide | 2.16 (3H, s), 3.14 (3H, d, J=5.1 Hz), 5.35 (1H, d, J=5.7 Hz), 7.51 (1H, d, J=5.1 Hz), 7.99 (1H, s) | CDCl$_3$ (300 MHz) | 619 (M$^+$ + 1) |
| 360 | Methyl 7-deoxy-7-epi-7-(5-(5-methyl-2-nitrophenyl)-1,3,4-thiadiazol-2-ylthio)-6-N-((2S,4R)-4-propyl)pipecoloyl-1-thio-α-lincosamide | 2.20 (3H, s), 2.51 (3H, s), 5.35 (1H, d, J=5.7 Hz), 7.30-7.55 (2H, m), 7.13 (1H, s), 7.98 (1H, d, J=8.1 Hz) | CDCl$_3$ (300 MHz) | 642 (M$^+$ + 1) |
| 361 | Methyl 7-deoxy-7-epi-7-(5-(2-methylaminophenyl)-1,3,4-thiadiazol-2-ylthio)-6-N-((2S,4R)-4-propyl)pipecoloyl-1-thio-α-lincosamide | 2.14 (3H, s), 2.98 (3H, s), 5.35 (1H, d, J=5.7 Hz), 6.66 (1H, t, J=5.7 Hz), 6.76 (1H, d, J=5.7 Hz), 7.30-7.40 (2H, m), 8.00-8.10 (1H, m) | CDCl$_3$ (300 MHz) | 612 (M$^+$ + 1) |
| 362 | Methyl 7-deoxy-7-(5-(5-dimethylamino-4-fluoro-2-nitrophenyl)-1,3,4-thiadiazol-2-ylthio)-7-epi-6-N-((2S,4R)-4-propyl)-pipecoloyl-1-thio-α-lincosamide | 0.76-0.92 (3H, m), 1.55 (3H, d, J=6.8 Hz), 2.01 (3H, s), 5.28 (1H, d, J=14.4 Hz) | CD$_3$OD (400 MHz) | 689 (M$^+$ + 1) |
| 363 | Methyl 7-(6-aminobenzo[d]-thiazol-2-ylthio)-7-deoxy-7-epi-6-N-((2S,4R)-4-propyl)-pipecoloyl-1-thio-α-lincosamide | 1.94 (3H, s), 5.25 (1H, d, J=5.3 Hz), 6.85 (1H, dd, J=8.7, 2.4 Hz), 7.08 (1H, d, J=2.4 Hz), 7.59 (1H, d, J=8.7 Hz) | CD$_3$OD (400 MHz) | 571 (M$^+$ + 1) |
| 364 | Methyl 7-(4-amino-5-ethoxycarbonylpyrimidin-2-ylthio)-7-deoxy-7-epi-6-N-((2S,4R)-4-propyl)pipecoloyl-1-thio-α-lincosamide | 1.60 (3H, t, J=7.1 Hz), 2.08 (3H, s), 4.58 (2H, q, J=7.1 Hz), 5.46 (1H, d, J=5.6 Hz), 8.81 (1H, s) | CD$_3$OD (400 MHz) | 588 (M$^+$ + 1) |
| 365 | Methyl 7-deoxy-7-epi-7-(5-(2-nitrophenyl)-1,3,4-thiadiazol-2-ylthio)-6-N-((2S,4R)-4-propyl)-pipecoloyl-1-thio-α-lincosamide | 1.89 (3H, s), 5.17 (1H, d, J=6.2 Hz), 7.68-7.74 (3H, m), 8.00-8.02 (1H, m) | CD$_3$OD (400 MHz) | 628 (M$^+$ + 1) |
| 366 | Methyl 7-deoxy-7-epi-7-(5-(4-fluoro-2-nitrophenyl)-1,3,4-thiadiazol-2-ylthio)-6-N-((2S,4R)-4-propyl)pipecoloyl-1-thio-α-lincosamide | 1.98 (3H, s), 5.27 (1H, d, J=5.6 Hz), 7.61-7.66 (1H, m), 7.85 (1H, dd, J=8.5, 5.3 Hz), 7.98 (1H, dd, J=8.5, 2.7 Hz) | CD$_3$OD (400 MHz) | 646 (M$^+$ + 1) |
| 367 | Methyl 7-deoxy-7-epi-7-(5-nitropyridin-2-ylthio)-6-N-((2S,4R)-4-propyl)pipecoloyl-1-thio-α-lincosamide | 1.75 (3H, s), 4.54 (1H, dq, J=2.7, 6.9 Hz), 5.22 (1H, d, J=5.4 Hz), 7.48 (1H, dd, J=0.6, 9.0 Hz), 8.33 (1H, dd, J=2.7, 9.0 Hz), 9.22 (1H, dd, J=0.6, 2.7 Hz) | CD$_3$OD (300 MHz) | 545 (M$^+$ + 1) |
| 368 | Methyl 7-deoxy-7-(1-(4,5-dihydrothiazol-2-yl)-azetidin-3-ylthio)-7-epi-6-N-((2S,4R)-4-propyl)-pipecoloyl-1-thio-α-lincosamide | 0.92 (3H, t, J=7.3 Hz), 2.18 (3H, s), 5.25 (1H, d, J=5.6 Hz) | CD$_3$OD (400 MHz) | 563 (M$^+$ + 1) |

TABLE 19

| | | | | |
|---|---|---|---|---|
| 369 | Methyl 7-deoxy-7-epi-7-(5-(4-fluoro-5-methoxy-2-nitrophenyl)-1,3,4-thiadiazol-2-ylthio)-6-N-((2S,4R)-4-propyl)pipecoloyl-1-thio-α-lincosamide | 0.86-0.93 (3H, m), 2.01 (3H, s), 5.29 (1H, d, J=5.6 Hz), 7.44 (1H, d, J=8.0 Hz), 8.08 (1H, d, J=10.7 Hz) | CD$_3$OD (400 MHz) | 676 (M$^+$ + 1) |

TABLE 19-continued

| | | | | |
|---|---|---|---|---|
| 370 | Methyl 7-deoxy-7-epi-6-N-((2S,4R)-4-propyl)pipecoloyl-7-(4-(pyridin-3-yl)phenylthio)-1-thio-α-lincosamide | 1.95 (3H, s), 3.87-3.95 (1H, m), 5.29 (1H, d, J=5.4 Hz), 7.50 (1H, d, J=8.4 Hz), 7.52 (2H, d, J=8.4 Hz), 7.63 (2H, d, J=8.4 Hz), 8.09 (1H, ddd, J=1.5, 2.4, 8.4 Hz), 8.51 (1H, dd, J=1.5, 4.8 Hz), 8.80 (1H, dd, J=0.6, 2.4 Hz) | $CD_3OD$ (400 MHz) | 576 ($M^+ + 1$) |
| 371 | Methyl 7-(5-acetamidopyridin-2-ylthio)-7-deoxy-7-epi-6-N-((2S,4R)-4-propyl)pipecoloyl-1-thio-α-lincosamide | 1.89 (3H, s), 2.14 (3H, s), 4.11 (1H, dq, J=2.4, 6.9 Hz), 5.25 (1H, d, J=5.7 Hz), 7.34 (1H, d, J=8.7 Hz), 7.85 (1H, dd, J=2.4, 8.7 Hz), 8.73 (1H, d, J=2.1 Hz) | $CD_3OD$ (300 MHz) | 557 ($M^+ + 1$) |
| 372 | Methyl 7-deoxy-7-epi-7-(5-(2-methoxyacetamido)pyridin-2-ylthio)-6-N-((2S,4R)-4-propyl)-pipecoloyl-1-thio-α-lincosamide | 1.89 (3H, s), 3.48 (3H, s), 4.06 (2H, s), 4.16 (1H, dq, J=2.7, 6.9 Hz), 5.25 (1H, d, J=5.4 Hz), 7.36 (1H, d, J=8.4 Hz), 7.92 (1H, dd, J=2.7, 8.7 Hz), 8.80 (1H, d, J=2.4 Hz) | $CD_3OD$ (300 MHz) | 587 ($M^+ + 1$) |
| 373 | Methyl 7-deoxy-7-epi-7-(5-(piperidinocarbonyl)-1,3,4-thiadiazol-2-ylthio)-6-N-((2S,4R)-4-propyl)pipecoloyl-1-thio-α-lincosamide | 1.60-1.80 (6H, m), 2.10 (3H, s), 3.30-3.45 (4H, m), 5.32 (1H, d, J=5.7 Hz) | $CDCl_3$ (300 MHz) | 618 ($M^+ + 1$) |
| 374 | Methyl 7-deoxy-7-epi-7-(5-(piperidinocarbonyl)thiazol-2-ylthio)-6-N-((2S,4R)-4-propyl)pipecoloyl-1-thio-α-lincosamide | 1.60-1.80 (6H, m), 2.22 (3H, s), 3.30-3.45 (4H, m), 5.32 (1H, d, J=5.7 Hz), 7.77 (1H, s) | $CDCl_3$ (300 MHz) | 617 ($M^+ + 1$) |
| 375 | Methyl 7-deoxy-7-epi-7-(4-(piperidinocarbonyl)-phenylthio)-6-N-((2S,4R)-4-propyl)-pipecoloyl-1-thio-α-lincosamide | 1.89 (3H, s), 3.92 (1H, dq, J=2.4, 6.8 Hz), 5.26 (1H, d, J=5.6 Hz), 7.33 (2H, d, J=8.3 Hz), 7.44 (2H, d, J=8.3 Hz) | $CD_3OD$ (400 MHz) | 610 ($M^+ + 1$) |
| 376 | Methyl 7-deoxy-7-epi-7-(5-(piperidinocarbonyl)pyridin-2-ylthio)-6-N-((2S,4R)-4-propyl)pipecoloyl-1-thio-α-lincosamide | 1.76 (3H, s), 3.41 (2H, br), 3.69 (2H, br), 4.40 (1H, dq, J=2.4, 7.2 Hz), 5.22 (1H, d, J=5.7 Hz), 7.37 (1H, dd, J=0.9, 8.4 Hz), 7.63 (1H, dd, J=2.1, 8.4 Hz), 8.45 (1H, dd, J=0.9, 2.1 Hz) | $CD_3OD$ (300 MHz) | 611 ($M^+ + 1$) |
| 377 | Methyl 7-deoxy-7-epi-7-(5-(morpholinocarbonyl)pyridin-2-ylthio)-6-N-((2S,4R)-4-propyl)pipecoloyl-1-thio-α-lincosamide | 1.76 (3H, s), 3.70 (4H, br), 4.41 (1H, dq, J=2.4, 6.9 Hz), 5.23 (1H, d, J=5.7 Hz), 7.38 (1H, dd, J=0.9, 8.1 Hz), 7.67 (1H, dd, J=2.4, 8.1 Hz), 8.49 (1H, dd, J=0.9, 2.4 Hz) | $CD_3OD$ (300 MHz) | 613 ($M^+ + 1$) |
| 378 | Methyl 7-(4-amino-5-(piperidinocarbonyl)pyrimidin-2-ylthio)-7-deoxy-7-epi-6-N-((2S,4R)-4-propyl)pipecoloyl-1-thio-α-lincosamide | 1.84 (3H, s), 5.21 (1H, d, J=5.6 Hz), 7.92 (1H, s) | $CD_3OD$ (400 MHz) | 627 ($M^+ + 1$) |
| 379 | Methyl 7-deoxy-7-epi-7-(4-(morpholinocarbonyl)-phenylthio)-6-N-((2S,4R)-4-propyl)-pipecoloyl-1-thio-α-lincosamide | 1.88 (3H, s), 5.27 (1H, d, J=5.6 Hz), 7.38 (2H, d, J=8.7 Hz), 7.45 (2H, d, J=8.6 Hz) | $CD_3OD$ (400 MHz) | 612 ($M^+ + 1$) |
| 380 | Methyl 7-deoxy-7-epi-7-(5-(5-methylamino-2-nitrophenyl)-1,3,4-thiadiazol-2-ylthio)-6-N-((2S,4R)-4-propyl)pipecoloyl-1-thio-α-lincosamide | 2.19 (3H, s), 2.91 (3H, s), 5.33 (1H, d, J=5.7 Hz) | $CD_3OD/CDCl_3$ (300 MHz) | 657 ($M^+ + 1$) |
| 381 | Methyl 7-deoxy-7-(5-(4-dimethylamino-2-nitrophenyl)-1,3,4-thiadiazol-2-ylthio)-7-epi-6-N-((2S,4R)-4-propyl)-pipecoloyl-1-thio-α-lincosamide | 1.99 (3H, s), 3.10 (6H, s), 5.26 (1H, d, J=5.6 Hz), 6.99-7.02 (1H, m), 7.21-7.21 (1H, m), 7.54-7.57 (1H, m) | $CD_3OD$ (400 MHz) | 671 ($M^+ + 1$) |
| 382 | Methyl 7-deoxy-7-epi-7-(5-(5-methoxy-2-nitrophenyl)-1,3,4-thiadiazol-2-ylthio)-6-N-((2S,4R)-4-propyl)pipecoloyl-1-thio-α-lincosamide | 2.15 (3H, s), 3.94 (3H, s), 5.36 (1H, d, J=5.7 Hz), 7.11 (1H, d, J=8.4 Hz), 7.13 (1H, s), 8.15 (1H, d, J=8.4 Hz) | $CDCl_3$ (300 MHz) | 658 ($M^+ + 1$) |

TABLE 20

| | | | | |
|---|---|---|---|---|
| 383 | Methyl 7-deoxy-7-epi-6-N-((2S,4R)-1-methyl-4-propyl)-pipecoloyl-7-(5-nitropyridin-2-ylthio)-1-thio-α-lincosamide | 1.79 (3H, s), 2.28 (3H, s), 4.52 (1H, dq, J=3.0, 6.9 Hz), 5.23 (1H, d, J=5.4 Hz), 7.49 (1H, d, J=9.0 Hz), 8.34 (1H, dd, J=2.7, 9.0 Hz), 9.23 (1H, d, J=2.7 Hz) | CD₃OD (300 MHz) | 559 (M⁺ + 1) |
| 384 | Methyl 7-(5-acetamidopyridin-2-ylthio)-7-deoxy-7-epi-6-N-((2S,4R)-1-methyl-4-propyl)-pipecoloyl-1-thio-α-lincosamide | 1.98 (3H, s), 2.16 (3H, s), 2.30 (3H, s), 4.07 (1H, dq, J=2.4, 6.9 Hz), 5.26 (1H, d, J=5.4 Hz), 7.38 (1H, d, J=8.4 Hz), 7.82 (1H, dd, J=2.4, 8.4 Hz), 8.85 (1H, d, J=2.1 Hz) | CD₃OD (300 MHz) | 571 (M⁺ + 1) |
| 385 | Methyl 7-deoxy-7-epi-7-(5-(2-methoxyacetamido)pyridin-2-ylthio)-6-N-((2S,4R)-1-methyl-4-propyl)pipecoloyl-1-thio-α-lincosamide | 1.97 (3H, s), 2.28 (3H, s), 3.49 (3H, s), 4.06 (2H, s), 5.25 (1H, d, J=5.7 Hz), 7.39 (1H, dd, J=0.6, 9.0 Hz), 7.89 (1H, dd, J=2.4, 9.0 Hz), 8.90 (1H, dd, J=0.6, 2.4 Hz) | CD₃OD (300 MHz) | 601 (M⁺ + 1) |
| 386 | Methyl 7-deoxy-7-epi-6-N-((2S,4R)-1-methyl-4-propyl)-pipecoloyl-7-(5-(morpholino-carbonyl)pyridin-2-ylthio)-1-thio-α-lincosamide | 1.81 (3H, s), 2.28 (3H, s), 3.70 (4H, br), 4.38 (1H, dq, J=2.7, 6.9 Hz), 5.23 (1H, d, J=6.0 Hz), 7.39 (1H, dd, J=0.9, 8.1 Hz), 7.68 (1H, dd, J=2.4, 8.1 Hz), 8.50 (1H, dd, J=0.9, 2.4 Hz) | CD₃OD (300 MHz) | 627 (M⁺ + 1) |
| 387 | Methyl 7-deoxy-7-epi-6-N-((2S,4R)-1-methyl-4-propyl)-pipecoloyl-7-(5-(piperidino-carbonyl)pyridin-2-ylthio)-1-thio-α-lincosamide | 1.81 (3H, s), 2.30 (3H, s), 3.42 (2H, br), 3.69 (2H, br), 5.22 (1H, d, J=5.7 Hz), 7.38 (1H, dd, J=0.9, 8.1 Hz), 7.64 (1H, dd, J=2.1, 8.4 Hz), 8.46 (1H, dd, J=0.9, 2.4 Hz) | CD₃OD (300 MHz) | 625 (M⁺ + 1) |
| 388 | Methyl 7-deoxy-7-(1-(4,5-dihydrothiazol-2-yl)azetidin-3-ylthio)-7-epi-6-N-((2S,4R)-1-methyl-4-propyl)-pipecoloyl-1-thio-α-lincosamide | 0.87-0.94 (3H, m), 2.18 (3H, s), 2.26 (3H, s), 5.26 (1H, d, J=5.6 Hz) | CD₃OD (400 MHz) | 577 (M⁺ + 1) |
| 389 | Methyl 7-deoxy-7-epi-7-(5-(4-fluoro-2-nitrophenyl)-1,3,4-thiadiazol-2-ylthio)-6-N-((2S,4R)-1-methyl-4-propyl)-pipecoloyl-1-thio-α-lincosamide | 1.99 (3H, s), 2.25 (3H, s), 5.27 (1H, d, J=5.6 Hz), 7.61-7.66 (1H, m), 7.85 (1H, dd, J=8.5, 5.3 Hz), 7.98 (1H, dd, J=8.5, 2.4 Hz) | CD₃OD (400 MHz) | 660 (M⁺ + 1) |
| 390 | Methyl 7-(4-amino-5-piperidinocarbonyl)-pyrimidine-7-deoxy-7-epi-6-N-((2S,4R)-1-methyl-4-propyl)pipecoloyl-1-thio-α-lincosamide | 1.88 (3H, s), 2.26 (3H, s), 5.22 (1H, d, J=5.6 Hz), 7.92 (1H, s) | CD₃OD (400 MHz) | 641 (M⁺ + 1) |
| 391 | Methyl 7-deoxy-7-epi-6-N-((2S,4R)-1-methyl-4-propyl)-pipecoloyl-7-(4-(morpholinocarbonyl)-phenylthio)-1-thio-α-lincosamide | 1.89 (3H, s), 2.29 (3H, s), 5.27 (1H, d, J=5.6 Hz), 7.38 (2H, d, J=8.0 Hz), 7.98 (2H, d, J=8.5 Hz) | CD₃OD (400 MHz) | 626 (M⁺ + 1) |
| 392 | Methyl 7-deoxy-7-epi-6-N-((2S,4R)-1-methyl-4-propyl)-pipecoloyl-7-(4-(piperidino-carbonyl)-phenylthio)-1-thio-α-lincosamide | 1.90 (3H, s), 2.32 (3H, s), 3.94 (1H, dq, J=2.6, 7.0 Hz), 5.25 (1H, d, J=5.6 Hz), 7.33 (2H, ddd, J=8.6, 2.0, 2.0 Hz), 7.44 (2H, ddd, J=8.6, 2.0, 2.0 Hz) | CD₃OD (400 MHz) | 624 (M⁺ + 1) |
| 393 | Methyl 7-deoxy-7-epi-6-N-((2S,4R)-1-methyl-4-propyl)pipecoloyl-7-(4-(pyridin-3-yl)phenylthio)-1-thio-α-lincosamide | 1.97 (3H, s), 2.34 (3H, s), 3.93 (1H, dq, J=2.7, 6.6 Hz), 5.31 (1H, d, J=5.4 Hz), 7.51 (1H, dd, J=4.8, 8.1 Hz), 7.53 (2H, d, J=8.4 Hz), 7.64 (2H, d, J=8.7 Hz), 8.09 (1H, ddd, J=1.5, 2.1, 8.1 Hz), 8.51 (1H, dd, J=1.5, 4.8 Hz), 8.80 (1H, dd, J=0.6, 2.1 Hz) | CD₃OD (300 MHz) | 590 (M⁺ + 1) |
| 394 | Methyl 7-deoxy-7-epi-6-N-((2S,4R)-4-ethyl)pipecoloyl-7-(4-fluoro-2-nitrophenyl)-1,3,4-thiadiazol-2-ylthio)-1-thio-α-lincosamide | 2.08 (3H, s), 5.34 (1H, d, J=5.4 Hz), 7.35-7.50 (1H, m), 7.65-7.80 (2H, m) | CD₃OD (300 MHz) | 632 (M⁺ + 1) |
| 395 | Methyl 7-deoxy-7-epi-6-N-((2S,4R)-4-ethyl)pipecoloyl-7-(5-(2-nitrophenyl)-1,3,4-thiadiazol-2-ylthio)-1-thio-α-lincosamide | 2.11 (3H, s), 5.35 (1H, d, J=5.7 Hz), 7.60-7.80 (3H, m), 8.02 (1H, d, J=8.1 Hz) | CD₃OD (300 MHz) | 614 (M⁺ + 1) |

TABLE 20-continued

| 396 | Methyl 7-deoxy-7-epi-6-N-((2S,4R)-4-ethyl-1-methyl)pipecoloyl-7-(5-(4-fluoro-2-nitrophenyl)-1,3,4-thiadiazol-2-ylthio)-1-thio-α-lincosamide | 2.20 (3H, s), 2.23 (3H, s), 5.35 (1H, d, J=5.4 Hz), 7.45-7.55 (1H, m), 7.75-7.85 (2H, m) | $CD_3OD$ (300 MHz) | 646 ($M^+ + 1$) |
|---|---|---|---|---|

TABLE 21a

| 397 | Methyl 6-N-((2S,4R)-4-butyl)pipecoloyl-7-deoxy-7-epi-7-(5-(5-methylaminothiazol-4-yl)-1,3,4-thiadiazol-2-ylthio)-1-thio-α-lincosamide | 2.15 (3H, s), 3.13 (3H, d, J=5.1 Hz), 5.38 (1H, d, J=5.7 Hz), 7.52 (1H, d, J=5.1 Hz), 7.98 (1H, s) | $CD_3OD$ (300 MHz) | 633 ($M^+ + 1$) |
|---|---|---|---|---|
| 398 | Methyl 6-N-((2S,4R)-4-butyl)pipecoloyl-7-(5-(2-cyanophenyl)-1,3,4-thiadiazol-2-ylthio)-7-deoxy-7-epi-1-thio-α-lincosamide | 1.92 (3H, s), 2.51 (3H, s), 5.35 (1H, d, J=5.1 Hz), 7.75-7.95 (4H, m) | $CD_3OD$ (300 MHz) | 622 ($M^+ + 1$) |
| 399 | Methyl 6-N-((2S,4R)-4-butyl)pipecoloyl-7-deoxy-7-epi-7-(5-(4-fluoro-2-nitrophenyl)-1,3,4-thiadiazol-2-ylthio)-1-thio-α-lincosamide | 0.71-0.83 (3H, m), 1.98 (3H, s), 5.28 (1H, d, J=5.8 Hz), 7.60-7.67 (1H, m), 7.81-7.88 (1H, m), 7.94-8.00 (1H, m) | $CD_3OD$ (400 MHz) | 660 ($M^+ + 1$) |
| 400 | Methyl 6-N-((2S,4R)-4-butyl)-pipecoloyl-7-deoxy-7-epi-7-(5-(2-nitrophenyl)-1,3,4-thiadiazol-2-ylthio)-1-thio-α-lincosamide | 0.80-0.92 (3H, m), 1.56 (3H, d, J=7.1 Hz), 1.99 (3H, s), 5.29 (1H, d, J=5.6 Hz), 7.75-7.86 (3H, m), 8.08-8.11 (1H, m) | $CD_3OD$ (400 MHz) | API 642 ($M^+ + 1$) |
| 401 | Methyl 6-N-((2S,4R)-4-butyl)-pipecoloyl-7-deoxy-7-epi-7-(4-(morpholinocarbonyl)-phenylthio)-1-thio-α-lincosamide | 1.88 (3H, s), 3.93 (1H, dq, J=2.4, 6.8 Hz), 5.29 (1H, d, J=5.6 Hz), 7.37 (2H, ddd, J=8.5, 1.9, 1.9 Hz), 7.45 (2H, ddd, J=8.5, 1.9, 1.9 Hz) | $CD_3OD$ (400 MHz) | 626 ($M^+ + 1$) |
| 402 | Methyl 7-(4-amino-5-(piperidinocarbonyl)pyrimidin-2-ylthio)-6-N-((2S,4R)-4-butyl)pipecoloyl-7-deoxy-7-epi-1-thio-α-lincosamide | 1.84 (3H, s), 5.22 (1H, d, J=5.6 Hz), 7.92 (1H, s) | $CD_3OD$ (400 MHz) | 641 ($M^+ + 1$) |
| 403 | Methyl 7-(5-acetamidopyridin-2-ylthio)-6-N-((2S,4R)-4-butyl)pipecoloyl-7-deoxy-7-epi-1-thio-α-lincosamide | 1.88 (3H, s), 2.13 (3H, s), 5.26 (1H, d, J=5.4 Hz), 7.34 (1H, d, J=8.7 Hz), 7.84 (1H, dd, J=2.7, 8.7 Hz), 8.74 (1H, d, J=1.8 Hz) | $CD_3OD$ (300 MHz) | 571 ($M^+ + 1$) |
| 404 | Methyl 6-N-((2S,4R)-4-butyl-1-methyl)pipecoloyl-7-deoxy-7-epi-7-(5-(5-(methylamino)thiazol-4-yl)-1,3,4-thiadiazol-2-ylthio)-1-thio-α-lincosamide | 2.19 (6H, s), 3.14 (3H, d, J=5.1 Hz), 5.35 (1H, d, J=5.7 Hz), 7.58 (1H, d, J=5.1 Hz), 7.99 (1H, s) | $CDCl_3$ (300 MHz) | 647 ($M^+ + 1$) |
| 405 | Methyl 6-N-((2S,4R)-4-butyl-1-methyl)pipecoloyl-7-deoxy-7-epi-7-(5-(4-fluoro-2-nitrophenyl)-1,3,4-thiadiazol-2-ylthio)-1-thio-α-lincosamide | 0.86-0.91 (3H, m), 1.57 (3H, d, J=6.8 Hz), 1.99 (3H, s), 2.27 (3H, s), 5.28 (1H, d, J=5.6 Hz), 7.60-7.67 (1H, m), 7.82-7.87 (1H, m), 7.95-8.00 (1H, m) | $CDCl_3$ (300 MHz) | 674 ($M^+ + 1$) |
| 406 | Methyl 6-N-((2S,4R)-4-butyl-1-methyl)pipecoloyl-7-deoxy-7-epi-7-(5-(2-nitrophenyl)-1,3,4-thiadiazol-2-ylthio)-1-thio-α-lincosamide | 0.85-0.91 (3H, m), 1.57 (3H, d, J=7.0 Hz), 2.00 (3H, s), 2.26 (3H, s), 5.28 (1H, d, J=5.6 Hz), 7.76-7.86 (3H, m), 8.07-8.13 (1H, m) | $CD_3OD$ (400 MHz) | API 656 ($M^+ + 1$) |
| 407 | Methyl 7-(5-acetamidopyridin-2-ylthio)-6-N-((2S,4R)-4-butyl-1-methyl)pipecoloyl-7-deoxy-7-epi-1-thio-α-lincosamide | 1.88 (3H, s), 2.13 (3H, s), 5.26 (1H, d, J=5.4 Hz), 7.34 (1H, d, J=8.7 Hz), 7.84 (1H, dd, J=2.7, 8.7 Hz), 8.74 (1H, d, J=1.8 Hz) | $CD_3OD$ (300 MHz) | 585 ($M^+ + 1$) |
| 408 | Methyl 7-((4-amino-5-piperidinocarbonyl)-pyrimidin-2-ylthio)-6-N-((2S,4R)-4-butyl-1-methyl)pipecoloyl-7-deoxy-7-epi-1-thio-α-lincosamide | 1.89 (3H, s), 2.25 (3H, s), 5.22 (1H, d, J=5.6 Hz), 7.95 (1H, s) | $CD_3OD$ (400 MHz) | 655 ($M^+ + 1$) |

TABLE 21a-continued

| | | | | |
|---|---|---|---|---|
| 409 | 7-(6-Aminobenzo[d]thiazol-2-ylthio)-7-deoxylincomycin | 2.24 (3H, s), 2.43 (3H, s), 5.37 (1H, d, J=5.4 Hz), 6.78 (1H, dd, J=2.4, 8.4 Hz), 7.01 (1H, d, J=2.4 Hz), 7.76 (1H, d, J=8.4 Hz) | CDCl$_3$ (300 MHz) | 571 (M$^+$ + 1) |
| 410 | 7-(5-Amino-1,3,4-thiadiazol-2-ylthio)-7-deoxy-2-o-(2,6-dichlorobenzyl)-7-epilincomycin | 2.04 (3H, s), 2.33 (3H, s), 5.43 (1H, d, J=5.6 Hz), 7.26-7.32 (1H, s), 7.35-7.40 (1H, m) | CD$_3$OD (400 MHz) | 680 (M$^+$ + 1) |
| 411 | 7-(5-Amino-1,3,4-thiadiazol-2-ylthio)-7-deoxy-7-epi-2-o-methyl-carbamoylmethyllincomycin | 2.12 (3H, s), 2.41 (3H, s), 2.79 (3H, s), 5.54 (1H, d, J=5.3 Hz) | CD$_3$OD (400 MHz) | 593 (M$^+$ + 1) |
| 412 | 7-Deoxy-7-epi-7-(5-(5-(methylamino)-thiazol-4-yl)-2-o-methylcarbamoylmethyl-1,3,4-thiadiazol-2-ylthio)lincomycin | 2.04 (3H, s), 2.46 (3H, s), 2.78 (3H, s), 3.12 (3H, s), 5.54 (1H, d, J=5.4 Hz), 8.13 (1H, s) | CD$_3$OD (400 MHz) | 690 (M$^+$ + 1) |

TABLE 21b

| | | | | |
|---|---|---|---|---|
| 413 | 7-(5-(5-(Azetidin-1-yl)-2-nitrophenyl)-1,3,4-thiadiazol-2-ylthio)-7-deoxy-7-epilincomycin | 2.17 (3H, s), 2.39 (3H, s), 2.51 (2H, t, J=7.5 Hz), 4.10 (4H, t, J=7.5 Hz), 5.36 (1H, d, J=5.4 Hz), 6.40 (1H, s), 6.42 (1H, d, J=8.7 Hz), 8.14 (1H, d, J=8.7 Hz) | CDCl$_3$ (300 MHz) | 683 (M$^+$ + 1) |
| 414 | 7-Deoxy-7-epi-7-(5-(1-methyl-5-nitro-1H-pyrazol-4-yl)-1,3,4-thiadiazol-2-ylthio)lincomycin | 2.14 (3H, s), 2.41 (3H, s), 4.05 (3H, s), 5.34 (1H, d, J=5.4 Hz), 8.33 (1H, s) | CDCl$_3$ (300 MHz) | 632 (M$^+$ + 1) |
| 415 | 7-(5-(4-Amino-2-nitrophenyl)-1,3,4-thiadiazol-2-ylthio)-7-deoxy-7-epilincomycin | 2.08 (3H, s), 2.65 (3H, s), 5.25 (1H, d, J=5.4 Hz), 6.82 (1H, d, J=8.7 Hz), 7.10 (1H, s), 7.36 (1H, d, J=8.7 Hz) | CDCl$_3$ (300 MHz) | 643 (M$^+$ + 1) |
| 416 | 7-Deoxy-7-epi-7-(5-(1-methyl-4-nitro-1H-pyrazol-5-yl)-1,3,4-thiadiazol-2-ylthio)lincomycin | 2.16 (3H, s), 2.40 (3H, s), 4.15 (3H, s), 5.36 (1H, d, J=5.4 Hz), 8.23 (1H, s) | CDCl$_3$ (300 MHz) | 632 (M$^+$ + 1) |
| 417 | 7-Deoxy-7-epi-7-(5-(1-methyl-4-nitro-1H-imidazol-2-yl)-1,3,4-thiadiazol-2-ylthio)-lincomycin | 2.11 (3H, s), 2.43 (3H, s), 4.26 (3H, s), 5.35 (1H, d, J=5.7 Hz), 7.91 (1H, s) | CDCl$_3$ (300 MHz) | 632 (M$^+$ + 1) |
| 418 | 7-Deoxy-7-epi-7-(5-(1-methyl-4-nitro-1H-pyrazol-3-yl)-1,3,4-thiadiazol-2-ylthio)lincomycin | 2.15 (3H, s), 2.41 (3H, s), 4.08 (3H, s), 5.35 (1H, d, J=5.4 Hz), 8.33 (1H, s) | CDCl$_3$ (300 MHz) | 632 (M$^+$ + 1) |
| 419 | 7-(5-(4-Chloro-2-nitrophenyl)-oxazol-2-ylthio)-7-deoxy-7-epilincomycin | 2.06 (3H, s), 2.36 (3H, s), 5.26 (1H, d, J=5.6 Hz), 6.72 (1H, ddd, J=7.5, 7.5, 1.0 Hz), 6.84 (1H, dd, J=8.0, 1.2 Hz), 7.10-7.18 (2H, m), 7.78 (1H, s) | CD$_3$OD (400 MHz) | 645 (M$^+$ + 1) |
| 420 | 7-(5-(2-Cyanophenyl)oxazol-2-ylthio)-7-deoxy-7-epilincomycin | 2.00 (3H, s), 2.37 (3H, s), 5.26 (1H, d, J=5.6 Hz), 7.51 (1H, ddd, J=7.8, 7.8, 1.2 Hz), 7.76 (1H, ddd, J=7.8, 7.8, 1.2 Hz), 7.83-7.87 (3H, m) | CD$_3$OD (400 MHz) | 591 (M$^+$ + 1) |
| 421 | 7-Deoxy-7-epi-7-(5-(pyridin-4-yl)oxazol-2-ylthio)lincomycin | 1.98 (3H, s), 2.37 (3H, s), 5.26 (1H, d, J=5.6 Hz), 7.66 (2H, dd, J=4.7, 1.7 Hz), 7.83 (1H, s), 8.58 (2H, dd, J=4.7, 1.7 Hz) | CD$_3$OD (400 MHz) | 567 (M$^+$ + 1) |
| 422 | 7-Deoxy-7-epi-7-(5-(4,5-dimethoxy-2-nitrophenyl)oxazol-2-ylthio)-7-epilincomycin | 2.01 (3H, s), 2.38 (3H, s), 3.94 (3H, s), 3.96 (3H, s), 5.26 (1H, d, J=5.6 Hz), 7.15 (1H, s), 7.40 (1H, s), 7.61 (1H, s) | CD$_3$OD (400 MHz) | 671 (M$^+$ + 1) |
| 423 | 7-Deoxy-7-epi-7-(5-(pyridin-3-yl)oxazol-2-ylthio)lincomycin | 2.00 (3H, s), 2.37 (3H, s), 5.26 (1H, d, J=5.6 Hz), 7.51 (1H, dd, J=8.0, 4.9 Hz), 7.68 (1H, s), 8.09 (1H, ddd, J=8.0, 2.2, 2.2 Hz), 8.50 (1H, dd, J=4.9, 2.2 Hz), 8.86 (1H, d, J=2.2 Hz) | CD$_3$OD (400 MHz) | 567 (M$^+$ + 1) |
| 424 | 7-Deoxy-7-epi-7-(5-(4-dimethylamino-2-nitrophenyl)oxazol-2-ylthio)-7-epilincomycin | 2.01 (3H, s), 2.36 (3H, s), 3.07 (3H, s), 3.07 (3H, s), 5.26 (1H, d, J=5.6 Hz), 6.99 (1H, dd, J=8.8, 2.4 Hz), 7.11 (1H, d, J=2.4 Hz), 7.20 (1H, s), 7.49 (1H, d, J=8.8 Hz) | CD$_3$OD (400 MHz) | 654 (M$^+$ + 1) |
| 425 | 7-Deoxy-7-epi-7-(5-phenyl oxazol-2-ylthio)lincomycin | 2.01 (3H, s), 2.36 (3H, s), 5.26 (1H, d, J=5.6 Hz), 7.33-7.36 (1H, m), 7.42-7.46 (2H, m), 7.50 (1H, s), 7.64-7.66 (2H, m) | CD$_3$OD (400 MHz) | 566 (M$^+$ + 1) |
| 426 | 7-Deoxy-7-epi-7-(5-(pyridin-2-yl)oxazol-2-ylthio)lincomycin | 2.00 (3H, s), 2.36 (3H, s), 5.26 (1H, d, J=5.6 Hz), 7.35 (1H, ddd, J=7.5, 5.0, 1.0 Hz), 7.73-7.75 (2H, m), 7.89-7.93 (1H, m), 8.56-8.58 (1H, m) | CD$_3$OD (400 MHz) | 567 (M$^+$ + 1) |

TABLE 21b-continued

| | | | | |
|---|---|---|---|---|
| 427 | 7-Deoxy-7-(5-(2,4-dimethoxy-6-(methoxycarbonyl)phenyl)-oxazol-2-ylthio)-7-epilincomycin | 2.03 (3H, s), 2.30 (3H, s), 3.83 (3H, s), 3.88 (3H, s), 3.90 (3H, s), 5.26 (1H, d, J=5.6 Hz), 6.81 (1H, d, J=2.4 Hz), 6.83 (1H, d, J=2.4 Hz), 7.23 (1H, s) | $CD_3OD$ (400 MHz) | 684 ($M^+$ + 1) |
| 428 | 7-Deoxy-7-epi-7-(5-(4-methyl-1,2,3-thiadiazol-5-yl)oxazol-2-ylthio)lincomycin | 1.98 (3H, s), 2.38 (3H, s), 2.84 (3H, s), 5.25 (1H, d, J=5.6 Hz), 7.66 (1H, s) | $CD_3OD$ (400 MHz) | 588 ($M^+$ + 1) |

TABLE 21c

| | | | | |
|---|---|---|---|---|
| 429 | 7-Deoxy-7-(4-(2,4-diamino-1,3,5-triazin-6-yl)phenylthio)-7-epilincomycin | 2.17 (3H, s), 2.40 (3H, s), 5.37 (1H, d, J=5.7 Hz), 7.45-7.55 (4H, m) | $CDCl_3$ (300 MHz) | 608 ($M^+$ + 1) |
| 430 | 7-Deoxy-7-epi-7-(4-(1H-imidazol-1-yl)phenylthio)-lincomycin | 2.13 (3H, s), 2.41 (3H, s), 5.39 (1H, d, J=5.1 Hz), 7.22 (1H, s), 7.27 (1H, s), 7.36 (2H, d, J=8.7 Hz), 7.53 (2H, d, J=8.7 Hz), 7.88 (1H, s) | $CDCl_3$ (300 MHz) | 565 ($M^+$ + 1) |
| 431 | 7-Deoxy-7-epi-7-(4-(1-methyl-1H-pyrazol-4-yl)-phenylthio)-lincomycin | 2.17 (3H, s), 2.35 (3H, s), 3.96 (3H, s), 5.38 (1H, d, J=5.4 Hz), 7.40-7.55 (4H, m), 7.62 (1H, s), 7.78 (1H, s) | $CDCl_3$ (300 MHz) | 579 ($M^+$ + 1) |
| 432 | 7-Deoxy-7-epi-7-(4-(6-fluoro-pyridin-3-yl)phenylthio)-lincomycin | 2.12 (3H, s), 2.40 (3H, s), 5.39 (1H, d, J=4.8 Hz), 7.00-7.05 (1H, m), 7.45-7.58 (4H, m), 8.10-8.15 (1H, m), 8.42 (1H, s) | $CDCl_3$ (300 MHz) | 594 ($M^+$ + 1) |
| 433 | 7-(4-(6-Aminopyridin-3-yl)phenylthio)-7-deoxy-7-epilincomycin | 2.15 (3H, s), 2.36 (3H, s), 5.39 (1H, d, J=5.1 Hz), 6.59 (1H, d, J=8.4 Hz), 7.45-7.58 (4H, m), 7.66 (1H, d, J=8.4 Hz), 8.30 (1H, s) | $CDCl_3$ (300 MHz) | 591 ($M^+$ + 1) |
| 434 | 7-Deoxy-7-epi-7-(4-(imidazo[2,1-b]thiazol-6-yl)phenylthio)lincomycin | 2.15 (3H, s), 2.33 (3H, s), 5.30 (1H, d, J=5.7 Hz), 7.45-7.60 (4H, m), 7.66 (1H, s), 7.99 (1H, s) | $CDCl_3$ (300 MHz) | 621 ($M^+$ + 1) |
| 435 | 7-Deoxy-7-(2,6-difluoro-4-(1H-tetrazol-1-yl)phenylthio)-7-epilincomycin | 2.27 (3H, s), 2.47 (3H, s), 5.36 (1H, d, J=5.7 Hz), 7.61 (2H, d, J=6.6 Hz), 9.53 (1H, s) | $CDCl_3$ (300 MHz) | 603 ($M^+$ + 1) |
| 436 | 7-Deoxy-7-epi-7-(5-(pyridin-2-yl)thiophen-2-ylthio)lincomycin | 2.24 (3H, s), 2.32 (3H, s), 5.40 (1H, d, J=5.7 Hz), 7.21 (1H, d, J=3.9 Hz), 7.48 (1H, d, J=3.9 Hz), 7.63 (1H, d, J=7.8 Hz), 7.72 (1H, t, J=7.8 Hz), 7.94 (1H, d, J=7.8 Hz), 8.57 (1H, s) | $CDCl_3$ (300 MHz) | 582 ($M^+$ + 1) |
| 437 | 7-(6-Aminopyridin-3-ylthio)-7-deoxy-7-epilincomycin | 2.28 (3H, s), 2.31 (3H, s), 5.38 (1H, d, J=5.4 Hz), 6.46 (1H, d, J=8.4 Hz), 7.53 (1H, d, J=8.4 Hz), 8.18 (1H, s) | $CDCl_3$ (300 MHz) | 515 ($M^+$ + 1) |
| 438 | 7-(5-Aminopyrazin-2-ylthio)-7-deoxy-7-epilincomycin | 2.16 (3H, s), 2.30 (3H, s), 5.35 (1H, d, J=5.4 Hz), 7.90 (1H, s), 8.10 (1H, s) | $CDCl_3$ (300 MHz) | 516 ($M^+$ + 1) |
| 439 | 7-(2-Carbamoylimidazo[2,1-b]thiazol-2-ylthio)-7-deoxy-7-epilincomycin | 2.17 (3H, s), 2.18 (3H, s), 5.27 (1H, d, J=5.7 Hz), 7.68 (1H, s), 8.02 (1H, s) | $CDCl_3$ (300 MHz) | 588 ($M^+$ + 1) |
| 440 | 7-Deoxy-7-(2-N,N-dimethylcarbamoylimidazo[2,1-b]thiazol-2-ylthio)-7-epilincomycin | 2.21 (3H, s), 2.26 (3H, s), 3.01 (3H, s), 3.50 (3H, s), 5.36 (1H, d, J=5.4 Hz), 7.65 (1H, s), 8.00 (1H, s) | $CDCl_3$ (300 MHz) | 616 ($M^+$ + 1) |
| 441 | 7-Deoxy-7-epi-7-(2-(4-(trifluoro-methoxy)-phenyl)imidazo[1,2-a]pyridin-6-ylthio)lincomycin | 2.19 (3H, s), 2.24 (3H, s), 5.37 (1H, d, J=5.7 Hz), 7.29 (2H, d, J=6.6 Hz), 7.31 (1H, d, J=9.6 Hz), 7.61 (1H, d, J=9.6 Hz), 7.97 (2H, d, J=6.6 Hz), 7.86 (1H, s), 8.36 (1H, s) | $CDCl_3$ (300 MHz) | 699 ($M^+$ + 1) |
| 442 | 7-(4-(5-Cyanopyridin-3-yl)phenylthio)-7-deoxy-7-epilincomycin | 2.08 (3H, s), 2.43 (3H, s), 5.37 (1H, d, J=6.3 Hz), 7.54 (4H, s), 8.13 (1H, s), 8.87 (1H, s), 9.09 (1H, s) | $CDCl_3$ (300 MHz) | 601 ($M^+$ + 1) |
| 443 | 7-Deoxy-7-epi-7-(4-(2-fluoropyridin-3-yl)phenylthio)-lincomycin | 2.09 (3H, s), 2.39 (3H, s), 5.38 (1H, d, J=5.4 Hz), 7.28-7.33 (1H, m), 7.52 (4H, s), 7.87 (1H, t, J=7.8 Hz) 8.21 (1H, d, J=4.5 Hz) | $CDCl_3$ (300 MHz) | 594 ($M^+$ + 1) |
| 444 | 7-Deoxy-7-epi-7-(4-(5-fluoropyridin-3-yl)phenylthio)-lincomycin | 2.11 (3H, s), 2.40 (3H, s), 5.39 (1H, d, J=5.7 Hz), 7.53 (4H, s), 7.57 (1H, d, J=9.3 Hz), 8.47 (1H, d, J=2.1 Hz), 8.66 (1H, s) | $CDCl_3$ (300 MHz) | 594 ($M^+$ + 1) |

TABLE 21d

| | | | | |
|---|---|---|---|---|
| 445 | 7-Deoxy-7-epi-7-(4-(2-methoxypyridin-3-yl)-phenylthio)lincomycin | 2.13 (3H, s), 2.38 (3H, s), 3.97 (3H, s), 5.38 (1H, d, J=5.4 Hz), 6.99 (1H, t, J=7.5 Hz), 7.44 (2H, d, J=8.7 Hz), 7.57 (2H, d, J=8.7 Hz), 7.60 (1H, d, J=7.5 Hz), 8.15 (1H, d, J=7.5 Hz) | CDCl$_3$ (300 MHz) | 606 (M$^+$ + 1) |
| 446 | 7-Deoxy-7-epi-7-(4-(2-nitropyridin-3-yl)phenylthio)-lincomycin | 1.90 (3H, s), 2.42 (3H, s), 5.25 (1H, d, J=5.6 Hz), 7.33 (2H, ddd, J=8.5, 2.0, 2.0 Hz), 7.49 (2H, ddd, J=8.5, 2.0, 2.0 Hz), 7.77 (1H, dd, J=7.8, 4.8 Hz), 8.09 (1H, dd, J=7.8, 1.7 Hz), 8.51 (1H, dd, J=4.8, 1.7 Hz) | CD$_3$OD (400 MHz) | 621 (M$^+$ + 1) |
| 447 | 7-Deoxy-7-epi-7-(4-(4-nitro-1-oxidopyridin-3-yl)-phenylthio)lincomycin | 1.90 (3H, s), 2.43 (3H, s), 5.25 (1H, d, J=5.6 Hz), 7.35 (2H, ddd, J=8.5, 1.9, 1.9 Hz), 7.49 (2H, ddd, J=8.5, 1.9, 1.9 Hz), 8.11 (1H, d, J=7.1 Hz), 8.39-8.43 (2H, m) | CD$_3$OD (400 MHz) | 637 (M$^+$ + 1) |
| 448 | 7-Deoxy-7-epi-7-(2-nitropyridin-3-ylthio)lincomycin | 1.85 (3H, s), 2.38 (3H, s), 5.19 (1H, d, J=5.6 Hz), 7.69 (1H, dd, J=8.2, 4.4 Hz), 8.29 (1H, dd, J=8.2, 1.5 Hz), 8.34 (1H, dd, J=4.4, 1.5 Hz) | CD$_3$OD (400 MHz) | 545 (M$^+$ + 1) |
| 449 | 7-Deoxy-7-epi-7-(5-(4-fluoro-5-hydroxy-2-nitrophenyl)-1,3,4-thiadiazol-2-ylthio)-lincomycin | 1.56 (3H, d, J=6.8 Hz), 2.02 (3H, s), 2.71 (3H, s), 5.29 (1H, d, J=5.6 Hz), 6.81 (1H, d, J=8.5 Hz), 7.97 (1H, d, J=11.7 Hz) | CD$_3$OD (400 MHz) | 662 (M$^+$ + 1) |
| 450 | 7-Deoxy-7-epi-7-(5-(3-nitropyridin-2-yl)-1,3,4-thiadiazol-2-ylthio)lincomycin | 1.58 (3H, d, J=6.8 Hz), 2.01 (3H, s), 2.37 (3H, s), 5.26 (1H, d, J=5.6 Hz), 7.74 (1H, dd, J=4.9, 8.3 Hz), 8.29 (1H, d, J=8.3 Hz), 8.85 (1H, d, J=4.9 Hz) | CD$_3$OD (400 MHz) | 629 (M$^+$ + 1) |
| 451 | 7-Deoxy 7-(5-(4,5-dimethoxy-2-nitrophenyl)-1,3,4-oxadiazol-2-ylthio)-7-epilincomycin | 1.57 (3H, d, J=6.8 Hz), 2.07 (3H, s), 2.39 (3H, s), 5.27 (1H, d, J=5.7 Hz), 7.35 (1H, s), 7.78 (1H, s) | CD$_3$OD (400 MHz) | 627 (M$^+$ + 1) |
| 452 | 7-Deoxy-7-epi-7-(4-(pyridin-3-ylamino)phenylthio)-lincomycin | 2.13 (3H, s), 2.37 (3H, s), 5.29 (1H, d, J=5.7 Hz), 7.09 (2H, ddd, J=2.1, 2.7, 9.3 Hz), 7.29 (1H, ddd, J=0.6, 4.8, 8.4 Hz), 7.40 (2H, ddd, J=2.1, 2.7, 9.3 Hz), 7.58 (1H, ddd, J=1.5, 2.7, 8.4 Hz), 8.02 (1H, dd, J=1.5, 4.8 Hz), 8.30 (1H, dd, J=0.6, 2.7 Hz) | CD$_3$OD (300 MHz) | 591 (M$^+$ + 1) |
| 453 | 7-Deoxy-7-epi-7-(4-(methyl(pyridin-3-yl)amino)-phenylthio)lincomycin | 2.07 (3H, s), 2.42 (3H, s), 3.33 (3H, s), 5.29 (1H, d, J=5.4 Hz), 7.05 (2H, ddd, J=1.8, 2.7, 8.7 Hz), 7.31 (1H, ddd, J=0.6, 4.8, 8.4 Hz), 7.41 (2H, ddd, J=1.8, 2.7, 8.7 Hz), 7.44 (1H, ddd, J=1.5, 2.7, 8.4 Hz), 8.08 (1H, dd, J=1.5, 4.8 Hz), 8.21 (1H, d, J=2.7 Hz) | CD$_3$OD (300 MHz) | 605 (M$^+$ + 1) |
| 454 | 7-Deoxy-7-epi-7-(4-nicotinoylphenylthio)lincomycin | 1.85 (3H, s), 2.43 (3H, s), 5.25 (1H, d, J=5.4 Hz), 7.52 (2H, d, J=8.7 Hz), 7.60 (1H, dd, J=5.1, 7.8 Hz), 7.76 (2H, d, J=8.1 Hz), 8.17 (1H, ddd, J=1.8, 2.1, 7.8 Hz), 8.77 (1H, dd, J=1.8, 5.1 Hz), 8.86 (1H, d, J=2.1 Hz) | CD$_3$OD (300 MHz) | 604 (M$^+$ + 1) |
| 455 | 7-(Biphenyl-4-ylthio)-7-deoxy-7-epilincomycin | 2.01 (3H, s), 2.41 (3H, s), 5.27 (1H, d, J=5.7 Hz), 7.30-7.36 (1H, m), 7.39-7.46 (2H, m), 7.47-7.53 (2H, m), 7.56-7.63 (4H, m) | CD$_3$OD (300 MHz) | 575 (M$^+$ + 1) |
| 456 | 7-(3'-Aminobiphenyl-4-ylthio)-7-deoxy-7-epilincomycin | 2.01 (3H, s), 2.40 (3H, s), 5.28 (1H, d, J=5.7 Hz), 6.71 (1H, ddd, J=0.9, 2.1, 8.1 Hz), 6.92 (1H, ddd, J=0.9, 1.8, 7.5 Hz), 6.97 (1H, dd, J=1.8, 2.1 Hz), 7.16 (1H, d, J=7.5, 8.1 Hz), 7.46 (2H, d, J=8.7 Hz), 7.54 (2H, d, J=8.4 Hz) | CD$_3$OD (300 MHz) | 590 (M$^+$ + 1) |
| 457 | 7-Deoxy-7-((3'-dimethylamino)biphenly-4-ylthio)-7-epilincomycin | 2.02 (3H, s), 2.38 (3H, s), 2.96 (6H, s), 5.29 (1H, d, J=5.7 Hz), 6.74-6.80 (1H, m), 6.90-6.93 (2H, m), 7.25 (1H, dd, J=7.5, 8.4 Hz), 7.47 (2H, d, J=8.4 Hz), 7.56 (2H, d, J=8.4 Hz) | CD$_3$OD (300 MHz) | 618 (M$^+$ + 1) |
| 458 | 7-Deoxy-7-epi-7-(4-(5-methoxypyridin-3-yl)phenylthio)lincomycin | 1.98 (3H, s), 2.43 (3H, s), 3.94 (3H, s), 5.30 (1H, d, J=5.4 Hz), 7.52 (2H, d, J=8.4 Hz), 7.59 (1H, dd, J=1.8, 2.7 Hz), 7.64 (2H, d, J=8.4 Hz), 8.21 (1H, d, J=2.7 Hz), 8.38 (1H, d, J=2.1 Hz) | CD$_3$OD (300 MHz) | 606 (M$^+$ + 1) |

TABLE 21d-continued

| | | | | |
|---|---|---|---|---|
| 459 | 7-Deoxy-7-epi-7-(3'-methoxybiphenyl-4-ylthio)lincomycin | 2.01 (3H, s), 2.39 (3H, s), 3.84 (3H, s), 5.28 (1H, d, J=6.0 Hz), 6.91 (1H, dd, J=2.4, 8.1 Hz), 7.12-7.14 (1H, m), 7.17 (1H, d, J=7.5 Hz), 7.34 (1H, dd, J=7.8, 8.1 Hz), 7.49 (2H, d, J=8.1 Hz), 7.58 (2H, d, J=8.1 Hz) | $CD_3OD$ (300 MHz) | 605 ($M^+ + 1$) |
| 460 | 7-Deoxy-7-epi-7-(4-(6-methoxypyridin-3-yl)phenylthio)lincomycin | 2.01 (3H, s), 2.40 (3H, s), 3.94 (3H, s), 5.30 (1H, d, J=5.4 Hz), 6.86 (1H, dd, J=0.6, 8.4 Hz), 7.49 (2H, d, J=8.7 Hz), 7.55 (2H, d, J=9.0 Hz), 7.92 (1H, dd, J=2.7, 8.7 Hz), 8.37 (1H, dd, J=0.6, 2.7 Hz) | $CD_3OD$ (300 MHz) | 606 ($M^+ + 1$) |

TABLE 21e

| | | | | |
|---|---|---|---|---|
| 461 | 7-Deoxy-7-epi-7-(3'-methylbiphenyl-4-ylthio)-lincomycin | 2.01 (3H, s), 2.38 (3H, s), 2.40 (3H, s), 5.30 (1H, d, J=5.4 Hz), 7.15 (1H, d, J=7.5 Hz), 7.29 (1H, t, J=7.5 Hz), 7.38 (1H, d, J=8.4 Hz), 7.41 (1H, s), 7.47 (2H, d, J=8.7 Hz), 7.56 (2H, d, J=8.7 Hz) | $CD_3OD$ (300 MHz) | 589 ($M^+ + 1$) |
| 462 | 7-Deoxy-7-epi-7-((3'-methylthio)biphenyl-4-ylthio)lincomycin | 2.00 (3H, s), 2.40 (3H, s), 2.50 (3H, s), 5.29 (1H, d, J=5.7 Hz), 7.20-7.26 (1H, m), 7.33-7.36 (2H, m), 7.44-7.46 (1H, m), 7.47 (2H, d, J=8.7 Hz), 7.55 (2H, d, J=8.4 Hz) | $CD_3OD$ (300 MHz) | 621 ($M^+ + 1$) |
| 463 | 7-(3'-Cyanobiphenyl-4-ylthio)-7-deoxy-7-epilincomycin | 1.97 (3H, s), 2.43 (3H, s), 5.29 (1H, d, J=5.4 Hz), 7.51 (2H, d, J=8.4 Hz), 7.62 (2H, d, J=8.7 Hz), 7.69 (1H, ddd, J=1.2, 1.5, 7.8 Hz), 7.93 (1H, ddd, J=1.5, 1.8, 7.8 Hz), 7.98 (1H, dd, J=1.2, 1.5 Hz) | $CD_3OD$ (300 MHz) | 600 ($M^+ + 1$) |
| 464 | 7-(3'-Acetamidobiphenyl-4-ylthio)-7-deoxy-7-epilincomycin | 2.00 (3H, s), 2.15 (3H, s), 2.38 (3H, s), 5.29 (1H, d, J=5.7 Hz), 7.31-7.39 (2H, m), 7.48 (2H, d, J=8.4 Hz), 7.51 (1H, ddd, J=1.5, 2.1, 7.2 Hz), 7.57 (2H, d, J=8.4 Hz), 7.88 (1H, s) | $CD_3OD$ (300 MHz) | 632 ($M^+ + 1$) |
| 465 | 7-Deoxy-7-epi-7-(4-(isoquinolin-4-yl)phenylthio)-lincomycin | 2.01 (3H, s), 2.45 (3H, s), 5.31 (1H, d, J=5.4 Hz), 7.45 (2H, d, J=8.4 Hz), 7.58 (2H, d, J=8.1 Hz), 7.68-7.79 (2H, m), 7.87 (1H, d, J=8.4 Hz), 8.16 (1H, dd, J=1.2, 8.4 Hz), 8.34 (1H, s), 9.23 (1H, s) | $CD_3OD$ (300 MHz) | 626 ($M^+ + 1$) |
| 466 | 7-Deoxy-7-epi-7-((S)-4-(2-((methylamino)methyl)-pyrrolidine-1-carbonyl)phenylthio)-lincomycin | 1.89 (3H, s), 2.42 (3H, s), 2.58 (3H, s), 2.91-3.17 (2H, m), 3.46-3.68 (2H, m), 4.42-4.48 (1H, m), 5.26 (1H, d, J=5.7 Hz), 7.44-7.54 (4H, m) | $CD_3OD$ (300 MHz) | 639 ($M^+ + 1$) |
| 467 | 7-((S)-4-(2-(Aminomethyl)pyrrolidine-1-carbonyl)phenylthio)-7-deoxy-7-epilincomycin | 1.87 (3H, s), 2.40 (3H, s), 2.84-3.04 (2H, m), 3.34-3.52 (3H, m), 5.26 (1H, d, J=5.4 Hz), 7.45 (2H, d, J=8.1 Hz), 7.80 (2H, d, J=8.4 Hz) | $CD_3OD$ (300 MHz) | 625 ($M^+ + 1$) |
| 468 | 7-Deoxy-7-((S)-4-(2-((dimethylamino)methyl)-pyrrolidine-1-carbonyl)-phenylthio)-7-epilincomycin | 1.90 (3H, s), 2.38 (6H, s), 2.41 (3H, s), 2.48 (1H, d, J=9.0 Hz), 2.77 (1H, dd, J=3.6, 12.0 Hz), 3.35-3.45 (1H, br), 3.49-3.58 (1H, br), 4.34-4.45 (1H, br), 5.26 (1H, d, J=5.4 Hz), 7.47 (4H, d, J=3.0 Hz) | $CD_3OD$ (300 MHz) | 653 ($M^+ + 1$) |
| 469 | 7-Deoxy-7-epi-7-(4-(methoxy-methyl)phenylthio)-lincomycin | 1.99 (3H, s), 2.38 (3H, s), 3.36 (3H, s), 4.42 (2H, s), 5.28 (1H, d, J=5.4 Hz), 7.29 (2H, d, J=8.4 Hz), 7.41 (2H, d, J=8.1 Hz) | $CD_3OD$ (300 MHz) | 543 ($M^+ + 1$) |
| 470 | 7-(6-(3-Aminophenyl)-pyridin-3-ylthio)-7-deoxy-7-epilincomycin | 2.02 (3H, s), 2.38 (3H, s), 5.27 (1H, d, J=5.7 Hz), 6.80 (1H, ddd, J=1.5, 2.1, 7.8 Hz), 7.20 (1H, t, J=7.8 Hz), 7.25 (1H, dt, J=1.5, 7.8 Hz), 7.32 (1H, dd, J=1.5, 1.8 Hz), 7.75 (1H, d, J=8.7 Hz), 7.92 (1H, dd, J=2.4, 8.4 Hz), 8.60 (1H, d, J=2.1 Hz) | $CD_3OD$ (300 MHz) | 591 ($M^+ + 1$) |
| 471 | 7-Deoxy-7-epi-7-(6-nitroquinolin-3-yl)lincomycin | 1.86 (3H, s), 2.38 (3H, s), 5.24 (1H, d, J=5.4 Hz), 8.16 (1H, d, J=9.0 Hz), 8.43 (1H, dd, J=2.4, 9.3 Hz), 8.60 (1H, d, J=2.1 Hz), 8.89 (1H, d, J=2.4 Hz), 8.97 (1H, d, J=2.1 Hz) | $CD_3OD$ (300 MHz) | 595 ($M^+ + 1$) |

TABLE 21e-continued

| | | | | |
|---|---|---|---|---|
| 472 | 7-Deoxy-7-epi-7-(4-(1,3-di hydroxypropan-2-ylcarbamoyl)-phenylthio)lincomycin | 1.87 (3H, s), 2.54 (3H, s), 3.70-3.77 (5H, m), 5.28 (1H d, J=5.6 Hz), 7.43 (2H, d, J=8.3 Hz), 7.49 (2H, d, J=8.3 Hz) | CD$_3$OD (400 MHz) | 617 (M$^+$+1) |
| 473 | 7-Deoxy-7-epi-7-(4-((R)-3-methoxypyrrolidine-1-carbonyl)-phenylthio)lincomycin | 1.87 (3H, s), 2.54 (3H, s), 3.25 (3H, s) 5.26 (1H, d, J=5.6 Hz), 7.45 (2H, d, J=8.3 Hz), 7.49 (2H, d, J=8.3 Hz) | CD$_3$OD (400 MHz) | 627 (M$^+$+1) |
| 474 | 7-Deoxy-7-epi-7-(4-(3-hydroxy-propylcarbamoyl)phenylthio)-lincomycin | 1.33-1.38 (2H, m), 1.87 (3H, s), 2.40 (3H, s), 3.47 (1H, t, J=6.9 Hz), 3.64 (1H, t, J=6.2 Hz), 5.26 (1H, d, J=5.6 Hz), 7.45 (2H, dd, J=8.8, 1.9 Hz), 7.49 (2H, dd, J=8.8, 1.9 Hz) | CD$_3$OD (400 MHz) | 600 (M$^+$+1) |
| 475 | 7-Deoxy-7-epi-7-(4-((2-hydroxyethyl)-(3-hydroxypropyl)-carbamoyl)phenylthio)lincomycin | 1.92 (3H, s), 2.43 (3H, s), 5.27 (1H, d, J=5.6 Hz), 7.38-7.47 (4H, m) | CD$_3$OD (400 MHz) | 645 (M$^+$+1) |
| 476 | 7-Deoxy-7-epi-7-(4-(1,4-oxazepane-4-carbonyl)phenylthio)-lincomycin | 1.91 (3H, s), 2.42 (3H, s), 5.26 (1H, d, J=5.6 Hz), 7.38-7.49 (4H, m) | CD$_3$OD (400 MHz) | 627 (M$^+$+1) |

TABLE 21f

| | | | | |
|---|---|---|---|---|
| 477 | 7-Deoxy-7-epi-7-(4-((2-methoxyethyl)(3-methoxypropyl)-carbamoyl)-phenylthio)lincomycin | 1.91 (3H, s), 2.42 (3H, s), 5.26 (1H, d, J=5.6 Hz), 7.32-7.47 (4H, m) | CD$_3$OD (400 MHz) | 673 (M$^+$+1) |
| 478 | 7-Deoxy-7-epi-7-(4-((R)-1-hydroxybutan-2-ylcarbamoyl)-phenylthio)lincomycin | 0.97 (3H, t, J=7.5 Hz), 1.88 (3H, s), 2.41 (3H, s), 3.61 (2H, d, J=7.1 Hz), 5.26 (1H, d, J=5.3 Hz), 7.44 (2H, d, J=8.6 Hz), 7.79 (2H, d, J=8.6 Hz) | CD$_3$OD (400 MHz) | 615 (M$^+$+1) |
| 479 | 7-(4-((S)-2-(Allyloxymethyl)-pyrrolidine-1-carbonyl)-phenylthio)-7-deoxy-7-epilincomycin | 1.77 (3H, s), 2.30 (3H, s), 5.24 (1H, brd), 5.86 (1H, brs), 7.31-7.41 (4H, m) | DMSO (400 MHz) | 667 (M$^+$+1) |
| 480 | 7-Deoxy-7-epi-7-(4-(3-(methoxymethyl)-morpholine-4-carbonyl)phenylthio)-lincomycin | 1.90 (3H, s), 2.43 (3H, s), 5.25 (1H, d, J=5.6 Hz), 7.39 (2H, d, J=8.2 Hz), 7.46 (2H, d, J=8.2 Hz) | CD$_3$OD (400 MHz) | 657 (M$^+$+1) |
| 481 | 7-Deoxy-7-(4-(1,3-dimethoxypropan-2-ylcarbamoyl)phenylthio)-7-epilincomycin | 1.88 (3H, s), 2.42 (3H, s), 2.42 (3H, s), 3.36 (3H, s), 3.36 (3H, s), 5.25 (1H, d, J=5.6 Hz), 7.44 (2H, d, J=8.7 Hz), 7.77 (2H, d, J=8.7 Hz) | CD$_3$OD (400 MHz) | 645 (M$^+$+1) |
| 482 | 7-(4-(Cyanomethyl)-phenylthio)-7-deoxy-7-epilincomycin | 1.87 (3H, s), 2.30 (3H, s), 2.42 (3H, s), 3.36 (3H, s), 3.79 (2H, s), 5.18 (1H, d, J=5.6 Hz), 7.22 (2H, d, J=8.7 Hz), 7.33 (2H, d, J=8.7 Hz) | CD$_3$OD (400 MHz) | 539 (M$^+$+1) |
| 483 | 7-Deoxy-7-epi-7-(4-(4-methylmorpholin-2-yl)-phenylthio)lincomycin | 1.97 (3H, d, J=1.5 Hz), 2.02 (1H, t, J=11.3 Hz), 2.25 (1H, dt, J=3.4, 11.7 Hz), 2.33 (3H, s), 2.40 (3H, d, J=1.9 Hz), 2.79 (1H, d, J=11.6 Hz), 2.91 (1H, d, = 11.7 Hz), 3.78 (1H, dt, J=2.2, 11.7 Hz), 4.02 (1H, dd, J=2.7, 11.7 Hz), 4.51 (1H, d, J=9.5 Hz), 5.26 (1H, d, J=5.6 Hz), 7.33 (2H, d, J=8.3 Hz), 7.41 (2H, d, J=8.3 Hz). | CD$_3$OD (400 MHz) | 599 (M$^+$+1) |
| 484 | 7-Deoxy-7-epi-7-(4-(4-(2-methoxyethyl)-morpholin-2-yl-)phenylthio)-lincomycin | 1.98 (3H, s), 2.08 (1H, t, J=11.4 Hz), 2.31 (1H, dt, J=3.4, 11.7 Hz), 2.40 (3H, d, J=2.4 Hz), 2.62 (2H, t, J=5.3 Hz), 2.88 (1H, d, J=11.7 Hz), 2.98 (1H, d, J=11.7 Hz), 3.33 (3H, s), 3.55 (2H, t, J=5.3 Hz), 3.80 (1H, dt, J=2.4, 11.7 Hz), 3.98 (1H, dd, J=2.5, 11.5 Hz), 4.54 (1H, d, J=8.8 Hz), 5.26 (1H, d, J=5.6 Hz), 7.33 (2H, d, J=8.5 Hz), 7.41 (2H, d, J=8.3 Hz). | CD$_3$OD (400 MHz) | 643 (M$^+$+1) |
| 485 | 7-Deoxy-7-epi-7-(4-(4-propylmorpholin-2-yl)-phenylthio)lincomycin | 0.93 (3H, t, J=7.3 Hz), 1.51-1.61 (2H, m), 1.97 (3H, d, J=1.2 Hz), 2.02 (1H, t, J=11.4 Hz), 2.23 (1H, dt, J=3.4, 11.7 Hz), 2.37 (2H, t, J=8.1 Hz), 2.39 (3H, d, J=2.5 Hz), 2.87 (1H, d, J=11.7 Hz), 2.95 (1H, d, J=11.7 Hz), 3.79 (1H, dt, J=2.4, | CD$_3$OD (400 MHz) | 627 (M$^+$+1) |

TABLE 21f-continued

| | | | | |
|---|---|---|---|---|
| | | 11.4 Hz), 4.01 (1H, dd, J=2.5, 11.7 Hz), 4.52 (1H, d, J=8.8 Hz), 5.26 (1H, d, J=5.6 Hz), 7.33 (2H, d, J=8.3 Hz), 7.41 (2H, d, J=8.3 Hz) | | |
| 486 | 7-Deoxy-7-epi-7-(4-((2-oxopiperidin-1-yl)methyl)-phenylthio)lincomycin | 1.77-1.82 (4H, m), 1.97 (3H, s), 2.40 (3H, s), 2.40-2.44 (2H, m), 3.23-3.28 (2H, m), 4.56 (2H, s), 5.27 (1H, d, J=5.6 Hz), 7.23 (2H, d, J=8.3 Hz), 7.40 (2H, d, J=8.3 Hz) | CD$_3$OD (400 MHz) | 611 (M$^+$ + 1) |
| 487 | 7-Deoxy-7-epi-7-(4-(2-morpholineacetyl)-phenylthio)-lincomycin | 1.82 (3H, s), 2.43 (3H, s), 2.61 (2H, t, J=4.6 Hz), 3.73 (2H, t, J=4.6 Hz), 3.89 (2H, s), 5.25 (1H, d, J=5.6 Hz), 7.45 (2H, d, J=8.7 Hz), 7.95 (2H, d, J=8.7 Hz) | CD$_3$OD (400 MHz) | 627 (M$^+$ + 1) |
| 488 | 7-Deoxy-7-epi-7-((S)-4-(2-(methylthiomethyl)-pyrrolidine-1-carbonyl)-phenylthio)lincomycin | 1.90 (3H, s), 2.18 (3H, s), 2.41 (3H, s), 2.98-3.03 (2H, m), 3.40-3.47 (1H, m), 3.54-3.65 (1H, m), 4.36-4.44 (1H, br), 5.26 (1H, d, J=5.6 Hz), 7.45 (2H, d, J=8.3 Hz), 7.48 (2H, d, J=8.3 Hz) | CD$_3$OD (400 MHz) | 657 (M$^+$ + 1) |
| 489 | 7-Deoxy-7-epi-7-((R)-4-(3-ethylmorpholin-4-carbonyl)phenylthio)-lincomycin | 0.91-0.95 (3H, m), 1.70-1.85 (2H, br), 1.98 (3H, s), 2.42 (3H, s), 3.35-3.93 (7H, m), 5.25 (1H, d, J=5.6 Hz), 7.36 (2H, d, J=8.5 Hz), 7.48 (2H, d, J=8.5 Hz) | CD$_3$OD (400 MHz) | 641 (M$^+$ + 1) |
| 490 | 7-Deoxy-7-epi-7-(5-(2-methoxy-carbonylphenyl)-thiazol-2-ylthio)lincomycin | 2.06 (3H, s), 2.42 (3H, s), 3.77 (3H, s), 5.27 (1H, d, J=5.6 Hz), 7.48-7.54 (2H, m), 7.58-7.62 (2H, m), 7.82-7.85 (1H, m) | CD$_3$OD (400 MHz) | 640 (M$^+$ + 1) |
| 491 | 7-Deoxy-7-(5-(2-dimethylcarbamoyl-4,6-dimethoxyphenyl)oxazol-2-ylthio)-7-epilincomycin | 2.08 (3H, s), 2.25 (3H, s), 2.81 (6H, s), 3.88 (3H, s), 3.98 (3H, s), 5.29 (1H, d, J=5.3 Hz), 6.54 (1H, s), 6.77 (1H, s), 7.91 (1H, s) | CD$_3$OD (400 MHz) | 697 (M$^+$ + 1) |

TABLE 21g

| | | | | |
|---|---|---|---|---|
| 492 | 7-((R)-4-(3-Acetamidopyrrolidine-1-carbonyl)phenylthio)-7-deoxy-7-epilincomycin | 1.89 (3H, d, J=3.9 Hz), 1.90 (3H, s), 2.51 (3H, s), 3.45-3.85 (4H, m), 4.25-4.47 (1H, m), 5.25 (1H, d, J=5.6 Hz), 7.44-7.52 (4H, m) | CD$_3$OD (400 MHz) | 654 (M$^+$ + 1) |
| 493 | 7-((S)-4-(3-Acetamidopyrrolidin-1-carbonyl)phenylthio)-7-deoxy-7-epilincomycin | 1.78 (3H, s), 1.80 (3H, s), 2.36 (3H, s), 3.35-3.76 (4H, m), 4.14-4.38 (1H, m), 5.16 (1H, d, J=5.6 Hz), 7.34-7.42 (4H, m) | CD$_3$OD (400 MHz) | 654 (M$^+$ + 1) |
| 494 | 7-Deoxy-7-epi-7-(R-4-(3-hydroxypyrrolidine-1-carbonyl)phenylthio)-lincomycin | 1.90 (3H, s), 2.51 (3H, s), 3.46-3.80 (4H, m), 4.46-4.51 (1H, m), 5.26 (1H, d, J=5.6 Hz), 7.44-7.51 (4H, m) | CD$_3$OD (400 MHz) | 613 (M$^+$ + 1) |
| 495 | 7-Deoxy-7-epi-7-((R)-4-(3-hydroxypiperidine-1-carbonyl)phenylthio)-lincomycin | 1.92 (3H, s), 2.45 (3H, s), 3.40-4.20 (5H, m), 5.26 (1H, d, J=5.6 Hz), 7.35-7.42 (2H, br), 7.47 (2H, d, J=8.6 Hz) | CD$_3$OD (400 MHz) | 627 (M$^+$ + 1) |
| 496 | 7-Deoxy-7-epi-7-(4-(1-oxidopyridin-3-yl)-phenylthio)lincomycin | 1.94 (3H, s), 2.50 (3H, s), 5.26 (1H, d, J=5.6 Hz), 7.54 (2H, ddd, J=8.6, 1.9, 1.9 Hz), 7.61 (1H, dd, J=7.9, 4.8 Hz), 7.66 (2H, ddd, J=8.6, 1.9, 1.9 Hz), 7.89 (1H, ddd, J=7.9, 1.0, 1.0 Hz), 8.31 (1H, ddd, J=4.8, 1.0, 1.0 Hz), 8.62 (1H, dd, J=1.9, 1.9 Hz) | CD$_3$OD (400 MHz) | 592 (M$^+$ + 1) |
| 497 | 7-Deoxy-7-epi-7-(4-(4-nitropyridin-3-yl)phenylthio)-lincomycin | 1.91 (3H, s), 2.43 (3H, s), 5.25 (1H, d, J=5.6 Hz), 7.35 (2H, ddd, J=8.6, 2.0, 2.0 Hz), 7.51 (2H, ddd, J=8.6, 2.0, 2.0 Hz), 7.86 (1H, dd, J=5.4, 0.5 Hz), 8.79 (1H, d, J=0.5 Hz), 8.82 (1H, d, J=5.4 Hz) | CD$_3$OD (400 MHz) | 621 (M$^+$ + 1) |
| 498 | 7-Deoxy-7-epi-7-(5-(pyridin-3-yl)thiazol-2-ylthio)lincomycin | 2.02 (3H, s), 2.36 (3H, s), 5.26 (1H, d, J=5.6 Hz), 7.47-7.52 (1H, m), 8.03-8.07 (1H, m), 8.10 (1H, s), 8.50 (1H, dd, J=4.9, 1.4 Hz), 8.79 (1H, d, J=2.2 Hz) | CD$_3$OD (400 MHz) | 583 (M$^+$ + 1) |
| 499 | 7-Deoxy-7-epi-7-(5-(pyridin-4-yl)thiazol-2-ylthio)lincomycin | 1.99 (3H, s), 2.36 (3H, s), 5.26 (1H, d, J=5.6 Hz), 7.62 (2H, dd, J=4.7, 1.7 Hz), 8.26 (1H, s), 8.50 (2H, dd, J=4.7, 1.7 Hz) | CD$_3$OD (400 MHz) | 583 (M$^+$ + 1) |

TABLE 21g-continued

| | | | | |
|---|---|---|---|---|
| 500 | 7-Deoxy-7-epi-7-(5-(4-(hydroxymethyl)phenyl)-thiazol-2-ylthio)lincomycin | 2.04 (3H, s), 2.34 (3H, s), 4.62 (2H, s), 5.26 (1H, d, J=5.6 Hz), 7.41 (2H, d, J=8.5 Hz), 7.56 (2H, d, J=8.5 Hz), 7.97 (1H, s) | $CD_3OD$ (400 MHz) | 612 ($M^+ + 1$) |
| 501 | 7-Deoxy-7-epi-7-(5-(4-(methylthio)phenyl)thiazol-2-ylthio)lincomycin | 2.04 (3H, s), 2.34 (3H, s), 2.50 (3H, s), 5.26 (1H, d, J=5.7 Hz), 7.41 (2H, ddd, J=8.8, 2.2, 2.2 Hz), 7.56 (2H, ddd, J=8.8, 2.2, 2.2 Hz), 7.94 (1H, s) | $CD_3OD$ (400 MHz) | 628 ($M^+ + 1$) |
| 502 | 7-(5-(2-Carbamoylphenyl)-thiazol-2-ylthio)-7-deoxy-7-epilincomycin | 2.03 (3H, s), 2.97 (3H, s), 5.29 (1H, d, J=5.6 Hz), 7.51-7.57 (4H, m), 7.86 (1H, s) | $CD_3OD$ (500 MHz) | 625 ($M^+ + 1$) |
| 503 | 7-(5-(2-Acetamidophenyl)-thiazol-2-ylthio)-7-deoxy-7-epilincomycin | 2.04 (3H, s), 2.10 (3H, s), 2.36 (3H, s), 5.26 (1H, d, J=5.6 Hz), 7.32-7.41 (3H, m), 7.58 (1H, d, J=7.3 Hz), 7.85 (1H, s) | $CD_3OD$ (400 MHz) | 639 ($M^+ + 1$) |
| 504 | 7-Deoxy-7-epi-7-(5-(2-methylsulfonamidophenyl)-thiazol-2-ylthio)lincomycin | 2.06 (3H, s), 2.38 (3H, s), 2.99 (3H, s), 5.27 (1H, d, J=5.6 Hz), 7.35 (1H, ddd, J=7.6, 7.6, 1.7 Hz), 7.40 (1H, ddd, J=7.6, 7.6, 1.7 Hz), 7.48 (1H, dd, J=7.6, 1.7 Hz), 7.64 (1H, dd, J=7.5, 1.8 Hz), 8.00 (1H, s) | $CD_3OD$ (400 MHz) | 675 ($M^+ + 1$) |
| 505 | 7-(5-(3-Aminophenyl)-thiazol-2-ylthio)-7-deoxy-7-epilincomycin | 2.04 (3H, s), 2.33 (3H, s), 5.26 (1H, d, J=5.9 Hz), 6.67-6.70 (1H, m), 6.85-6.87 (1H, m), 6.91 (1H, dd, J=1.7, 1.7 Hz), 7.14 (1H, dd, J=7.9, 7.9 Hz), 7.89 (1H, s) | $CD_3OD$ (400 MHz) | 597 ($M^+ + 1$) |
| 506 | 7-Deoxy-7-epi-7-(5-(2-formamidophenyl)-thiazol-2-ylthio)-lincomycin | 2.06 (3H, s), 2.37 (3H, s), 5.26 (1H, d, J=5.6 Hz), 7.31-7.51 (3H, m), 7.71-7.73 (1H, m), 7.79 (1H, s), 8.25 (1H, s) | $CD_3OD$ (400 MHz) | 625 ($M^+ + 1$) |
| 507 | 7-Deoxy-7-epi-7-(5-(2-ethoxycarbonylphenyl)-thiazol-2-ylthio)lincomycin | 1.21 (3H, t, J=7.1 Hz), 2.07 (3H, s), 2.37 (3H, s), 4.22 (2H, q, J=7.1 Hz), 5.27 (1H, d, J=5.6 Hz), 7.47-7.54 (2H, m), 7.58-7.62 (2H, m), 7.82 (1H, dd, J=7.5, 1.5 Hz) | $CD_3OD$ (400 MHz) | 654 ($M^+ + 1$) |

TABLE 21h

| | | | | |
|---|---|---|---|---|
| 508 | 7-(5-(2-Aminophenyl)thiazol-2-ylthio)-7-deoxy-7-epilincomycin | 1.98 (3H, s), 2.37 (3H, s), 5.25 (1H, d, J=5.6 Hz), 7.49 (1H, s), 7.74-7.80 (2H, m), 7.99 (1H, d, J=1.9 Hz) | $CD_3OD$ (400 MHz) | 597 ($M^+ + 1$) |
| 509 | Methyl 7-(5-(5-(azetidin-1-yl)-2-nitrophenyl)-1,3,4-thiadiazol-2-ylthio)-7-deoxy-7-epi-6-N-((2S,4R)-4-propyl)pipecoloyl-1-thio-α-lincosamide | 2.13 (3H, s), 2.48 (2H, t, J=7.5 Hz), 4.10 (4H, t, J=7.5 Hz), 5.36 (1H, d, J=6.0 Hz), 6.36 (1H, s), 6.38 (1H, d, J=9.0 Hz), 8.13 (1H, d, J=9.0 Hz) | $CDCl_3$ (300 MHz) | 683 ($M^+ + 1$) |
| 510 | Methyl 7-deoxy-7-epi-7-(5-(5-methoxy-2-nitrophenyl)-1,3,4-thiadiazol-2-ylthio)-6-N-((2S,4R)-4-propyl)pipecoloyl-1-thio-α-lincosamide | 2.20 (3H, s), 2.51 (3H, s), 5.34 (1H, d, J=5.7 Hz), 6.66 (1H, t, J=5.7 Hz), 7.45 (1H, s), 7.47 (1H, d, J=9.0 Hz), 7.99 (1H, d, J=9.0 Hz) | $CDCl_3$ (300 MHz) | 658 ($M^+ + 1$) |
| 511 | Methyl 7-deoxy-7-epi-7-(5-(5-methyl-2-nitrophenyl)-1,3,4-thiadiazol-2-ylthio)-6-N-((2S,4R)-4-propyl)pipecoloyl-1-thio-α-lincosamide | 2.14 (3H, s), 3.94 (3H, s), 5.34 (1H, d, J=5.7 Hz), 6.66 (1H, t, J=5.7 Hz), 7.05 (1H, s), 7.07 (1H, d, J=9.0 Hz), 8.16 (1H, d, J=9.0 Hz) | $CDCl_3$ (300 MHz) | 642 ($M^+ + 1$) |
| 512 | Methyl 7-deoxy-7-epi-7-(5-(5-methylamino)-1,3,4-thiadiazol-2-ylthio)-6-N-((2S,4R)-4-propyl)-pipecoloyl-1-thio-α-lincosamide | 1.53 (3H, s), 2.94 (3H, s), 5.33 (1H, d, J=5.7 Hz), 6.62 (1H, s), 6.64 (1H, d, J=9.0 Hz), 8.16 (1H, d, J=9.0 Hz) | $CDCl_3$ (300 MHz) | 657 ($M^+ + 1$) |
| 513 | Methyl 7-deoxy-7-epi-7-(4-(1H-imidazol-1-yl)phenylthio)-6-N-((2S,4R)-4-propyl)-pipecoloyl-1-thio-α-lincosamide | 2.00 (3H, s), 5.40 (1H, d, J=4.8 Hz), 7.19 (1H, s), 7.26 (1H, s), 7.32 (2H, d, J=8.7 Hz), 7.51 (2H, d, J=8.7 Hz), 7.86 (1H, s), | $CDCl_3$ (300 MHz) | 565 ($M^+ + 1$) |
| 514 | Methyl 7-deoxy-7-epi-7-(5-(4,5-dimethoxy-2-nitrophenyl)oxazol-2-ylthio)-7-epi-6-N-((2S,4R)-4-propyl)pipecoloyl-1-thio-α-lincosamide | 1.99 (3H, s), 3.94 (3H, s), 3.96 (3H, s), 5.26 (1H, d, J=5.6 Hz), 7.14 (1H, s), 7.39 (1H, s), 7.61 (1H, s) | $CD_3OD$ (400 MHz) | 671 ($M^+ + 1$) |

TABLE 21h-continued

| | | | | |
|---|---|---|---|---|
| 515 | Methyl 7-deoxy-7-(5-(4,5-dlmethoxy-2-nitrophenyl)-1,3,4-thiadiazol-2-ylthio)-7-epi-6-N-((2S,4R)-4-propyl)pipecoloyl-1-thio-α-lincosamide | 1.56 (3H, d, J=7.2 Hz), 2.01 (3H, s), 3.96 (3H, s), 3.98 (3H, s), 5.28 (1H, d, J=5.6 Hz), 7.21 (1H, s), 7.76 (1H, s) | $CD_3OD$ (400 MHz) | 688 ($M^+ + 1$) |
| 516 | Methyl 7-deoxy-7-epi-7-(5-(1-methyl-4-nitro-1H-imidazol-2-yl)-1,3,4-thiadiazol-2-ylthio)-6-N-((2S,4R)-4-propyl)pipecoloyl-1-thio-α-lincosamide | 1.57 (3H, d, J=7.1 Hz), 1.97 (3H, s), 4.20 (3H, s), 5.29 (1H, d, J=5.6 Hz), 8.35 (1H, s) | $CD_3OD$ (400 MHz) | 632 ($M^+ + 1$) API |
| 517 | Methyl 7-deoxy-7-(5-(4,5-dimethoxy-2-nitrophenyl)-1,3,4-thiadiazol-2-ylthio)-7-epi-6-N-((2S,4R)-4-ethyl)pipecoloyl-1-thio-α-lincosamide | 1.56 (3H, d, J=6.8 Hz), 2.01 (3H, s), 3.96 (3H, s), 3.99 (3H, s), 5.29 (1H, d, J=5.6 Hz), 7.22 (1H, s), 7.77 (1H, s) | $CD_3OD$ (400 MHz) | 674 ($M^+ + 1$) |
| 518 | Methyl 6-N-((2S,4R)-4-butyl)pipecoloyl-7-deoxy-7-(5-(4,5-dimethoxy-2-nitrophenyl)-1,3,4-thiadiazol-2-ylthio)-7-epi-1-thio-α-lincosamide | 1.55 (3H, d, J=6.8 Hz), 2.01 (3H, s), 3.95 (3H, s), 3.98 (3H, s), 5.28 (1H, d, J=5.8 Hz), 7.21 (1H, s), 7.75 (1H, s) | $CD_3OD$ (400 MHz) | 702 ($M^+ + 1$) API |

TABLE 22

Formula (Ia)

| Compound No. | $R_2$ | $R_3$ | $R_4$ | R |
|---|---|---|---|---|
| 11 | methyl | n-propyl | H | $NH_2$ |
| 12 | methyl | n-propyl | H | $NHCH_3$ |
| 13 | methyl | n-propyl | H |  |
| 14 | methyl | n-propyl | H | 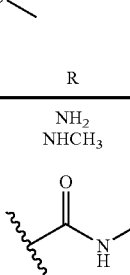 |
| 15 | methyl | n-propyl | H | 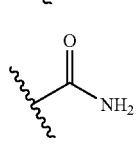 |
| 16 | methyl | n-propyl | H | 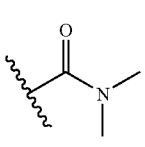 |
| 17 | methyl | n-propyl | H | 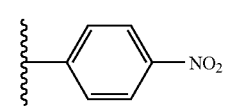 |
| 18 | methyl | n-propyl | H | 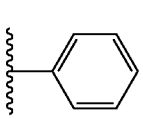 |
| 19 | methyl | n-propyl | H | 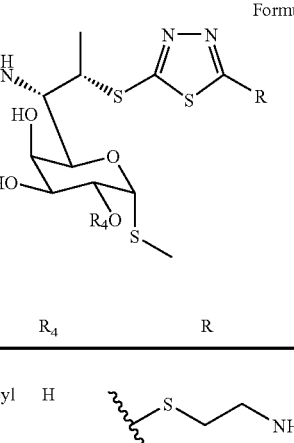 |
| 20 | methyl | n-propyl | H | 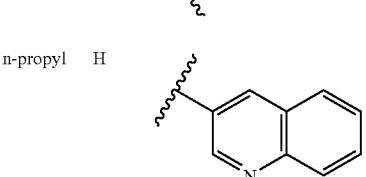 |
| 21 | methyl | n-propyl | H | 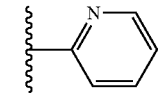 |
| 22 | methyl | n-propyl | H | 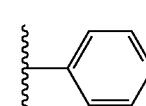 |

TABLE 22-continued

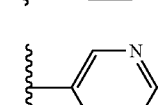

Formula (Ia)

TABLE 22-continued

Formula (Ia)

| Compound No. | R₂ | R₃ | R₄ | R |
|---|---|---|---|---|
| 23 | methyl | n-propyl | H | 2-nitrophenyl |
| 24 | methyl | n-propyl | H | 3-nitrophenyl |
| 25 | methyl | n-propyl | H | 2-naphthyl |
| 26 | methyl | n-propyl | H | 2-thienyl |
| 27 | methyl | n-propyl | H | 3,5-diaminophenyl |
| 28 | methyl | n-propyl | H | 3,4-diaminophenyl |
| 29 | methyl | n-propyl | H | 5-nitrofuran-2-yl |
| 30 | methyl | n-propyl | H | 2-(methylamino)thiazol-4-yl |
| 31 | methyl | n-propyl | H | furan-2-yl |
| 32 | methyl | n-propyl | H | 2-aminothiazol-4-yl |
| 33 | methyl | n-propyl | H | 5-amino-1-methyl-1H-pyrazol-4-yl |
| 34 | methyl | n-propyl | H | 2-cyanophenyl |
| 35 | methyl | n-propyl | H | 3-aminothien-2-yl |
| 36 | methyl | n-propyl | H | 4-methyl-1,2,3-thiadiazol-5-yl |
| 37 | methyl | n-propyl | H | 2-chlorophenyl |
| 38 | methyl | n-propyl | H | 2-(methylthio)phenyl |

TABLE 22-continued

Formula (Ia)

| Compound No. | R₂ | R₃ | R₄ | R |
|---|---|---|---|---|
| 39 | methyl | n-propyl | H | 2-(methylsulfonyl)phenyl |
| 40 | methyl | n-propyl | H | 2-methoxyphenyl |
| 41 | methyl | n-propyl | H | pyrazin-2-yl |
| 42 | methyl | n-propyl | H | 3-aminopyrazin-2-yl |
| 43 | methyl | n-propyl | H | 2-fluorophenyl |
| 44 | methyl | n-propyl | H | 4-methyl-1,2,3-thiadiazol-5-yl |
| 45 | methyl | n-propyl | H | —C(O)NHCH₂CH₂-pyrrolidin-1-yl |
| 46 | methyl | n-propyl | H | 4-chlorophenyl |
| 47 | methyl | n-propyl | H | 4-chloro-2-nitrophenyl |
| 48 | methyl | n-propyl | H | 2-methylphenyl |
| 49 | methyl | n-propyl | H | —NH-(4-(SCHF₂)phenyl) |
| 50 | methyl | n-propyl | H | —S-CH₂-C(O)NH₂ |

TABLE 23

Formula (Ia)

| Compound No. | R₂ | R₃ | R₄ | R |
|---|---|---|---|---|
| 51 | methyl | n-propyl | H | 4-fluoro-2-nitrophenyl |
| 52 | methyl | n-propyl | H | —C(O)OCH₂CH₃ |
| 53 | methyl | n-propyl | H | 4,5-difluoro-2-nitrophenyl |

TABLE 23-continued

Formula (Ia)

| Compound No. | R₂ | R₃ | R₄ | R |
|---|---|---|---|---|
| 54 | methyl | n-propyl | H | 2,4-dinitrophenyl |
| 55 | methyl | n-propyl | H | 2-(methylamino)phenyl |
| 56 | methyl | n-propyl | H | 5-fluoro-2-nitrophenyl |
| 57 | methyl | n-propyl | H | 3-cyano-2-nitrophenyl (NO₂/CN substituted) |
| 58 | methyl | n-propyl | H | 2-(methylsulfonyl)phenyl |
| 59 | methyl | n-propyl | H | 5-methyl-2-nitrophenyl |
| 118 | methyl | n-propyl | H | –NH–C(O)–CH₂–NH₂ |
| 119 | methyl | n-propyl | H | –N(CH₃)–C(O)–CH₂–NH₂ |
| 120 | methyl | n-propyl | H | thiazol-4-yl |
| 122 | methyl | n-propyl | H | 5-amino-thiazol-4-yl |
| 123 | methyl | n-propyl | H | 5-amino-1,3,4-thiadiazol-2-yl |
| 124 | methyl | n-propyl | H | 2-aminopyridin-3-yl |
| 125 | methyl | n-propyl | H | 6-aminopyridin-3-yl |
| 135 | methyl | n-propyl | H | 4,5-dimethoxy-2-nitrophenyl |
| 136 | methyl | n-propyl | H | 2-(methoxycarbonyl)phenyl |
| 183 | methyl | n-propyl | H | 4-aminophenyl |
| 184 | methyl | n-propyl | H | 2-aminophenyl |

TABLE 23-continued

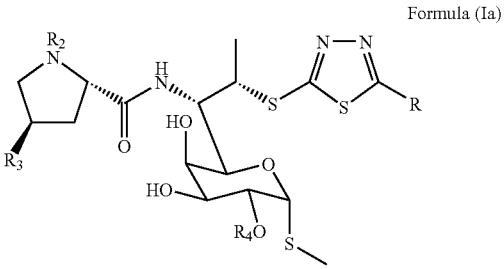

Formula (Ia)

| Compound No. | R₂ | R₃ | R₄ | R |
|---|---|---|---|---|
| 185 | methyl | n-propyl | H | 3-aminophenyl |
| 194 | methyl | n-propyl | H | NHC(O)CH₃ |
| 195 | methyl | n-propyl | H | NHC(O)CH₂OCH₃ |
| 217 | methyl | n-propyl | H | C(O)-morpholinyl |
| 218 | methyl | n-propyl | H | C(O)-piperidinyl |
| 219 | methyl | n-propyl | H | C(O)-(2,6-dimethylmorpholinyl) |
| 220 | methyl | n-propyl | H | C(O)-pyrrolidinyl |
| 267 | methyl | n-propyl | H | 3-nitro-4-(dimethylamino)phenyl |

TABLE 23-continued

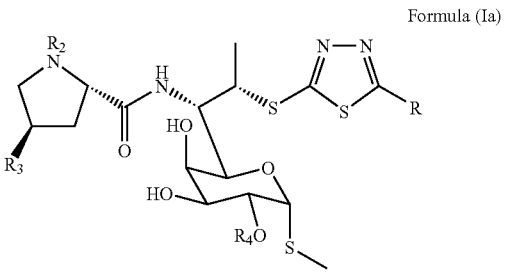

Formula (Ia)

| Compound No. | R₂ | R₃ | R₄ | R |
|---|---|---|---|---|
| 268 | methyl | n-propyl | H | 3-nitro-4-(dimethylamino)phenyl |
| 269 | methyl | n-propyl | H | 3-nitro-4-(methylamino)phenyl |
| 270 | methyl | n-propyl | H | 2-nitro-4-aminophenyl |
| 271 | methyl | n-propyl | H | 3-nitro-4-(2-hydroxyethylamino)phenyl |
| 272 | methyl | n-propyl | H | 4-nitro-2-fluoro-5-(2-hydroxyethylamino)phenyl |
| 273 | methyl | n-propyl | H | 4-nitro-2-fluoro-5-(dimethylamino)phenyl |

TABLE 23-continued

Formula (Ia)

| Compound No. | R₂ | R₃ | R₄ | R |
|---|---|---|---|---|
| 274 | methyl | n-propyl | H | 4-nitro-2-fluoro-5-(methylamino)phenyl |
| 275 | methyl | n-propyl | H | 2-nitro-5-methoxyphenyl |

TABLE 23-continued

Formula (Ia)

| Compound No. | R₂ | R₃ | R₄ | R |
|---|---|---|---|---|
| 276 | methyl | n-propyl | H | 2-nitro-4-fluoro-5-methoxyphenyl |

TABLE 24

Formula (Ia)

| Compound No. | R₂ | R₃ | R₄ | R |
|---|---|---|---|---|
| 296 | H | n-propyl | H | pyridin-2-yl |
| 298 | H | n-propyl | H | 2-nitrophenyl |
| 299 | H | n-propyl | H | NH₂ |
| 300 | H | n-propyl | H | 5-(methylamino)thiazol-4-yl |

TABLE 24-continued

Formula (Ia)

| Compound No. | R₂ | R₃ | R₄ | R |
|---|---|---|---|---|
| 301 | H | n-propyl | H | 5-nitrofuran-2-yl |
| 302 | H | n-propyl | H | 5-amino-1-methyl-1H-pyrazol-4-yl |
| 303 | H | n-propyl | H | 2-cyanophenyl |
| 304 | H | n-propyl | H | 3-aminothiophen-2-yl |
| 305 | H | n-propyl | H | 3-aminopyrazin-2-yl |
| 306 | H | n-propyl | H | 4-fluoro-2-nitrophenyl |
| 307 | H | n-propyl | H | 4,5-difluoro-2-nitrophenyl |
| 317 | H | n-propyl | H | 2-aminophenyl |

TABLE 24-continued

Formula (Ia)

| Compound No. | R₂ | R₃ | R₄ | R |
|---|---|---|---|---|
| 320 | H | n-propyl | H | 2-methoxy-4-fluoro-5-nitrophenyl (OMe, F, O₂N substituted phenyl) |
| 339 | H | (E)-2-butenyl | H | $NH_2$ |
| 340 | H | (E)-2-butenyl | H | 2-nitrophenyl ($NO_2$) |
| 341 | methyl | (E)-2-butenyl | H | $NH_2$ |
| 342 | methyl | (E)-2-butenyl | H | 2-nitrophenyl ($NO_2$) |
| 343 | H | n-butyl | H | $NH_2$ |
| 344 | H | n-butyl | H | 2-nitrophenyl ($NO_2$) |
| 345 | methyl | n-butyl | H | $NH_2$ |
| 346 | methyl | n-butyl | H | 2-nitrophenyl ($NO_2$) |
| 321 | isopropyl | n-propyl | H | 2-nitrophenyl ($O_2N$) |
| 322 | isopropyl | n-propyl | H | $NH_2$ |

TABLE 24-continued

Formula (Ia)

| Compound No. | R₂ | R₃ | R₄ | R |
|---|---|---|---|---|
| 323 | ⟿CH₂CH₂OH | n-propyl | H | 4-position of thiazole with 5-NH- |
| 324 | ⟿CH₂CH₂OH | n-propyl | H | 2-nitrophenyl |
| 325 | ⟿CH₂CH₂NH₂ | n-propyl | H | 4-position of thiazole with 5-NH- |
| 326 | ⟿CH₂CH₂OH | n-propyl | H | NH₂ |
| 327 | ⟿CH₂CH₂NH₂ | n-propyl | H | NH₂ |
| 328 | ⟿CH₂CH(OH)CH₃ | n-propyl | H | 4-position of thiazole with 5-NH- |
| 329 | 4-methylthiazol-5-ylmethyl | n-propyl | H | 4-position of thiazole with 5-NH- |
| 334 | ⟿C(O)CH₂NH₂ | n-propyl | H | NH₂ |

TABLE 24-continued

Formula (Ia)

| Compound No. | R₂ | R₃ | R₄ | R |
|---|---|---|---|---|
| 335 | acetyl (C(=O)CH₃) | n-propyl | H | 5-(methylamino)thiazol-4-yl |
| 336 | -C(=O)CH₂OH | n-propyl | H | 5-(methylamino)thiazol-4-yl |
| 347 | H | (E)-2-pentenyl | H | 2-nitrophenyl |
| 348 | H | (E)-2-pentenyl | H | NH₂ |
| 349 | H | (E)-2-pentenyl | H | 5-(methylamino)thiazol-4-yl |
| 351 | methyl | (E)-2-pentenyl | H | 2-nitrophenyl |
| 352 | methyl | (E)-2-pentenyl | H | NH₂ |

TABLE 25

Formula (Ia)

| Compound No. | R₂ | R₃ | R₄ | R |
|---|---|---|---|---|
| 353 | H | n-pentyl | H | 2-nitrophenyl |
| 354 | H | n-pentyl | H | 5-(methylamino)thiazol-4-yl |
| 355 | H | n-pentyl | H | NH₂ |
| 356 | methyl | n-pentyl | H | NH₂ |
| 357 | methyl | n-pentyl | H | 2-nitrophenyl |
| 358 | methyl | n-pentyl | H | 5-(methylamino)thiazol-4-yl |
| 410 | methyl | n-propyl | NH₂ | 2,6-dichlorobenzyl |
| 411 | methyl | n-propyl | NH₂ | -CH₂C(O)NHCH₃ |
| 412 | methyl | n-propyl | 5-(methylamino)thiazol-4-yl | -CH₂C(O)NHCH₃ |

TABLE 26

Formula (Ib)

| Compound No. | R₂ | R₃ | R |
|---|---|---|---|
| 359 | H | n-propyl | 5-(methylamino)thiazol-4-yl |
| 360 | H | n-propyl | 2-nitro-4-methylphenyl |
| 361 | H | n-propyl | 2-(methylamino)phenyl |
| 362 | H | n-propyl | 5-nitro-2-fluoro-4-(dimethylamino)phenyl |
| 365 | H | n-propyl | 2-nitrophenyl |
| 366 | H | n-propyl | 2-nitro-4-fluorophenyl |
| 369 | H | n-propyl | 2-nitro-4-fluoro-5-methoxyphenyl |

TABLE 26-continued

Formula (Ib)

| Compound No. | R₂ | R₃ | R |
|---|---|---|---|
| 373 | H | n-propyl | 1-piperidinyl carbonyl |
| 380 | H | n-propyl | 2-nitro-5-(methylamino)phenyl |
| 381 | H | n-propyl | 2-nitro-5-(dimethylamino)phenyl |
| 382 | H | n-propyl | 2-nitro-5-methoxyphenyl |
| 389 | methyl | n-propyl | 2-nitro-4-fluorophenyl |
| 394 | H | ethyl | 2-nitro-4-fluorophenyl |
| 395 | H | ethyl | 2-nitrophenyl |

TABLE 26-continued

Formula (Ib)

| Compound No. | R₂ | R₃ | R |
|---|---|---|---|
| 396 | methyl | ethyl | 2-nitro-4-fluorophenyl |
| 397 | H | n-butyl | 5-(methylamino)thiazol-4-yl |
| 398 | H | n-butyl | 2-cyanophenyl |
| 399 | H | n-butyl | 2-nitro-4-fluorophenyl |
| 400 | H | n-butyl | 2-nitrophenyl |
| 404 | methyl | n-butyl | 5-(methylamino)thiazol-4-yl |

TABLE 26-continued

Formula (Ib)

| Compound No. | R₂ | R₃ | R |
|---|---|---|---|
| 405 | methyl | n-butyl | 2-nitro-4-fluorophenyl |
| 406 | methyl | n-butyl | 2-nitrophenyl |

TABLE 27

Formula (Ic)

| Compound No. | Rb | Rc |
|---|---|---|
| 137 | H | methyl ester (—C(O)OMe) |
| 138 | methyl ester (—C(O)OMe) | H |
| 139 | H | —S(O)₂Me |

TABLE 27-continued

Formula (Ic)

| Compound No. | Rb | Rc |
|---|---|---|
| 235 | H | —C(O)-piperidinyl |
| 236 | H | —C(O)-morpholinyl |
| 237 | —C(O)-morpholinyl | H |

TABLE 28

Formula (Id)

| Compound No. | Rb | Rc | Rd |
|---|---|---|---|
| 9 | NO₂ | H | H |
| 10 | H | NO₂ | H |
| 112 | Cl | H | methyl |
| 181 | NH₂ | H | H |
| 182 | H | NH₂ | H |
| 210 | H | —NHC(O)CH₃ | H |

TABLE 29
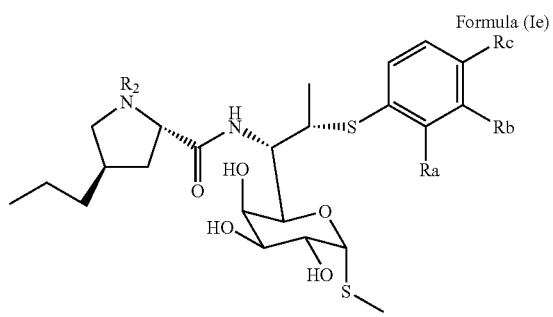
Formula (Ie)
| Compound No. | R₂ | Ra | Rb | Rc |
|---|---|---|---|---|
| 113 | methyl | H | H | 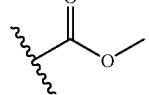 |
| 114 | methyl | H | H | NO₂ |
| 116 | methyl | H | NO₂ | H |
| 128 | methyl | H | H | F |
| 129 | methyl | H | H | CF₃ |
| 130 | methyl | H | H | Cl |
| 131 | methyl | H | H | 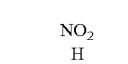 |
| 132 | methyl | H | Cl | H |
| 134 | methyl | H | 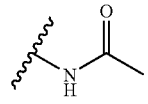 | H |
| 141 | methyl | H | 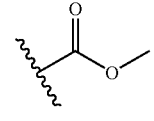 | H |
| 142 | methyl | H | 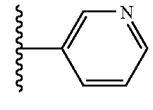 | H |
| 143 | methyl | H | 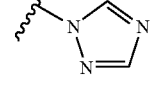 | H |
| 145 | methyl | H | H | 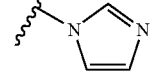 |
| 146 | methyl | H | H |  |
| 147 | methyl | H | H | 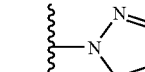 |
| 148 | methyl | H | H | 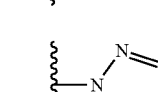 |
| 149 | methyl | H | H | 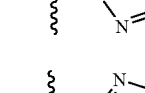 |
| 150 | methyl | H | H | 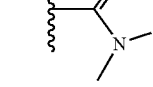 |
| 151 | methyl | H | H | 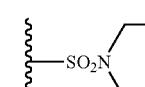 |
| 152 | methyl | H | H | 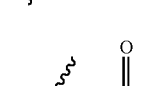 |
| 312 | H | H | H | 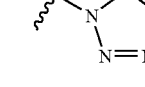 |
| 313 | H | H | H | 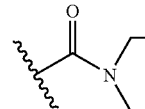 |
| 314 | H | H | H | 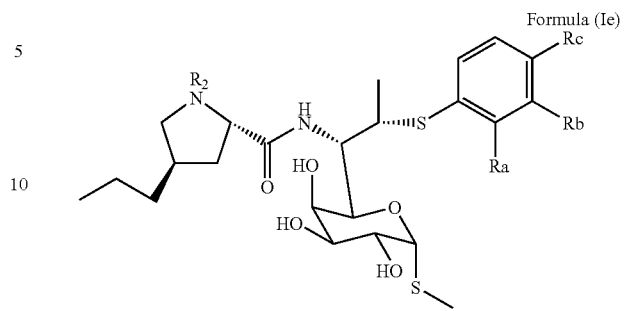 |

TABLE 29-continued

Formula (Ie)

| Compound No. | R₂ | Ra | Rb | Rc |
|---|---|---|---|---|
| 153 | methyl | H | H | triazolone (N-linked, 3-oxo-2,4-dihydro-1,2,4-triazol-1-yl) |
| 154 | methyl | H | H | C(=O)N(OMe)Me |
| 155 | methyl | H | H | pyridin-2-yl |
| 156 | methyl | H | H | pyridin-4-yl |
| 157 | methyl | H | H | C(=O)CH₂CH₂CH₂CH₃ |
| 158 | methyl | H | H | 4-methyl-5-oxo-4,5-dihydro-1,2,4-triazol-1-yl |
| 159 | methyl | H | H | 4-methyl-5-oxo-4,5-dihydro-tetrazol-1-yl |
| 162 | methyl | H | H | CN |
| 163 | methyl | H | F | CN |
| 164 | methyl | H | H | C(=O)CH₃ |
| 165 | methyl | H | F | C(=O)-morpholin-4-yl |
| 166 | methyl | H | F | C(=O)-piperidin-1-yl |
| 169 | methyl | H | H | N(Me)C(=O)CH₃ |
| 170 | methyl | H | H | N(Me)C(=O)CH₂OMe |
| 171 | methyl | H | H | N(nPr)C(=O)CH₂OMe |
| 172 | methyl | H | H | CH₂-morpholin-4-yl |
| 173 | methyl | H | NO₂ | C(=O)-morpholin-4-yl |
| 174 | methyl | H | H | SO₂-morpholin-4-yl |
| 175 | methyl | H | methyl | C(=O)-morpholin-4-yl |

TABLE 29-continued
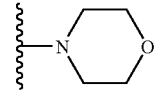
Formula (Ie)
| Compound No. | R₂ | Ra | Rb | Rc |
|---|---|---|---|---|
| 176 | methyl | H | (morpholine via N) | F |
| 315 | H | H | H | (C(=O)NH-propyl) |
| 316 | H | H | H | (3-pyridyl) |
| 319 | H | H | H | (C(=O)NH-CH₂-OCH₃) |
TABLE 30
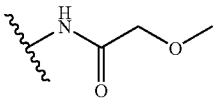
Formula (Ie)
| Compound No. | R₂ | Ra | Rb | Rc |
|---|---|---|---|---|
| 177 | methyl | H | H | (morpholine via N) |
| 178 | methyl | H | H | (prolinol acyl) |
| 179 | methyl | H | H | (2-methoxymethyl-pyrrolidinyl acyl) |

TABLE 30-continued

Formula (Ie)

| Compound No. | R₂ | Ra | Rb | Rc |
|---|---|---|---|---|
| 187 | methyl | H | H | NH₂ |
| 189 | methyl | H | NH₂ | H |
| 204 | methyl | H | H | -NHC(O)CH₂CH₃ |
| 205 | methyl | H | H | -NHC(O)CH₂CH₂CH₃ |
| 206 | methyl | H | H | -NHC(O)CH₂OCH₃ |
| 207 | methyl | H | H | -NHC(O)CH=CH₂ |
| 208 | methyl | H | H | -NHC(O)CH₂NHCH₃ |
| 209 | methyl | H | H | -NHC(O)-morpholinyl |
| 211 | methyl | H | H | -NHS(O)₂CH₃ |
| 227 | methyl | H | H | -C(O)N(CH₃)₂ |
| 228 | methyl | H | H | -C(O)-pyrrolidinyl |

TABLE 30-continued

Formula (Ie)

| Compound No. | R₂ | Ra | Rb | Rc |
|---|---|---|---|---|
| 229 | methyl | H | H | -C(O)NH-propyl |
| 230 | methyl | H | H | -C(O)NH-CH₂CH₂OH |
| 231 | methyl | H | -C(O)NH-methyl | H |
| 232 | methyl | H | H | -C(O)NH₂ |
| 233 | methyl | H | H | -C(O)NH-methyl |
| 234 | methyl | H | H | -CH₂OH |
| 167 | methyl | F | H | -C(O)-morpholinyl |
| 168 | methyl | F | H | -C(O)-piperidinyl |
| 239 | methyl | H | H | -C(O)NH-adamantyl |

TABLE 30-continued
Formula (Ie)
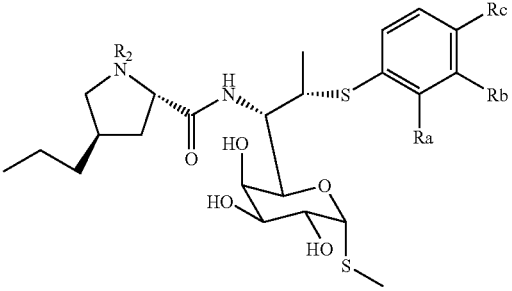
| Compound No. | R₂ | Ra | Rb | Rc |
|---|---|---|---|---|
| 244 | methyl | H | H | 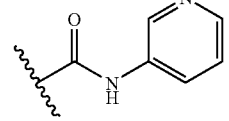 |
| 245 | methyl | H | H | 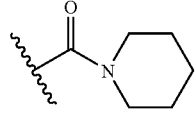 |
| 246 | methyl | H | H | 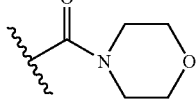 |
| 247 | methyl | H | H | 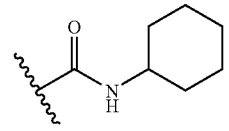 |
| 248 | methyl | H | H | 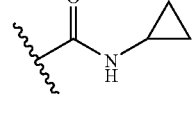 |
| 249 | methyl | H | H | 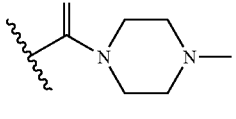 |
| 250 | methyl | H | H | 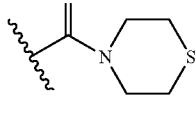 |
| 251 | methyl | H | H | 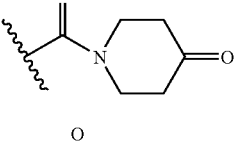 |
| 252 | methyl | H | H | 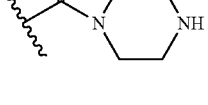 |

TABLE 30-continued
Formula (Ie)
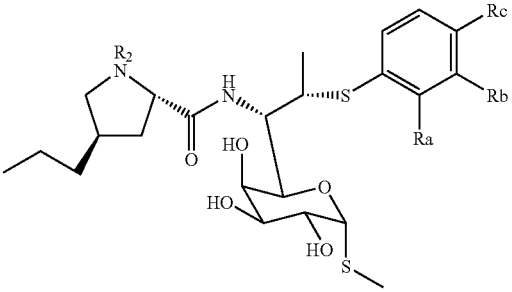
| Compound No. | R₂ | Ra | Rb | Rc |
|---|---|---|---|---|
| 253 | methyl | H | H | 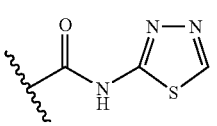 |
| 254 | methyl | H | H | 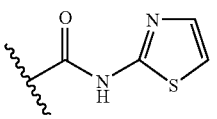 |
| 255 | methyl | H | H | 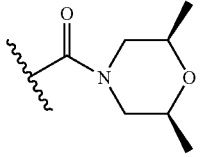 |
| 256 | methyl | H | 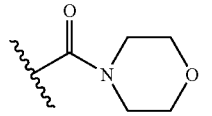 | H |
| 257 | methyl | H | 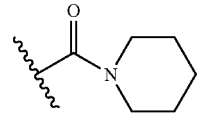 | H |
| 258 | methyl | H | 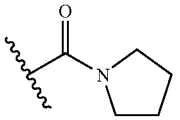 | H |
| 259 | methyl | H | H | 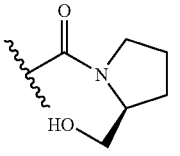 |
| 115 | methyl | NO₂ | H | H |
| 127 | methyl | F | H | H |
| 133 | methyl | Cl | H | H |
| 188 | methyl | NH₂ | H | H |

TABLE 30-continued

Formula (Ie)

| Compound No. | R₂ | Ra | Rb | Rc |
|---|---|---|---|---|
| 243 | methyl | (C(=O)-pyrrolidin-1-yl) | H | H |

TABLE 31

Formula (If)

| Compound No. | R₂ | R₃ | R |
|---|---|---|---|
| 370 | H | n-propyl | pyridin-3-yl |
| 375 | H | n-propyl | C(=O)-piperidin-1-yl |
| 379 | H | n-propyl | C(=O)-morpholin-4-yl |
| 391 | methyl | n-propyl | C(=O)-morpholin-4-yl |

TABLE 31-continued

Formula (If)

| Compound No. | R₂ | R₃ | R |
|---|---|---|---|
| 392 | methyl | n-propyl | C(=O)-piperidin-1-yl |
| 393 | methyl | n-propyl | pyridin-3-yl |
| 401 | H | n-butyl | C(=O)-morpholin-4-yl |

TABLE 32
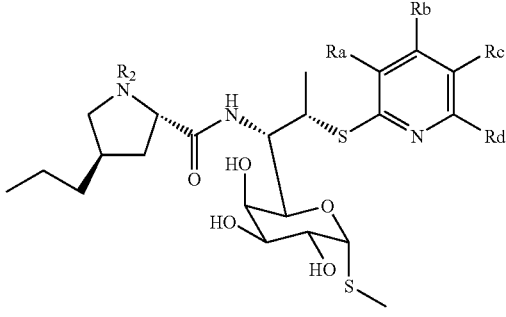
Formula (Ig)
| Compound No. | R₂ | Ra | Rb | Rc | Rd |
|---|---|---|---|---|---|
| 85 | methyl | H | H | $NO_2$ | H |
| 86 | methyl | H | H | 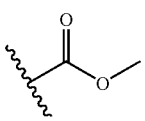 | H |
| 95 | methyl | H | H | $CF_3$ | H |
| 186 | methyl | H | H | $NH_2$ | H |
| 190 | methyl | H | H | 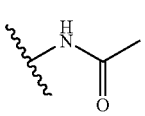 | H |
| 191 | methyl | H | H | 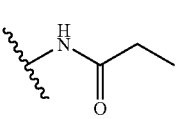 | H |
| 96 | methyl | CN | 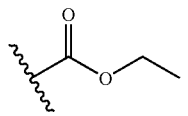 | H | methyl |
| 97 | methyl | CN | $CF_3$ | H | 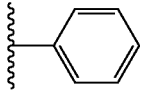 |
| 192 | methyl | H | H | 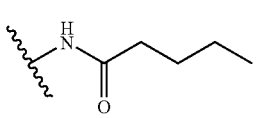 | H |
| 193 | methyl | H | H | 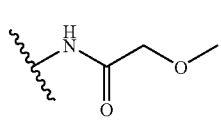 | H |
| 240 | methyl | H | H | 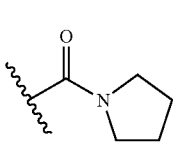 | H |

TABLE 32-continued
Formula (Ig)
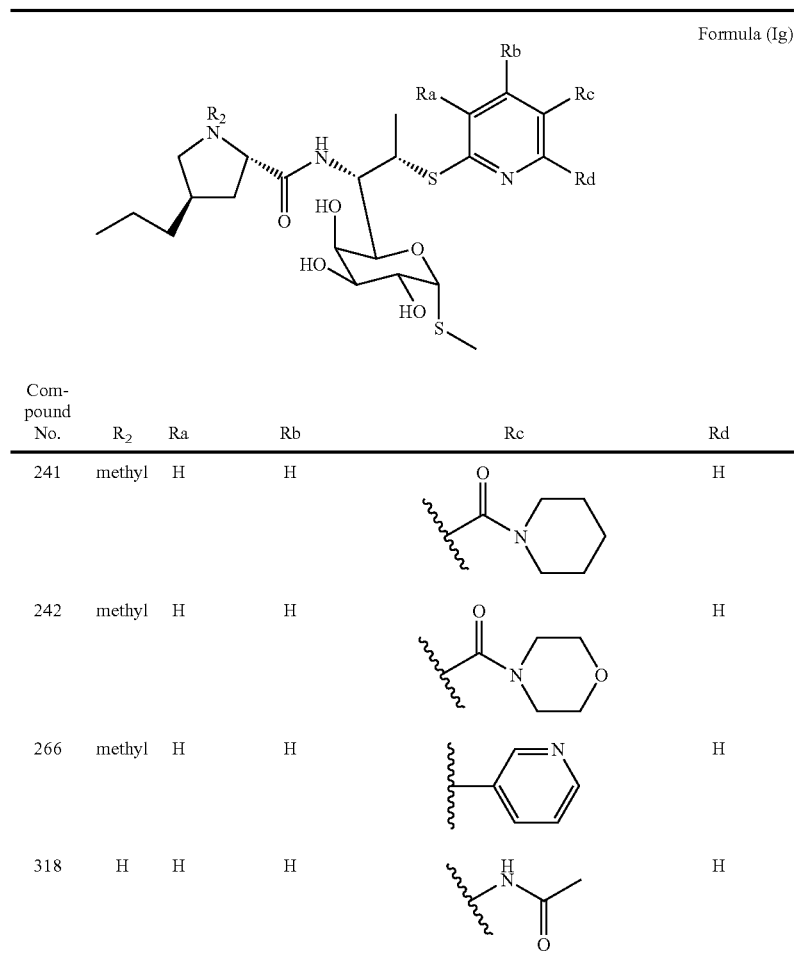
| Compound No. | R₂ | Ra | Rb | Rc | Rd |
|---|---|---|---|---|---|
| 241 | methyl | H | H | (piperidinyl carbonyl) | H |
| 242 | methyl | H | H | (morpholinyl carbonyl) | H |
| 266 | methyl | H | H | (pyridin-3-yl) | H |
| 318 | H | H | H | (NHC(O)CH₃) | H |
TABLE 33
Formula (Ih)
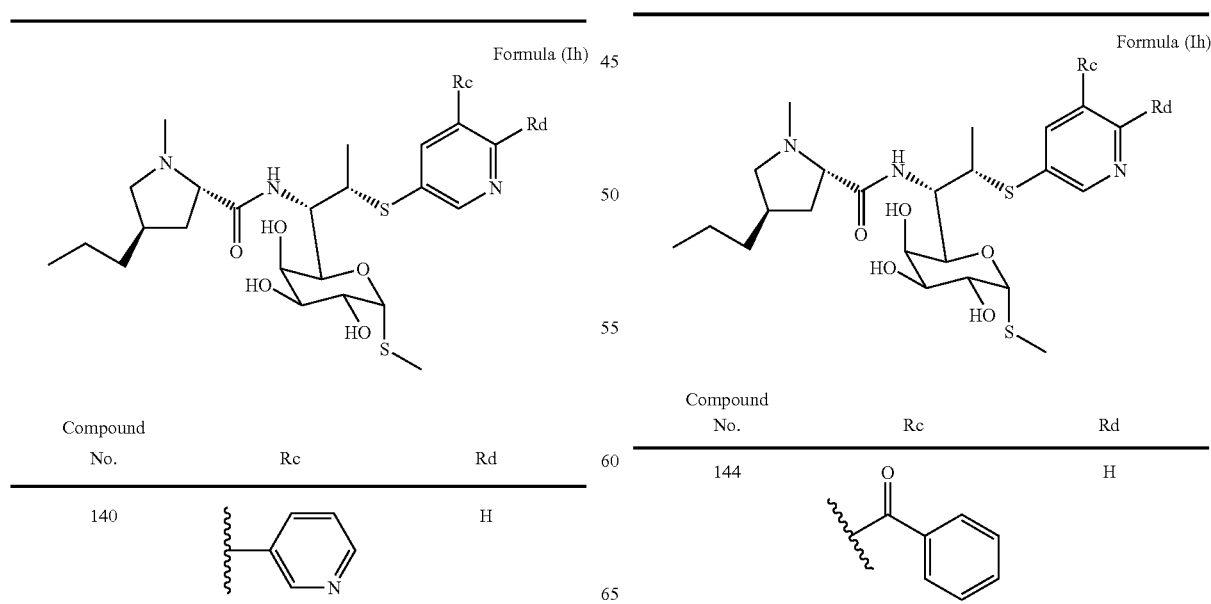
| Compound No. | Rc | Rd |
|---|---|---|
| 140 | (pyridin-3-yl) | H |
| 144 | (benzoyl) | H |

TABLE 33-continued

Formula (Ih)

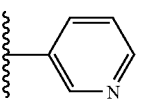

| Compound No. | Rc | Rd |
|---|---|---|
| 265 | H | 3-pyridyl |

TABLE 34

Formula (Ii)

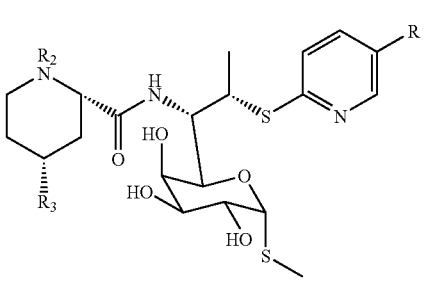

| Compound No. | R₂ | R₃ | R |
|---|---|---|---|
| 367 | H | n-propyl | NO₂ |
| 371 | H | n-propyl | NHC(O)CH₃ |
| 372 | H | n-propyl | NHC(O)CH₂OCH₃ |
| 376 | H | n-propyl | C(O)-piperidinyl |

TABLE 34-continued

Formula (Ii)

| Compound No. | R₂ | R₃ | R |
|---|---|---|---|
| 377 | H | n-propyl | C(O)-morpholinyl |
| 403 | H | n-butyl | NHC(O)CH₃ |
| 383 | CH₃ | n-propyl | NO₂ |
| 384 | CH₃ | n-propyl | NHC(O)CH₃ |
| 385 | CH₃ | n-propyl | NHC(O)CH₂OCH₃ |
| 386 | CH₃ | n-propyl | C(O)-morpholinyl |
| 387 | CH₃ | n-propyl | C(O)-piperidinyl |
| 407 | CH₃ | n-butyl | NHC(O)CH₃ |

TABLE 35
Formula (Ij)
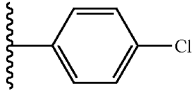
| Compound No. | R₂ | Rb | Rc |
|---|---|---|---|
| 87 | methyl | 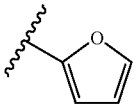 4-chlorophenyl | H |
| 98 | methyl | H | 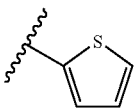 2-furyl |
| 99 | methyl | H | 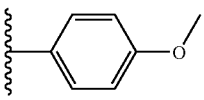 2-thienyl |
| 100 | methyl | H | 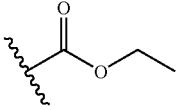 4-methoxyphenyl |
| 101 | methyl | 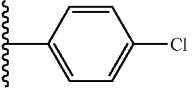 ethoxycarbonyl | $NH_2$ |
| 102 | methyl | H | 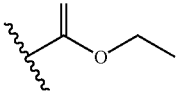 4-chlorophenyl |
| 126 | methyl | H | $NH_2$ |
| 310 | H | 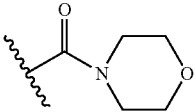 ethoxycarbonyl | $NH_2$ |
| 238 | methyl | 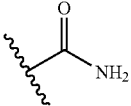 morpholinocarbonyl | $NH_2$ |
| 260 | methyl | carbamoyl | $NH_2$ |

TABLE 35-continued
Formula (Ij)
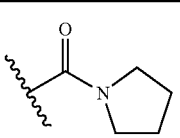
| Compound No. | R₂ | Rb | Rc |
|---|---|---|---|
| 261 | methyl | 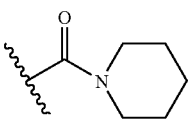 | NH₂ |
| 262 | methyl | 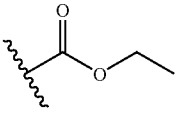 | NH₂ |
| 330 | pentyl | 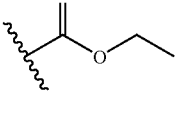 | NH₂ |
| 331 | ethyl | 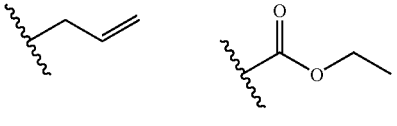 | NH₂ |
| 332 | 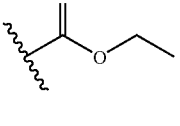 | 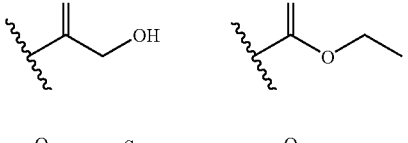 | NH₂ |
| 333 |  |  | NH₂ |
| 337 |  |  | NH₂ |
| 338 |  |  | NH₂ |

TABLE 36
Formula (Ik)
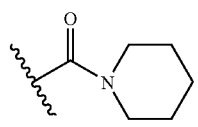
| Compound No. | R2 | R3 | Rb | Rc |
|---|---|---|---|---|
| 378 | H | n-propyl | 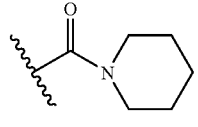 | NH2 |
| 390 | methyl | n-propyl | 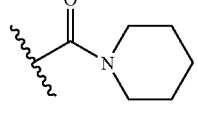 | NH2 |
| 402 | H | n-butyl | 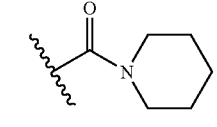 | NH2 |
TABLE 36-continued
Formula (Ik)
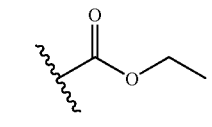
| Compound No. | R2 | R3 | Rb | Rc |
|---|---|---|---|---|
| 408 | methyl | n-butyl | 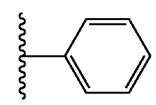 | NH2 |
| 364 | H | n-propyl | 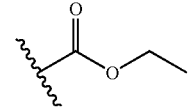 | NH2 |
TABLE 37
Formula (Il)
| Compound No. | R2 | Ra | Rb |
|---|---|---|---|
| 60 | methyl | phenyl | H |
| 61 | methyl | H | NO2 |
| 62 | methyl | ethyl ester | H |

TABLE 37-continued
Formula (II)
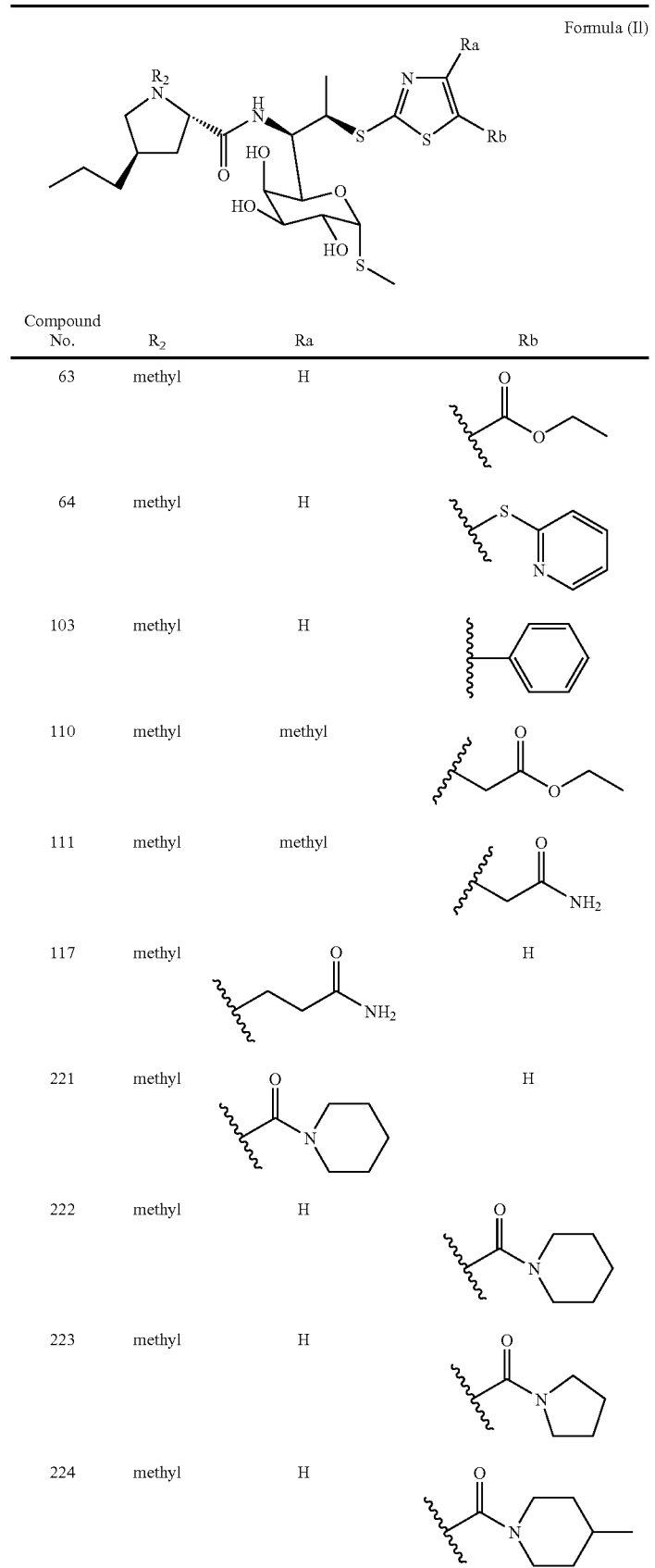
| Compound No. | R₂ | Ra | Rb |
|---|---|---|---|
| 63 | methyl | H | ethyl ester (–C(=O)OEt) |
| 64 | methyl | H | –S-(2-pyridyl) |
| 103 | methyl | H | phenyl |
| 110 | methyl | methyl | –CH₂C(=O)OEt |
| 111 | methyl | methyl | –CH₂C(=O)NH₂ |
| 117 | methyl | –CH₂CH₂C(=O)NH₂ | H |
| 221 | methyl | –C(=O)-piperidinyl | H |
| 222 | methyl | H | –C(=O)-piperidinyl |
| 223 | methyl | H | –C(=O)-pyrrolidinyl |
| 224 | methyl | H | –C(=O)-(4-methylpiperidinyl) |

TABLE 37-continued
Formula (II)
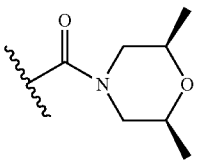
| Compound No. | R₂ | Ra | Rb |
|---|---|---|---|
| 225 | methyl | H | 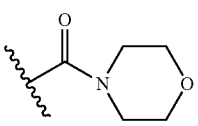 |
| 226 | methyl | H | 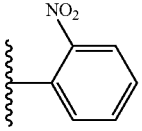 |
| 263 | methyl | H | 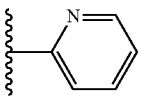 |
| 264 | methyl | H | 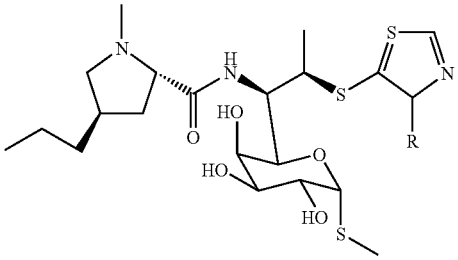 |
| 308 | H | H | NO₂ |
TABLE 38
Formula (Im)
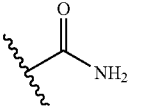
| Compound No. | R |
|---|---|
| 65 | 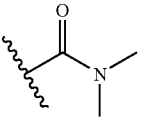 |
TABLE 38-continued
Formula (Im)
| Compound No. | R |
|---|---|
| 66 |  |

TABLE 39

Formula (In)

| Compound No. | R₂ | R₃ | R |
|---|---|---|---|
| 67 | methyl | n-propyl | phenyl |
| 68 | methyl | n-propyl | pyridin-3-yl |
| 69 | methyl | n-propyl | pyridin-4-yl |
| 70 | methyl | n-propyl | 2,6-dichloropyridin-4-yl |
| 71 | methyl | n-propyl | 5-(methylamino)thiazol-4-yl |
| 72 | methyl | n-propyl | 5-amino-1-thio-pyrazol-4-yl |
| 73 | methyl | n-propyl | 3-aminothiophen-2-yl |
| 74 | methyl | n-propyl | 3-aminopyrazin-2-yl |

TABLE 39-continued

Formula (In)

| Compound No. | R₂ | R₃ | R |
|---|---|---|---|
| 309 | H | n-propyl | 5-(methylamino)thiazol-4-yl |
| 350 | H | (E)-2-pentenyl | 5-(methylamino)thiazol-4-yl |

TABLE 40

Formula (Io)

| Compound No. | R₂ | R |
|---|---|---|
| 104 | methyl | 2-nitrophenyl |
| 105 | methyl | 4-methoxyphenyl |
| 106 | methyl | 4-chlorophenyl |
| 311 | H | 2-nitrophenyl |

TABLE 41

Formula (Ip)

| Compound No. | Ra | Rc |
|---|---|---|
| 91 | H | ethyl ester |
| 92 | H | phenyl |
| 107 | methyl | ethyl ester |
| 108 | methyl | phenyl |
| 109 | methyl | 4-chlorophenyl |

TABLE 42

Formula (Iq)

| Compound No. | Ra | Rb |
|---|---|---|
| 75 | methyl | ethyl ester |
| 76 | methyl | 4-chlorophenyl |

TABLE 42-continued

Formula (Iq)

| Compound No. | Ra | Rb |
|---|---|---|
| 77 | ethyl | phenyl |
| 78 | phenyl | phenyl |
| 79 | ethyl | 4-chlorophenyl |
| 80 | phenyl | 3-chlorophenyl |
| 81 | H | phenyl |
| 82 | NH$_2$ | phenyl |
| 83 | NH$_2$ | 4-pyridyl |
| 93 | ethyl | 4-chlorophenyl |
| 94 | methyl | amide (C(O)NH$_2$) |

TABLE 43

Formula (Ir)

| Compound No. | R |
|---|---|
| 160 | —C(O)OCH₃ |
| 161 | —C(O)-morpholine |

TABLE 44

Formula (Is)

| Compound No. | R |
|---|---|
| 121 | 4,5-dihydrothiazol-2-yl |
| 277 | —C(O)N(CH₃)₂ |
| 278 | —C(O)-morpholine |
| 279 | —C(O)-(4-ethyl-2,3-dioxopiperazin-1-yl) |

TABLE 44-continued

Formula (Is)

| Compound No. | R |
|---|---|
| 280 | —C(O)-phenyl |
| 281 | —C(O)-(2-nitrophenyl) |
| 282 | —C(O)-(4-methylaminothiazol-5-yl) |
| 283 | —C(O)CH₂-morpholine |
| 284 | —S(O)₂-phenyl |
| 285 | —CH₂CH₂CN |
| 286 | —CH₂CH₂C(O)N(CH₃)₂ |
| 287 | —CH₂CH₂C(O)OCH₃ |

TABLE 44-continued
Formula (Is)
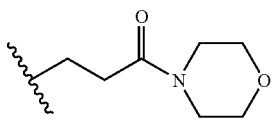
| Compound No. | R |
|---|---|
| 288 | 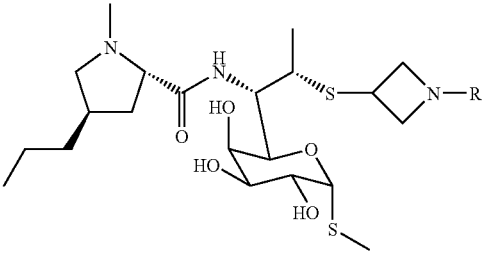 |
| 289 | 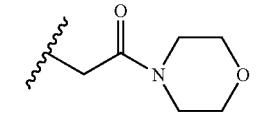 |
| 290 | 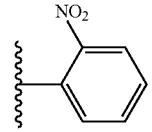 |
| 291 | 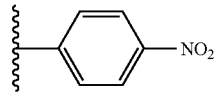 |
| 292 | 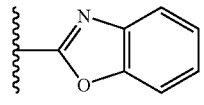 |
| 293 | 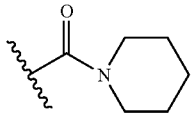 |
| 294 | 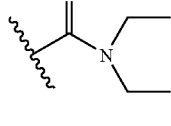 |
| 295 | 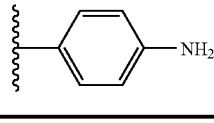 |
TABLE 45
Formula (It)
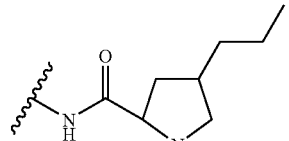
| Compound No. | $R_2$ | Ra | Rb |
|---|---|---|---|
| 1 | methyl | H | $NH_2$ |
| 2 | methyl | Cl | H |
| 3 | methyl | H | F |
| 4 | methyl | $NO_2$ | H |
| 5 | methyl | H | CN |
| 6 | methyl | H | $COOCHPh_2$ |
| 7 | methyl | H | $NHC_2H_5$ |
| 8 | methyl | H | $NO_2$ |
| 180 | methyl | $NH_2$ | H |
| 196 | methyl | H | 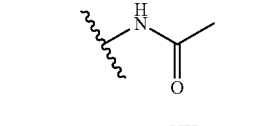 |
| 197 | methyl | H | 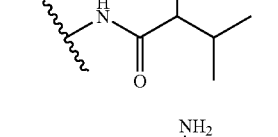 |
| 198 | methyl | H | 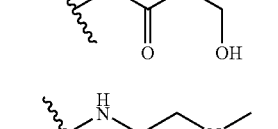 |
| 199 | methyl | H | 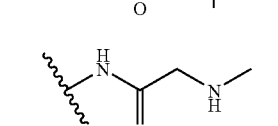 |
| 200 | methyl | H | 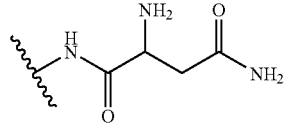 |
| 201 | methyl | H | 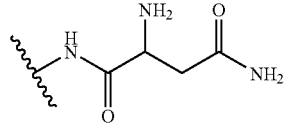 |
| 202 | methyl | H | 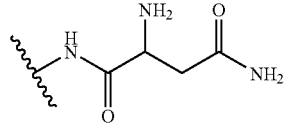 |

TABLE 45-continued
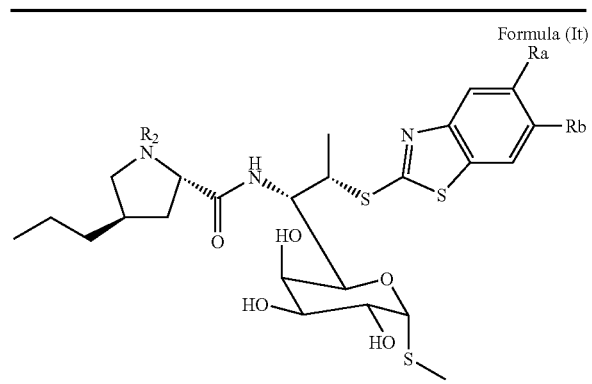
Formula (It)
| Compound No. | R₂ | Ra | Rb |
|---|---|---|---|
| 203 | methyl | H | (NHCH₂C(O)NH₂ group) |
| 212 | methyl | H | (NH-allyl group) |
| 213 | methyl | H | (C(O)NH₂ group) |
| 214 | methyl | H | (C(O)N(CH₃)₂ group) |
| 215 | methyl | H | (C(O)-azetidinyl group) |
TABLE 45-continued
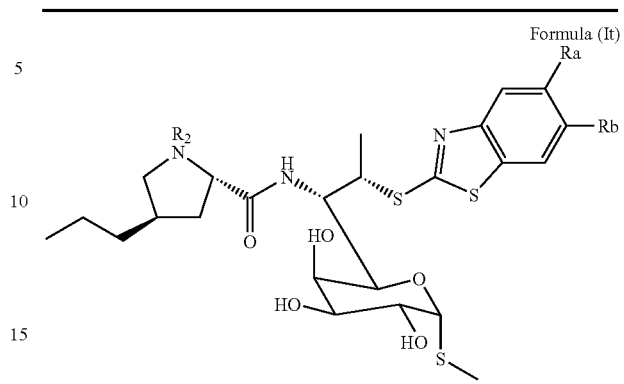
Formula (It)
| Compound No. | R₂ | Ra | Rb |
|---|---|---|---|
| 216 | methyl | H | (C(O)NHCH₃ group) |
| 297 | H | H | NH₂ |
TABLE 46
Formula (Iu)
| Compound No. | R₂ |
|---|---|
| 368 | H |
| 388 | methyl |
TABLE 47
| Compound No. |
|---|
| 84 |
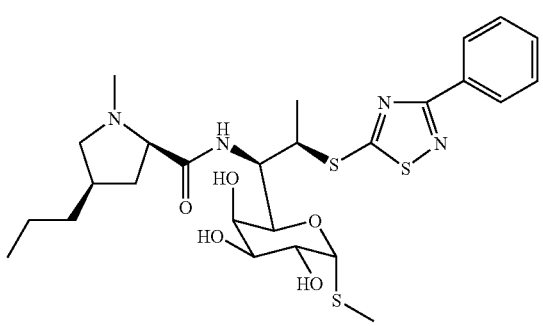

TABLE 47-continued
| Compound No. | |
|---|---|
| 88 | 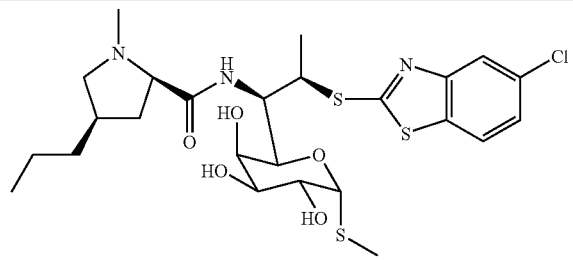 |
| 89 | 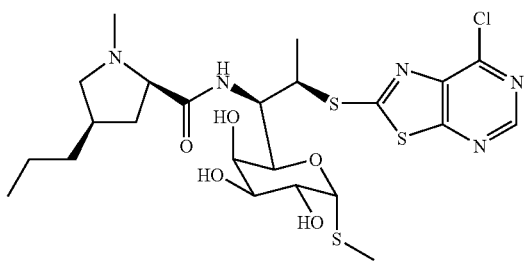 |
| 90 | 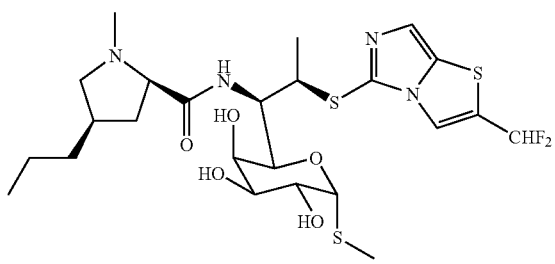 |
| 363 | 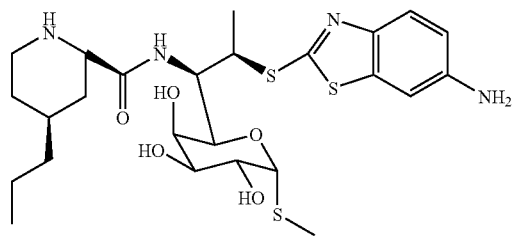 |
| 374 | 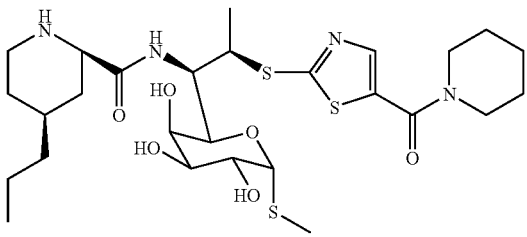 |
| 409 | 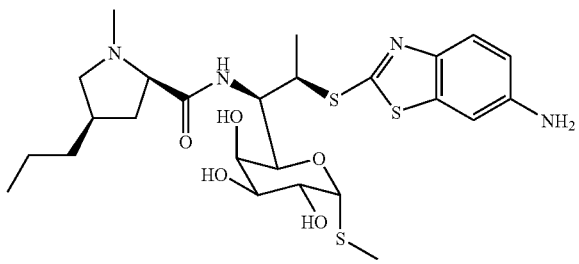 |

TABLE 48
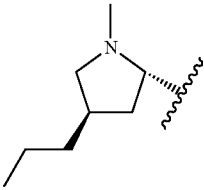
| Compound No. | Rx | Ry |
|---|---|---|
| 452 | 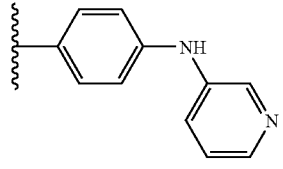 | 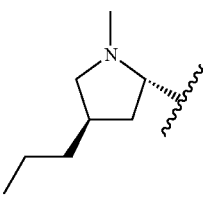 |
| 453 | 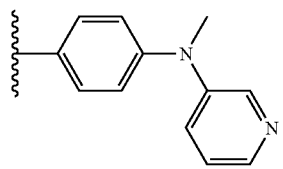 | 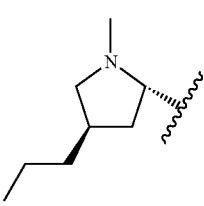 |
| 454 | 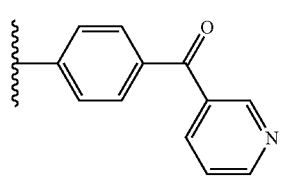 | 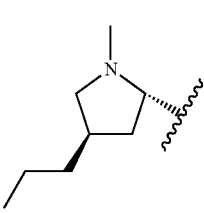 |
| 455 | 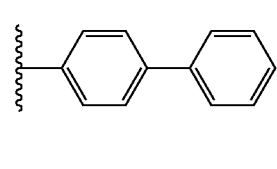 | 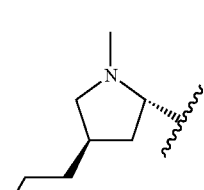 |
| 456 | 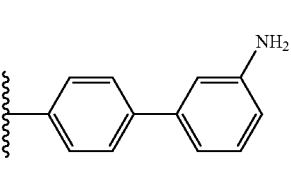 | 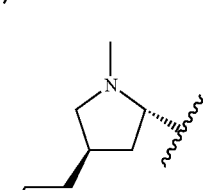 |
| 457 | 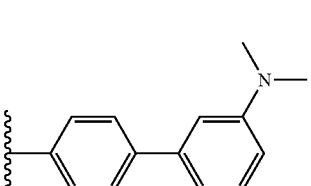 | |

TABLE 48-continued
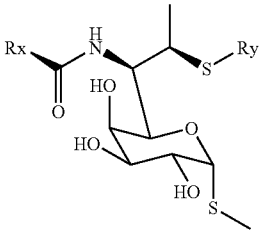
| Compound No. | Rx | Ry |
|---|---|---|
| 458 | 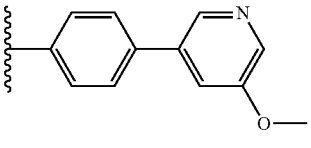 | 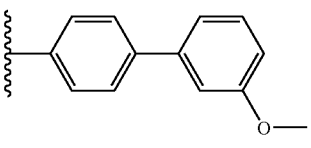 |
| 459 | 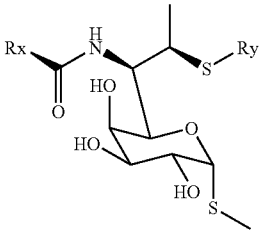 | 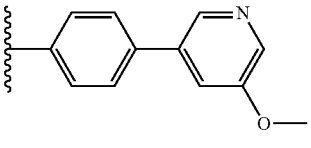 |
| 460 | 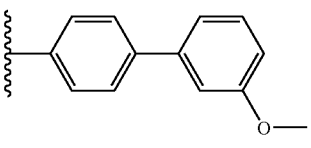 | 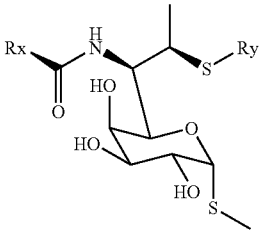 |
| 461 | 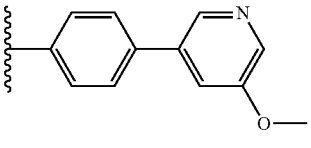 | 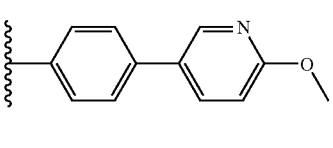 |
| 462 | 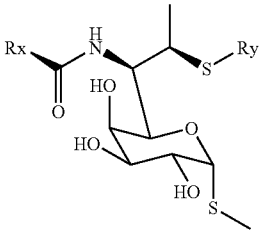 | 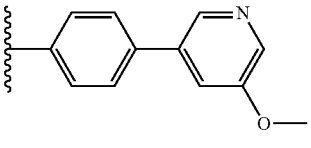 |
| 463 | 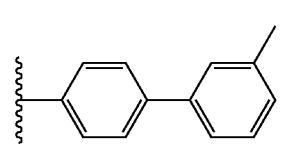 | 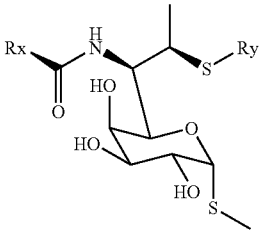 |

TABLE 48-continued

| Compound No. | Rx | Ry |
|---|---|---|
| 429 | 1-methyl-4-propylpyrrolidin-2-yl | 4-(4,6-diamino-1,3,5-triazin-2-yl)phenyl |
| 430 | 1-methyl-4-propylpyrrolidin-2-yl | 4-(1H-imidazol-1-yl)phenyl |
| 446 | 1-methyl-4-propylpyrrolidin-2-yl | 4-(2-nitropyridin-3-yl)phenyl |
| 431 | 1-methyl-4-propylpyrrolidin-2-yl | 4-(1-methyl-1H-pyrazol-4-yl)phenyl |
| 464 | 1-methyl-4-propylpyrrolidin-2-yl | 3'-acetamido-[1,1'-biphenyl]-4-yl |
| 447 | 1-methyl-4-propylpyrrolidin-2-yl | 4-(5-nitro-1-oxidopyrimidin-3-yl)phenyl |

TABLE 48-continued

| Compound No. | Rx | Ry |
|---|---|---|
| 496 | 1-methyl-4-propylpyrrolidin-2-yl | 4-(pyridin-3-yl N-oxide)phenyl |
| 432 | 1-methyl-4-propylpyrrolidin-2-yl | 4-(6-fluoropyridin-3-yl)phenyl |

TABLE 49

| Compound No. | Rx | Ry |
|---|---|---|
| 433 | 1-methyl-4-propylpyrrolidin-2-yl | 4-(6-aminopyridin-3-yl)phenyl |
| 497 | 1-methyl-4-propylpyrrolidin-2-yl | 4-(4-nitropyridin-3-yl)phenyl |

TABLE 49-continued

| Compound No. | Rx | Ry |
|---|---|---|
| 465 | 1-methyl-4-propylpyrrolidin-2-yl | 4-(isoquinolin-1-yl)phenyl |
| 434 | 1-methyl-4-propylpyrrolidin-2-yl | 4-(imidazo[2,1-b]thiazol-6-yl)phenyl |
| 483 | 1-methyl-4-propylpyrrolidin-2-yl | 4-(4-methylmorpholin-2-yl)phenyl |
| 484 | 1-methyl-4-propylpyrrolidin-2-yl | 4-(4-(2-methoxyethyl)morpholin-2-yl)phenyl |
| 485 | 1-methyl-4-propylpyrrolidin-2-yl | 4-(4-propylmorpholin-2-yl)phenyl |
| 466 | 1-methyl-4-propylpyrrolidin-2-yl | 4-(2-(methylaminomethyl)pyrrolidine-1-carbonyl)phenyl |

TABLE 49-continued

| Compound No. | Rx | Ry |
|---|---|---|
| 467 | 1-methyl-4-propyl-pyrrolidin-2-yl | 4-[(2-(aminomethyl)pyrrolidin-1-yl)carbonyl]phenyl |
| 468 | 1-methyl-4-propyl-pyrrolidin-2-yl | 4-[(2-((dimethylamino)methyl)pyrrolidin-1-yl)carbonyl]phenyl |
| 495 | 1-methyl-4-propyl-pyrrolidin-2-yl | 4-[(3-hydroxypiperidin-1-yl)carbonyl]phenyl |
| 486 | 1-methyl-4-propyl-pyrrolidin-2-yl | 4-[(2-oxopiperidin-1-yl)methyl]phenyl |
| 487 | 1-methyl-4-propyl-pyrrolidin-2-yl | 4-(2-morpholin-4-yl-acetyl)phenyl |
| 492 | 1-methyl-4-propyl-pyrrolidin-2-yl | 4-[(3-acetamidopyrrolidin-1-yl)carbonyl]phenyl |

TABLE 49-continued

| Compound No. | Rx | Ry |
|---|---|---|
| 493 | 1-methyl-4-propylpyrrolidin-2-yl | 4-[(3-acetamidopyrrolidin-1-yl)carbonyl]phenyl |
| 494 | 1-methyl-4-propylpyrrolidin-2-yl | 4-[(3-hydroxypyrrolidin-1-yl)carbonyl]phenyl |
| 488 | 1-methyl-4-propylpyrrolidin-2-yl | 4-{[2-(methylthiomethyl)pyrrolidin-1-yl]carbonyl}phenyl |
| 489 | 1-methyl-4-propylpyrrolidin-2-yl | 4-[(3-ethylmorpholin-4-yl)carbonyl]phenyl |
| 472 | 1-methyl-4-propylpyrrolidin-2-yl | 4-{[(1,3-dihydroxy-2-propyl)amino]carbonyl}phenyl |
| 473 | 1-methyl-4-propylpyrrolidin-2-yl | 4-[(3-methoxypyrrolidin-1-yl)carbonyl]phenyl |

TABLE 50

| Compound No. | Rx | Ry |
|---|---|---|
| 474 | 1-methyl-4-propylpyrrolidin-2-yl | 4-[(3-hydroxypropyl)carbamoyl]phenyl |
| 475 | 1-methyl-4-propylpyrrolidin-2-yl | 4-[N-(2-hydroxyethyl)-N-(3-hydroxypropyl)carbamoyl]phenyl |
| 476 | 1-methyl-4-propylpyrrolidin-2-yl | 4-(1,4-oxazepan-4-ylcarbonyl)phenyl |
| 477 | 1-methyl-4-propylpyrrolidin-2-yl | 4-[N-(2-methoxyethyl)-N-(3-methoxypropyl)carbamoyl]phenyl |
| 478 | 1-methyl-4-propylpyrrolidin-2-yl | 4-{[1-(hydroxymethyl)propyl]carbamoyl}phenyl |

TABLE 50-continued

| Compound No. | Rx | Ry |
|---|---|---|
| 479 | 1-methyl-4-propylpyrrolidin-2-yl | 4-[(2-(allyloxymethyl)pyrrolidin-1-yl)carbonyl]phenyl |
| 480 | 1-methyl-4-propylpyrrolidin-2-yl | 4-[(3-(methoxymethyl)morpholin-4-yl)carbonyl]phenyl |
| 481 | 1-methyl-4-propylpyrrolidin-2-yl | 4-[N-(1,3-dimethoxyprop-2-yl)carbamoyl]phenyl |
| 482 | 1-methyl-4-propylpyrrolidin-2-yl | 4-(cyanomethyl)phenyl |
| 469 | 1-methyl-4-propylpyrrolidin-2-yl | 4-(methoxymethyl)phenyl |
| 435 | 1-methyl-4-propylpyrrolidin-2-yl | 3,5-difluoro-4-(1H-tetrazol-1-yl)phenyl |

TABLE 50-continued

| Compound No. | Rx | Ry |
|---|---|---|
| 442 | 1-methyl-4-propylpyrrolidin-2-yl | 4-(5-cyanopyridin-3-yl)phenyl |
| 443 | 1-methyl-4-propylpyrrolidin-2-yl | 4-(2-fluoropyridin-3-yl)phenyl |
| 444 | 1-methyl-4-propylpyrrolidin-2-yl | 4-(5-fluoropyridin-3-yl)phenyl |
| 445 | 1-methyl-4-propylpyrrolidin-2-yl | 4-(2-methoxypyridin-3-yl)phenyl |
| 498 | 1-methyl-4-propylpyrrolidin-2-yl | 5-(pyridin-3-yl)thiazol-2-yl |
| 499 | 1-methyl-4-propylpyrrolidin-2-yl | 5-(pyridin-4-yl)thiazol-2-yl |

TABLE 50-continued

[Structure: Rx-C(=O)-NH-CH(CH3)-CH(S-Ry)-sugar(OH,HO,HO)-O-S-CH3]

| Compound No. | Rx | Ry |
|---|---|---|
| 500 | 1-methyl-4-propylpyrrolidin-2-yl | 5-(4-(hydroxymethyl)phenyl)thiazol-2-yl |
| 501 | 1-methyl-4-propylpyrrolidin-2-yl | 5-(4-(methylthio)phenyl)thiazol-2-yl |
| 502 | 1-methyl-4-propylpyrrolidin-2-yl | 5-(2-carbamoylphenyl)thiazol-2-yl |

TABLE 51

[Structure: Rx-C(=O)-NH-CH(CH3)-CH(S-Ry)-sugar(OH,HO,HO)-O-S-CH3]

| Compound No. | Rx | Ry |
|---|---|---|
| 503 | 1-methyl-4-propylpyrrolidin-2-yl | 5-(2-acetamidophenyl)thiazol-2-yl |

TABLE 51-continued

| Compound No. | Rx | Ry |
|---|---|---|
| 504 | 1-methyl-4-propylpyrrolidin-2-yl | 5-(2-(methylsulfonamido)phenyl)thiazol-2-yl |
| 505 | 1-methyl-4-propylpyrrolidin-2-yl | 5-(3-aminophenyl)thiazol-2-yl |
| 506 | 1-methyl-4-propylpyrrolidin-2-yl | 5-(2-formamidophenyl)thiazol-2-yl |
| 419 | 1-methyl-4-propylpyrrolidin-2-yl | 5-(4-chloro-2-nitrophenyl)oxazol-2-yl |
| 507 | 1-methyl-4-propylpyrrolidin-2-yl | 5-(2-(ethoxycarbonyl)phenyl)thiazol-2-yl |
| 508 | 1-methyl-4-propylpyrrolidin-2-yl | 5-(2-aminophenyl)thiazol-2-yl |

TABLE 51-continued
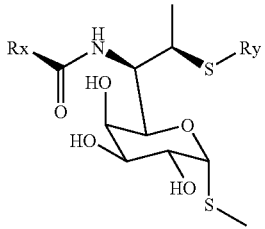
| Compound No. | Rx | Ry |
|---|---|---|
| 490 | 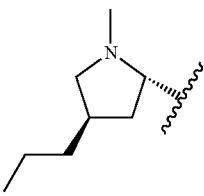 | 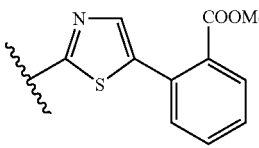 |
| 420 | 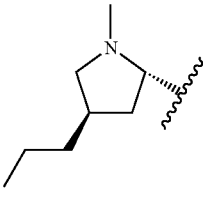 | 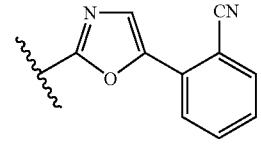 |
| 421 | 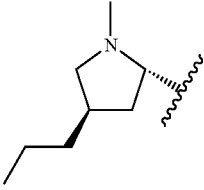 | 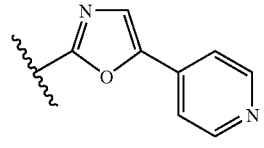 |
| 422 | 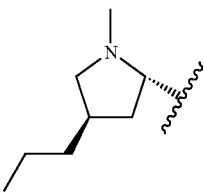 | 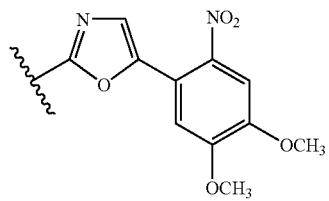 |
| 423 | 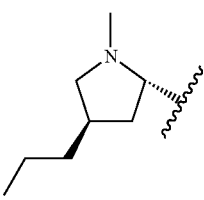 | 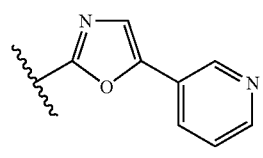 |
| 424 | 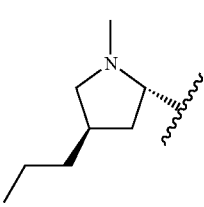 | 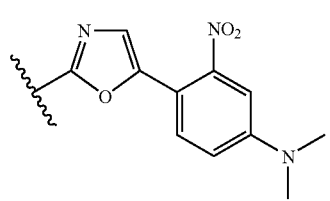 |

TABLE 51-continued

| Compound No. | Rx | Ry |
|---|---|---|
| 425 | 1-methyl-4-propyl-pyrrolidin-2-yl | 5-phenyl-oxazol-2-yl |
| 426 | 1-methyl-4-propyl-pyrrolidin-2-yl | 5-(pyridin-2-yl)-oxazol-2-yl |
| 427 | 1-methyl-4-propyl-pyrrolidin-2-yl | 5-(2-methoxycarbonyl-3,5-dimethoxyphenyl)-oxazol-2-yl |
| 428 | 1-methyl-4-propyl-pyrrolidin-2-yl | 5-(4-methyl-1,2,3-thiadiazol-5-yl)-oxazol-2-yl |
| 491 | 1-methyl-4-propyl-pyrrolidin-2-yl | 5-(2-(N,N-dimethylcarbamoyl)-3,5-dimethoxyphenyl)-oxazol-2-yl |
| 413 | 1-methyl-4-propyl-pyrrolidin-2-yl | 5-(5-(azetidin-1-yl)-2-nitrophenyl)-1,3,4-thiadiazol-2-yl |

TABLE 51-continued
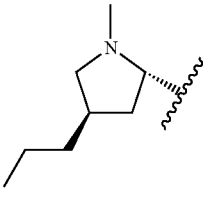
| Compound No. | Rx | Ry |
|---|---|---|
| 414 | 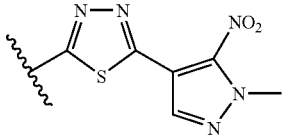 | 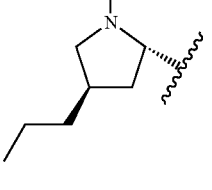 |
TABLE 52
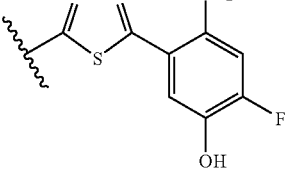
| Compound No. | Rx | Ry |
|---|---|---|
| 449 | 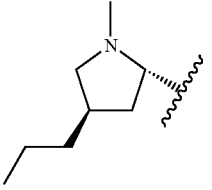 | 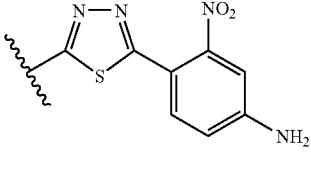 |
| 415 | 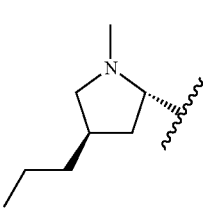 | 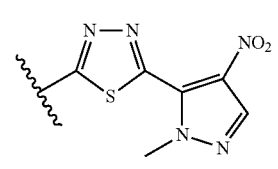 |
| 416 | | |

TABLE 52-continued
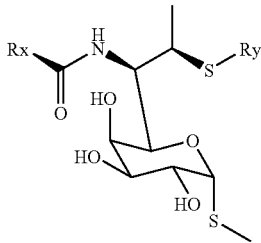
| Compound No. | Rx | Ry |
|---|---|---|
| 417 | 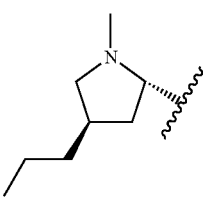 | 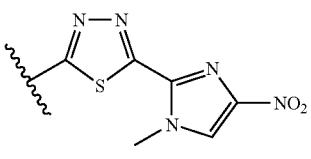 |
| 418 | 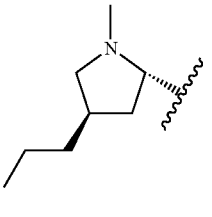 | 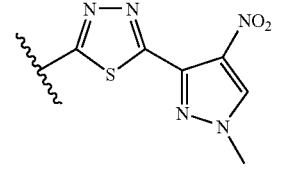 |
| 450 | 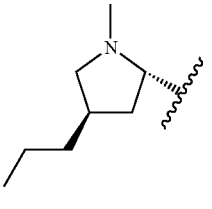 | 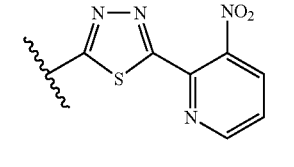 |
| 451 | 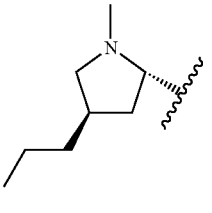 | 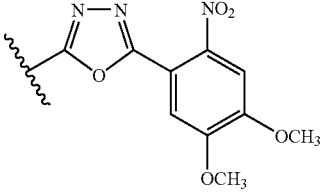 |
| 436 | 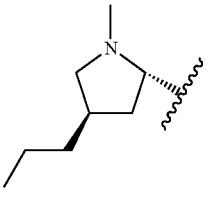 | 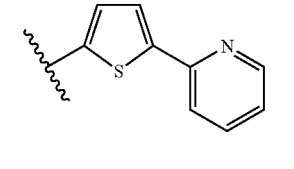 |
| 448 | 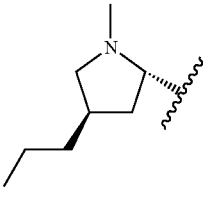 | 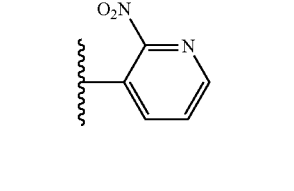 |

TABLE 52-continued
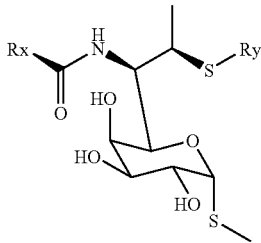
| Compound No. | Rx | Ry |
|---|---|---|
| 437 | 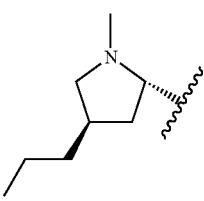 | 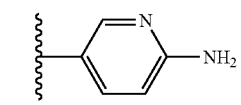 |
| 470 | 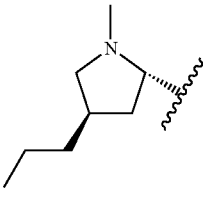 | 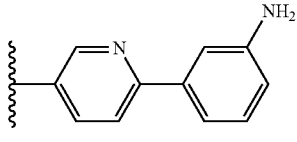 |
| 438 | 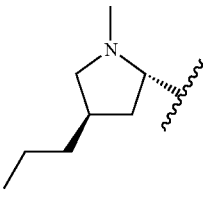 | 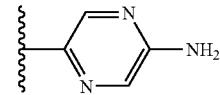 |
| 439 | 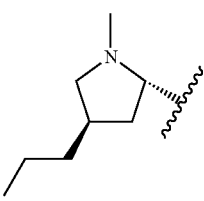 | 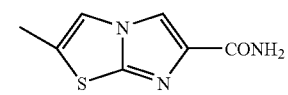 |
| 440 | 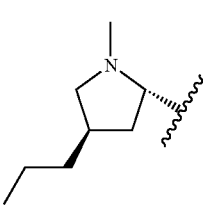 | 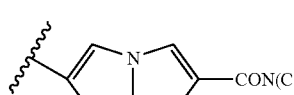 |
| 441 | 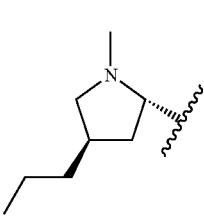 | 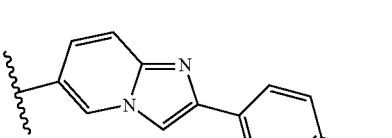 |

TABLE 52-continued
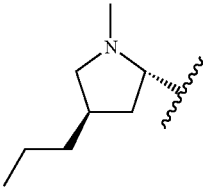
| Compound No. | Rx | Ry |
|---|---|---|
| 471 | 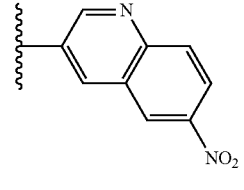 | 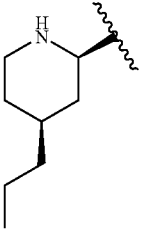 |
TABLE 53
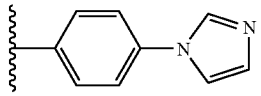
| Compound No. | Rx | Ry |
|---|---|---|
| 513 | 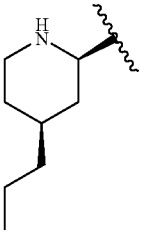 | 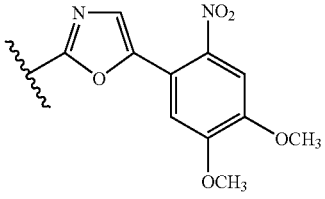 |
| 514 | | |

US 7,871,982 B2
291
292
TABLE 53-continued
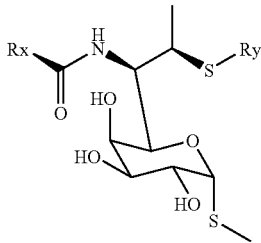
| Compound No. | Rx | Ry |
|---|---|---|
| 509 | 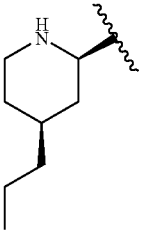 | 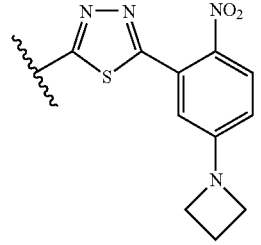 |
| 515 | 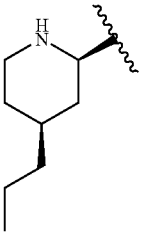 | 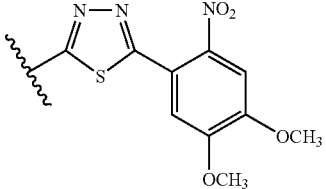 |
| 518 | 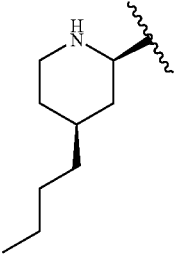 | 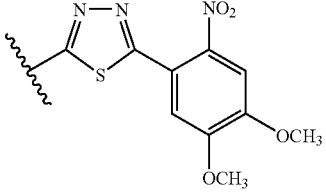 |
| 517 | 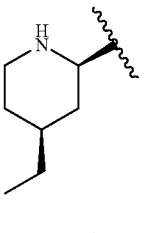 | 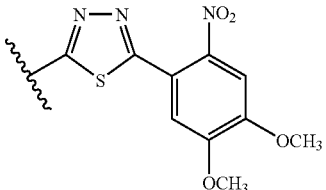 |
| 516 | 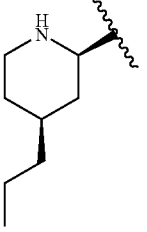 | 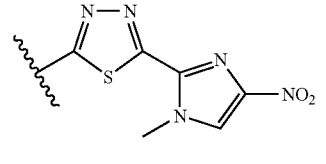 |

TABLE 53-continued
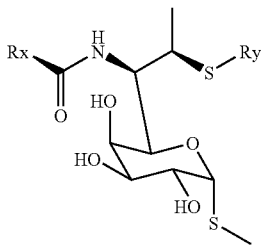
| Compound No. | Rx | Ry |
|---|---|---|
| 510 | 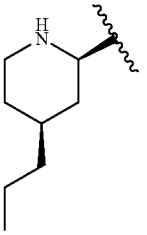 | 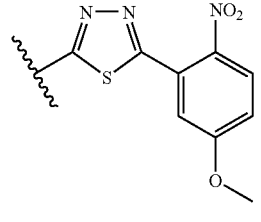 |
| 511 | 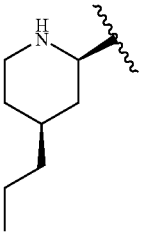 | 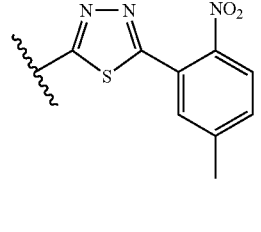 |
| 512 | 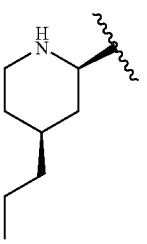 | 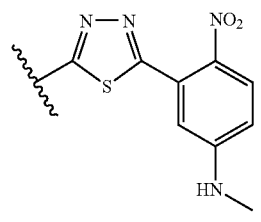 |
| 519 | 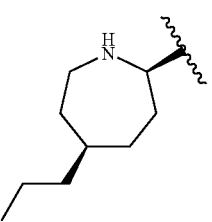 | 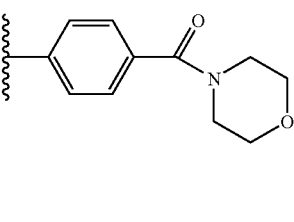 |
| 520 | 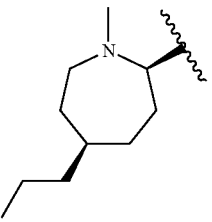 | 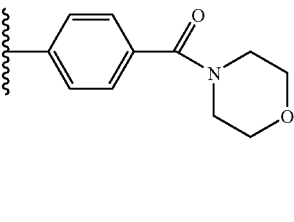 |

The invention claimed is:
1. A compound of formula (I) or its pharmacologically acceptable salt:

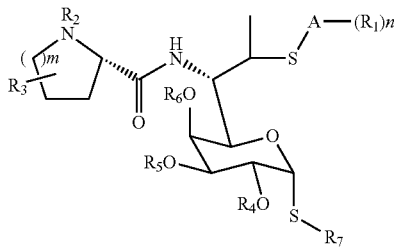

wherein
A represents
  aryl optionally substituted by a group selected from the group consisting of benzyl and $C_{1-6}$ alky; or
  a monocyclic or bicyclic heterocyclic group in which each ring is a four- to seven-membered ring and which is optionally substituted by a group selected from the group consisting of $C_{1-6}$ alkyl and halogenated $C_{1-6}$ alkyl,
  wherein the heterocyclic group contains one to four heteroatoms selected from the group consisting of nitrogen, oxygen, and sulfur atoms,
$R_1$ represents
  a halide;
  cyano;
  nitro;
  substituted $C_{1-6}$ alkyl
    wherein the $C_{1-6}$ alkyl group is substituted by one or more groups selected from the group consisting of hydroxy, halides, carbamoyl, $C_{1-6}$ alkyloxycarbonyl, cyano, di-$C_{1-6}$ alkylcarbamoyl, $C_{1-6}$ alkyloxy, heterocyclic carbonyl, and heterocyclic groups, and the heterocyclic carbonyl and heterocyclic groups are optionally substituted by one or more groups selected from the group consisting of halides, nitro, $C_{1-6}$ alkyl, $C_{1-6}$ alkylamino, amino, cyano, di-$C_{1-6}$ alkylamino, $C_{1-6}$ alkyloxy, hydroxy, acylamino, oxo, carbamoyl, di-$C_{1-6}$ alkylaminocarbonyl, and $C_{1-6}$ alkylaminocarbonyl;
  optionally substituted amino
    wherein the amino group is optionally substituted by one or more groups selected from the group consisting of $C_{1-6}$ alkyl, $C_{2-6}$ alkenyl, $C_{1-6}$ acyl, optionally substituted heterocyclic groups, and optionally substituted aryl, the heterocyclic group, which can substitute the amino group, is optionally substituted by one or more groups selected from the group consisting of halides, nitro, cyano, di-$C_{1-6}$ alkylamino, $C_{1-6}$ alkyloxy, hydroxy, acylamino, $C_{1-6}$ alkyl, $C_{1-6}$ alkylamino, amino, oxo, carbamoyl, di-$C_{1-6}$ alkylaminocarbonyl, and $C_{1-6}$ alkylaminocarbony, and the aryl group is optionally substituted by one or more groups selected from the group consisting of halides, nitro, amino, $C_{1-6}$ alkyl, cyano, $C_{1-6}$ alkylthio, halogenated $C_{1-6}$ alkylthio, $C_{1-6}$ alkylsulfonyl, $C_{1-6}$ alkyloxy, hydroxy $C_{1-6}$ alkylamino, $C_{1-6}$ alkylamino, di-$C_{1-6}$ alkylamino, $C_{1-6}$ alkylsulfinyl, $C_{1-6}$ alkyloxycarbonyl, carbamoyl, and di-$C_{1-6}$ alkylaminocarbonyl;

N-amino-$C_1$-6 alkylcarbonyl-N—$C_{1-6}$ alkylamino;
N—$C_{1-6}$ alkyloxycarbonyl-$C_{1-6}$ alkyl-N—$_{1-6}$ alkylamino;
N—$C_{1-6}$ alkyloxy substituted $C_{1-6}$ alkylcarbonyl-N—$C_{1-6}$ alkylamino;
$C_{1-6}$ alkylcarbonylamino optionally substituted by one or more groups selected from the group consisting of amino and hydroxy;
$C_{1-6}$ alkylamino-$C_{1-6}$ alkylcarbonylamino;
(di-$C_{1-6}$ alkylamino)-$C_{1-6}$ alkylcarbonylamino;
$C_{1-6}$ alkyloxy-$C_{1-6}$ alkylcarbonylamino;
N—$C_{2-6}$ alkenylcarbonylamino;
$C_{1-6}$ alkyloxycarbonylamino;
heterocyclic carbonylamino optionally substituted by one or more $C_{1-6}$ alkyl;
$C_{1-6}$ alkylsulfonylamino;
(S)-2-amino-3-succinamide;
carbamoyl;
N—$C_{1-6}$ alkyl substituted carbamoyl;
N—$C_{1-6}$ alkyl-N—$C_{1-6}$ alkyloxy substituted carbamoyl;
N,N-di-$C_{1-6}$ alkyl substituted carbamoyl;
N—$C_{3-6}$ cycloalkyl substituted carbamoyl;
N-adamantyl substituted carbamoyl;
N-amino substituted carbamoyl;
N-heterocyclic $C_{1-6}$ alkyl substituted carbamoyl;
N-(hydroxy-$C_{1-6}$ alkyl) substituted carbamoyl;
N-(dihydroxy-$C_{1-6}$ alkyl) substituted carbamoyl;
N-(di-$C_{1-6}$ alkyloxy-$C_{1-6}$ alkyl) substituted carbamoyl;
N,N-di(hydroxy-$C_{1-6}$ alkyl) substituted carbamoyl;
N,N-di($C_{1-6}$ alkyloxy-$C_{1-6}$ alkyl) substituted carbamoyl;
carboxyl;
$C_{1-6}$ alkylcarbonyl;
heterocyclic-$C_{1-6}$ alkylcarbonyl;
$C_{1-6}$ alkyloxycarbonyl;
heterocyclic aminocarbonyl;
optionally substituted arylcarbonyl
  wherein the arylcarbonyl group is optionally substituted by one or more groups selected from the group consisting of halides, nitro, amino, $C_{1-6}$ alkyl, cyano, $C_{1-6}$ alkylthio, $C_{1-6}$ alkylsulfonyl, $C_{1-6}$ alkyloxy, hydroxy $C_{1-6}$ alkylamino, $C_{1-6}$ alkylamino, di-$C_{1-6}$ alkylamino, $C_{1-6}$ alkylsulfinyl, $C_{1-6}$ alkyloxycarbonyl, carbamoyl, and di-$C_{1-6}$ alkylaminocarbonyl;
optionally substituted 4- to 7-membered heterocyclic carbonyl
  wherein the heterocyclic carbonyl group is optionally substituted by one or more groups selected from the group consisting of $C_{1-6}$ alkyl, hydroxy $C_{1-6}$ alkyl, cyano, di-$C_{1-6}$ alkylamino, $C_{1-6}$ alkyloxy; $C_{2-6}$ alkenyloxy-$C_{1-6}$ alkyl, hydroxy, $C_{1-6}$ alkylcarbonylamino, $C_{1-6}$ alkylthio-$C_{1-6}$ alkyl, amino-$C_{1-6}$ alkyl, $C_{1-6}$ alkyloxy-$C_{1-6}$ alkyl, oxo, $C_{1-6}$ alkylamino, carbamoyl, di-$C_{1-6}$ alkylaminocarbonyl, $C_{1-6}$ alkylaminocarbonyl, $C_{1-6}$ alkylamino-$C_{1-6}$ alkyl, di-$C_{1-6}$ alkylamino-$C_{1-6}$ alkyl, $C_{1-6}$ alkylsulfonyl-$C_{1-6}$ alkyl, cyano, halides, amino, acylamino $C_{1-6}$ alkyl, and acylamino;
$C_{1-6}$ alkylthio substituted by amino or carbamoyl;
pyridylthio;
$C_{1-6}$ alkylsulfonyl;
arylsulfonyl;
heterocyclic sulfonyl;
pyridyloxy;
optionally substituted aryl wherein the aryl group is optionally substituted by one or more groups, which may be the same or different, selected from the group consisting of a fluorine atom, a chlorine atom, nitro, amino, $C_{1-6}$ alkyl, cyano, $C_{1-6}$ alkyloxy, halogenated $C_{1-6}$ alkyloxy, hydroxy $C_{1-6}$ alkyl, hydroxy $C_{1-6}$ alkylamino, $C_{1-6}$ alkylamino, di-$C_{1-6}$ alkylamino, $C_{1-6}$ alkylthiocarbamoyl, $C_{1-6}$ alkylcarbonylamino, $C_{1-6}$ alkylsulfonylamino, formylamino, $C_{1-6}$ alkyloxycarbonyl, and azetidinyl;

an optionally substituted four- to seven-membered monocyclic heterocyclic group wherein the heterocyclic group is optionally substituted by one or more groups selected from the group consisting of halides, nitro, cyano, di-$C_{1-6}$ alkylamino, $C_{1-6}$ alkyloxy, hydroxy, acylamino, $C_{1-6}$ alkyl, $C_{1-6}$ alkylamino, amino, oxo, carbamoyl, di-$C_{1-6}$ alkylaminocarbonyl, $C_{1-6}$ alkylaminocarbonyl, $C_{1-6}$ alkyloxy-$C_{1-6}$ alkyl, and N-oxide; or a bicyclic heterocyclic group in which each ring is a four- to seven-membered ring, when n is 2, individual $R_1$s may be the same or different, $R_2$ represents a hydrogen atom;

optionally substituted $C_{1-6}$ alkyl;

optionally substituted $C_{2-6}$ alkenyl;

optionally substituted acyl; or optionally substituted $C_{1-6}$ alkyloxycarbonyl wherein the $C_{1-6}$ alkyl, $C_{2-6}$ alkenyl, acyl, and $C_{1-6}$ alkyloxycarbonyl groups are optionally substituted by one or more groups selected from the group consisting of heterocyclic rings optionally substituted by $C_{1-6}$ alkyl; amino; hydroxy; and cyano, $R_3$ represents optionally substituted $C_{1-6}$ alkyl wherein the $C_{1-6}$ alkyl group is optionally substituted by one or more groups selected from the group consisting of halides, nitro, hydroxy, amino, $C_{1-6}$ alkyloxycarbonyl, carbamoyl, cyano, $C_{1-6}$ alkyloxy, oxo, heterocyclic ring, carbamoyl, azide, $C_{1-6}$ alkylaminocarbonyl, di-$C_{1-6}$ alkylaminocarbonyl, and optionally substituted aryl; or $C_{2-6}$ alkenyl, $R_4$, $R_5$, and $R_6$, which may be the same or different, represent a hydrogen atom;

optionally substituted $C_{1-6}$ alkyl; or optionally substituted acyl wherein the $C_{1-6}$ alkyl group and hydrogen atoms on the acyl group are optionally substituted by one or more groups selected from the group consisting of halides; nitro; hydroxy; amino; $C_{1-6}$ alkyloxycarbonyl; carbamoyl; cyano; nitro halide; $C_{1-6}$ alkyloxy; oxo; heterocyclic rings; carbamoyl; azide; $C_{1-6}$ alkylaminocarbonyl; di-$C_{1-6}$ alkylaminocarbonyl; and aryl optionally substituted by a halide, hydroxy or $C_{1-4}$ alkyl, $R_7$ represents $C_{1-6}$ alkyl optionally substituted by one or more groups selected from the group consisting of halides and hydroxy, m is 1 to 3, and n is 1 or 2.

2. The compound according to claim 1, wherein formula (I) is of formula (II), or its pharmacologically acceptable salt:

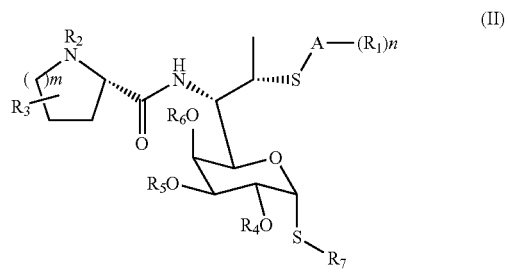

(II)

wherein A, $R_1$, $R_2$, $R_3$, $R_4$, $R_5$, $R_6$, $R_7$, m, and n are as defined in formula (I) of claim 1.

3. The compound according to claim 1 or 2 or its pharmacologically acceptable salt, wherein A represents a group selected from the group consisting of 1,3,4-thiadiazolyl, 1,2,4-thiadiazolyl, thiazolyl, thienyl, imidazolyl, azetidinyl, oxazolyl, 1,3,4-oxadiazolyl, 1,2,4-triazolyl, tetrazolyl, phenyl, pyridyl, pyrimidinyl, benzothiazolyl, benzooxazolyl, thiazolo[5,4-b]pyridyl, thiazolo[5,4-b]pyrimidinyl, imidazo[1,2-a]pyridyl, and imidazo[5,1-b]thiazolyl.

4. The compound according to claim 1 or 2 or its pharmacologically acceptable salt, wherein A represents 1,3,4-thiadiazolyl.

5. The compound according to claim 1 or 2 or its pharmacologically acceptable salt, wherein A represents phenyl.

6. The compound according to claim 1 or 2 or its pharmacologically acceptable salt, wherein $R_1$ represents a group selected from the group consisting of:

halides, cyano, nitro, substituted $C_{1-6}$ alkyl wherein the substituent is as defined in claim 1, amino optionally substituted by $C_{1-6}$ acyl, N—$C_{1-6}$ alkylamino, N,N-di-$C_{1-6}$ alkylamino, pyridylamino, $C_{1-6}$ alkylcarbonyl-N—$C_{1-6}$ alkylamino substituted by N—$C_{1-6}$ alkyloxy, $C_{1-6}$ alkylcarbonylamino, N—$C_{1-6}$ alkyl-N—$C_{1-6}$ alkylcarbonylamino, $C_{1-6}$ alkyloxy-$C_{1-6}$ alkylcarbonylamino, $C_{1-6}$ alkylcarbonylamino substituted by amino, $C_{1-6}$ alkylcarbonylamino substituted by amino and hydroxy, $C_{1-6}$ alkylamino-$C_{1-6}$ alkylcarbonylamino, (di-$C_{1-6}$ alkylamino)-$C_{1-6}$ alkylcarbonylamino, morpholino $C_{1-6}$ alkylcarbonyl, (S)-2-amino-3-succinamide, carbamoyl, carbamoyl substituted by N—$C_{1-6}$ alkyl, carbamoyl substituted by N,N-di-$C_{1-6}$ alkyl, $C_{1-6}$ alkyloxycarbonyl, azetidin-1-ylcarbonyl, optionally substituted 4- to 7-membered heterocyclic carbonyl wherein the substituent is as defined in claim 1, and the heterocyclic group in this group is selected from the group consisting of morpholino, 1,4-perhydroxazepinyl, piperidyl, and pyrrolidyl, optionally substituted phenyl wherein the substituent is as defined in claim 1, and optionally substituted 4- to 7-membered heterocyclic groups wherein the substituent is as defined in claim 1, and the heterocyclic group is selected from the group consisting of pyridyl, furyl, thiazolyl, pyrazolyl, imidazolyl, tetrazolyl, thiazolyl, 1,2,3-thiadiazolyl, and 1,3,6-triazinyl.

7. The compound according to claim 6 or its pharmacologically acceptable salt, wherein $R_1$ represents a group selected from the group consisting of:

halides, nitro, $C_{1-6}$ alkyl substituted by hydroxy, halide or $C_{1-6}$ alkyloxy, amino optionally substituted by $C_{1-6}$ acyl, pyridylamino, $C_{1-6}$ alkyloxycarbonyl, morpholino $C_{1-6}$ alkylcarbonyl, carbamoyl, N—$C_{1-6}$ alkyl substituted carbamoyl, N,N-di-$C_{1-6}$ alkyl substituted carbamoyl, optionally substituted 4- to 7-membered heterocyclic carbonyl wherein the heterocyclic carbonyl group is optionally substituted by one or more groups selected from the group consisting of $C_{1-6}$ alkyl, hydroxy $C_{1-6}$ alkyl, $C_{1-6}$ alkyloxy-$C_{1-6}$ alkyl, oxo, $C_{1-6}$ alkyloxy, hydroxy, $C_{1-6}$ alkylcarbonylamino, amino-$C_{1-6}$ alkyl, $C_{1-6}$ alkylamino-$C_{1-6}$ alkyl, di-$C_{1-6}$ alkylamino-$C_{1-6}$ alkyl, $C_{2-6}$ alkenyloxy-$C_{1-6}$ alkyl, and $C_{1-6}$ alkylthio-$C_{1-6}$ alkyl, and the heterocyclic group in this group is selected from the group consisting of morpholino, 1,4-perhydroxazepinyl, piperidyl, and pyrrolidyl, optionally substituted phenyl wherein the phenyl is optionally substituted by one or more groups selected from the group consisting of a fluorine atom, a chlorine atom, nitro, amino, $C_{1-6}$ alkyl, cyano, $C_{1-6}$ alkylthio, $C_{1-6}$ alkylsulfonyl, $C_{1-6}$ alkyloxy, hydroxy $C_{1-6}$ alkylamino, $C_{1-6}$ alkylamino, $C_{1-6}$ alkylcarbonylamino, di-$C_{1-6}$ alkylamino, $C_{1-6}$ alkylsulfinyl, $C_{1-6}$ alkyloxycarbonyl, carbamoyl, di-$C_{1-6}$ alkylaminocarbonyl, hydroxy, and azetidinyl, and optionally substituted 4- to 7-membered heterocyclic group wherein the heterocyclic group is optionally substituted by one or more groups selected from the group consisting of nitro, $C_{1-6}$ alkyl, $C_{1-6}$ alkylamino, amino, $C_{1-6}$ alkyloxy, N-oxide, $C_{1-6}$ alkyloxy-$C_{1-6}$ alkyl, halides, and oxo, and the heterocyclic group is selected from the group consisting of pyridyl, furyl, thiazolyl, pyrazolyl, imidazolyl, tetrazolyl, thiazolyl, 1,2,3-thiadiazolyl, and 1,3,6-triazinyl.

8. The compound according to claim 1 or 2 or its pharmacologically acceptable salt, wherein -A-$(R_1)_n$ in formula (I) or (II) represents a group selected from the group consisting of:

optionally substituted phenyl-1,3,4-thiadiazol-2-yl,
optionally substituted phenyloxazol-2-yl,
optionally substituted pyrazolyl-1,3,4-thiadiazol-2-yl,
optionally substituted pyridyloxazol-2-yl,
optionally substituted phenylthiazol-2-yl,
optionally substituted pyrrolidylcarbonylphenyl,
optionally substituted imidazolyl-1,3,4-thiadiazol-2-yl,
optionally substituted imidazolylphenyl,
optionally substituted 1,3,6-triazinylphenyl,
optionally substituted thiazolyl-1,3,4-oxadiazol-2-yl,
optionally substituted thiazolyl-1,3,4-thiadiazol-2-yl,
tetrazolyl phenyl,
1,4-perhydroxazepinecarbonylphenyl,
1,2,3-thiadiazolyloxazol-2-yl,
imidazo[5,1-b]thiazolylphenyl,
phenylimidazo[1,2-a]pyridin-6-yl,
optionally substituted phenyl-1,3,4-oxadiazol-2-yl,
optionally substituted pyridyl-1,3,4-thiadiazol-2-yl,
optionally substituted pyridylphenyl,
optionally substituted pyridylthiazol-2-yl,
optionally substituted pyridyloxazol-2-yl,
optionally substituted phenyloxazol-2-yl,
optionally substituted biphenyl,
optionally substituted morpholinocarbonylphenyl,
optionally substituted pyridylthiophen-2-yl,
optionally substituted pyrazolylphenyl,
optionally substituted phenylpyridyl,
optionally substituted morpholylphenyl, and
pyridylcarbonylphenyl.

9. The compound according to claim 1 or 2 or its pharmacologically acceptable salt, wherein $R_2$ represents a hydrogen atom;

optionally substituted $C_{1-6}$ alkyl wherein the $C_{1-6}$ alkyl group is optionally substituted by one or more groups selected from the group consisting of amino, hydroxy, heterocyclic rings substituted by $C_{1-6}$ alkyl, and cyano;

$C_{2-6}$ alkenyl;

$C_{1-6}$ acyl wherein the acyl group is optionally substituted by one or more groups selected from the group consisting of hydroxy, heterocyclic rings, and amino; or $C_{1-6}$ alkyloxycarbonyl.

10. The compound according to claim 1 or 2 or its pharmacologically acceptable salt, wherein $R_3$ represents n-$C_{1-6}$ alkyl or $C_{2-6}$ alkenyl.

11. The compound according to claim 1 or 2 or its pharmacologically acceptable salt, wherein A represents 1,3,4-thiadiazolyl, $R_1$ represents a group selected from the group consisting of amino optionally substituted by acyl, $C_{1-6}$ alkyloxycarbonyl, 4- to 7-membered heterocyclic carbonyl optionally substituted by $C_{1-6}$ alkyl, optionally substituted aryl wherein the aryl is optionally substituted by one or more groups selected from the group consisting of a fluorine atom, a chlorine atom, nitro, amino, $C_{1-6}$ alkyl, cyano, $C_{1-6}$ alkylthio, $C_{1-6}$ alkylsulfonyl, $C_{1-6}$ alkyloxy, hydroxy $C_{1-6}$ alkylamino, $C_{1-6}$ alkylamino, di-$C_{1-6}$ alkylamino, $C_{1-6}$ alkylsulfinyl, $C_{1-6}$ alkyloxycarbonyl, carbamoyl, di-$C_{1-6}$ alkylaminocarbonyl, hydroxy, and azetidinyl, and optionally substituted 4- to 7-membered monocyclic heterocyclic groups wherein the heterocyclic group is optionally substituted by one or more groups selected from the group consisting of nitro, $C_{1-6}$ alkyl, $C_{1-6}$ alkylamino, and amino, $R_2$ represents a hydrogen atom or optionally substituted $C_{1-6}$ alkyl wherein the $C_{1-6}$ alkyl group is optionally substituted by one or more groups selected from the group consisting of amino, hydroxy, and $C_{1-6}$ alkyl substituted heterocyclic ring, $R_3$ represents n-$C_{1-6}$ alkyl, all of $R_4$, $R_5$, and $R_6$ represent a hydrogen atom, $R_7$ represents $C_{1-6}$ alkyl, m is 1 or 2, and
n is 1.

12. The compound according to claim 1 or 2 or its pharmacologically acceptable salt, wherein A represents phenyl, $R_1$ represents a group selected from the group consisting of
halides,
nitro,
$C_{1-6}$ alkyl substituted by hydroxy, a halide, or $C_{1-6}$ alkyloxy,
amino optionally substituted by acyl,
heterocyclic amino,
$C_{1-6}$ alkyloxycarbonyl,
heterocyclic-$C_{1-6}$ alkylcarbonyl, and,
N-(hydroxy-$C_{1-6}$ alkyl) substituted carbamoyl,
N-(dihydroxy-$C_{1-6}$ alkyl) substituted carbamoyl,
N-(di-$C_{1-6}$ alkyloxy-$C_{1-6}$ alkyl) substituted carbamoyl,
N,N-di(hydroxy-$C_{1-6}$ alkyl) substituted carbamoyl,
N,N-di($C_{1-6}$ alkyloxy-$C_{1-6}$ alkyl) substituted carbamoyl,
optionally substituted 4- to 7-membered heterocyclic carbonyl
wherein the heterocyclic carbonyl group is optionally substituted by one or more groups selected from the group consisting of $C_{1-6}$ alkyl, hydroxy $C_{1-6}$ alkyl, $C_{1-6}$ alkyloxy-$C_{1-6}$ alkyl, oxo, $C_{1-6}$ alkyloxy, hydroxy, $C_{1-6}$ alkylcarbonylamino, amino-$C_{1-6}$ alkyl, $C_{1-6}$ alkylamino-$C_{1-6}$ alkyl, di-$C_{1-6}$ alkylamino-$C_{1-6}$ alkyl, $C_{2-6}$ alkenyloxy-$C_{1-6}$ alkyl, and $C_{1-6}$ alkylthio-$C_{1-6}$ alkyl,
optionally substituted aryl
wherein the aryl group is optionally substituted by one or more groups selected from the group consisting of cyano, amino, $C_{1-6}$ alkyl, $C_{1-6}$ alkylcarbonylamino, $C_{1-6}$ alkyloxy, $C_{1-6}$ alkylthio, and di-$C_{1-6}$ alkylamino, and
optionally substituted 4- to 7-membered monocyclic heterocyclic groups
wherein the heterocyclic group is optionally substituted by one or more groups selected from the group consisting of $C_{1-6}$ alkyl, $C_{1-6}$ alkyloxy, N-oxide, nitro, $C_{1-6}$ alkyloxy-$C_{1-6}$ alkyl, amino, halide, and oxo, $R_2$ represents a hydrogen atom or $C_{1-6}$ alkyl,
$R_3$ represents n-$C_{1-6}$ alkyl,
all of $R_4$, $R_5$, and $R_6$ represent a hydrogen atom,
$R_7$ represents $C_{1-6}$ alkyl,
m is 1 or 2, and
n is 1.

13. A pharmaceutical composition comprising a compound according to claim 1 or 2 or its pharmacologically acceptable salt and a pharmaceutically acceptable carrier.

14. The pharmaceutical composition according to claim 13, which further comprises an additive for a pharmaceutical preparation.

15. The pharmaceutical composition according to claim 13 for use as an antimicrobial agent.

16. The pharmaceutical composition according to claim 13 for use in the treatment of bacterial infectious diseases in respiratory organs.

17. A method for treating bacterial infectious diseases, comprising administering a therapeutically effective amount of a compound according to claim 1 or 2 or its pharmacologically acceptable salt together with a pharmaceutically acceptable carrier to a mammal.

18. The method according to claim 17, wherein the infectious disease is a bacterial infectious disease in a respiratory organ.

* * * * *